(12) United States Patent
Kamen et al.

(10) Patent No.: US 11,615,886 B2
(45) Date of Patent: *Mar. 28, 2023

(54) SYRINGE PUMP AND RELATED METHOD

(71) Applicant: DEKA Products Limited Partnership, Manchester, NH (US)

(72) Inventors: Dean Kamen, Bedford, NH (US); Larry B. Gray, Merrimack, NH (US); Jesse T. Bodwell, Manchester, NH (US); John M. Kerwin, Manchester, NH (US); Dirk A. van der Merwe, Canterbury, NH (US); Stephen L. Fichera, Salem, NH (US); Jonathan R. Thurber, Deerfield, NH (US); Martin D. Desch, Newburyport, MA (US)

(73) Assignee: DEKA Products Limited Partnership, Manchester, NH (US)

( * ) Notice: Subject to any disclaimer, the term of this patent is extended or adjusted under 35 U.S.C. 154(b) by 452 days.

This patent is subject to a terminal disclaimer.

(21) Appl. No.: 16/788,531

(22) Filed: Feb. 12, 2020

(65) Prior Publication Data
US 2020/0171241 A1    Jun. 4, 2020

Related U.S. Application Data

(63) Continuation of application No. 15/635,391, filed on Jun. 28, 2017, now Pat. No. 10,561,787, which is a
(Continued)

(51) Int. Cl.
*A61M 31/00* (2006.01)
*G16H 40/67* (2018.01)
(Continued)

(52) U.S. Cl.
CPC .......... *G16H 40/67* (2018.01); *A61M 5/142* (2013.01); *A61M 5/14236* (2013.01);
(Continued)

(58) Field of Classification Search
CPC ........ G16H 40/67; G16H 20/17; G16H 40/63; A61M 5/142; A61M 5/14236; A61M 5/172
(Continued)

(56) References Cited

U.S. PATENT DOCUMENTS

| 3,964,139 A | 6/1976 | Kleinmann et al. |
| D263,997 S | 4/1982 | Preussner |

(Continued)

FOREIGN PATENT DOCUMENTS

| AU | 659748 B2 | 5/1995 |
| CN | 1298313 A | 6/2001 |

(Continued)

OTHER PUBLICATIONS

AAMI and FDA, Infusing Patients Safely: Priority Issues from the AAMI/FDA Infusion Device Summit, Symposium, Oct. 5-6, 2010, pp. 1-48, AAMI, Arlington, VA, USA.
(Continued)

*Primary Examiner* — Tai T Nguyen
(74) *Attorney, Agent, or Firm* — Ira Stickler

(57) ABSTRACT

A syringe pump includes a lead screw, a motor, and a sliding block assembly. The lead screw has threads and the motor is coupled to the lead screw to rotate it. The half-nut housing has a half nut and a barrel cam. The half nut is disposed within the half-nut housing. The half nut has half-nut threads at an end adjacent to the lead screw void. The half nut engages or disengages with the threads of the lead screw. The half nut includes a half-nut cam-follower surface and a half nut slot. The barrel cam is disposed within the half-nut housing and engages with the half-nut cam-follower surface. The barrel cam includes a pin to fit within the half nut slot such that the barrel cam rotates between a first position and a second position to actuate the half nut between the
(Continued)

engagement position and the disengagement position, respectively.

34 Claims, 97 Drawing Sheets

Related U.S. Application Data continuation of application No. 13/833,432, filed on Mar. 15, 2013, now Pat. No. 9,744,300, which is a continuation-in-part of application No. 13/724,568, filed on Dec. 21, 2012, now Pat. No. 9,295,778, and a continuation-in-part of application No. 13/723,238, filed on Dec. 21, 2012, now Pat. No. 9,759,369, and a continuation-in-part of application No. 13/725,790, filed on Dec. 21, 2012, now Pat. No. 9,677,555, and a continuation-in-part of application No. 13/723,251, filed on Dec. 21, 2012, now Pat. No. 9,636,455, and a continuation-in-part of application No. PCT/US2012/071131, filed on Dec. 21, 2012, and a continuation-in-part of application No. 13/723,253, filed on Dec. 21, 2012, now Pat. No. 11,210,611, and a continuation-in-part of application No. PCT/US2012/071112, filed on Dec. 21, 2012, and a continuation-in-part of application No. PCT/US2012/071490, filed on Dec. 21, 2012, and a continuation-in-part of application No. 13/723,242, filed on Dec. 21, 2012, now Pat. No. 10,911,515, and a continuation-in-part of application No. 13/723,235, filed on Dec. 21, 2012, now Pat. No. 9,400,873, and a continuation-in-part of application No. 13/723,244, filed on Dec. 21, 2012, now Pat. No. 9,151,646, and a continuation-in-part of application No. PCT/US2012/071142, filed on Dec. 21, 2012, and a continuation-in-part of application No. 13/723,239, filed on Dec. 21, 2012, now Pat. No. 10,108,785, said application No. 13/725,790 is a continuation-in-part of application No. 13/333,574, filed on Dec. 21, 2011, now Pat. No. 10,453,157, said application No. PCT/US2012/071490 is a continuation-in-part of application No. PCT/US2011/066588, filed on Dec. 21, 2011, said application No. 13/723,238 is a continuation-in-part of application No. PCT/US2011/066588, filed on Dec. 21, 2011, said application No. 13/833,432 is a continuation-in-part of application No. 13/333,574, filed on Dec. 21, 2011, now Pat. No. 10,453,157, said application No. PCT/US2012/071142 is a continuation-in-part of application No. 13/333,574, filed on Dec. 21, 2011, now Pat. No. 10,453,157, said application No. 13/723,235 is a continuation-in-part of application No. PCT/US2011/066588, filed on Dec. 21, 2011, said application No. 13/725,790 is a continuation-in-part of application No. PCT/US2011/066588, filed on Dec. 21, 2011, said application No. PCT/US2012/071490 is a continuation-in-part of application No. 13/333,574, filed on Dec. 21, 2011, now Pat. No. 10,453,157, said application No. 13/723,238 is a continuation-in-part of application No. 13/333,574, filed on Dec. 21, 2011, now Pat. No. 10,453,157, said application No. 13/723,251 is a continuation-in-part of application No. 13/333,574, filed on Dec. 21, 2011, now Pat. No. 10,453,157, said application No. 13/723,244 is a continuation-in-part of application No. 13/333,574, filed on Dec. 21, 2011, now Pat. No. 10,453,157, said application No. PCT/US2012/071131 is a continuation-in-part of application No. 13/333,574, filed on Dec. 21, 2011, now Pat. No. 10,453,157, said application No. 13/723,253 is a continuation-in-part of application No. PCT/US2011/066588, filed on Dec. 21, 2011, said application No. 13/723,244 is a continuation-in-part of application No. PCT/US2011/066588, filed on Dec. 21, 2011, said application No. PCT/US2012/071131 is a continuation-in-part of application No. PCT/US2011/066588, filed on Dec. 21, 2011, said application No. 13/723,253 is a continuation-in-part of application No. 13/333,574, filed on Dec. 21, 2011, now Pat. No. 10,453,157, said application No. PCT/US2012/071142 is a continuation-in-part of application No. PCT/US2011/066588, filed on Dec. 21, 2011, said application No. 13/723,235 is a continuation-in-part of application No. 13/333,574, filed on Dec. 21, 2011, now Pat. No. 10,453,157, said application No. 13/723,239 is a continuation-in-part of application No. PCT/US2011/066588, filed on Dec. 21, 2011, said application No. 13/723,251 is a continuation-in-part of application No. PCT/US2011/066588, filed on Dec. 21, 2011, said application No. 13/724,568 is a continuation-in-part of application No. PCT/US2011/066588, filed on Dec. 21, 2011, said application No. 13/833,432 is a continuation-in-part of application No. PCT/US2011/066588, filed on Dec. 21, 2011, said application No. 13/724,568 is a continuation-in-part of application No. 13/333,574, filed on Dec. 21, 2011, now Pat. No. 10,453,157, said application No. PCT/US2012/071112 is a continuation-in-part of application No. 13/333,574, filed on Dec. 21, 2011, now Pat. No. 10,453,157, said application No. 13/723,239 is a continuation-in-part of application No. 13/333,574, filed on Dec. 21, 2011, now Pat. No. 10,453,157, said application No. PCT/US2012/071112 is a continuation-in-part of application No. PCT/US2011/066588, filed on Dec. 21, 2011.

(60) Provisional application No. 61/679,117, filed on Aug. 3, 2012, provisional application No. 61/651,322, filed on May 24, 2012, provisional application No. 61/578,674, filed on Dec. 21, 2011, provisional application No. 61/578,649, filed on Dec. 21, 2011, provisional application No. 61/578,658, filed on Dec. 21, 2011.

(51) Int. Cl.
    *A61M 5/172*     (2006.01)
    *A61M 5/142*     (2006.01)
    *G16H 20/17*     (2018.01)
    *G16H 40/63*     (2018.01)

(52) U.S. Cl.
    CPC ............ *A61M 5/172* (2013.01); *G16H 20/17* (2018.01); *G16H 40/63* (2018.01); *A61M 2205/103* (2013.01); *A61M 2205/16* (2013.01); *A61M 2205/18* (2013.01); *A61M 2205/332* (2013.01); *A61M 2205/3331* (2013.01); *A61M 2205/3334* (2013.01); *A61M 2205/3365* (2013.01); *A61M 2205/3584* (2013.01); *A61M 2205/50* (2013.01); *A61M 2205/505* (2013.01); *A61M 2205/52* (2013.01); *A61M 2205/581* (2013.01); *A61M 2205/587* (2013.01); *A61M 2205/6054* (2013.01); *A61M 2205/8206* (2013.01)

(58) Field of Classification Search
USPC .................................................... 604/500
See application file for complete search history.

(56) References Cited

U.S. PATENT DOCUMENTS

| | | | |
|---|---|---|---|
| 4,424,720 A | 1/1984 | Bucchianeri | |
| D289,395 S | 4/1987 | Bowers | |
| D309,662 S | 7/1990 | Gorton | |
| 4,976,696 A | 12/1990 | Sanderson et al. | |
| 4,991,433 A | 2/1991 | Warnaka et al. | |
| 5,176,502 A | 1/1993 | Sanderson et al. | |
| 5,256,157 A | 10/1993 | Samiotes et al. | |
| 5,295,966 A | 3/1994 | Stern et al. | |
| D348,730 S | 7/1994 | Walker et al. | |
| D353,667 S | 12/1994 | Tsubota et al. | |
| 5,395,321 A | 3/1995 | Kawahara et al. | |
| 5,472,324 A | 12/1995 | Atwater | |
| 5,501,665 A | 3/1996 | Jhuboo et al. | |
| 5,505,709 A | 4/1996 | Funderburk et al. | |
| 5,533,981 A | 7/1996 | Mandro et al. | |
| 5,545,140 A | 8/1996 | Conero et al. | |
| 5,637,095 A | 6/1997 | Nason et al. | |
| 5,662,612 A | 9/1997 | Niehoff | |
| 5,681,285 A | 10/1997 | Ford et al. | |
| D390,654 S | 2/1998 | Alsberg et al. | |
| D393,072 S | 3/1998 | Rogler | |
| 5,755,563 A | 5/1998 | Clegg et al. | |
| 5,781,442 A | 7/1998 | Engleson et al. | |
| 5,800,387 A | 9/1998 | Duffy et al. | |
| 5,810,568 A | 9/1998 | Whitefield et al. | |
| 5,814,015 A | 9/1998 | Gargano et al. | |
| 5,836,910 A | 11/1998 | Duffy et al. | |
| 5,879,360 A | 3/1999 | Crankshaw | |
| 5,954,527 A | 9/1999 | Jhuboo et al. | |
| 5,954,697 A | 9/1999 | Srisathapat et al. | |
| D425,017 S | 5/2000 | Leung | |
| 6,179,569 B1 | 1/2001 | Kojima et al. | |
| D440,575 S | 4/2001 | Wang et al. | |
| 6,269,340 B1* | 7/2001 | Ford .............. | G16H 40/63 604/890.1 |
| 6,305,541 B1 | 10/2001 | Tanner et al. | |
| 6,305,908 B1 | 10/2001 | Hermann et al. | |
| 6,328,712 B1 | 12/2001 | Cartledge | |
| 6,338,200 B1 | 1/2002 | Baxa et al. | |
| 6,339,616 B1 | 1/2002 | Kovalev | |
| 6,346,886 B1 | 2/2002 | De La Huerga | |
| 6,347,553 B1 | 2/2002 | Morris et al. | |
| 6,348,777 B1 | 2/2002 | Brown et al. | |
| 6,358,225 B1 | 3/2002 | Butterfield | |
| 6,407,335 B1 | 6/2002 | Franklin-Lees et al. | |
| 6,408,330 B1 | 6/2002 | DeLaHuerga | |
| 6,423,035 B1 | 7/2002 | Das et al. | |
| 6,428,509 B1 | 8/2002 | Fielder | |
| 6,458,465 B1 | 10/2002 | Uchibori | |
| 6,485,465 B2 | 11/2002 | Moberg et al. | |
| 6,519,569 B1 | 2/2003 | White et al. | |
| 6,551,277 B1 | 4/2003 | Ford | |
| D475,134 S | 5/2003 | Randolph | |
| 6,575,930 B1 | 6/2003 | Trombley, III et al. | |
| 6,575,936 B1 | 6/2003 | Kojima et al. | |
| 6,592,551 B1 | 7/2003 | Cobb | |
| 6,593,528 B2 | 7/2003 | Franklin-Lees et al. | |
| 6,645,177 B1 | 11/2003 | Shearn | |
| 6,656,148 B2 | 12/2003 | Das et al. | |
| 6,659,980 B2 | 12/2003 | Moberg et al. | |
| 6,723,072 B2 | 4/2004 | Mahoney et al. | |
| D491,523 S | 6/2004 | Chi et al. | |
| 6,790,198 B1 | 9/2004 | White et al. | |
| D499,740 S | 12/2004 | Ombao et al. | |
| 6,932,242 B2 | 8/2005 | Gerlach et al. | |
| D512,151 S | 11/2005 | Ward et al. | |
| 6,976,349 B2 | 12/2005 | Baldwin et al. | |
| 6,997,905 B2 | 2/2006 | Gillespie, Jr. et al. | |
| 7,150,724 B2 | 12/2006 | Morris et al. | |
| 7,153,290 B2 | 12/2006 | Wakabayashi et al. | |
| D551,243 S | 9/2007 | Young | |
| D557,272 S | 12/2007 | Glaser et al. | |
| 7,311,879 B2 | 12/2007 | Hodson | |
| D559,262 S | 1/2008 | Young | |
| D568,814 S | 5/2008 | Hung | |
| 7,499,581 B2 | 3/2009 | Tribble et al. | |
| 7,543,516 B2 | 6/2009 | Siefert | |
| 7,553,294 B2 | 6/2009 | Lazzaro et al. | |
| 7,553,295 B2 | 6/2009 | Susi | |
| 7,556,616 B2 | 7/2009 | Fathallah et al. | |
| 7,561,986 B2 | 7/2009 | Vanderveen et al. | |
| 7,565,301 B2 | 7/2009 | Moubayed et al. | |
| D599,373 S | 9/2009 | Kobayashi et al. | |
| 7,608,060 B2 | 10/2009 | Gillespie, Jr. et al. | |
| D604,740 S | 11/2009 | Matheny et al. | |
| 7,611,503 B2 | 11/2009 | Spohn et al. | |
| 7,621,893 B2 | 11/2009 | Moberg et al. | |
| 7,623,249 B2 | 11/2009 | Sandberg et al. | |
| 7,635,349 B2 | 12/2009 | Tribe et al. | |
| 7,651,489 B2 | 1/2010 | Estes et al. | |
| 7,678,071 B2 | 3/2010 | Lebel et al. | |
| 7,699,806 B2 | 4/2010 | Ware et al. | |
| 7,743,975 B2 | 6/2010 | Miller | |
| D622,730 S | 8/2010 | Krum et al. | |
| 7,766,863 B2 | 8/2010 | Gillespie, Jr. et al. | |
| 7,766,873 B2 | 8/2010 | Moberg et al. | |
| 7,771,390 B2 | 8/2010 | Brown | |
| 7,794,429 B2 | 9/2010 | Niehoff | |
| 7,794,443 B2 | 9/2010 | Nelson et al. | |
| D625,322 S | 10/2010 | Guntaur et al. | |
| D625,323 S | 10/2010 | Matsushima et al. | |
| 7,819,843 B2 | 10/2010 | Mann et al. | |
| 7,823,287 B2 | 11/2010 | Gerlach et al. | |
| 7,824,374 B2 | 11/2010 | Niehoff | |
| 7,873,489 B2 | 1/2011 | Dolgos et al. | |
| 7,890,881 B1 | 2/2011 | Skidgel | |
| 7,892,206 B2 | 2/2011 | Moberg et al. | |
| 7,893,876 B2 | 2/2011 | Brown et al. | |
| D633,517 S | 3/2011 | Weir et al. | |
| 7,896,842 B2 | 3/2011 | Palmroos et al. | |
| 7,904,822 B2 | 3/2011 | Monteleone et al. | |
| 7,905,860 B2 | 3/2011 | Stempfle et al. | |
| 7,911,353 B2 | 3/2011 | Bedingfield | |
| 7,933,780 B2 | 4/2011 | De La Huerga | |
| 7,938,796 B2 | 5/2011 | Moubayed et al. | |
| 7,941,534 B2 | 5/2011 | de la Huerga | |
| 7,945,452 B2 | 5/2011 | Fathallah et al. | |
| 7,972,306 B2 | 7/2011 | Shearn | |
| 7,976,508 B2 | 7/2011 | Hoag | |
| 8,025,634 B1 | 9/2011 | Moubayed et al. | |
| 8,032,226 B2 | 10/2011 | Miller et al. | |
| 8,034,019 B2 | 10/2011 | Nair et al. | |
| 8,062,257 B2 | 11/2011 | Moberg et al. | |
| D649,973 S | 12/2011 | Matas | |
| 8,070,732 B2 | 12/2011 | Rochette | |
| D652,050 S | 1/2012 | Chaudhri | |
| D655,301 S | 3/2012 | Ray et al. | |
| 8,133,197 B2 | 3/2012 | Blomquist et al. | |
| 8,134,459 B2 | 3/2012 | Smith et al. | |
| 8,149,131 B2 | 4/2012 | Blomquist | |
| 8,161,810 B2 | 4/2012 | Cadieux et al. | |
| D660,313 S | 5/2012 | Williams et al. | |
| 8,182,461 B2 | 5/2012 | Pope et al. | |
| 8,185,322 B2 | 5/2012 | Schroeder et al. | |
| D662,051 S | 6/2012 | Saunders et al. | |
| 8,192,394 B2 | 6/2012 | Estes et al. | |
| 8,209,060 B2 | 6/2012 | Ledford | |
| 8,231,578 B2 | 7/2012 | Fathallah et al. | |
| D664,988 S | 8/2012 | Gleasman et al. | |
| D665,401 S | 8/2012 | Rai et al. | |
| D666,208 S | 8/2012 | Spears et al. | |
| 8,235,938 B2 | 8/2012 | Eggers et al. | |
| 8,250,483 B2 | 8/2012 | Blomquist | |
| 8,267,893 B2 | 9/2012 | Moberg et al. | |
| D668,262 S | 10/2012 | Gleasman et al. | |
| D669,096 S | 10/2012 | Katsura | |
| D669,165 S | 10/2012 | Estes et al. | |
| D671,550 S | 11/2012 | Chen et al. | |
| D671,551 S | 11/2012 | Deng et al. | |

(56) References Cited

U.S. PATENT DOCUMENTS

| | | |
|---|---|---|
| D673,168 S | 12/2012 | Frijlink et al. |
| D675,224 S | 1/2013 | Lee et al. |
| 8,359,338 B2 | 1/2013 | Butterfield et al. |
| D675,727 S | 2/2013 | Collins et al. |
| 8,378,837 B2 | 2/2013 | Wang et al. |
| D678,320 S | 3/2013 | Kanalakis, Jr. et al. |
| 8,388,598 B2 | 3/2013 | Steinkogler |
| 8,414,523 B2 | 4/2013 | Blomquist et al. |
| 8,435,206 B2 | 5/2013 | Evans et al. |
| D685,817 S | 7/2013 | Kunieda et al. |
| D689,195 S | 9/2013 | Nelsen |
| D690,729 S | 10/2013 | Abratowski et al. |
| D691,259 S | 10/2013 | Estes et al. |
| D692,378 S | 10/2013 | Esses |
| D696,684 S | 12/2013 | Yuk et al. |
| D696,686 S | 12/2013 | Yuk et al. |
| D698,362 S | 1/2014 | Ramesh et al. |
| D701,232 S | 3/2014 | Na et al. |
| D704,213 S | 5/2014 | Agnew |
| D705,244 S | 5/2014 | Arnold et al. |
| D705,248 S | 5/2014 | McCormack et al. |
| D708,626 S | 7/2014 | Klein et al. |
| D708,627 S | 7/2014 | Klein et al. |
| D709,085 S | 7/2014 | Wen |
| 8,814,830 B2 | 8/2014 | Morris et al. |
| D712,920 S | 9/2014 | Sloo et al. |
| D715,320 S | 10/2014 | McCormack et al. |
| D716,332 S | 10/2014 | Chotin et al. |
| D717,814 S | 11/2014 | Zuckerberg et al. |
| D718,776 S | 12/2014 | Hobbs et al. |
| D718,777 S | 12/2014 | Hobbs et al. |
| D718,778 S | 12/2014 | Hobbs et al. |
| D719,963 S | 12/2014 | Hobbs et al. |
| D719,964 S | 12/2014 | Hobbs et al. |
| 8,911,403 B2 | 12/2014 | Flachbart et al. |
| D721,719 S | 1/2015 | Lee |
| D722,612 S | 2/2015 | Lee et al. |
| D722,614 S | 2/2015 | Williams et al. |
| D723,052 S | 2/2015 | Lai et al. |
| D725,670 S | 3/2015 | Zhang et al. |
| D728,779 S | 5/2015 | Sabin et al. |
| D731,509 S | 6/2015 | Sueishi et al. |
| D732,062 S | 6/2015 | Kwon |
| D732,063 S | 6/2015 | Kwon |
| D732,567 S | 6/2015 | Moon et al. |
| D733,740 S | 7/2015 | Lee et al. |
| D733,741 S | 7/2015 | Lee et al. |
| D735,319 S | 7/2015 | Sabin et al. |
| D735,746 S | 8/2015 | Zuckerberg et al. |
| D736,370 S | 8/2015 | Sabin et al. |
| D740,848 S | 10/2015 | Bolts et al. |
| D741,358 S | 10/2015 | Seo et al. |
| 9,151,646 B2 | 10/2015 | Kamen et al. |
| D745,661 S | 12/2015 | Collins et al. |
| D749,206 S | 2/2016 | Johnson et al. |
| D751,689 S | 3/2016 | Peret et al. |
| D751,690 S | 3/2016 | Peret et al. |
| D752,209 S | 3/2016 | Peret et al. |
| 9,295,778 B2 | 3/2016 | Kamen et al. |
| D754,065 S | 4/2016 | Gray et al. |
| D756,386 S | 5/2016 | Kendler et al. |
| D758,399 S | 6/2016 | Kendler et al. |
| D760,288 S | 6/2016 | Kendler et al. |
| D760,289 S | 6/2016 | Kendler et al. |
| 9,364,394 B2 | 6/2016 | Demers et al. |
| 9,372,486 B2 | 6/2016 | Peret et al. |
| D760,782 S | 7/2016 | Kendler et al. |
| D760,888 S | 7/2016 | Gill et al. |
| 9,400,873 B2 | 7/2016 | Kamen et al. |
| 9,408,966 B2 | 8/2016 | Kamen |
| D767,756 S | 9/2016 | Sabin |
| 9,435,455 B2 | 9/2016 | Peret et al. |
| D768,716 S | 10/2016 | Kendler et al. |
| 9,465,919 B2 | 10/2016 | Kamen et al. |
| 9,488,200 B2 | 11/2016 | Kamen et al. |
| D774,645 S | 12/2016 | Gill et al. |
| 9,518,958 B2 | 12/2016 | Wilt et al. |
| 9,636,455 B2 | 5/2017 | Kamen et al. |
| D789,516 S | 6/2017 | Gill et al. |
| 9,675,756 B2 | 6/2017 | Kamen et al. |
| 9,677,555 B2 | 6/2017 | Kamen et al. |
| 9,687,417 B2 | 6/2017 | Demers et al. |
| D792,963 S | 7/2017 | Gill |
| D795,424 S | 8/2017 | Sloss |
| D795,805 S | 8/2017 | Gray et al. |
| 9,719,964 B2 | 8/2017 | Blumberg |
| 9,724,465 B2 | 8/2017 | Peret et al. |
| 9,724,466 B2 | 8/2017 | Peret et al. |
| 9,730,731 B2 | 8/2017 | Langenfeld et al. |
| 9,744,300 B2 | 8/2017 | Kamen et al. |
| 9,746,093 B2 | 8/2017 | Peret et al. |
| 9,746,094 B2 | 8/2017 | Peret et al. |
| 9,759,343 B2 | 9/2017 | Peret et al. |
| 9,759,369 B2 | 9/2017 | Gray et al. |
| 9,772,044 B2 | 9/2017 | Peret et al. |
| D799,025 S | 10/2017 | Johnson et al. |
| D801,519 S | 10/2017 | Sabin et al. |
| 9,789,247 B2 | 10/2017 | Kamen et al. |
| D802,118 S | 11/2017 | Peret et al. |
| D803,386 S | 11/2017 | Sabin et al. |
| D803,387 S | 11/2017 | Bodwell et al. |
| D804,017 S | 11/2017 | Sabin |
| 9,808,572 B2 | 11/2017 | Kamen et al. |
| D805,183 S | 12/2017 | Sabin et al. |
| 9,856,990 B2 | 1/2018 | Peret et al. |
| D813,376 S | 3/2018 | Peret et al. |
| D814,021 S | 3/2018 | Sabin |
| D815,730 S | 4/2018 | Collins et al. |
| D816,685 S | 5/2018 | Kendler et al. |
| D816,829 S | 5/2018 | Peret et al. |
| D817,479 S | 5/2018 | Sabin et al. |
| D817,480 S | 5/2018 | Sabin et al. |
| 9,968,730 B2 | 5/2018 | Blumberg, Jr. et al. |
| 9,976,665 B2 | 5/2018 | Peret et al. |
| 10,044,791 B2 | 8/2018 | Kamen et al. |
| 10,228,683 B2 | 3/2019 | Peret et al. |
| 10,391,241 B2 | 8/2019 | Desch et al. |
| 10,561,787 B2 | 2/2020 | Kamen et al. |
| 10,722,645 B2 | 7/2020 | Kamen et al. |
| 2001/0018937 A1 | 9/2001 | Nemoto |
| 2001/0024502 A1 | 9/2001 | Ohkuma et al. |
| 2001/0044602 A1 | 11/2001 | Angersbach et al. |
| 2003/0009133 A1 | 1/2003 | Ramey |
| 2003/0106553 A1 | 6/2003 | Vanderveen |
| 2003/0161744 A1 | 8/2003 | Vilks et al. |
| 2003/0216692 A1 | 11/2003 | Fago et al. |
| 2003/0229311 A1 | 12/2003 | G. Morris et al. |
| 2004/0158193 A1 | 8/2004 | Bui et al. |
| 2005/0004514 A1 | 1/2005 | Hochman |
| 2005/0029277 A1 | 2/2005 | Tachibana |
| 2005/0050301 A1 | 3/2005 | Whittle et al. |
| 2005/0143735 A1 | 6/2005 | Kyle |
| 2005/0220639 A1 | 10/2005 | Sasaki et al. |
| 2005/0267827 A1 | 12/2005 | Grant, Jr. et al. |
| 2006/0167414 A1 | 7/2006 | Scott et al. |
| 2006/0184123 A1 | 8/2006 | Gillespie et al. |
| 2006/0258985 A1 | 11/2006 | Russell |
| 2007/0074596 A1 | 4/2007 | Siefert |
| 2007/0100281 A1 | 5/2007 | Morris et al. |
| 2007/0109325 A1 | 5/2007 | Eveleigh |
| 2007/0191770 A1 | 8/2007 | Moberg et al. |
| 2007/0201992 A1 | 8/2007 | Mernoe |
| 2008/0262440 A1 | 10/2008 | Rochette |
| 2008/0281272 A1 | 11/2008 | Blundred et al. |
| 2009/0005736 A1 | 1/2009 | Flachbart et al. |
| 2009/0040875 A1 | 2/2009 | Buzescu et al. |
| 2009/0144620 A1 | 6/2009 | Bauchot et al. |
| 2009/0153058 A1 | 6/2009 | Feng et al. |
| 2009/0188311 A1 | 7/2009 | Cadieux et al. |
| 2009/0203329 A1 | 8/2009 | White et al. |
| 2009/0254037 A1 | 10/2009 | Bryant, Jr. et al. |
| 2009/0270810 A1 | 10/2009 | DeBelser et al. |
| 2010/0063447 A1 | 3/2010 | Stempfle et al. |
| 2010/0153872 A1 | 6/2010 | Ahn et al. |

(56) References Cited

U.S. PATENT DOCUMENTS

| | | |
|---|---|---|
| 2010/0169389 A1 | 7/2010 | Weber et al. |
| 2010/0169783 A1 | 7/2010 | Weber et al. |
| 2010/0214110 A1 | 8/2010 | Wang et al. |
| 2011/0085778 A1 | 4/2011 | Iwase et al. |
| 2011/0097229 A1 | 4/2011 | Cauley, III et al. |
| 2011/0106318 A1 | 5/2011 | Ledford |
| 2011/0161806 A1 | 6/2011 | Stern et al. |
| 2011/0184383 A1 | 7/2011 | Hasegawa |
| 2011/0190694 A1* | 8/2011 | Lanier, Jr. ......... A61M 5/16881 604/67 |
| 2011/0213329 A1 | 9/2011 | Yodfat et al. |
| 2011/0218514 A1 | 9/2011 | Rebours |
| 2011/0224614 A1 | 9/2011 | Moberg et al. |
| 2011/0231204 A1 | 9/2011 | De La Huerga |
| 2011/0241878 A1 | 10/2011 | Hoag |
| 2011/0264383 A1 | 10/2011 | Moberg et al. |
| 2011/0271221 A1 | 11/2011 | Lategan |
| 2011/0313789 A1 | 12/2011 | Kamen et al. |
| 2011/0320049 A1 | 12/2011 | Chossat et al. |
| 2012/0016295 A1 | 1/2012 | Tsoukalis |
| 2012/0025995 A1 | 2/2012 | Moberg et al. |
| 2012/0035581 A1 | 2/2012 | Travis |
| 2012/0049543 A1 | 3/2012 | Park |
| 2012/0066609 A1 | 3/2012 | Howard et al. |
| 2012/0078222 A1 | 3/2012 | Smith et al. |
| 2012/0079416 A1 | 3/2012 | Fagans |
| 2012/0083760 A1 | 4/2012 | Ledford et al. |
| 2012/0124174 A1 | 5/2012 | Nudelman et al. |
| 2012/0130308 A1 | 5/2012 | Silkaitis et al. |
| 2012/0157920 A1 | 6/2012 | Flachbart et al. |
| 2012/0172802 A1 | 7/2012 | Blomquist |
| 2012/0176394 A1 | 7/2012 | Vik et al. |
| 2012/0177507 A1 | 7/2012 | Bennett et al. |
| 2012/0179130 A1 | 7/2012 | Barnes et al. |
| 2012/0185267 A1 | 7/2012 | Kamen et al. |
| 2012/0203195 A1 | 8/2012 | Pope et al. |
| 2012/0209197 A1 | 8/2012 | Lanigan et al. |
| 2012/0215169 A1 | 8/2012 | Moberg et al. |
| 2012/0215170 A1 | 8/2012 | Traversaz et al. |
| 2012/0215199 A1 | 8/2012 | Moberg et al. |
| 2012/0234099 A1 | 9/2012 | Rochette |
| 2012/0241525 A1 | 9/2012 | Borges et al. |
| 2012/0245525 A1 | 9/2012 | Pope et al. |
| 2012/0254044 A1 | 10/2012 | Flanagan et al. |
| 2012/0259282 A1* | 10/2012 | Alderete, Jr. ....... A61M 5/5086 604/131 |
| 2012/0266964 A1 | 10/2012 | West et al. |
| 2012/0283691 A1 | 11/2012 | Barnes et al. |
| 2012/0299737 A1 | 11/2012 | Fujioka et al. |
| 2012/0310205 A1 | 12/2012 | Lee et al. |
| 2013/0012880 A1 | 1/2013 | Blomquist |
| 2013/0023848 A1 | 1/2013 | Nelson et al. |
| 2013/0053820 A1 | 2/2013 | Estes et al. |
| 2013/0091191 A1 | 4/2013 | Levin et al. |
| 2013/0104120 A1 | 4/2013 | Arrizza et al. |
| 2013/0127870 A1 | 5/2013 | Baudel et al. |
| 2013/0129532 A1 | 5/2013 | Flachbart et al. |
| 2013/0133036 A1 | 5/2013 | Wang et al. |
| 2013/0141329 A1 | 6/2013 | Halbert et al. |
| 2013/0177455 A1 | 7/2013 | Kamen et al. |
| 2013/0182381 A1 | 7/2013 | Gray et al. |
| 2013/0184676 A1 | 7/2013 | Kamen et al. |
| 2013/0188040 A1 | 7/2013 | Kamen et al. |
| 2013/0191513 A1 | 7/2013 | Kamen |
| 2013/0197693 A1 | 8/2013 | Kamen et al. |
| 2013/0204188 A1 | 8/2013 | Kamen |
| 2013/0272773 A1 | 10/2013 | Kamen |
| 2013/0281965 A1 | 10/2013 | Kamen |
| 2013/0297330 A1 | 11/2013 | Kamen |
| 2013/0310990 A1 | 11/2013 | Peret et al. |
| 2013/0317753 A1 | 11/2013 | Kamen |
| 2013/0317837 A1 | 11/2013 | Ballantyne |
| 2013/0318429 A1 | 11/2013 | Dantas et al. |
| 2013/0325154 A1 | 12/2013 | Oh et al. |
| 2013/0336814 A1 | 12/2013 | Kamen |
| 2013/0339049 A1 | 12/2013 | Blumberg, Jr. |
| 2013/0346108 A1 | 12/2013 | Kamen |
| 2014/0152585 A1 | 6/2014 | Andersson Reimer |
| 2014/0165703 A1 | 6/2014 | Wilt |
| 2014/0180711 A1 | 6/2014 | Kamen |
| 2014/0188076 A1 | 7/2014 | Kamen et al. |
| 2014/0188516 A1 | 7/2014 | Kamen |
| 2014/0195639 A1 | 7/2014 | Kamen |
| 2014/0227021 A1 | 8/2014 | Kamen |
| 2014/0237419 A1 | 8/2014 | Ryu |
| 2014/0243745 A1 | 8/2014 | Ueda et al. |
| 2014/0318639 A1 | 10/2014 | Peret |
| 2014/0343492 A1 | 11/2014 | Kamen |
| 2014/0343533 A1 | 11/2014 | Gerlach et al. |
| 2014/0359443 A1 | 12/2014 | Hwang |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0018766 A1 | 1/2015 | Nakanishi et al. |
| 2015/0023808 A1 | 1/2015 | Zhu |
| 2015/0033823 A1 | 2/2015 | Blumberg, Jr. |
| 2015/0089364 A1 | 3/2015 | Meller et al. |
| 2015/0151057 A1 | 6/2015 | Nakanishi |
| 2015/0154364 A1 | 6/2015 | Biasi et al. |
| 2015/0157791 A1* | 6/2015 | Desch ............... A61M 5/16859 702/50 |
| 2015/0238228 A1 | 8/2015 | Langenfeld et al. |
| 2015/0257974 A1 | 9/2015 | Demers et al. |
| 2015/0314083 A1 | 11/2015 | Blumberg, Jr. et al. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0131272 A1 | 5/2016 | Yoo |
| 2016/0158437 A1 | 6/2016 | Biasi et al. |
| 2016/0179086 A1 | 6/2016 | Peret et al. |
| 2016/0184510 A1 | 6/2016 | Kamen et al. |
| 2016/0203292 A1 | 7/2016 | Kamen et al. |
| 2016/0262977 A1 | 9/2016 | Demers et al. |
| 2016/0319850 A1 | 11/2016 | Kamen et al. |
| 2016/0346056 A1 | 12/2016 | Demers et al. |
| 2016/0362234 A1 | 12/2016 | Peret et al. |
| 2017/0011202 A1 | 1/2017 | Kamen et al. |
| 2017/0045478 A1 | 2/2017 | Wilt et al. |
| 2017/0216516 A1 | 8/2017 | Dale et al. |
| 2017/0224909 A1 | 8/2017 | Kamen et al. |
| 2017/0259230 A1 | 9/2017 | Demers et al. |
| 2017/0266378 A1 | 9/2017 | Kamen et al. |
| 2017/0268497 A1 | 9/2017 | Kamen et al. |
| 2017/0284968 A1 | 10/2017 | Blumberg, Jr. |
| 2017/0296745 A1 | 10/2017 | Kamen et al. |
| 2017/0303969 A1 | 10/2017 | Langenfeld et al. |
| 2017/0321841 A1 | 11/2017 | Gray et al. |
| 2017/0333623 A1 | 11/2017 | Kamen et al. |
| 2017/0335988 A1 | 11/2017 | Peret et al. |
| 2018/0038501 A1 | 2/2018 | Peret et al. |
| 2018/0066648 A1 | 3/2018 | Kamen et al. |
| 2018/0080605 A1 | 3/2018 | Janway et al. |
| 2018/0106246 A1 | 4/2018 | Kamen et al. |
| 2018/0128259 A1 | 5/2018 | Kamen et al. |
| 2019/0009018 A1 | 1/2019 | Kamen et al. |
| 2019/0175821 A1 | 6/2019 | Kamen et al. |
| 2019/0328964 A1 | 10/2019 | Desch et al. |
| 2020/0171241 A1 | 6/2020 | Kamen et al. |

FOREIGN PATENT DOCUMENTS

| | | |
|---|---|---|
| CN | 2717611 Y | 8/2005 |
| CN | 102106062 A | 6/2011 |
| CN | 202126188 U | 1/2012 |
| EP | 467657 A1 | 1/1992 |
| EP | 477551 B1 | 1/1995 |
| EP | 760244 A1 | 3/1997 |
| EP | 960627 A2 | 12/1999 |
| EP | 1640028 A2 | 3/2006 |

(56) References Cited

FOREIGN PATENT DOCUMENTS

| EP | 1526884 | B1 | 10/2006 |
|---|---|---|---|
| EP | 1722310 | A1 | 11/2006 |
| EP | 2554197 | A1 | 2/2013 |
| GB | 1018502 | A | 1/1966 |
| JP | 06339528 | A | 12/1994 |
| JP | 2002191693 | A | 7/2002 |
| JP | 2008515600 | A | 5/2008 |
| JP | 2008540117 | A | 11/2008 |
| WO | WO9310835 | A1 | 6/1993 |
| WO | WO9408647 | A1 | 4/1994 |
| WO | WO9814234 | A1 | 4/1998 |
| WO | WO9952575 | A1 | 10/1999 |
| WO | WO0018298 | A1 | 2/2000 |
| WO | WO02100262 | A1 | 12/2002 |
| WO | WO03094091 | A1 | 11/2003 |
| WO | WO2004012043 | A2 | 2/2004 |
| WO | WO2004029853 | A2 | 4/2004 |
| WO | WO2004052429 | A1 | 6/2004 |
| WO | WO2005089263 | A2 | 9/2005 |
| WO | WO2005102416 | A1 | 11/2005 |
| WO | WO2006040557 | A1 | 4/2006 |
| WO | WO2006044341 | A2 | 4/2006 |
| WO | WO2006061558 | A1 | 6/2006 |
| WO | WO2006124634 | A1 | 11/2006 |
| WO | WO2008022880 | A1 | 2/2008 |
| WO | WO2008024814 | A2 | 2/2008 |
| WO | WO2008139459 | A1 | 11/2008 |
| WO | WO2008153985 | A1 | 12/2008 |
| WO | WO2009003196 | A1 | 12/2008 |
| WO | WO2009003196 | A8 | 2/2009 |
| WO | WO2009039203 | A2 | 3/2009 |
| WO | WO2010111505 | A2 | 9/2010 |
| WO | WO2010129720 | A2 | 11/2010 |
| WO | WO2011032960 | A1 | 3/2011 |
| WO | WO2011066556 | A1 | 6/2011 |
| WO | WO2011091998 | A1 | 8/2011 |
| WO | WO2011119810 | A1 | 9/2011 |
| WO | WO2011121918 | A1 | 10/2011 |
| WO | WO2012114417 | A1 | 8/2012 |
| WO | WO2013095459 | A1 | 6/2013 |
| WO | WO2013095459 | A9 | 6/2013 |
| WO | WO2013096713 | A2 | 6/2013 |
| WO | WO2013096718 | A2 | 6/2013 |
| WO | WO2013096722 | A2 | 6/2013 |
| WO | WO2013096909 | A2 | 6/2013 |
| WO | WO2013176770 | A2 | 11/2013 |
| WO | WO2013177357 | A1 | 11/2013 |
| WO | WO2014100557 | A2 | 6/2014 |
| WO | WO2014100571 | A2 | 6/2014 |
| WO | WO2014100658 | A1 | 6/2014 |
| WO | WO2014100687 | A2 | 6/2014 |
| WO | WO2014100736 | A2 | 6/2014 |
| WO | WO2014100744 | A2 | 6/2014 |
| WO | WO2014144557 | A2 | 9/2014 |
| WO | WO2015017275 | A1 | 2/2015 |

OTHER PUBLICATIONS

Anestfusor, Anestfusor Series II Standard, User Manual, 2002-2010, pp. 1-37, version 2.6.2, rev. 1.0, SMB—University of Chile School of Medicine.
Argus, Syringe Pump Green Stream SY-P ARGUS 600, Service Manual, Dec. 8, 2004, pp. 1-31, ARGUS Medical AG.
Ascor, Syringe Pump AP 14, Operating Manual, May 6, 2007, pp. 1-52, version 1.1.2, pub. 001, Ascor S.A.
Ascor, Syringe Pump: Model AP 14, Operating Manual, Nov. 2007, pp. 1-52, version 1.2.3, pub. 001, Ascor S.A.
B. Braun, Outlook 100 Safety Infusion System, Operator's Manual, 2005, 76 pgs., B. Braun Medical Inc.
B. Braun, Outlook ES Safety Infusion System, 2008, 16 pgs., B. Braun Medical, Inc.
B. Braun, Perfusor Secura FT, Service-Manual, Sep. 23, 1998, 93 pgs., B. Braun Melsungen AG.
B. Braun, Perfusor Space PCA and Accessories: Instructions for Use, manual, Nov. 2010, 1-46, B. Braun Melsungen AG.
B. Braun, Perfusor Space, Service Manual, 132 pgs., Version 1.3, Mar. 25, 2009.
B. Braun, SpaceControl for Automated Glucose Control: Instructions for use, manual, Dec. 2010, 1-43, B. Braun Melsungen AG.
B. Braun, Vista basic Infusion Pump: Quick Reference, manual, 2002, 2 pgs., B. Braun Medical Inc.
Butterfield, Alaris SE Pump, Monitoring and Detection of IV Line Occlusions, 2010, 4 pgs., CareFusion Corporation.
Carayon et al., Observing Nurse Interaction with Infusion Pump Technologies, Advances in Patient Safety: From Research to Implementation, Feb. 2005, pp. 349-364, vol. 2: Concepts and Methodology.
Cardinal Health, Alaris DS Docking Station, Technical Service Manual, 2002-2007, pp. 1-31, Issue 2, Cardinal Health, Inc.
Cardinal Health, Alaris Syringe Pumps, Technical Service Manual, 2002-2006, pp. 1-88, Issue 9, Cardinal Health, Inc.
Cardinal Health, IVAC PCAM Syringe Pump, 2000-2007, 34 pgs., Issue 2, Cardinal Health, Inc.
Cardinal Health, IVAC PCAM Syringe Pump, Technical Service Manual, 2005-2006, pp. 1-106, Issue 2, Cardinal Health, Inc.
Cardinal Health, IVAC Syringe Pumps: Models P7000, P6000, TIVA, TCI, & TIVA, Technical Service Manual, 1998-2006, pp. 1-105, Issue 3, Cardinal Health, Inc.
Care Everywhere, Gateway User Manual: V 1.0.13 W/CQI 1.6: For use with the Sigma Spectrum Pump: Care Everywhere Document No. CE-100-003-IFU, manual, 1-55, CareEverywhere LLC, 9 Tech Circle, Natick, MA, USA. ©2010.
Carefusion, Alaris GH Syringe Pump, Alaris Products brochure, 2010, 2 pgs., Issue 1, CareFusion Corporation.
Carefusion, Alaris GH Syringe Pump, direction for use, 2000-2010, pp. 1-34, Issue 1, CareFusion Corporation.
Carefusion, Alaris PK Anaethesia Syringe Pump Specifications, specifications sheet, 2011, 2 pgs., CareFusion Corporation.
Carefusion, Alaris PK Syringe Pump, directions for use, 2000-2012, pp. 1-47, Issue 4, CareFusion Corporation.
Carefusion, Alaris SE Pump: Models 7100/7130 and 7200/7230, Rev2.X—User Manual, manual, Apr. 2011, pp. i-126, CareFusion Corporation, San Diego, CA, United States.
Carefusion, Alaris Syringe Pump (with Plus Software), directions for use, 2009-2010, pp. 1-48, Issue 1, CareFusion Corporation.
Carefusion, Alaris Syringe Pump, Technical Service Manual, 2002-2010, pp. 1-86, Issue 18, CareFusion Corporation.
Carefusion, Directions for Use: Alaris System (with Alaris PC unit, Model 8015), directions for use, Dec. 2011, 360 pgs., CareFusion Corporation.
Carefusion, Infusion Products, brochure, 2011, 16 pgs., CareFusion Corporation.
Carefusion, IVAC PCAM Syringe Pump, Technical Service Manual, 2002-2011, pp. 1-92, Issue 9, CareFusion Corporation.
Carefusion, Technical Service Manual: Alaris Syringe Module, 8110 Series / Alaris PCA Module, 8120 Series, technical service manual, Nov. 2010, 172 pgs., CareFusion Corporation.
ECRI Institute, Evaluation: Large-Volume Infusion Pumps, Health Devices, Dec. 2009, pp. 402-410, Dec. 2009 issue, ECRI Institute.
ECRI, Product Comparison: Infusion Pumps, General-Purpose, Aug. 2005, pp. 1-47, ECRI.
FDA, Medical Devices: SEDASYS Computer-Assisted Personalized Sedation System—P080009, Recently-Approved Devices, Mar. 24, 2013, 2 pgs., U.S. Food and Drug Administration.
Fresenius, Master PCA, Technical Manual, 1998, 47 pgs., Fresenius Vial S.A.
Fresenius, Module DPS Visio, Technical Manual, 1998 (ed. Nov. 2002), pp. 1-140, Fresenius Vial S.A.S.
Fresenius, Orchestra Modul DPS, Technical handbook, Apr. 2003, pp. 1-56, MC Medizintchnik GmbH, Fresenius Vial S.A.
Fresenius, Pilot A2, CE2, Technical Manual, 1998, pp. 1-136, Fresenius Vial S.A.
Fresenius, Pilot Anaesthesia 2, Technical Manual, 1998, 78 pgs., Rev.A1, Fresenius Vial S.A.

(56) References Cited

OTHER PUBLICATIONS

Fresenius, Pilote Hyperbaric: Syringe Pump certified for Hyperbaric Caisson, data sheet, 2 pgs., rev. 0, Fresenius Vial, dated Jun. 16, 2003.
Fresenius, Syringe Pump: Pilot A2, Operator's Guide, Fresenius Vial Infusion Technology, Dec. 9, 2003, pp. 1-16, Fresenius Vial S.A.
Fresenius, Syringe Pumps: Model Pilot C, Technical Sheet, Jun. 1, 2003, 1 pg., Fresenius Vial.
Gieras, Innovative Infusion Pump Technologies, Engineering in Medicine & Biology Society, Jun. 15, 2010, pp. 1-53, IEEE Long Island Chapter.
Goldman et al., Advancing the Adoption of Medical Device "Plug-and-Play" Interoperability to Improve Patient Safety and Healthcare Efficiency, a white paper from the MD PnP Program, 2006-2009 (rev Sep. 2009), pp. 1-3, MD PnP Program.
Graseby, Graseby 3400 Syringe Pump, Instruction Manual, 2002, pp. 1-26, Graseby Medical Limited.
Graseby, Omnifuse Syringe Pump, Technical User Manual, Jan. 2004, 47 pgs., Graseby Medical Limited.
Hawk, III, The Role of Color Coding in Medication Error Reduction, Action of the AMA House of Delegates 2004 Annual Meeting: Report of the Council on Scientific Affairs, CSA Report 5-A-04, pp. 1-8.
Hoenich, Hemodialysis Horizons: The Current Status and Future Directions of Hemodialysis Machine Technology, 2006 pp. 38-44, AAMI.org.
Hofmann, Modeling Medical Devices for Plug-and-Play Interoperability, Master of Engineering thesis, Massachusetts Institute of Technology, Jun. 2007, pp. 1-187, Robert Matthew Hofmann, MMVII.
Infusion Nurses Society, Infusion Nursing Standards of Practice, Journal of Infusion Nursing, Jan./Feb. 2011, pp. S1-S110, vol. 34, No. 1S, Infusion Nurses Society.
Infusion Nurses Society, Policies and Procedures for Infusion Nursing, 2011, 1-162, 4th edition, Infusion Nurses Society, Inc.
International Preliminary Report on Patentability dated Jul. 2, 2015, received in International patent application No. PCT/US2013/077077 (L50WO), 9 pgs.
International Preliminary Report on Patentability dated Jul. 3, 2014, received in International patent application No. PCT/US2012/071112 (J81WO), 12 pgs.
International Search Report & Written Opinion dated Jul. 15, 2015, received in International patent application No. PCT/US2015/016796 (P41WO), 16 pgs.
International Search Report & Written Opinion dated Jul. 31, 2013, received in International patent application No. PCT/US2012/071112 (J81WO), 17 pgs.
International Search Report & Written Opinion dated May 9, 2014, received in International patent application No. PCT/US2013/077077 (L50WO), 14 pgs.
Invitation to Pay Additional Fees and, Where Applicable, Protest Fee dated May 8, 2015, received in International patent application No. PCT/US2015/016796 (P41WO), 6 pgs.
Jetley et al., "Safety Requirements Based Analysis of Infusion Pump Software", Proceedings of the IEEE Real Time Systems Symposium, Tuscon, Dec. 2007 pp. 1-4.
King et al. Prototyping closed loop physiologic control with the medical device coordination framework. In SEHC 2010: Proceedings of the 2010 ICSE Workshop on Software Engineering in Health Care (pp. 1-11). New York, NY: ACM. (2010).
Medex, Medfusion 3500: Syringe Infusion Pump, Operation Manual, 1998-2004, pgs. i-78, rev. 5, Medex Inc. (Publication date unknown but assumed to be prior to the filing date.).
MSD, Biomedical Rental Equipment—I.V. Infusion Pumps / Enteral Pumps, catalogue, pp. 21-25, MSP (Publication date unknown but assumed to be prior to the filing date.).
National Patient Safety Agency, Design for Patient Safety: A Guide to the Design of Electronic Infusion Devices, booklet, 2010, pp. 1-96, Edition 1, National Patient Safety Agency, London, USA.
Nemeth et al., Making Information Technology a Team Player in Safety: The Case of Infusion Devices, Advances in Patient Safety: Interface Design for Infusion Devices, pp. 319-330, vol. 1, Feb. 2005.
Notice for Reason for Rejection, dated Jun. 23, 2015, received in Japanese patent application National Publication No. 2014-548929 (J81JP), 12 pgs. Chinese Language and English Translation.
Pfiedler Enterprises, A Comprehensive Surgical Checklist: Using Technology to Help Optimize Preparedness, Patient Safety and Performance (A Continuing Education Self-Study Activity), 2011, pp. 1-20, Pfiedler Enterprises.
Prusch et al., IV Interoperability: Smart Pump and BCMA Integration, Oct. 5, 2010, 13 pgs., Lancaster General Health.
Rafferty, Proposal for Wireless Transmission of Non-invasive Respiratory Data to the Servo Module of an Opioid Infusion-Pump for Real-Time Patient Safety Feedback Control, Yale School of Medicine (Publication date unknown but assumed to be prior to the filing date. Try the society of Society for Technology in Anesthesia 2008?).
Sims Graseby, Graseby 3100 Syringe Pump, Instruction Manual, 1998, pp. 1-18, SIMS Graseby Limited.
Sprunk et al., System Design for Simultaneous Data Acquisition from Patient Monitor and Syringe Pumps in Intensive Care Unit, Dec. 17-19, 2010, 878-882, IEEE EMBS International Conference on Biomedical Engineering and Sciences, Langkawi.
Vanderveen, Technology Focus: Using Data to Improve Smart Intravenous Infusion Pumps, Human Factors Horizons, 2010, pp. 57-63, Human Factors Horizons.
International Preliminary Report on Patentability dated Sep. 1, 2016, received in International patent application PCT/US2015/016796 (P41WO), 11 pgs.
First Office Action dated Jun. 2, 2016, received in Republic of China patent application No. 201380072074.X (L50CN), 3 pgs.
Second Office Action dated Jan. 26, 2017, received in Republic of China patent application No. 201380072074.X (L50CN), 7 pgs.
First Examination Report from The Intellectual Property Office of New Zealand for Application 709295 (L50NZ), dated Jan. 19, 2017, 4 pgs.
Invitation to Respond to Written Opinion from The Intellectual Property Office of Singapore for Application 11201504881W (L50SG), dated Jun. 13, 2016, 15 pgs.
Invitation to Respond to Written Opinion from The Intellectual Property Office of Singapore for Application 11201504881W (L50SG), dated Dec. 29, 2016, 5 pgs.
Supplementary Search Report from The Intellectual Property Office of Singapore for Application 11201504881W (L50SG), dated Nov. 3, 2016, 3 pgs.
Second Supplementary Search Report from The Intellectual Property Office of Singapore for Application 11201504881W (L50SG), dated Nov. 3, 2016, 3 pgs.
New Creations Direction dated Aug. 8, 2015, received in Columbian application No. 15-168135-2 (L50CO), 4 pgs.
New Creations Direction dated Feb. 11, 2016, received in Columbian application No. 15-168135-2 (R18CO), 5 pgs.
New Creations Direction dated Feb. 11, 2016, received in Columbian application No. 15-306238-1 (R19CO), 6 pgs.
English Translation of New Creations Direction dated Jun. 28, 2016, received in Columbian application No. 16-155497-1 (S29CO), 2 pgs.
English Translation of New Creations Direction dated Jun. 28, 2016, received in Columbian application No. 16-155512-1 (S30CO), 2 pgs.
Further Examination Report from The Intellectual Property Office of New Zealand for Application 709295 (L50NZ), dated May 25, 2017, 2 pgs.
First Office Action dated Nov. 22, 2017, received in Australian patent application No. 2013361072 (L50AU), 3 pgs.
Notice for Reason for Rejection, dated Sep. 5, 2017, received in Japanese patent application National Publication No. 2015-549799 (L50JP), 4 pgs.
U.S. Appl. No. 13/724,568, filed Dec. 21, 2012, US20130184676A1.
U.S. Appl. No. 13/833,432, filed Mar. 15, 2013, US20130281965A1.
U.S. Appl. No. 61/894,801, filed Oct. 23, 2013.

(56) References Cited

OTHER PUBLICATIONS

U.S. Appl. No. 61/904,123, filed Nov. 14, 2013.
PCT/US13/77077, Dec. 20, 2013, WO/2014/100658A1.
U.S. Appl. No. 14/135,784, filed Dec. 20, 2013, US20140188076A1.
U.S. Appl. No. 61/942,986, filed Feb. 21, 2014.
U.S. Appl. No. 61/990,330, filed May 8, 2014.
U.S. Appl. No. 14/627,287, filed Feb. 20, 2015, US20150157791A1.
PCT/US15/16796, Feb. 27, 2015, WO/2015/127189A1.
U.S. Appl. No. 15/059,394, filed Mar. 3, 2016, US20160184510A1.
U.S. Appl. No. 15/635,391, filed Jun. 28, 2017, US20170296745A1.
U.S. Appl. No. 15/673,814, filed Aug. 10, 2017, US2017033623A1.
U.S. Appl. No. 16/124,644, filed Sep. 2, 2018, US20190009018A1.
U.S. Appl. No. 16/277,179, filed Feb. 15, 2019, US20190175821A1.
U.S. Appl. No. 16/509,989, filed Jul. 12, 2019, US20190328964A1.
U.S. Appl. No. 15/635,391, filed Jun. 28, 2017.
U.S. Appl. No. 13/833,432, filed Mar. 15, 2013.
U.S. Appl. No. 15/635,391, B16, C100.
U.S. Appl. No. 13/833,432, B1, B2, B3, B4, B5, B6, B7, B8, B9, B10, B11, B12, B13, B14, B15, B17, B18, B19, B20, B21, B22, B23, B24, B25, B26, B27, B28, B29, B30, B31, B32, B33, B34, B35, B36, B37, B38, B39, B40, B41, B42, B43, B44, B46, B47, B48, B49, B50, B51, B52, B53, B54, B55, B56, B57, B58, B59, B60, B61, B62, B63, B64, B65, C1, C2, C3, C4, C5, C6, C7, C8, C9, C10, C11, C12, C13, C14, C15.
CN202126188U, English Translation.
EP477551B1, English Abstract.
EP960627A2, English Abstract.
JP06339528A, English Translation.
JP2002191693A, English Translation.
JP2008515600A, English Abstract.
JP2008540117A, English Translation.
WO2008022880A1, English Abstract.
WO2011091998A1, English Abstract.
WO2011121918A1, See EP2554197A1 for English Translation.
WO2012114417A1, English Machine Translation.
First Office Action dated Jun. 2, 2016, received in Republic of China patent application No. 201380072074.X (L50CN), 3 pgs., English Translation.
Second Office Action dated Jan. 26, 2017, received in Republic of China patent application No. 201380072074.X (L50CN), 7 pgs, English Translation.
New Creations Direction dated Aug. 8, 2015, received in Columbian application No. 15-168135-2 (L50CO), 4 pgs, English Translation.
New Creations Direction dated Feb. 11, 2016, received in Columbian application No. 15-168135-2 (R18CO), 5 pgs, English Translation.
New Creations Direction dated Feb. 11, 2016, received in Columbian application No. 15-306238-1 (R19CO), 6 pgs., English Translation.
Notice for Reason for Rejection, dated Sep. 5, 2017, received in Japanese patent application National Publication No. 2015-549799 (L50JP), 4 pgs, English Translation.

\* cited by examiner

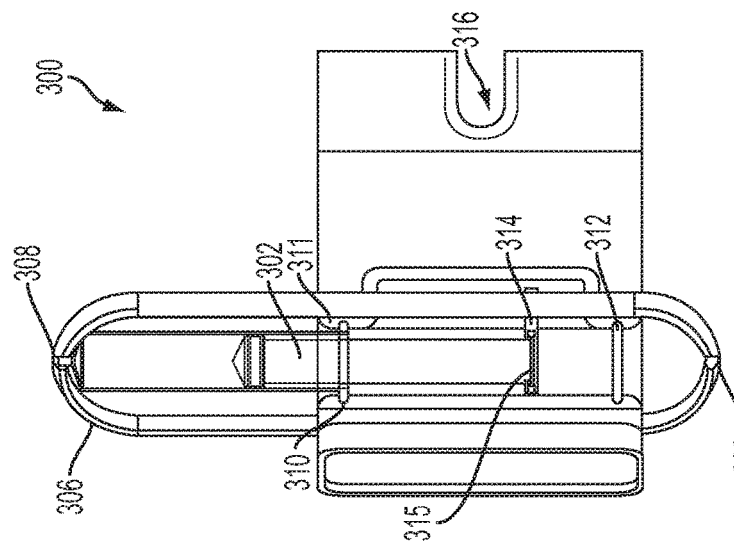
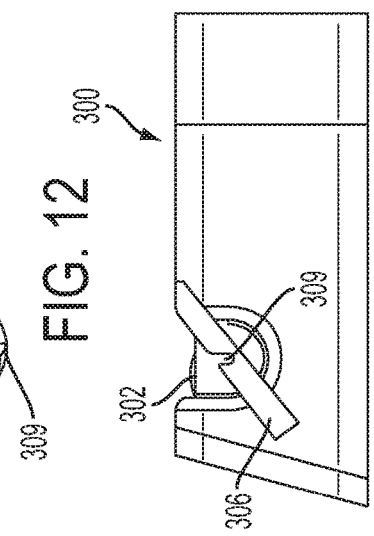
FIG. 12
FIG. 13
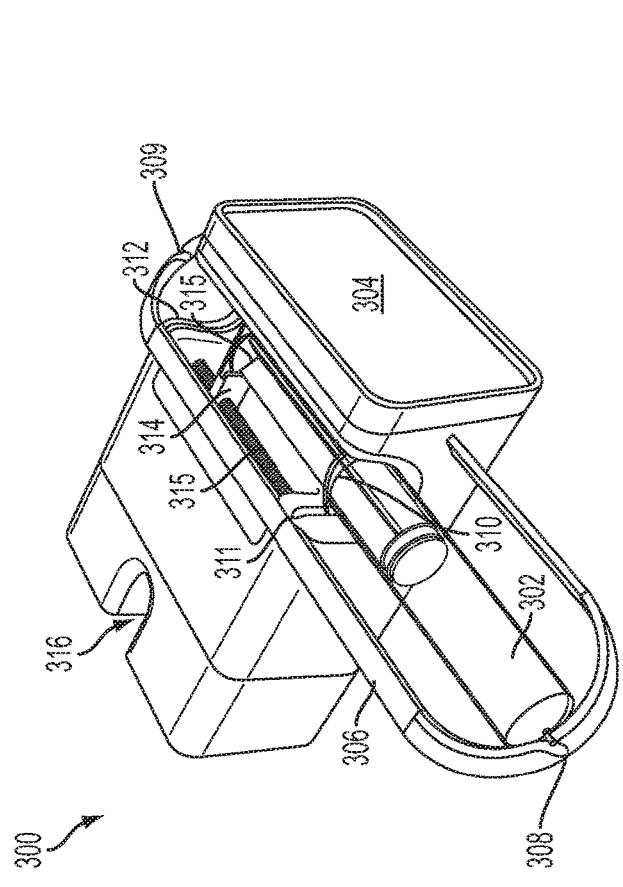
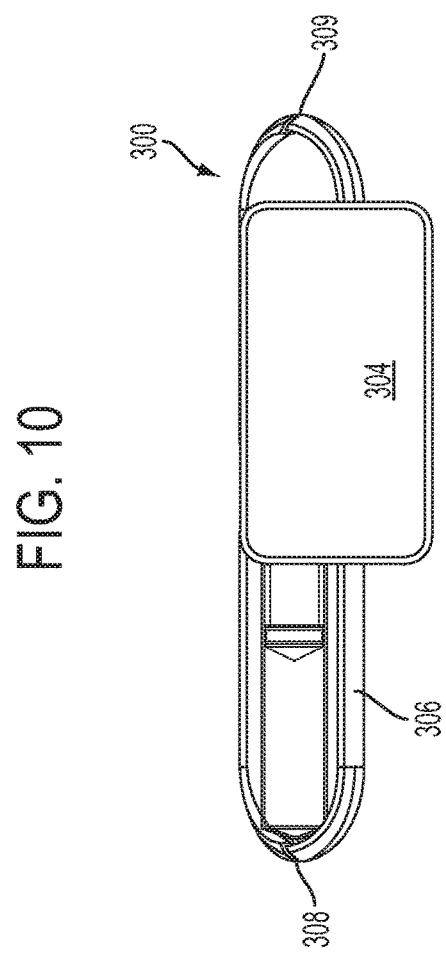
FIG. 10
FIG. 11

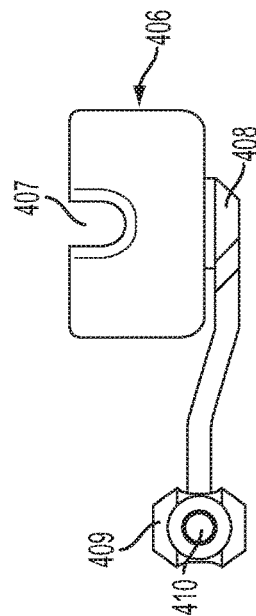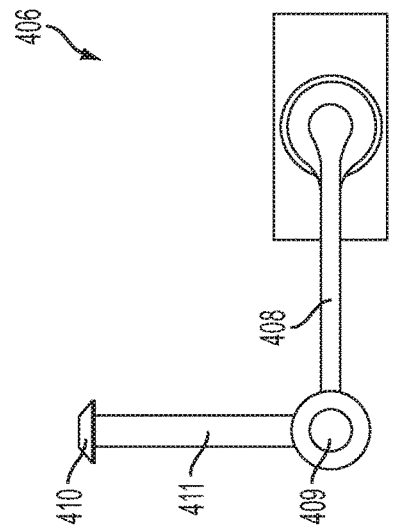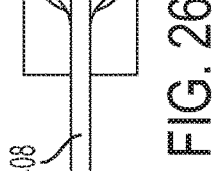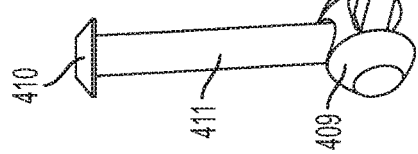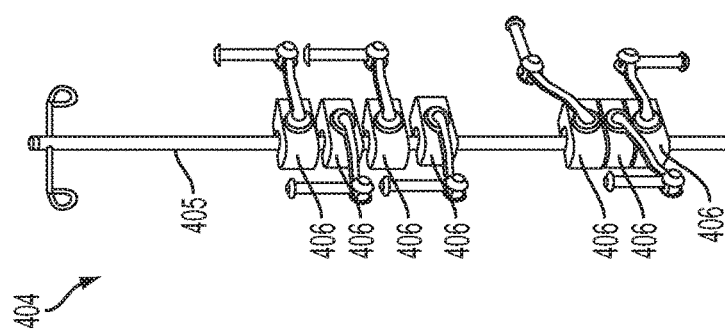

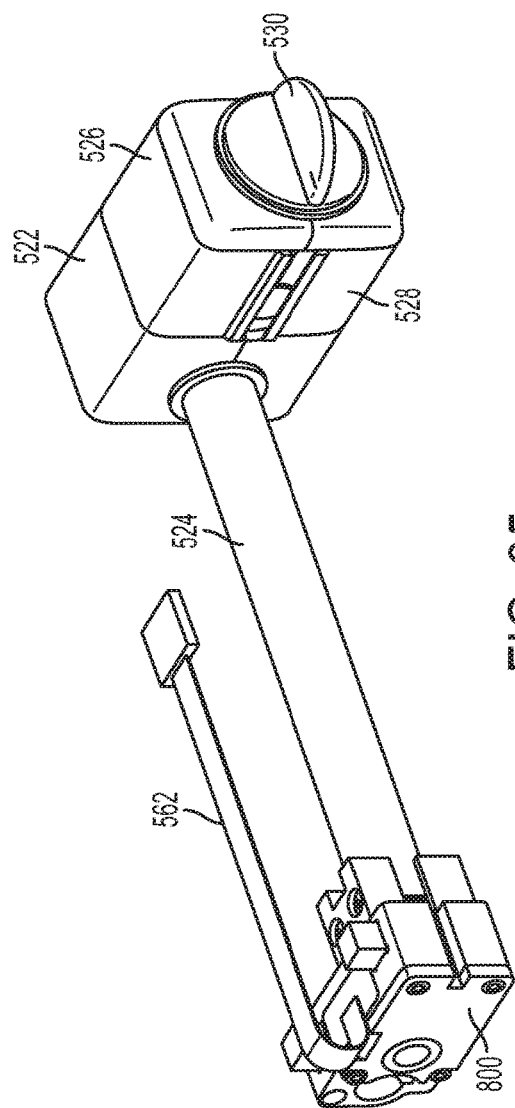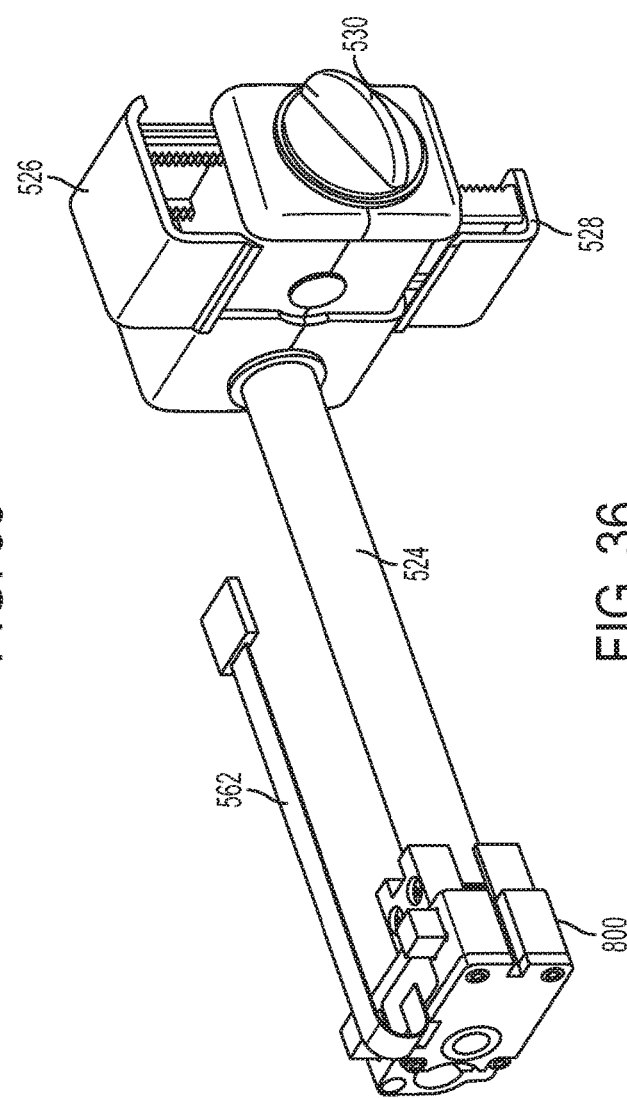

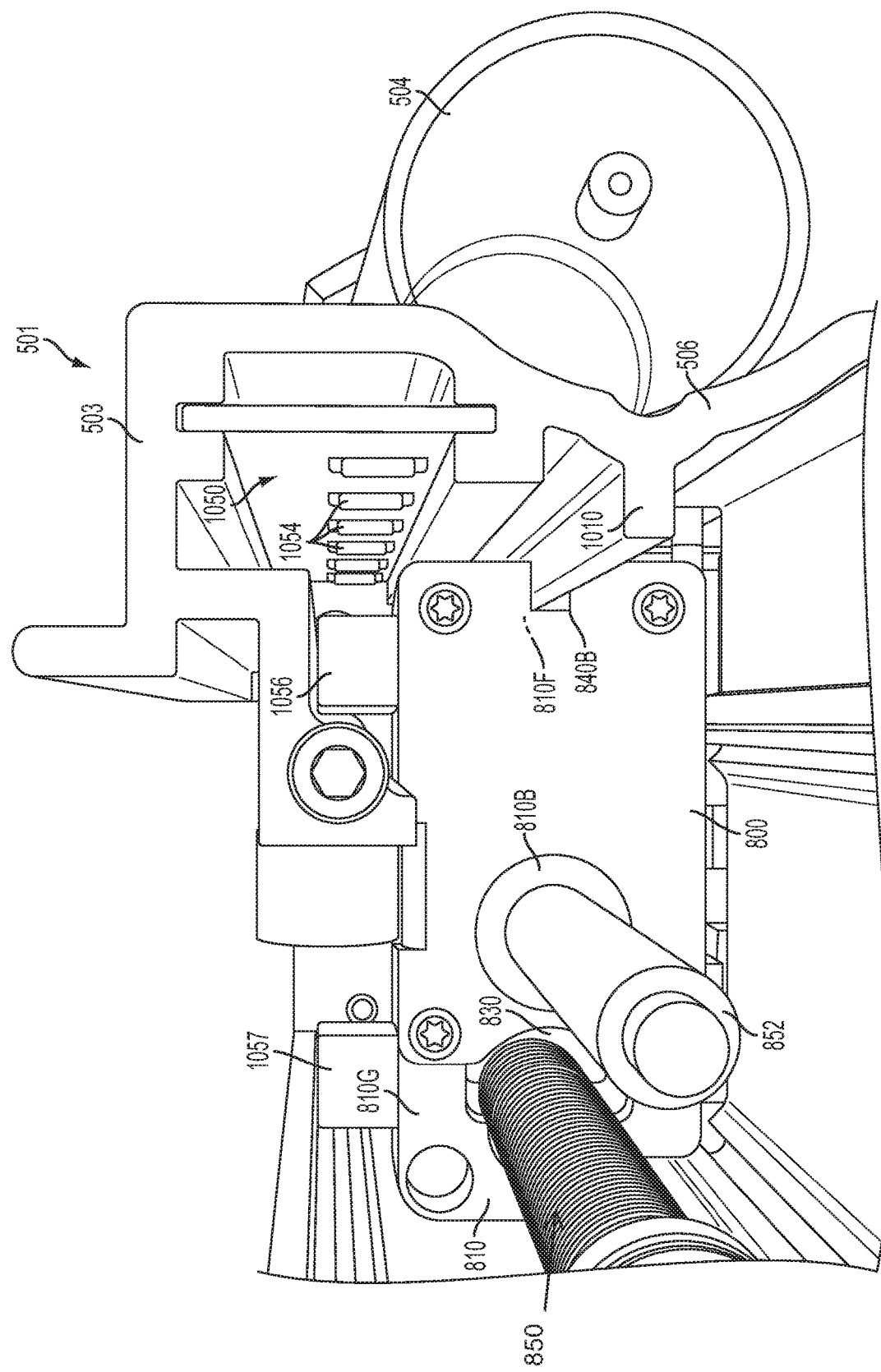

TPS3813 PIN CONFIGURATIONS

WDT, WDR = 00 = 10-200 MS WINDOW
WDT, WDR = 01 = 2.5-200 MS WINDOW
WDT, WDR = 10 = 100-2000 MS WINDOW
WDT, WDR = 11 = 25-2000 MS WINDOW

SYRINGE PUMP AND RELATED METHOD

CROSS REFERENCE TO RELATED APPLICATIONS

The present application is a continuation application of U.S. patent application Ser. No. 15/635,391, filed on Jun. 28, 2017 and entitled "Syringe Pump and Related Method", and will be U.S. Pat. No. 10,561,787, issuing on Feb. 18, 2020, which is a continuation application of U.S. patent application Ser. No. 13/833,432, filed on Mar. 15, 2013 and entitled "Syringe Pump and Related Method", now U.S. Pat. No. 9,744,300, issued on Aug. 29, 2017, which claims priority to and the benefit of the following:

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, claims priority to and is also a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, claims priority to and is also a Continuation-in-Part Application of U.S. patent application Ser. No. 13/723,238, filed Dec. 21, 2012 and entitled System, Method, and Apparatus for Clamping, now U.S. Pat. No. 9,759,369, issued on Sep. 12, 2017, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/723,238, filed Dec. 21, 2012 and entitled System, Method, and Apparatus for Clamping, now U.S. Pat. No. 9,759,369, issued on Sep. 12, 2017 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, claims priority to and is also a Continuation-in-Part Application of U.S. patent application Ser. No. 13/723,235, filed Dec. 21, 2012 and entitled System, Method, and Apparatus for Dispensing Oral Medications, now U.S. Pat. No. 9,400,873, issued on Jul. 26, 2016, which claims priority to and benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/723,235, filed Dec. 21, 2012 and entitled System, Method, and Apparatus for Dispensing Oral Medications, now U.S. Pat. No. 9,400,873, issued on Jul. 26, 2016 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, is also a Continuation-In-Part Application of PCT Application Serial No. PCT/US 12/71131, filed Dec. 21, 2012 and entitled System, Method, and Apparatus for Dispensing Oral Medications, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US12/71131 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, claims priority to and is also a Continuation-In-Part Application of U.S. patent application Ser. No. 13/724,568, filed Dec. 21, 2012 and entitled System, Method, and Apparatus for Estimating Liquid Delivery, now U.S. Pat. No. 9,295,778, issued on Mar. 29, 2016, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/724,568, filed Dec. 21, 2012 and entitled Syringe Pump, now U.S. Pat. No. 9,295,778, issued on Mar. 29, 2016 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, claims priority to and is also a Continuation-In-Part Application of U.S. patent application Ser. No. 13/725,790, filed Dec. 21, 2012 and entitled System, Method, and Apparatus for Infusing Fluid, now U.S. Pat. No. 9,677,555, issued Jun. 13, 2017, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/725,790, filed Dec. 21, 2012 and entitled System, Method, and Apparatus for Infusing Fluid, now U.S. Pat. No. 9,677,555, issued Jun. 13, 2017 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, is also a Continuation-In-Part Application of PCT Application Serial No. PCT/US12/71490, filed Dec. 21, 2012 and entitled System, Method, and Apparatus for Infusing Fluid, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

PCT Application Serial No. PCT/US12/71490 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, claims priority to and is also a Continuation-In-Part Application of U.S. patent application Ser. No. 13/723,239, filed Dec. 21, 2012 and entitled System, Method, and Apparatus for Electronic Patient Care, now U.S. Pat. No. 10,108,785, issued Oct. 23, 2018, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,239, filed Dec. 21, 2012 and entitled System, Method, and Apparatus for Electronic Patient Care, now U.S. Pat. No. 10,108,785, issued Oct. 23, 2018 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, claims priority to and is also a Continuation-In-Part Application of U.S. patent application Ser. No. 13/723,242, filed Dec. 21, 2012 and entitled System, Method, and Apparatus for Electronic Patient Care, now U.S. Pat. No. 10,911,515 issued on Feb. 2, 2021, which claims priority to and the benefit of the following:

U.S. Provisional Patent Application Ser. No. 61/651,322, filed May 24, 2012 and entitled System, Method, and Apparatus for Electronic Patient Care, which is hereby incorporated herein by reference in its entirety.

U.S. patent application Ser. No. 13/833,432, filed Mar. 15, 2013 and entitled Syringe Pump and Related Method, now U.S. Pat. No. 9,744,300, issued on Aug. 29, 2017, claims priority to and is also a Continuation-In-Part Application of U.S. patent application Ser. No. 13/723,244, filed Dec. 21, 2012 and entitled System, Method, and Apparatus for Monitoring, Regulating, or Controlling Fluid Flow, now U.S. Pat. No. 9,151,646, issued on Oct. 6, 2015, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,244, filed Dec. 21, 2012 and entitled System, Method, and Apparatus for Monitoring, Regulating, or Controlling Fluid Flow, now U.S. Pat. No. 9,151,646, issued on Oct. 6, 2015 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, claims priority to and is also a Continuation-In-Part Application of PCT Application Serial No. PCT/US12/71142, filed Dec. 21, 2012 and entitled System, Method, and Apparatus for Monitoring, Regulating, or Controlling Fluid Flow, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US12/71142, filed Dec. 21, 2012 and entitled System, Method, and Apparatus for Monitoring, Regulating, or Controlling Fluid Flow, claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, claims priority to and is also a Continuation-In-Part Application of U.S. patent application Ser. No. 13/723,251, filed Dec. 21, 2012 and entitled System, Method, and Apparatus for Estimating Liquid Delivery, now U.S. Pat. No. 9,636,455, issued on May 2, 2017, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,251, filed Dec. 21, 2012 and entitled System, Method, and Apparatus for Estimating Liquid Delivery, now U.S. Pat. No. 9,636,455, issued on May 2, 2017 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, is also a Continuation-In-Part Application of PCT Application Serial No. PCT/US12/71112, filed Dec. 21, 2012 and entitled System, Method, and Apparatus for Estimating Liquid Delivery, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US12/71112, filed Dec. 21, 2012 and entitled System, Method, and Apparatus for Estimating Liquid Delivery, claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, claims priority to and is also a Continuation-In-Part Application of U.S. patent application Ser. No. 13/723,253, filed Dec. 21, 2012 and entitled System, Method, and Apparatus for Electronic Patient Care, now U.S. Pat. No. 11,210,611, issued on Dec. 28, 2021, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,253, filed Dec. 21, 2012 and entitled System, Method, and Apparatus for Electronic Patient Care, now U.S. Pat. No. 11,210,611, issued on Dec. 28, 2021 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Pat. No. 10,453,157, issued Oct. 22, 2019, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/833,432, filed Mar. 15, 2013 and entitled Syringe Pump and Related Method, now U.S. Pat. No. 9,744,300, issued on Aug. 29, 2017, may also be related to one or more of the following U.S. patent applications filed on Mar. 15, 2013, all of which are hereby incorporated herein by reference in their entireties:

Nonprovisional Application for Apparatus for Infusing Fluid having the Ser. No. 13/840,339, filed Mar. 15, 2013, now U.S. Pat. No. 9,675,756, issued on Jun. 13, 2017;

PCT Application for Apparatus for Infusing Fluid having the Serial No.PCT/US13/32445, filed Mar. 15, 2013;

Nonprovisional Application for System and Apparatus for Electronic Patient Care having the Ser. No. 13/836,497, filed Mar. 15, 2013, now U.S. Pat. No. 10,242,159, issued on Mar. 26, 2019;

Nonprovisional Application for System, Method and Apparatus for Clamping having the Ser. No. 13/833,712, filed Mar. 15, 2013, now U.S. Pat. No. 9,488,200, issued on Nov. 8, 2016; and Nonprovisional Application for System, Method, and Apparatus for Monitoring, Regulating, or Controlling Fluid Flow having the Ser. No. 13/834,030, filed Mar. 15, 2013, now U.S. Pat. No. 9,372,486, issued on Jun. 21, 2016.

BACKGROUND

Relevant Field

The present disclosure relates to pumps. More particularly, the present disclosure relates to a system, method, and apparatus for estimating liquid delivery of a syringe pump.

Description of Related Art

Syringe pumps are used in a variety of medical applications, such as for intravenous delivery of liquid medications, for example a patient in an intensive-care unit (ICU), for an extended length of time. Syringe pumps may be designed so that needles, tubing, or other attachments are attachable to the syringe pump. Syringe pumps typically include a plunger mounted to a shaft that pushes a liquid out of a reservoir. The reservoir may be a tube-shaped structure having a port at one end such that the plunger can push (i.e., discharge) the liquid out of the syringe pump. Syringe pumps can be coupled to an actuator that mechanically drives the plunger to control the delivery of liquid to the patient.

Syringe pumps may also be used to deliver various drugs including analgesics, antiemetics, or other fluids. The medication may be administered via an intravenous liquid line very quickly (e.g., in a bolus) or over a length of time. Syringe pumps may also be used in non-medical applications, such as in microreactors, in laboratory testing, and/or in chemical processing applications.

SUMMARY

In accordance with one embodiment of the present disclosure, a pump for administering an agent to a patient may comprise a housing. Within said housing may be a motor, a gearbox operatively connected to said motor, a means for sensing rotation of said motor, a controller acting to control operation of said motor and monitor the quantity of said agent delivered to said patient, and a pump assembly. The pump may be configured such that the pump is interchangeable from a syringe pump or peristaltic pump respectively to a peristaltic pump or syringe pump via supplanting one pump assembly with a differing pump assembly.

In some embodiments, the pump may be field interchangeable from a syringe pump or peristaltic pump respectively to a peristaltic pump or syringe pump via supplanting one pump assembly with a differing pump assembly.

In accordance with another embodiment of the present disclosure, a syringe pump for administering an agent to a patient may comprise a housing, a lead screw, and a sliding block assembly. The sliding block assembly may comprise a cam, a cam projection fixedly coupled to the cam, and a threaded portion capable of engaging and disengaging from the lead screw. The threaded portion may be configured to be actuated between engagement and disengagement on the lead screw via rotation of the cam and cam projection.

In some embodiments, the sliding block assembly may comprise a slot with a straight expanse and an acruated expanse.

In some embodiments, rotation of the cam may cause the cam projection to move within the slot. As the cam projection moves within the straight expanse of the slot, the threaded portion may be configured to be actuated between engagement and disengagement with the lead screw.

In some embodiments, the syringe pump may further comprise a clamping means configured for clamping any of a range of plunger flange sizes.

In some embodiments, the cam projection may not enter the straight expanse of the slot until the largest of the range of plunger flange sizes has been released by the means configured for clamping any of a range of plunger flange sizes.

In some embodiments, the syringe pump may further comprise a plunger head assembly coupled to the sliding block and operative to drive a plunger of a syringe into a barrel of the syringe. A plunger tube may couple the plunger head assembly to the sliding block.

In some embodiments, the plunger tube may perform at least one or more additional functions from a list consisting of: a bushing support for at least one rotating shaft, a channel for electrical conduits to and from the plunger head assembly, and a channel for data transmission conduits to and from the plunger head assembly.

In some embodiments, the syringe pump may further comprise a barrel flange clip configured to retain a barrel flange of a syringe.

In some embodiments, the barrel flange clip may comprise a means of detecting the presence of a barrel flange. The means of detecting the presence of a barrel flange may comprise an optical sensor and a light source. The light source may be obscured in the presence of the barrel flange.

In some embodiments, the location of the cam of the sliding block assembly may be adjustable such that a user may optimize engagement of the threaded portion on the lead screw.

In some embodiments, the sliding block assembly may further include at least one bias member. The bias member may be configured to bias the threaded portion to one of an engaged position on the lead screw and a disengaged position on the lead screw.

In accordance with another aspect of the present disclosure, a syringe pump for administering an agent to a patient may comprise a housing, a lead screw, and a sliding block assembly. The sliding block assembly may comprise a threaded section configured for engaging and disengaging from the lead screw. The syringe pump may further comprise a plunger head assembly coupled to said sliding block and operative to drive a plunger of a syringe into a barrel of said syringe. The syringe pump may further comprise a clamping means configured for clamping any of a range of plunger flange sizes. The means configured for clamping any of a range of plunger flange sizes may comprise at least a first plunger flange clamp jaw and a second plunger flange clamp jaw. The first and second plunger flange clamp jaws may be configured to be actuated from a first position to a position in which at least one point of each of the first and second plunger flange clamp jaws abut an edge of the plunger flange forcing the plunger flange against the plunger head assembly and acting as an anti-siphon mechanism.

In some embodiments, the means configured for clamping any of a range of plunger flange sizes may comprise a cam, at least one cam follower, and at least one bias member. The bias member may bias said means configured for clamping any of a range of plunger flange sizes toward a first position. In some embodiments, movement of the at least one cam follower along the cam may overcome the bias member and allow the means configured for clamping any of a range of plunger flange sizes to move toward a second position.

In some embodiments, the cam, at least one cam follower, and at least one bias member may be coupled to a rotatable shaft. The cam may not be rotatable with said shaft but may be displaceable along an axial dimension of said shaft. The at least one cam follower may be fixedly coupled to the shaft and rotatable with the shaft. Rotation of the shaft may cause movement of the at least one cam follower along the cam thereby displacing the cam along the axial dimension of the shaft.

In some embodiments, the bias member may automatically return the means configured for clamping any range of plunger flange sizes to the first position in the absence of a force sufficient to overcome the bias member.

In some embodiments, the cam may comprise at least one detent, each of said detents being reached by one of the at least one cam followers when the means configured for clamping any range of plunger flange sizes has been allowed to move to the second position.

In some embodiments, the plunger head assembly may further comprise a pressure sensor for monitoring the pressure of the agent being dispensed from the syringe.

In some embodiments, the plunger flange of the syringe may be held against the pressure sensor by the means configured for clamping any range of plunger flange sizes.

In some embodiments, the syringe pump may further comprise a barrel flange clip. The barrel flange clip may be configured to retain a barrel flange of the syringe.

In some embodiments, the barrel flange clip may comprise a means of detecting the presence of a barrel flange. The means of detecting the presence of a barrel flange may comprise an optical sensor and a light source. The light source may be obscured in the presence of said barrel flange.

In accordance with another aspect of the present disclosure a syringe pump for administering an agent to a patient may comprise a housing a lead screw and a sliding block assembly. The sliding block assembly may comprise a threaded section configured for engagement and disengagement with said lead screw and movable along said lead screw. The syringe pump may further comprise a plunger head assembly coupled to said sliding block assembly and operative to drive a plunger of a syringe into a barrel of said syringe. The syringe pump may further comprise a clamping means configured for clamping any of a range of plunger flange sizes. The syringe pump may further comprise a means of monitoring the clamping means. The means of monitoring the clamping means may be capable of generating data to determine at least one characteristic of the clamped syringe.

In some embodiments, the means of monitoring the clamping means may be a potentiometer.

In some embodiments, the data generated by the means of monitoring the clamping means may be evaluated by referencing said data against a database.

In some embodiments, the data generated by the means of monitoring the clamping means may be evaluated by referencing said data against a database and data generated by at least one other sensor.

In some embodiments, the clamping means may comprise a cam, at least one cam follower, and at least one bias member. The bias member may bias said clamping means toward a first position. Movement of the at least one cam follower along the cam may overcome the bias member and allow the clamping means to move toward a second position.

In some embodiments, the cam, at least one cam follower, and at least one bias member may be coupled to a rotatable shaft. In some specific embodiments, the cam may not be rotatable with the shaft but may be displaceable along an axial dimension of said shaft. The at least one cam follower may be fixedly coupled to the shaft and rotatable with the shaft. Rotation of the shaft may cause movement of the at least one cam follower along the cam displacing the cam along the axial dimension of the shaft.

In some embodiments, the bias member may automatically return the clamping means to the first position in the absence of a force sufficient to overcome the bias member.

In some embodiments, the cam may comprise at least one detent. Each of the detents may be reached by one of the at least one cam followers when the means for clamping any range of plunger flange sizes has been allowed to move to the second position.

In some embodiments, the plunger head assembly may further comprise a pressure sensor for monitoring the pressure of the agent being dispensed from the syringe.

In some embodiments, a plunger flange of the syringe may be held against the pressure sensor by the clamping means.

In some embodiments, the barrel flange clip may comprise a means of detecting the presence of a barrel flange. The means of detecting the presence of said barrel flange may comprise an optical sensor and a light source. The light source may be obscured in the presence of said barrel flange.

In accordance with another aspect of the present disclosure, a syringe pump for administering an agent to a patient may comprise a housing, a lead screw, and a plunger head assembly operatively coupled to drive a plunger of a syringe into the barrel of a syringe with rotation of said lead screw. The syringe pump may further comprise at least one set of redundant sensors. The redundant sensors may be configured such that if part of a set of redundant sensors is compromised, the syringe pump may function in a fail operative mode for at least the duration of a therapy. One or more of the set of redundant sensors are configured to monitor the volume being infused.

In accordance with another aspect of the present disclosure, a syringe pump for administering an agent to a patient may comprise a housing and a syringe barrel holder which may be movable between a first position and a second position. The syringe barrel holder may be biased by a bias member to either the first position or the second position. The syringe pump may further comprise a syringe barrel contacting member. The barrel contacting member may be coupled to said syringe barrel holder and configured to hold the syringe in place on the housing. The syringe pump may further comprise a detector capable of sensing the position of the syringe barrel holder and generating position data based on the position of the syringe barrel holder. When a syringe is in place on said housing, the syringe barrel holder may be biased such that the syringe is held in place on said housing. The position data generated by said detector may be indicative of at least one characteristic of the syringe and evaluated to determine said characteristic.

In some embodiments the detector may be a linear potentiometer.

In some embodiments, the detector may be a magnetic linear position sensor.

In some embodiments, the syringe barrel holder may be configured to be locked in at least one of the first position and second position.

In some embodiments, the bias member may cause the syringe barrel holder to automatically adjust to the size of the syringe.

In some embodiments, position data generated by the detector may be referenced against a database to determine the at least one characteristic of the syringe.

In some embodiments, the position data generated by the detector may be referenced against a database and data from at least one other sensor to determine the at least one characteristic of the syringe.

In accordance with another aspect of the present disclosure, a method of administering an agent to a patient via a syringe pump may comprise defining one or a number of parameters for an infusion through an interface of the syringe pump. The method may further comprise referencing said parameters against a medical database and placing restrictions on further parameters to be defined through the interface of the syringe pump. One of the further parameters may be an end of infusion behavior to be executed by the syringe pump after a volume to be infused has been infused. The method may further comprise infusing said agent to said patient in accordance with the defined parameters for infusion and executing the specified end of infusion behavior.

In some embodiments, the end of infusion behavior may be selected from a list consisting of: stopping an infusion, infusing at a keep vein open rate, and continuing to infuse at the rate of the finished infusion.

In some embodiments, referencing parameters against a database and placing restrictions on further parameters may comprise referencing the agent against the database.

In accordance with one embodiment of the present disclosure, a syringe pump includes a housing, a syringe seat, and a bumper. The syringe seat is coupled to the housing. The bumper is coupled to the housing adjacent to the syringe seat. The bumper may at least partially surround a corner of the syringe seat.

In another embodiment of the present disclosure, a syringe pump includes a housing, a syringe seat, and a power supply. The syringe seat is coupled to the housing. The power supply is coupled to the housing such that the housing is configured as a heat sink for the power supply. The syringe pump may include a motor, and the motor may be coupled to the housing such that the housing is a heat sink for the motor. The housing may be die casted. The housing may comprise at least one metal and/or may be a unitary body.

In another embodiment of the present disclosure, a syringe pump includes a user interface, an antenna, and a split-ring resonator. The user interface has a front side and a backside. The antenna is disposed on the back side of the user interface. The split-ring resonator is disposed in spaced relation to the user interface and is configured to operate with the antenna.

The user interface may include a touchscreen sensor. The split-ring resonator may be disposed on a backside of the touchscreen sensor. A frame may surround the touchscreen sensor that has a gap such that the frame defines the split-ring resonator. A dielectric may be disposed within the gap.

In another embodiment of the present disclosure, a syringe pump includes a housing, a lead screw, a motor, a rotary position sensor, a sliding block assembly, a linear position sensor, and one or more processors. The lead screw is rotatable within the housing. The motor is operatively coupled to the lead screw and is configured to rotate the lead screw. The motor has an integral motor rotation sensor configured to provide a motor rotation signal. The rotary position sensor is operatively coupled to the motor or the lead screw to provide a rotation signal. The rotary position sensor may be a magnetic encoder sensor. The sliding block assembly is configured to engage with the lead screw to actuate the sliding block assembly along the lead screw in accordance with rotation of the lead screw. The linear position sensor is operatively coupled to the sliding block assembly and is configured to provide a linear position signal. The one or more processors are configured to control rotation of the motor. The one or more processors operatively receive the motor rotation signal from the integral motor rotation sensor of the motor, the rotation signal from the rotary position sensor, and the linear position signal from the linear position sensor. The one or more processors are configured to determine if a discrepancy exists among the motor rotation signal, the rotation signal, and the linear position signal. The one or more processors may be further configured to continue an infusion treatment by ignoring an inoperative one of the integral motor rotation sensor, the rotary position sensor, and a linear position sensor.

In another embodiment of the present disclosure, a syringe pump includes a housing, a lead screw, a sliding block assembly, a plunger, and first and second pivotal jaw members. The lead screw is rotatable within the housing. The sliding block assembly is configured for engaging with the lead screw to move along the lead screw in accordance with rotation of the lead screw. The plunger head assembly is coupled to the sliding block assembly and is configured to drive a plunger of a syringe into a barrel of the syringe. The first and second pivotal jaw members are each pivotally coupled to the plunger head assembly. The first and second pivotal jaw members are configured to pivot toward each other to retain a plunger flange of the syringe. The first pivotal jaw member and/or the second pivotal jaw member includes a bend.

The syringe pump may further include a knob coupled to the sliding block assembly. The knob may be operatively coupled to the first and second pivotal jaw members to pivotally actuate the first and second pivotal jaw members. The pump may include a bias member configured to bias the knob in a direction of rotation. The bias member may be configured to automatically return the first and second pivotal jaw members to a position away from each other. The bias member may be configured to automatically return the first and second pivotal jaw members to a position toward each other.

In another embodiment, a syringe pump includes a housing, a syringe seat coupled to the housing, and a retaining finger. The retaining finger is pivotally coupled to the housing and is configured to rotate toward a syringe disposed within the syringe seat to retain the syringe.

In another embodiment of the present disclosure, a method is provided for removing the effects of slack in a syringe pump having a syringe loaded on the syringe pump. The syringe has a barrel and a plunger disposed within the barrel. The method includes the acts of: receiving a target flow rate of the syringe loaded on the syringe pump; determining a therapy actuation speed corresponding to the target flow rate; actuating the plunger of the syringe out of the barrel at a first predetermined speed until a force sensor coupled to the plunger measures a force that is less than a first predetermined force threshold; actuating the plunger of the syringe into the barrel at a second predetermined speed greater than the therapy actuation speed until the force sensor coupled to the plunger measures a force that exceeds a second predetermined threshold; and actuating the plunger of the syringe into the barrel at the therapy actuation speed. The therapy actuation speed may correspond to the target flow rate when there is no slack in the syringe pump or the syringe. The method may further include the acts of: estimating a volume discharged starting from the position of the plunger when the second predetermined threshold was exceeded; and/or stopping the syringe pump when the estimated volume discharged is equal to or exceeds a target delivery volume.

In another embodiment of the present disclosure, a method is provided for removing the effects of slack in a syringe pump having a syringe loaded on the syringe pump. The syringe has a barrel and a plunger disposed within the barrel. The method includes the acts of: receiving a target flow rate of the syringe loaded on the syringe pump; determining a therapy actuation speed corresponding to the target flow rate; actuating the plunger of the syringe out of the barrel at a first predetermined speed until a force sensor coupled to the plunger measures a force that is less than a first predetermined force threshold or the plunger travels out of the barrel by a first predetermined distance; actuating the plunger of the syringe into the barrel at a second predetermined speed greater than the therapy actuation speed until the force sensor coupled to the plunger measures a force that exceeds a second predetermined threshold or the plunger travels into the barrel by a second predetermined distance; and actuating the plunger of the syringe into the barrel at the therapy actuation speed.

The therapy actuation speed may correspond to the target flow rate when there is no slack in the syringe pump or the syringe. The method may further include the acts of: estimating a volume discharged starting from the position of the plunger when the second predetermined threshold was exceeded; stopping the syringe pump when the estimated volume discharged is equal to or exceeds a target delivery volume; and/or using an alarm if the plunger traveled into the barrel by the second predetermined distance without the force sensor measuring a force that exceeds the second predetermined threshold.

In another embodiment of the present disclosure, a syringe pump includes a housing, a syringe seat, a lead screw, a motor, a sliding block assembly, a plunger head assembly, and one or more processors. The syringe seat is coupled to the housing and is configured to retain a syringe having a barrel and a plunger disposed within the barrel. The lead screw is rotatable within the housing. The motor is coupled to the lead screw and is configured rotate the lead screw. The sliding block assembly may be configured for engaging with the lead screw to move along the lead screw in accordance with rotation of the lead screw. The plunger head assembly is coupled to the sliding block assembly and is configured to drive a plunger of a syringe into a barrel of the syringe. The plunger head assembly has a force sensor operatively coupled to the plunger of the syringe to measure a force of the plunger head assembly on the plunger of the syringe. The one or more processors are operatively coupled to the motor and are configured to control the rotation of the motor to thereby control actuation of the plunger head assembly. The one or more processors are also operatively coupled to the force sensor to receive a measured force therefrom and are configured to: receive a target flow rate of the syringe loaded on the syringe pump; determine a therapy actuation speed corresponding to the target flow rate; command the motor to actuate the plunger of the syringe out of the barrel at a first predetermined speed until the force sensor coupled to the plunger measures a force that is less than a first predetermined force threshold; command the motor to actuate the plunger of the syringe into the barrel at a second predetermined speed greater than the therapy actuation speed until the force sensor coupled to the plunger measures a force that exceeds a second predetermined threshold; and command the motor to actuate the plunger of the syringe into the barrel at the therapy actuation speed. The therapy actuation speed may correspond to the target flow rate when there is no slack in the syringe pump or the syringe.

The one or more processors may be configured to estimate a volume discharged starting from the position of the plunger when the second predetermined threshold was exceeded.

The one or more processors may be further configured to stop the syringe pump when the estimated volume discharged is equal to or exceeds a target delivery volume.

In yet another embodiment of the present disclosure, a syringe pump includes a housing, a syringe seat, a lead screw, a motor, a sliding block assembly, a plunger head assembly, and one or more processors. The syringe seat is coupled to the housing and is configured to retain a syringe having a barrel and a plunger disposed within the barrel. The lead screw is rotatable within the housing. The motor is coupled to the lead screw and is configured rotate the lead screw. The sliding block assembly may be configured for engaging with the lead screw to move along the lead screw in accordance with rotation of the lead screw. The plunger head assembly is coupled to the sliding block assembly and is configured to drive a plunger of a syringe into a barrel of the syringe. The plunger head assembly has a force sensor operatively coupled to the plunger of the syringe to measure a force of the plunger head assembly on the plunger of the syringe. The one or more processors are operatively coupled to the motor and are configured to control the rotation of the motor to thereby control actuation of the plunger head assembly. The one or more processors are also operatively coupled to the force sensor to receive a measured force therefrom and are configured to: receive a target flow rate of the syringe loaded on the syringe pump; determine a therapy actuation speed corresponding to the target flow rate; command the motor to actuate the plunger of the syringe out of the barrel at a first predetermined speed until a force sensor coupled to the plunger measures a force that is less than a first predetermined force threshold or the plunger travels out of the barrel by a first predetermined distance; command the motor to actuate the plunger of the syringe into the barrel at a second predetermined speed greater than the therapy actuation speed until the force sensor coupled to the plunger measures a force that exceeds a second predetermined threshold or the plunger travels into the barrel by a second predetermined distance; and command the motor to actuate the plunger of the syringe into the barrel at the therapy actuation speed. The therapy actuation speed may correspond to the target flow rate when there is no slack in the syringe pump or the syringe.

The one or more processors may be further configured to estimate a volume discharged starting from the position of the plunger when the second predetermined threshold was exceeded and/or to stop the syringe pump when the estimated volume discharged is equal to or exceeds a target delivery volume The one or more processors may be further configured to issue an alarm if the plunger traveled into the barrel by the second predetermined distance without the force sensor measuring a force that exceeds the second predetermined threshold.

The syringe pump described herein may further comprise a transceiver, and the one or more processors are configured to communicate via the transceiver with a monitoring client.

In some embodiments, the syringe pump includes a Patient-controlled analgesia ("PCA") button to deliver at least one pain medication.

BRIEF DESCRIPTION OF THE DRAWINGS

These and other aspects will become more apparent from the following detailed description of the various embodiments of the present disclosure with reference to the drawings wherein:

FIGS. 10-13 show several views of a syringe pump in accordance with an embodiment of the present disclosure;

FIG. 23 shows several mounts mounted on a pole in accordance with an embodiment of the present disclosure;

FIGS. 24-26 show several views of a mount of FIG. 23 in accordance with an embodiment of the present disclosure;

FIG. 35 is a view of an exemplary embodiment of the plunger head assembly, plunger tube, and sliding block assembly of the syringe pump assembly in accordance with an embodiment of the present disclosure;

FIG. 36 is another view of an exemplary embodiment of the plunger head assembly, plunger tube, and sliding block assembly of the syringe pump assembly in accordance with an embodiment of the present disclosure;

FIG. 57 is another interior view of an exemplary embodiment of the syringe pump assembly with the sliding block assembly and linear position sensors in place in accordance with an embodiment of the present disclosure;

DETAILED DESCRIPTION

Figure 1:
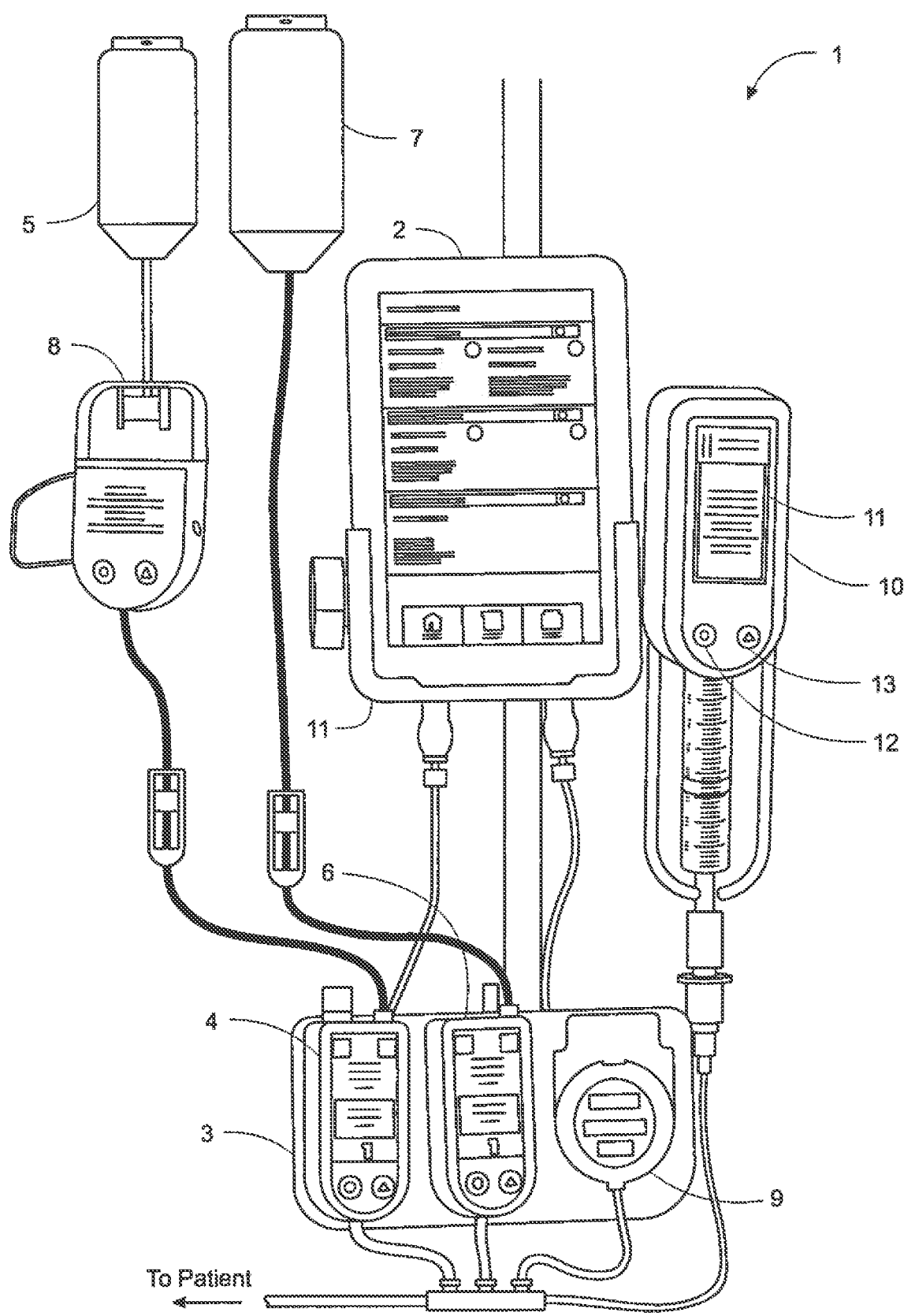
FIG. 1 is a illustration of an electronic patient-care system having a syringe pump in accordance with an embodiment of the present disclosure.

FIG. 1 shows an exemplary arrangement of a system 1 for electronic patient care in accordance with an embodiment of the present disclosure. The system 1 includes a monitoring client 2 that is linked to a number of patient-care devices via docks 3 and 11, including an infusion pump 4 connected to and delivering from a smaller bag of liquid 5, an infusion pump 6 connected to and delivering from a larger bag of liquid 7, a drip detection device 8 connected to tubing from the smaller bag 5, and a microinfusion pump 9. System 1 also includes a syringe pump 10 connected wirelessly to the monitoring client 2. In some embodiments, the monitoring client 2 may communicate with these patient-care devices in a wired fashion, as shown in FIG. 1 for the infusion pumps 4 and 6, and the microinfusion pump 9 (via docks 3 and 11). Additionally or alternatively, the monitoring client 2 may communicate wirelessly with patient-care devices, as suggested by the absence of a wired connection between the syringe pump 10 and the monitoring client 2.

In some embodiments, a wired connection between the monitoring client 2 and a patient-care device also affords an opportunity for electrical power to be supplied to the patient-care device from the monitoring client 2. In this exemplary embodiment, the monitoring client 2 may include the electronic circuitry necessary to convert the voltage to power the patient-care device from either a battery attached to the monitoring client 2 or from an Alternative Current ("AC") line voltage fed into the monitoring client 2 from a power outlet (not shown) in a patient's room. Additionally or alternatively, the dock 3 supplies power to the infusion pumps 4 and 6, and to the microinfusion pump 9, e.g., from a signal generated from an AC line voltage.

In an embodiment, the monitoring client 2 is capable of receiving information about each patient-care device with which it is linked either directly from the device itself, or via a docking station, such as, for example, the dock 3 onto which the patient-care device may be mounted. The dock 3 may be configured to receive one or more patient-care devices via a standardized connection mount, or in some cases via a connection mount individualized for the particular device. For example, infusion pumps 4 and 6 may be mounted to the dock 3 via a similar connection mount, whereas the microinfusion pump 9, for example, may be mounted to the dock 3 via a connection mount configured for the particular dimensions of the microinfusion pump's 9 housing.

The dock 3 may be configured to electronically identify the particular patient-care device being mounted on the docking station, and to transmit this identifying information to the monitoring client 2, either wirelessly or via a wired connection. Additionally or alternatively, wireless patient-care devices may transmit the identifying information wirelessly to the monitoring client 2, e.g., during a discovery protocol. Additionally, the particular patient-care device may be preprogrammed with treatment information (e.g., patient-treatment parameters such as an infusion rate for a predetermined infusion liquid) that is transmitted to the monitoring client 2. For example, the syringe pump 10 may include identity information and treatment information, such as what medication has been prescribed to the patient, what liquid is within the syringe pump's 10 reservoir, how much and how long the liquid is prescribed to be delivered to the patient, who are the authorized caregivers, etc. In some embodiments of the present disclosure, the monitoring client 2 communicates with EMR records to verify that the preprogrammed treatment information is safe for an identified patient and/or the preprogrammed treatment information matches the prescribed treatment stored in the EMR records.

In some embodiments, the drip detection device 8 may communicate with the monitoring client 2 either wirelessly or in a wired connection. If an aberrant liquid flow condition is detected (e.g., because the tubing to the patient has become occluded), a signal may be transmitted to monitoring client 2, which (1) may display the flow rate of liquid from the liquid container 5 in a user interface either locally on the monitoring client 2, or more remotely to a user interface at a nurse's station or a handheld communications device, (2) may trigger an auditory or visual alarm, and/or (3) may cause the monitoring client 2 to alter the rate of infusion of a pump 4 connected to a bag 5, by either terminating the infusion or otherwise changing the pumping rate. The aberrant liquid flow condition may also cause an audible alarm (and/or vibration alarm) on the infusion pump 4 or the drip detection device 8, or cause the infusion pump 4 to modify or stop the pumping, e.g., when the aberrant liquid flow condition exceed predefined ranges of operation.

The alarms may occur simultaneously on several devices or may follow a predetermined schedule. For example, when an occlusion occurs in a line connected to the infusion pump 4, (1) the drip detection device 8 alarms using its internal speaker and an internal vibration motor, (2) thereafter, the infusion pump 4 alarms using its internal speaker and an internal vibration motor, (3) next, the monitoring client 2 alarms using its internal speaker and an internal vibration motor, and (4) finally, a remote communicator (e.g., a smart phone, blackberry-based phone, Android-based phone, iphone, etc.) alarms using its internal speaker and an internal vibration motor. In some embodiments, the syringe pump 10 may be connected to the drip detection device 8 and detect aberrant liquid flow conditions as described above.

In some embodiments, the syringe pump 10 may be programmable to allow for continued operation at a predetermined pumping rate should communications fail between the monitoring client 2 and the syringe pump 10, either because of a malfunction in the monitoring client 2, in the communications channel between the monitoring client 2 and the syringe pump 10, or in the syringe pump 10 itself. In some embodiments, this independent function option is enabled when the medication being infused is pre-designated for not being suspended or held in the event of a malfunction in other parts of the system. In some embodiments, the syringe pump 10 is programmed to operate independently in a fail safe mode and may also be configured to receive information from a drip detection device 8 directly, rather than through a monitoring client 2 (e.g., in embodiment where the drip detection device 8 is used in conjunction with the syringe pump 10); with this option, the syringe pump 10 may be programmed, in some embodiments, to stop an infusion if the drip detection device 8 detects an aberrant flow condition (such as, e.g., a free-flow condition or an air bubble present in the infusion line). In some embodiments, one or more of the pumps 4, 6, and 10 may have internal liquid flow meters and/or can operate independently as a stand-alone device. Additionally or alternatively, an internal liquid flow meter of the syringe pump 10 may be independently determined by a flow meter of the drip detection device 8 by the monitoring client 2, in embodiments where the devices 8 and 10 are used together.

The monitoring client 2 may also remotely send a prescription to a pharmacy. The prescription may be a prescription for infusing a fluid using the syringe pump 10. The pharmacy may include one or more computers connected to a network, e.g., the internet, to receive the prescription and queue the prescription within the one or more computers. The pharmacy may use the prescription to compound the drug (e.g., using an automated compounding device coupled to the one or more computers or manually by a pharmacists viewing the queue of the one or more computers), pre-fill a fluid reservoir or cartridge of a syringe pump 10, and/or program the syringe pump 10 (e.g., a treatment regime is programmed into the syringe pump 10) at the pharmacy in accordance with the prescription. The reservoir or cartridge may be automatically filled by the automated compounding device and/or the syringe pump 10 may be automatically programmed by the automated compounding device. The automated compounding device may generate a barcode, RFID tag and/or data. The information within the barcode, RFID tag, and/or data may include the treatment regime, prescription, and/or patient information. The automated compounding device may: attach the barcode to the syringe pump 10 or to the reservoir, cartridge, or disposable portion of the syringe pump 10; attach the RFID tag to the syringe pump 10 or the reservoir, cartridge, or disposable portion of the syringe pump 10; and/or program the RFID tag or memory within the syringe pump 10 or the reservoir, cartridge, or disposable portion of the syringe pump 10 with the information or data. The data or information may be sent to a database that associates the prescription with the syringe pump 10 or the reservoir, cartridge, or disposable portion of the syringe pump 10, e.g., using a serial number or other identifying information within the barcode, RFID tag, or memory.

The syringe pump 10 may have a scanner, e.g., an RFID interrogator that interrogates a reservoir, disposable portion, or cartridge of the syringe pump 10 to determine that it is the correct fluid within the fluid reservoir or it is the correct fluid reservoir, disposable portion or cartridge, the treatment programmed into the syringe pump 10 corresponds to the fluid within the fluid reservoir, disposable portion or cartridge, and/or the syringe pump 10 and reservoir, disposable portion or cartridge of the syringe pump 10 are correct for the particular patient (e.g., as determined from a patient's barcode, RFID, or other patient identification). For example, a serial number of a reservoir, disposable portion as scanned by the syringe pump 10 is compared to a serial number in electronic medical records to determine if it correctly corresponds to a patient's serial number within the electronic medical records; the syringe pump 10 may scan a RFID tag or barcode of a patient to obtain a serial number of a patient which is also compared to the patient's serial number within the electronic medical records (e.g., the serial number of a reservoir, disposable portion, or cartridge of the syringe pump 10 or a serial number stored within memory of the syringe pump 10 should be associated with the patient's serial number as scanned within the electronic medical records). The syringe pump 10 may issue an error or alarm if the serial numbers do not match, in some specific embodiments. Additionally or alternatively, the monitoring client 2 may scan the reservoir, disposable portion, cartridge, or syringe pump 10 to determine that it is the correct fluid within the fluid reservoir, it is the correct fluid reservoir, the treatment programmed into the syringe pump 10 corresponds to the fluid within the fluid reservoir or cartridge, and/or the fluid reservoir and syringe pump 10 are correct for the particular patient (e.g., as determined from a patient's barcode, RFID, or other patient identification). Additionally or alternatively, the monitoring client 2 or syringe pump 10 may interrogate an electronic medical records database and/or the pharmacy to verify the prescription or download the prescription, e.g., using a barcode serial number on the syringe pump 10, or a reservoir, cartridge, or disposable portion of the syringe pump 10.

The liquid being delivered to a patient may be monitored by the monitoring client 2 to determine if all the medications being delivered are safe for the patient. For example, the monitoring client 2 may log the medication delivered from the syringe pump 10 as communicated by the syringe pump 10 to the monitoring client 2, and the monitoring client 2 may also log the medication being delivered by the infusion pumps 4 and 6, and/or the microinfusion pump 9. The monitoring client 1 may make a determination from the logged data to determine if the aggregate amounts and types of medication being delivered are safe. For example, the monitoring client 2 may determine if the IV bag 5 is contraindicated with the medication in the syringe pump 10. Additionally or alternatively, in some embodiments, the monitoring client 2 may monitor the delivery of the liquid in the IV bag 8 and one or more boluses delivered by the syringe pump 10 to determine if the total dose exceeds a predetermined threshold, e.g., the medication in the IV bag 5 and syringe pump 10 may be the same type or class of drug, and the monitoring client 2 may determine if the drugs are safe when combined as delivered to the patient. The syringe pump 10 may also communicate with the infusion pumps 4 and 6, and/or the microinfusion pump 9 to make the same determination; In this exemplary embodiment, the syringe pump 10 may communicate with the devices directly (via wirelessly or wired communications) or through the monitoring client 2 (via wirelessly or wired communications). In some embodiments of the present disclosures, one or more communication modules (e.g., each having the capabilities to communicate via one or more protocols) may be connected to the syringe pump 10 and/or may be connected together and then connected to the syringe pump 10 to enable the syringe pump 10 to communicate via the communication modules.

The syringe pump 10 includes a touch screen interface 11 (which may be detachable), a start button 12, and a stop button 13. However, in some alternative embodiments, the button 12 is a PCA button to deliver pain medicine to a patient. The user interface 11 may be used to program treatment regimes, such as flow rates, bolus amounts, or other treatment parameters. After a treatment regime is programmed into the syringe pump 10, the syringe pump 10 may query a database (e.g., Electronic Medical Records ("EMR"), Drug Error Reduction System ("DERS"), or other database) to determine if the treatment regime is safe for the particular patient or for any patient. For example, the syringe pump 10 may query the EMR database (e.g., via a wireless link, wired link, WiFi, cell-phone network, or other communications technology) to determine if the treatment regime from the syringe pump 10 is safe based upon patient information stored (e.g., age, weight, allergies, condition, etc.) in the EMR records. Additionally or alternatively, the syringe pump 10 may query the DERS database (e.g., via a wireless link, wired link, WiFi, cell-phone network, or other communications technology) to determine if the treatment regime from the syringe pump 10 is safe based upon predetermined safety criteria in the DERS records In some embodiments, if the treatment regime is determined to be safe, a prompt may request user confirmation of the treatment regime. After user confirmation, the user (e.g., caregiver, nurse, or other authorized person) may press the start button 12. In some embodiments, the stop button 13 may be pressed at any time to stop treatment.

In some embodiments, if the EMR and/or DERS determines that the treatment regime exceeds a first set of criteria, treatment may continue if the user confirms the treatment (e.g., with an additional warning, user passcode, and/or additional authentication or authorization, etc.); in this embodiment, the EMR or DERS may prevent the treatment from being delivered if the EMR and/or DERS determines that the treatment regime exceeds a second set of criteria, e.g., the treatment is not safe under any circumstances for any patient, for example.

Exemplary Bedside Arrangement

Figure 2:
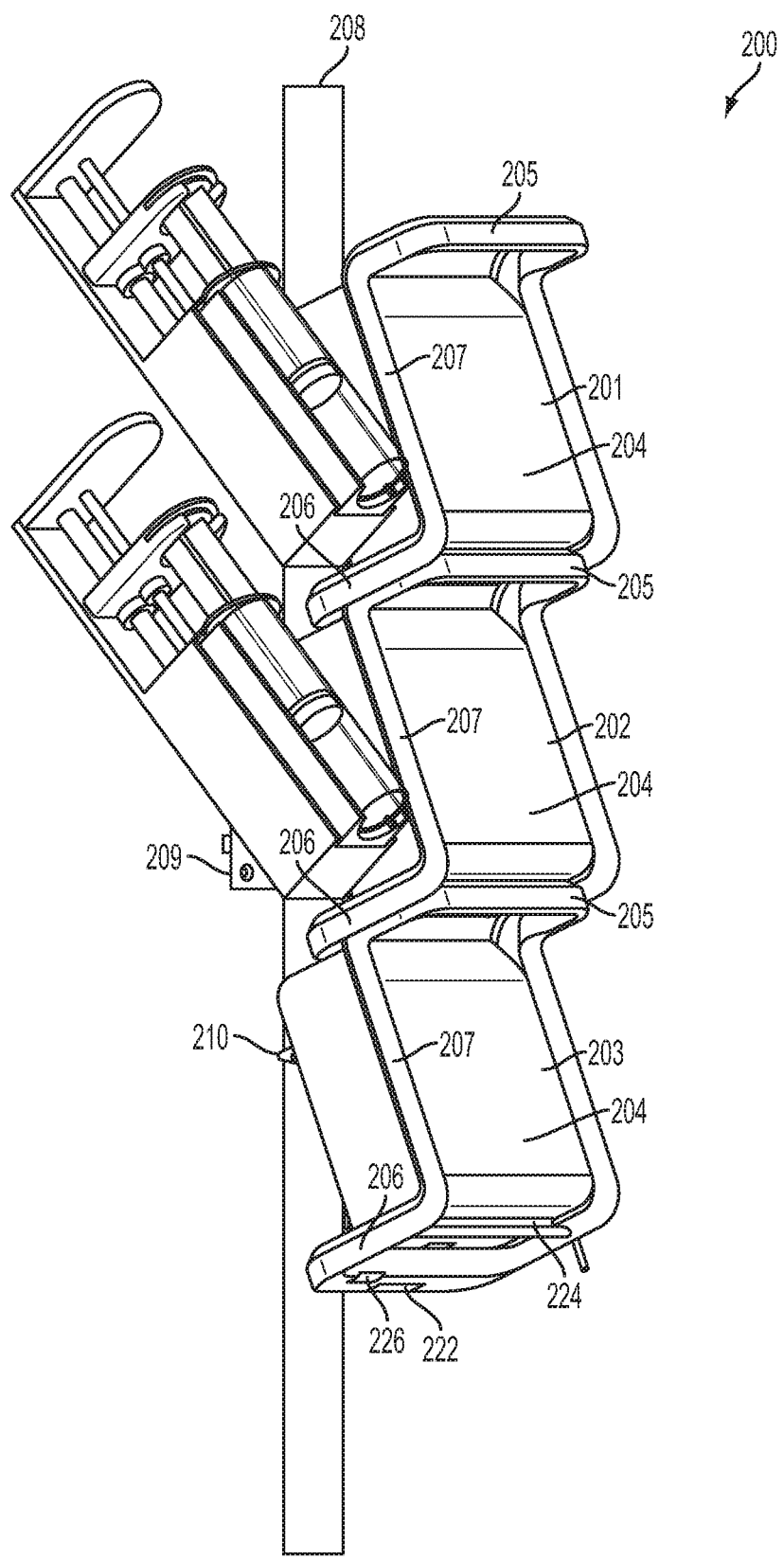
FIGS. 2-5 show several views of a patient bedside system in accordance with an embodiment of the present disclosure.

FIGS. 2-9 show various views related to a system 200. FIG. 2 shows a system 200 that includes several pumps 201, 202, and 203. The pumps 201, 202, 203 can be coupled together to form a group of pumps that are connectable to a pole 208. The system 200 includes two syringe pumps 201, 202 and a peristaltic pump 203; however, other combinations of various medical devices may be employed.

Each of the pumps 201, 202, 203 includes a touch screen 204 which may be used to control the pumps 201, 202, 203. One of the pumps' (e.g., 201, 202, 203) touch screen 204 may also be used to coordinate operation of all of the pumps 201, 202, 203 and/or to control the other ones of the pumps 201, 202, 203.

The pumps 201, 202, and 203 are daisy chained together such that they are in electrical communication with each other. Additionally or alternatively, the pumps 201, 202, and/or 203 may share power with each other or among each other; For example, one of the pumps 201, 202, and/or 203 may include an AC/DC converter that converts AC electrical power to DC power suitable to power the other pumps.

Within the system 200, the pumps 201, 202, and 203 are stacked together using respective Z-frames 207. Each of the Z-frames 207 includes a lower portion 206 and an upper portion 205. A lower portion 206 of one Z-frame 207 (e.g., the lower portion 206 of the pump 201) can engage an upper portion 205 of another Z-frame 207 (e.g., the upper portion 205 of the Z-frame 207 of the pump 202).

Figure 3:
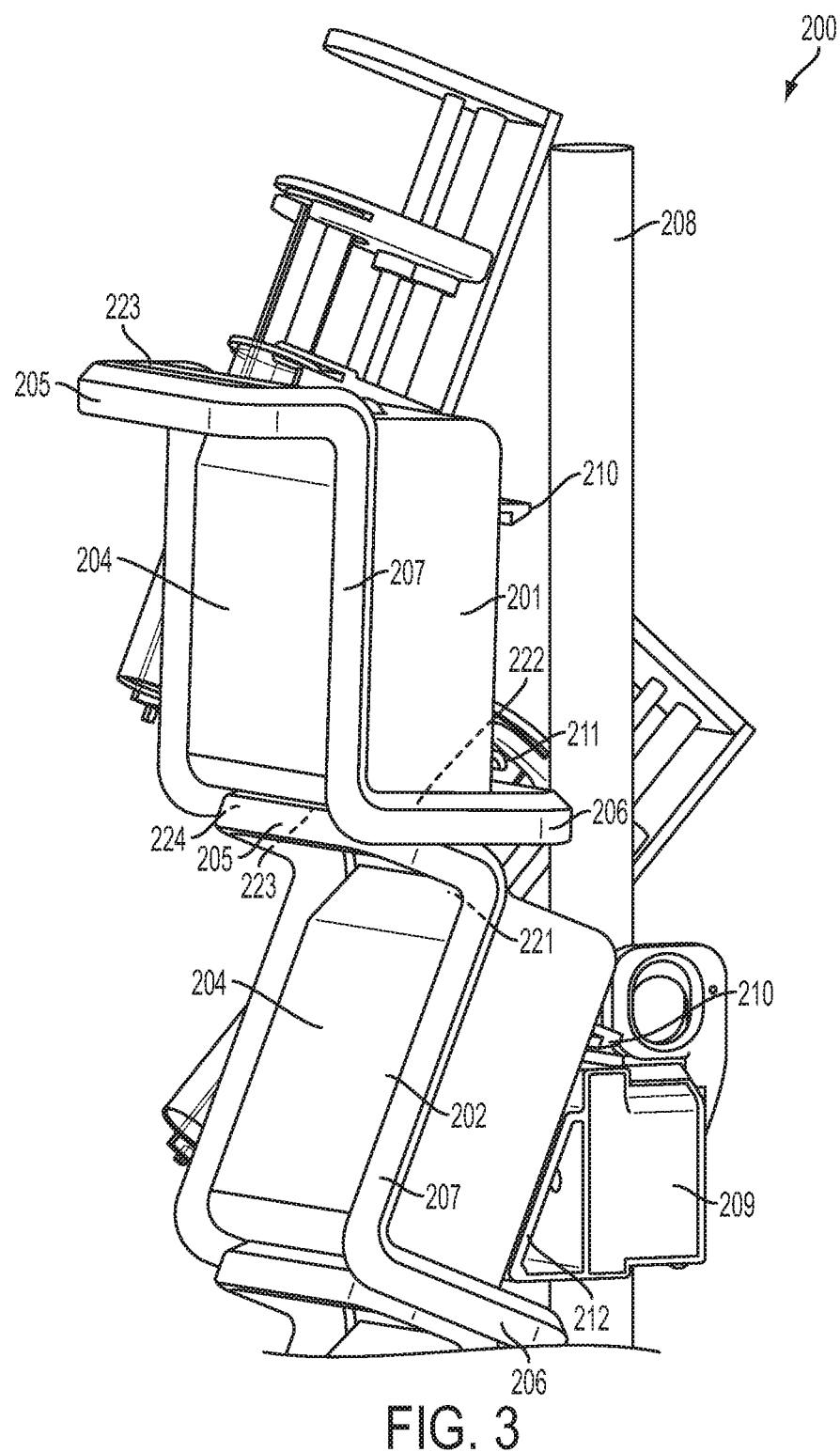
Figure 4:
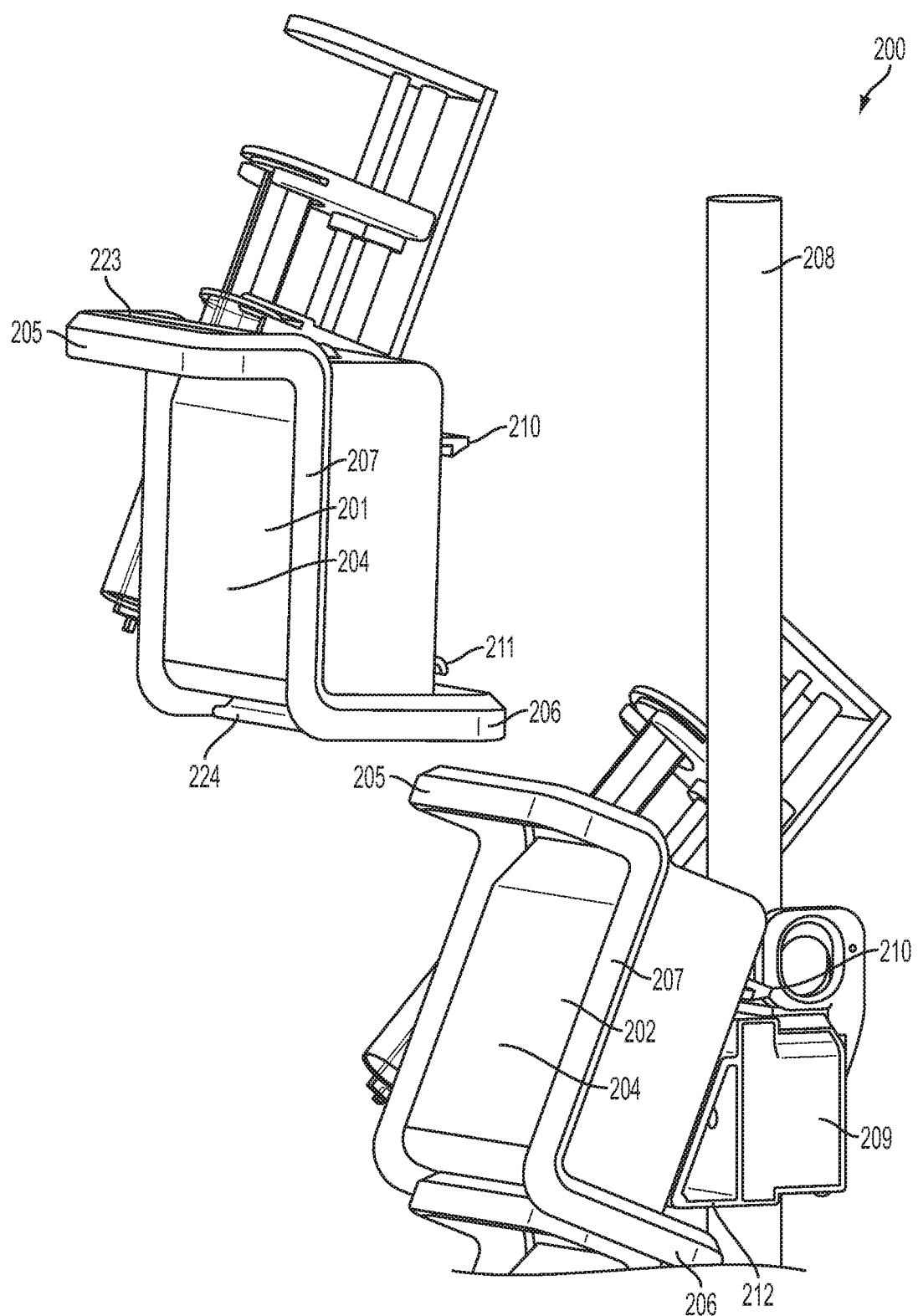
Figure 5:
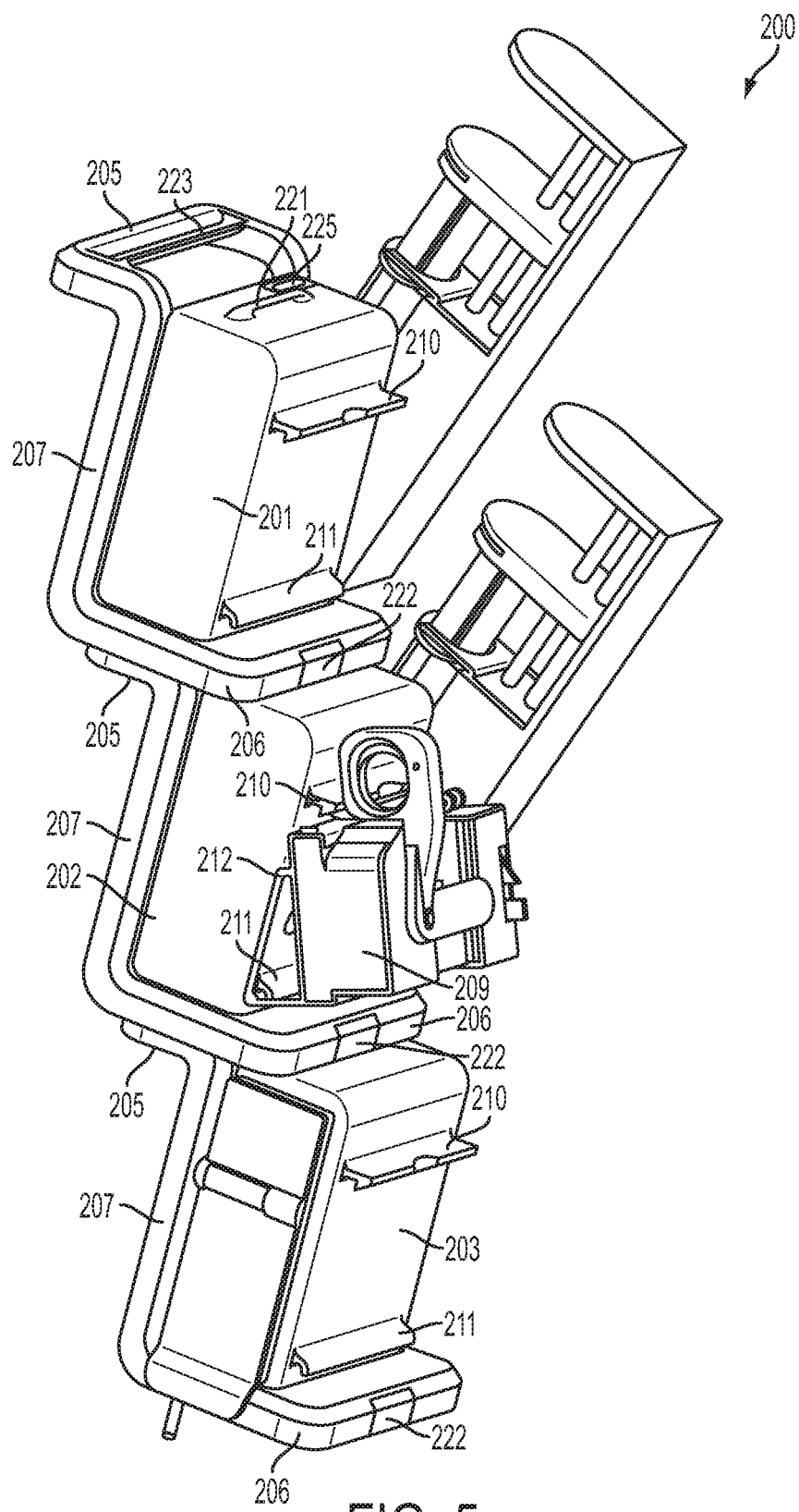

A clamp 209 may be coupled to one of the pumps 201, 202, 203 (e.g., the pump 202 as shown in FIG. 3). That is, the clamp 209 may be coupled to any one of the pumps 201, 202, 203. The clamp 209 is attachable to the back of any one of the pump 201, 202, 203. As is easily seen in FIG. 5, each of the pumps 201, 202, 203 includes an upper attachment member 210 and a lower attachment member 211. A clamp adapter 212 facilitates the attachment of the clamp 209 to the pump 202 via a respective pump's (e.g., 201, 202, or 203) upper attachment member 210 and lower attachment member 211. In some embodiments, the clamp adapter 212 may be integral with the clamp 209.

Figure 6:
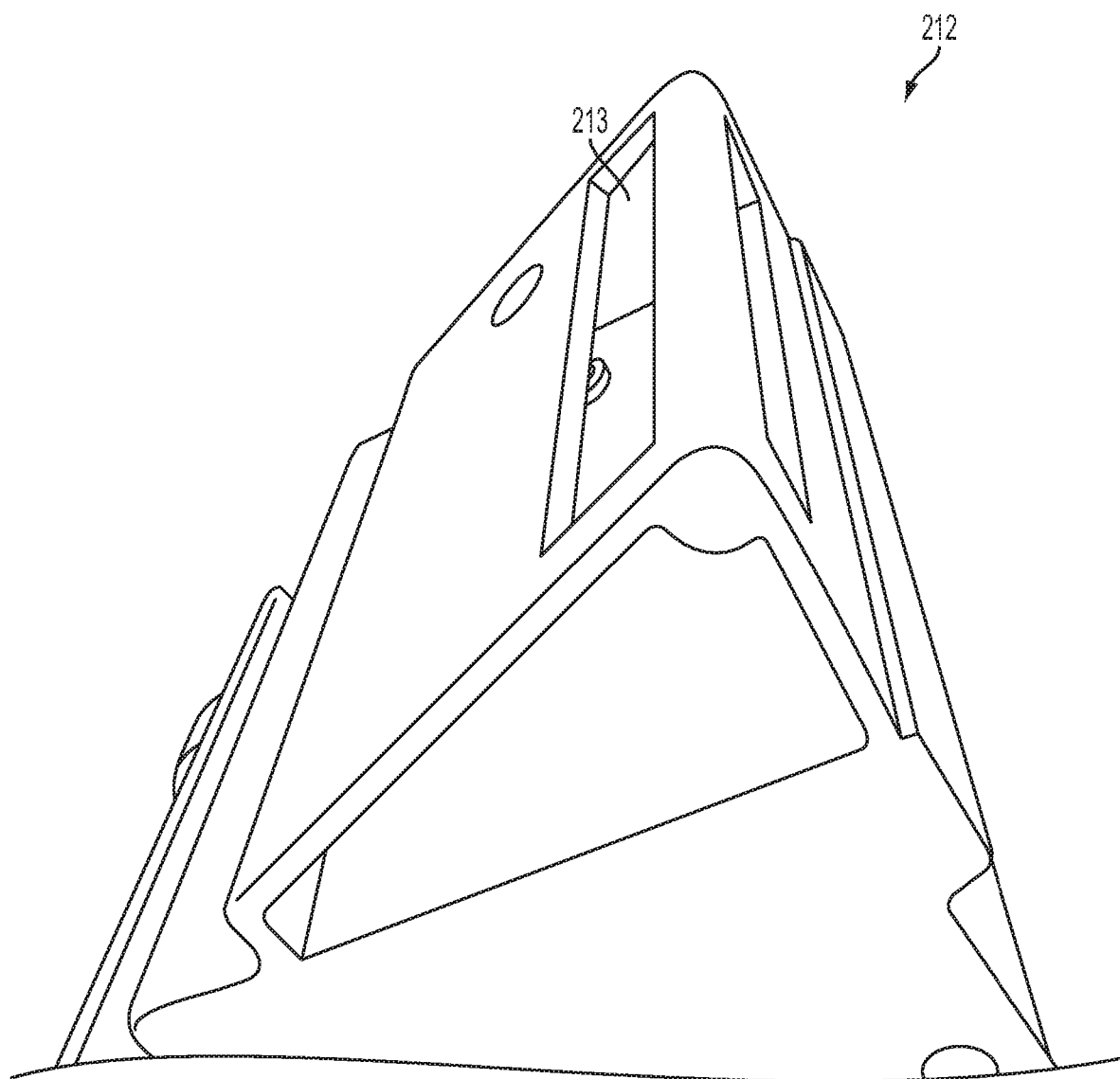
FIG. 6 shows a close-up view of a portion of an interface of a clamp that is attachable to a pump shown in FIGS. 2-5 in accordance with an embodiment of the present disclosure.

FIG. 6 shows a close-up view of a portion of an interface of a clamp (i.e., the clamp adapter 212) that is attachable to the pump 202 (or to pumps 201 or 203) shown in FIGS. 2-5 in accordance with an embodiment of the present disclosure. The clamp adapter 212 includes a hole 213 in which a lower attachment member 211 (see FIG. 5) may be attached to. That is, the lower attachment member 211 is a curved hook-like protrusion that may be inserted into the hole 213 and thereafter rotated to secure the lower attachment member 211 therein.

Figure 7:
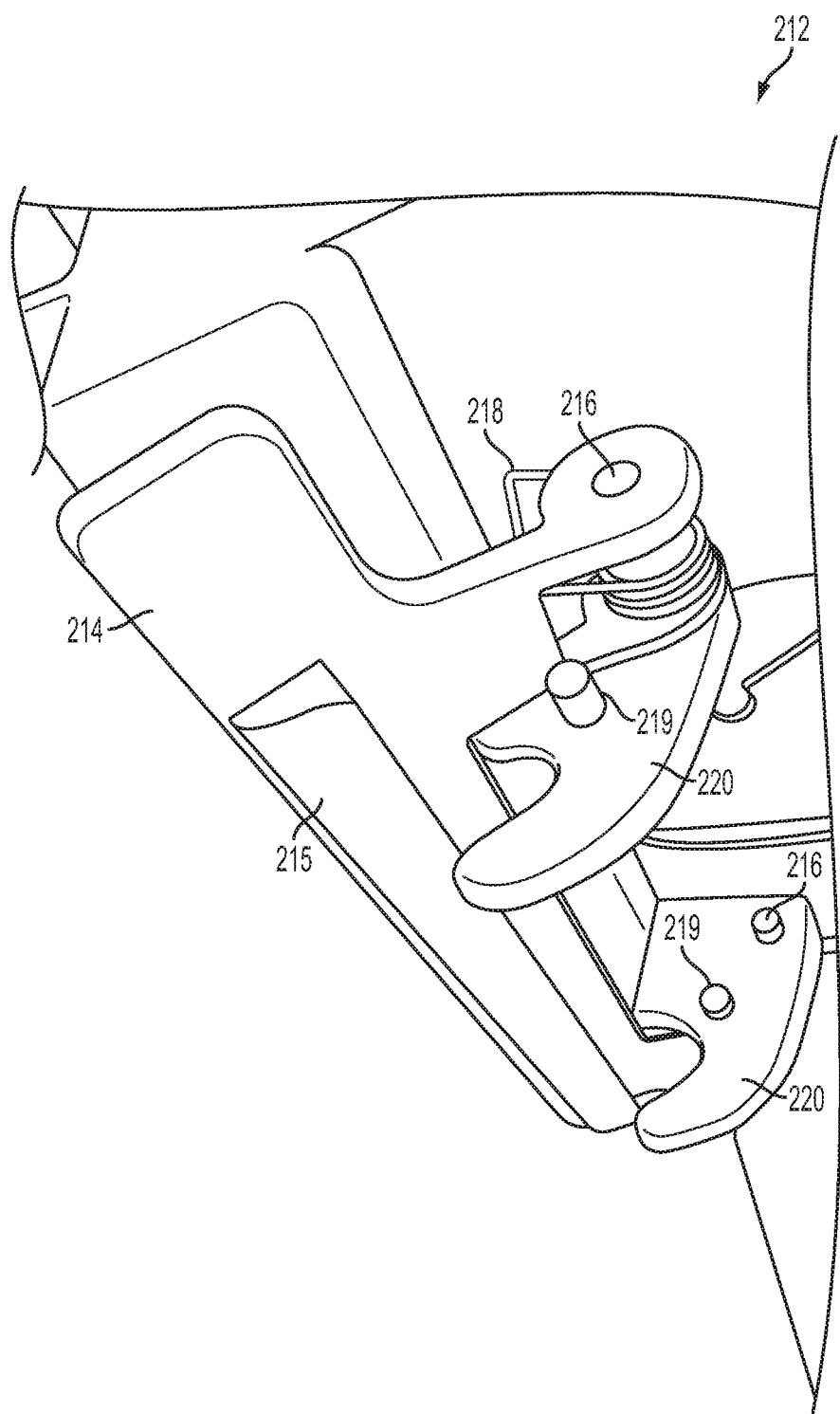
FIG. 7 shows another close-up view of another portion of the interface shown in FIG. 6 in accordance with an embodiment of the present disclosure.

As is easily seen in FIG. 7, the clamp adapter 212 also includes a latch 214. The latch 214 is pivotally mounted to the clamp adapter 212 via pivots 216. The latch 214 may be spring biased via springs 218 that are coupled to the hooks 220. Stop members 219 prevent the latch 214 from pivoting beyond a predetermined amount. After the hole 213 is inserted into the lower attachment member 211 (see FIGS. 5 and 6), the clamp adapter 212 may be rotated to bring the latch 214 towards the upper attachment member 210 such that the latch 214 is compressed down by the upper attachment member 210 until the protrusion 215 snaps into a complementary space of the upper attachment member 210. The hooks 220 help secure the clamp adapter 212 to the pump 202.

Figure 8:
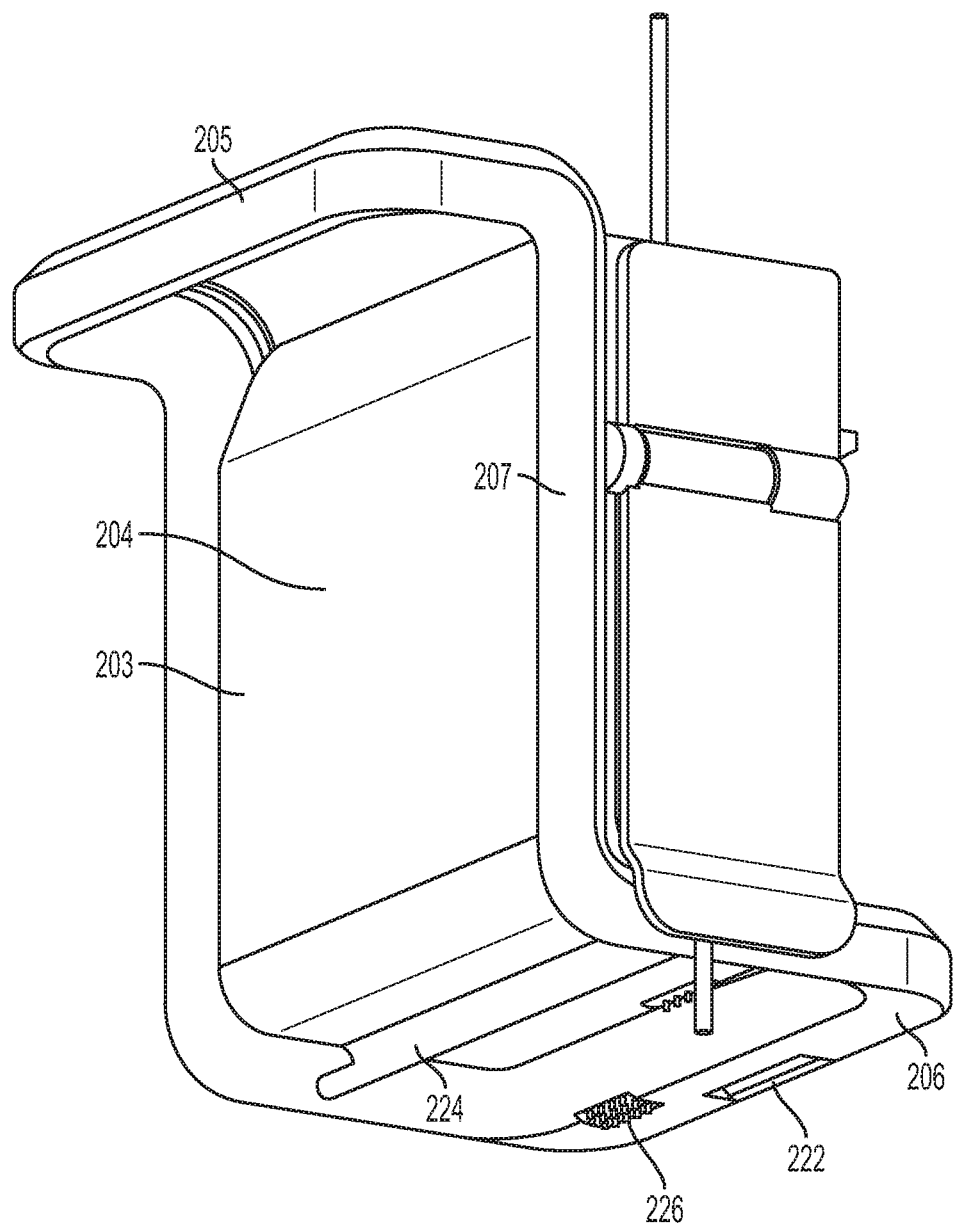
FIG. 8 shows a perspective view of a pump attachable to the patient bedside system of FIGS. 2-5 in accordance with an embodiment of the present disclosure.
Figure 9:
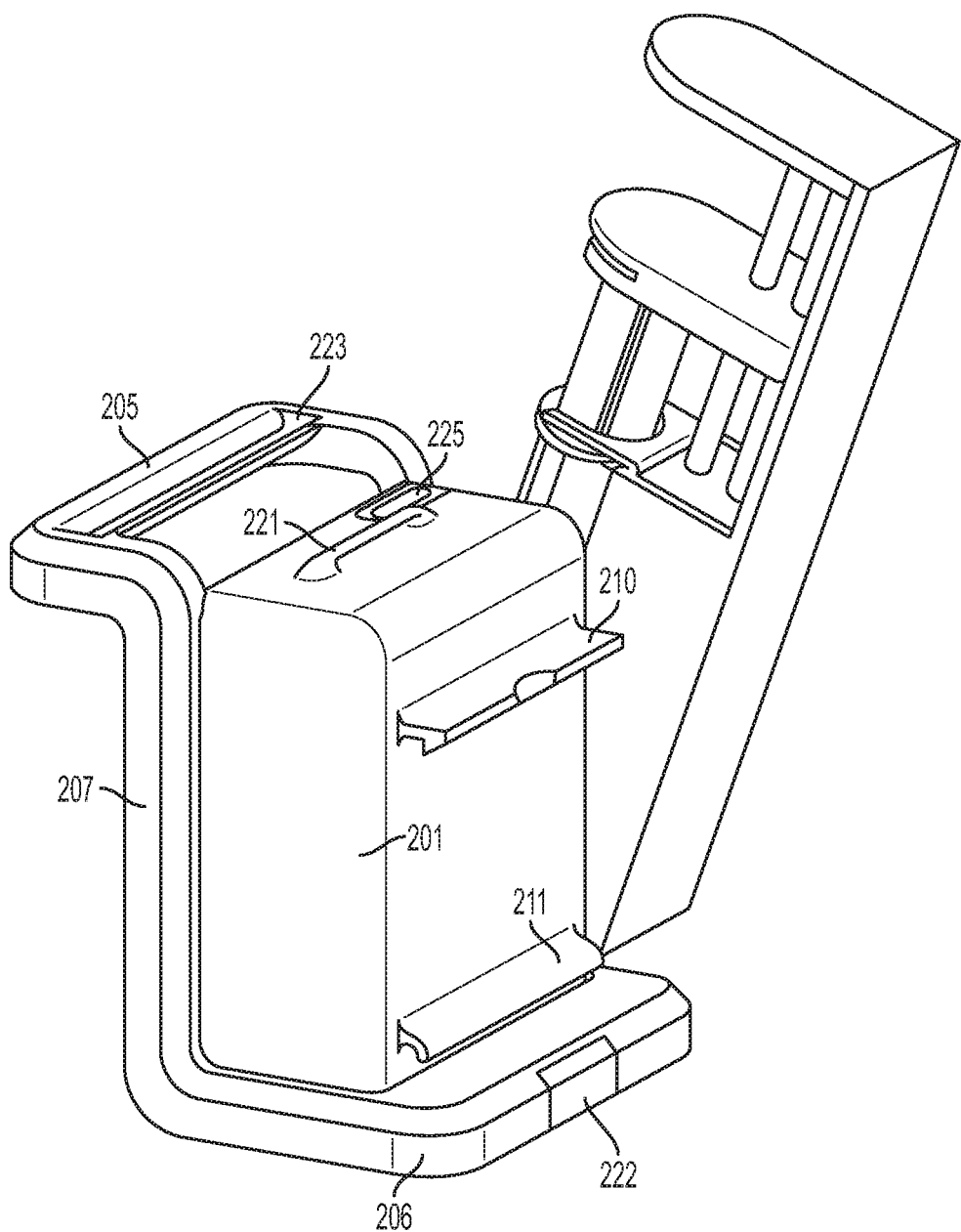
FIG. 9 shows a perspective view of a pump shown in FIGS. 2-5 in accordance with an embodiment of the present disclosure.

Each Z-frame 207 of the pumps 201, 202, 203 includes a recessed portion 223 (see FIG. 5) and a protrusion 224 (see FIG. 8). A protrusion 224 of the Z-frame 207 of one pump (e.g., pumps 201, 202, or 203) may engage a recessed portion 223 of another pump to enable the pump to be stacked on top of each other. Each of the pumps 201, 202, 203 includes a latch engagement member 221 that allows another one of the pumps 201, 202, 203 to be attached thereto via a latch 222 (see FIG. 8). The latch 222 may include a small spring loaded flange that can "snap" into the space formed under the latch engagement member 221. The latch 222 may be pivotally coupled to the lower portion 206 of the Z-frame 207.

As is seen in FIG. 3, the latch 222 of the pump 201 may be pulled to withdraw a portion of the latch 222 out of the space under the latch engagement member 221 of the pump 202. Thereafter, the pump 201 may be rotated to pull out the protrusion 224 of the pump 201 out of the recessed portion 223 of the Z-frame 207 of the pump 202 such that the pump 201 may be removed from the stack of pumps 202, 203 (see FIG. 4).

Each of the pumps 201, 202, 203 includes a top connector 225 (see FIG. 9) and a bottom connector 226 (see FIG. 8). The connectors 225 and 226 allow the stacked pumps 201, 202, and 203 to communication between each other and/or to provide power to each other. For example, if the battery of the middle pump 202 (see FIG. 2) fails, then the top pump 201 and/or the bottom pump 203 may provide power to the middle pump 202 as a reserve while audibly alarming.

Exemplary Syringe Pump Embodiment and Related Bedside Arrangement

FIGS. 10-13 show several views of a syringe pump 300 in accordance with an embodiment of the present disclosure. The syringe pump 300 may have a syringe 302 loaded either facing to the left (as shown in FIGS. 10-13) or to the right (refer to FIG. 16, described below). That is, the syringe pump 300 is a bidirectional syringe pump.

The syringe 302 may be loaded into a syringe holder 306 of the syringe pump 300. The flange endpiece 310 of the syringe 302 may be placed in the left flange receiver 311 or in the right flange receiver 312. When the flange endpiece 310 is inserted into the left flange receiver 311, the syringe 302 faces towards the left outlet 308, which may hold a tube that is fluidly coupled to the syringe 302. An engagement member 314 may be coupled to an end fitting 315 of the syringe 302 when or after the syringe 302 is loaded into the syringe holder 306. A threaded shaft 315 that is coupled to a motor may be rotated to move the engagement member 314 in any direction to discharge fluid from the syringe 302.

The syringe 302 may also be loaded to the right (not shown in FIGS. 10-13). The syringe holder 306 may be moved and/or adjusted such that it is moved to the right so the syringe 302 may be loaded. The syringe holder 306 may be manually moved and/or an electric motor may move the syringe holder 306 to the right. In some embodiments of the present disclosure, the syringe holder 306 extends sufficiently to the left and to the right such that no adjustment is used.

In the case where the syringe 302 is loaded facing the right, the flange endpiece 310 is loaded into the right flange receiver 312. The engagement member 314 thereafter moves to the right such that fluid may be discharged through a tube that traverses through a right outlet 309.

The pump 300 may be controlled via a touch screen 304 to set the flow rate, flow profile, and/or to otherwise monitor or control the syringe pump 300. A clamp 316 may be used to secure the syringe pump 300 to a pole (e.g., using a screw-type clamp).

Figure 14:
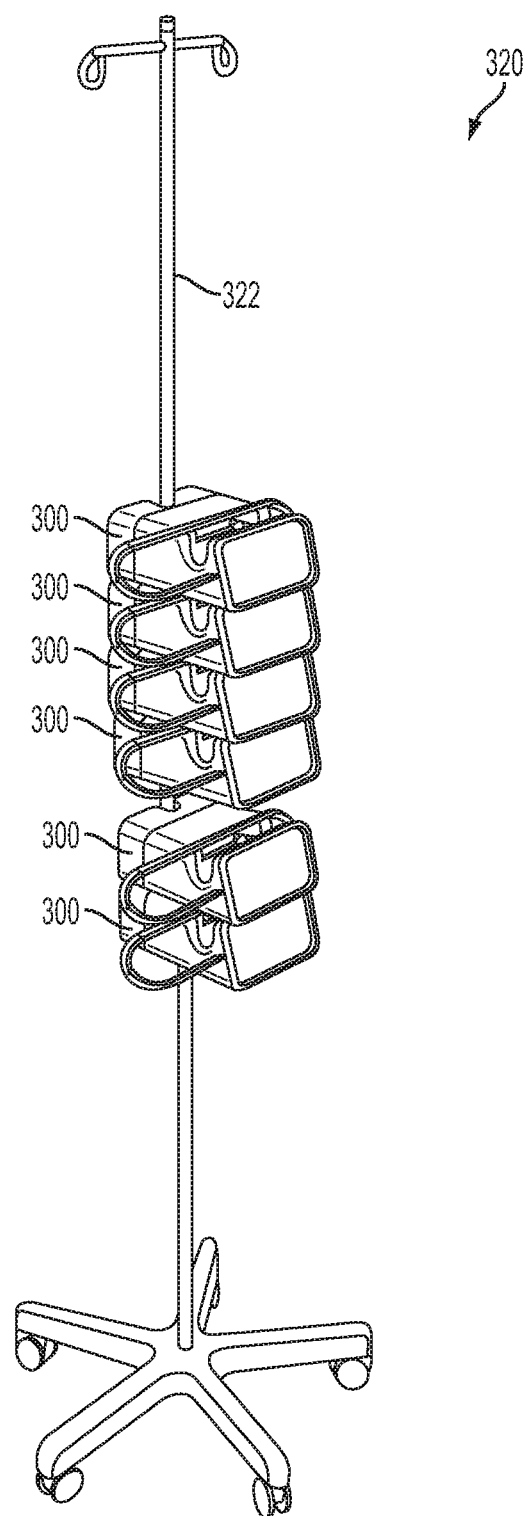
FIG. 14 shows several of the syringe pump of FIGS. 10-13 mounted on a pole in accordance with an embodiment of the present disclosure.

FIG. 14 shows several of the syringe pumps 300 of FIGS. 10-13 mounted on a pole 322 in accordance with an embodiment of the present disclosure. That is, FIG. 14 shows a system 320 that uses several syringe pumps 300 mounted on the pole 312. The pole 322 may be used in a hospital and/or in a home setting.

Figure 15:
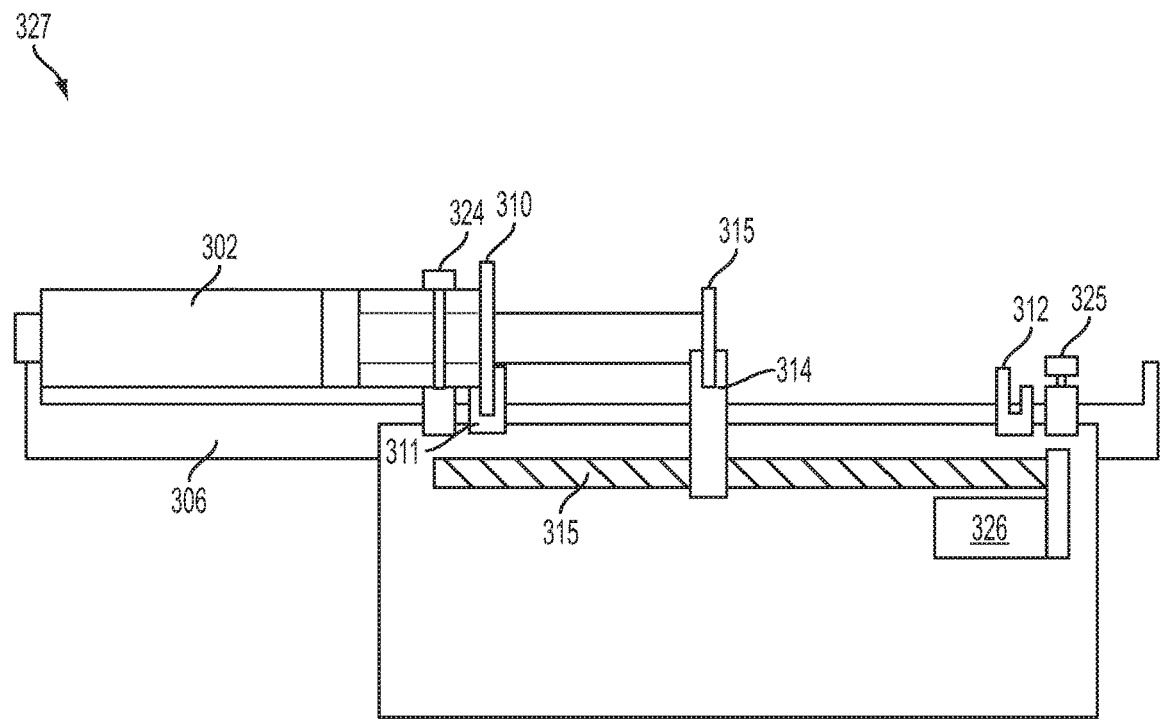
FIGS. 15-16 illustrate portions of the operation of the syringe pump of FIGS. 10-13 in accordance with an embodiment of the present disclosure.
Figure 16:
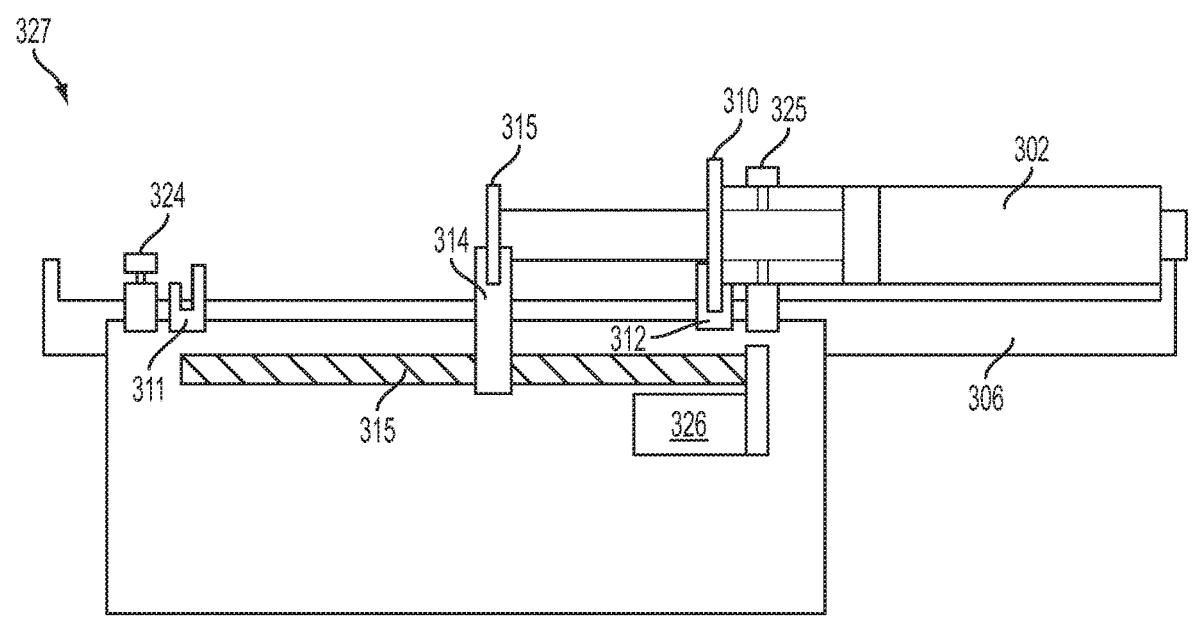
Figure 19:
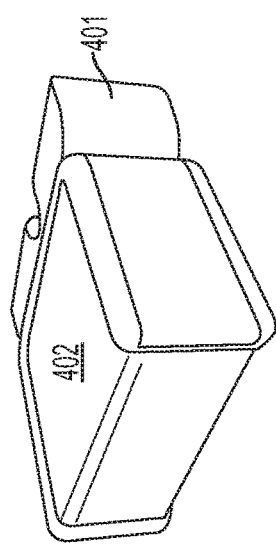
FIGS. 19-22 show several views of a medical device of FIGS. 17-18 in accordance with an embodiment of the present disclosure.
Figure 20:
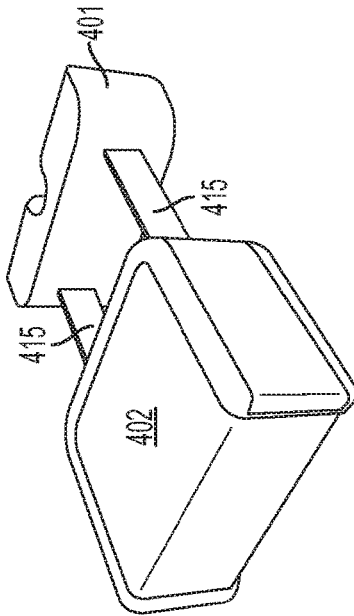
Figure 22:
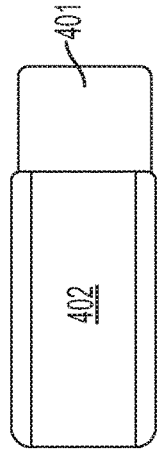
Figure 21:
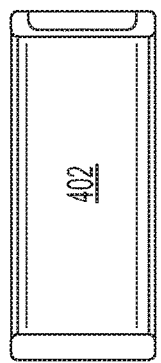

FIGS. 15-16 illustrate portions 327 of the operation of the syringe pump 300 of FIGS. 21-24 in accordance with an embodiment of the present disclosure. FIG. 15 shows the syringe 302 loaded facing the left, and FIG. 16 shows the syringe 302 loaded to the right. As shown in FIGS. 15-16, a motor 326 is coupled to the threaded shaft 315 such that the motor 326 can rotate the threaded shaft 315.

A left syringe diameter sensor 324 measures the diameter of the syringe 305 to estimate the cross-sectional size of the internal space of the barrel of the syringe 302. The left syringe diameter sensor 325 may be a bar that is attached to a post such that the bar is lifted to cover the syringe 302; the post's movement out of the body of the syringe pump 300 may be measured by a linear sensor to estimate the diameter of the barrel of the syringe 302. Any linear sensor may be used including a linear potentiometer technology, an optical linear sensor technology, a hall-effect sensor technology, etc. The motor's 326 movement may thereby be correlated to fluid discharged from the syringe 302 using the estimate of the diameter of the internal space of the barrel of the syringe 302. Similarly, the right syringe diameter sensor 325 may be used to estimate the internal diameter of the barrel of the syringe 302, which may be used to estimate the fluid discharged from the syringe 302 to the right.

In some embodiments of the present disclosure, the touch screen 304 requests information from the user when the syringe 302 is loaded into the syringe pump 300 (in either the left or right configuration) and the syringe diameter sensor 324 or 325 is used to estimate the diameter of the internal space of the barrel of the syringe 305; The user is prompted by a touch screen 304 request for the user to enter into the touch screen 304 the manufacturer of the syringe 305. An internal database within the syringe pump 300 may be used to narrow down the range of possible model numbers associated with an estimate of the diameter of the syringe 305. When the user enters in the manufacturer of the syringe 305, the database may be used to identify a particular model number of the syringe 305 and/or a subset of possible model numbers corresponding to the estimate of the diameter of the syringe 305 and the user entered information, which in turn, may provide a more accurate internal diameter value (as stored within the database). The user may be prompted by the display on the touch screen 304 to select the syringe model from a list or enter the model of the syringe that will deliver the medication. The user may be guided through a selection process on the touchscreen 304 to identify the syringe loaded into the machine using one or more of the following aspects: syringe barrel size, plunger head size, manufacturer names, images of syringes, and model numbers. The selection process may access a database of syringes including manufacturer, model, internal diameter and image. The syringe pump 300 may use the identified syringe to set the internal diameter value for volume calculations.

Exemplary Bedside Arrangements

Figure 18:
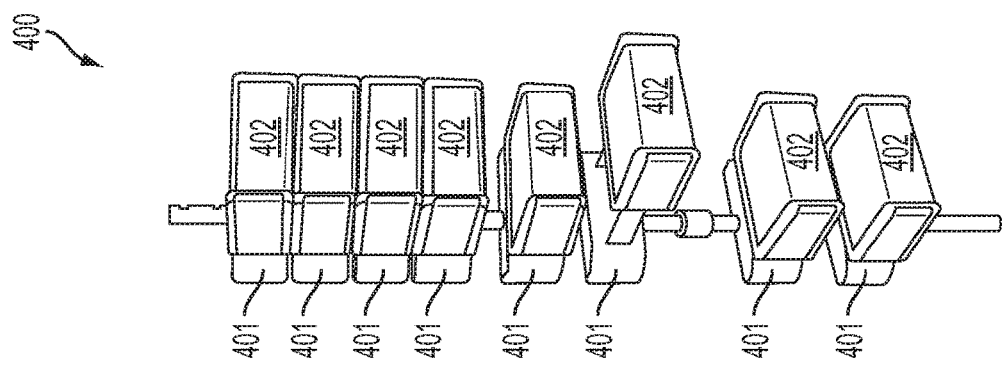
FIGS. 17-18 illustrate several medical devices mounted on a pole in accordance with an embodiment of the present disclosure.
Figure 17:
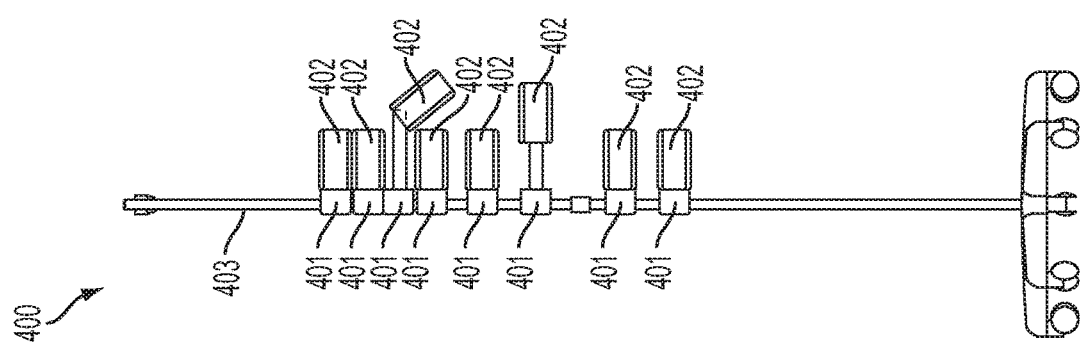

FIGS. 17-18 illustrate several medical devices 402 mounted on a pole 403 in accordance with an embodiment of the present disclosure. FIGS. 19-22 show several views of the medical device 402 of FIGS. 17-18. The medical device 402 is mounted to the pole via the clamp 401. The clamp 401 allows the medical device 402 to be pulled out and adjusted. The medical device 402 may be any medical device, such as an infusion pump, a syringe pump, a monitoring client, etc.

The medical device 402 is coupled to the pole 403 via arms 403 such that the medical device 402 may be pulled away from the pole (see FIG. 20) and/or pivoted on the arms 403.

FIG. 23 shows several mounts 406 mounted on a pole 405, and FIGS. 24-26 show several views of a mount of FIG. 23 in accordance with an embodiment of the present disclosure. Each of the mounts 406 includes a clamp 407 (e.g., a screw-type clamp), a first arm 408 pivotally mounted to the clamp 407, and a second arm 411 pivotally mounted to the first arm 408 via a hinge 409. The end of the second arm 411 includes a coupling member 410 that can be coupled to a medical device.

Exemplary Battery and Speaker Test

Figure 27:
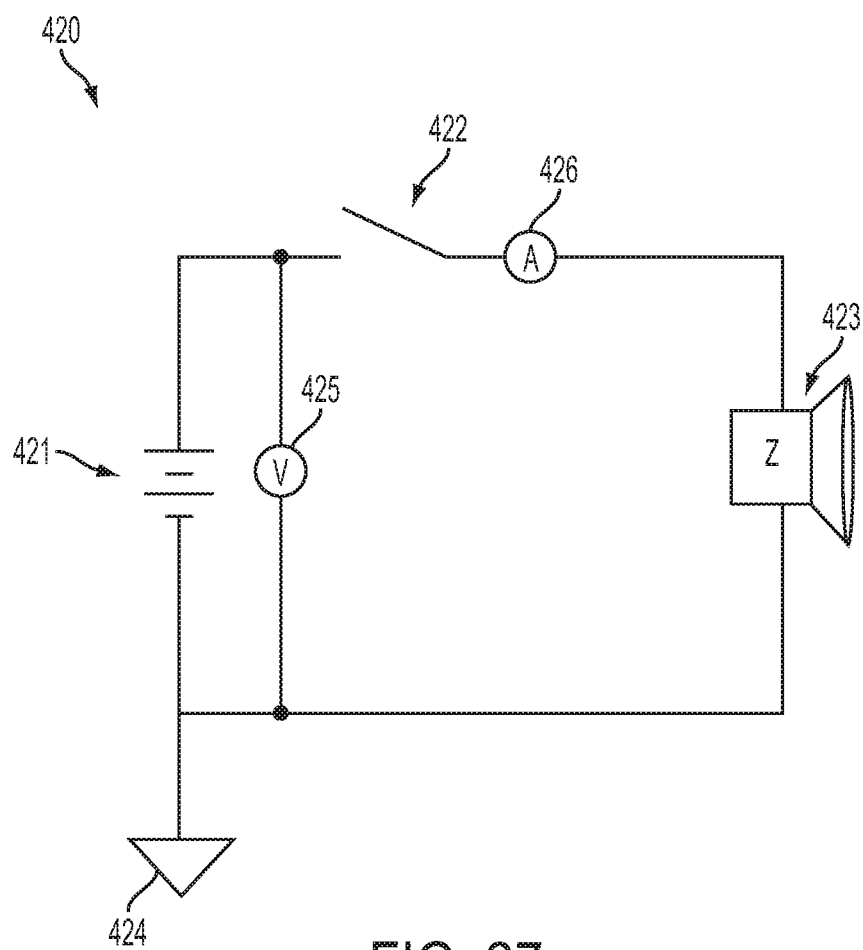
FIG. 27 shows a circuit diagram having a speaker and battery in accordance with an embodiment of the present disclosure.

FIG. 27 shows a circuit diagram 420 having a speaker 423 and a battery 421 in accordance with an embodiment of the present disclosure. The battery 421 may be a backup battery and/or the speaker 423 may be a backup alarm speaker. That is, the circuit 420 may be a backup alarm circuit, for example, a backup alarm circuit in a medical device, such as a syringe pump.

In some embodiments of the present disclosure, the battery 421 may be tested simultaneously with the speaker 423. When a switch 422 is in an open position, a voltmeter 425 may be used to measure the open circuit voltage of the battery 421. Thereafter, the switch 422 may be closed and the closed-circuit voltage from the battery 421 may be measured. The internal resistance of the battery 421 may be estimated by using the known impedance, Z, of the speaker 423. A processor may be used to estimate the internal resistance of the battery 421 (e.g., a processor of a syringe pump). The processor may correlate the internal resistance of the battery 421 to the battery's 421 health. In some embodiments of the present disclosure, if the closed-circuit voltage of the battery 421 is not within a predetermined range (the range may be a function of the open-circuit voltage of the battery 421), the speaker 423 may be determined to have failed.

In some additional embodiments of the present disclosure, the switch 422 may be modulated such that the speaker 423 is tested simultaneously with the battery 421. A microphone may be used to determine if the speaker 423 is audibly broadcasting a signal within predetermined operating parameters (e.g., volume, frequency, spectral compositions, etc.) and/or the internal impedance of the battery 421 may be estimated to determine if it is within predetermined operating parameters (e.g., the complex impedance, for example). The microphone may be coupled to the processor. Additionally or alternatively, a test signal may be applied to the speaker 423 (e.g., by modulating the switch 422) and the speaker's 423 current waveform may be monitored by an current sensor 426 to determine the total harmonic distortion of the speaker 423 and/or the magnitude of the current; a processor may be monitored these values using the current sensor 426 to determine if a fault condition exists within the speaker 423 (e.g., the total harmonic distortion or the magnitude of the current are not within predetermined ranges).

Various sine waves, periodic waveforms, and/or signals maybe applied to the speaker 423 to measure its impedance and/or to measure the impedance of the battery 421. For example, a processor of a syringe pump disclosed herein may modulate the switch 422 and measure the voltage across the battery 421 to determine if the battery 421 and the speaker 423 has an impedance within predetermined ranges; if the estimated impedance of the battery 421 is outside a first range, the processor will determine that the battery is in a fault condition, and/or if the estimated impedance of the speaker 423 is outside a second range, the processor will determine that the speaker 423 is in a fault condition. Additionally or alternatively, if the processor cannot determine if the battery 421 or the speaker 423 has a fault condition, but has determined that at least one exists in a fault condition, the processor may issue an alert or alarm that the circuit 420 is in a fault condition. The processor may alarm or alert a user or a remote server of the fault condition. In some embodiments of the present disclosure, the syringe pump will not operate until the fault is addressed, mitigated and/or corrected.

Exemplary Syringe Pump Embodiment

Figure 28:
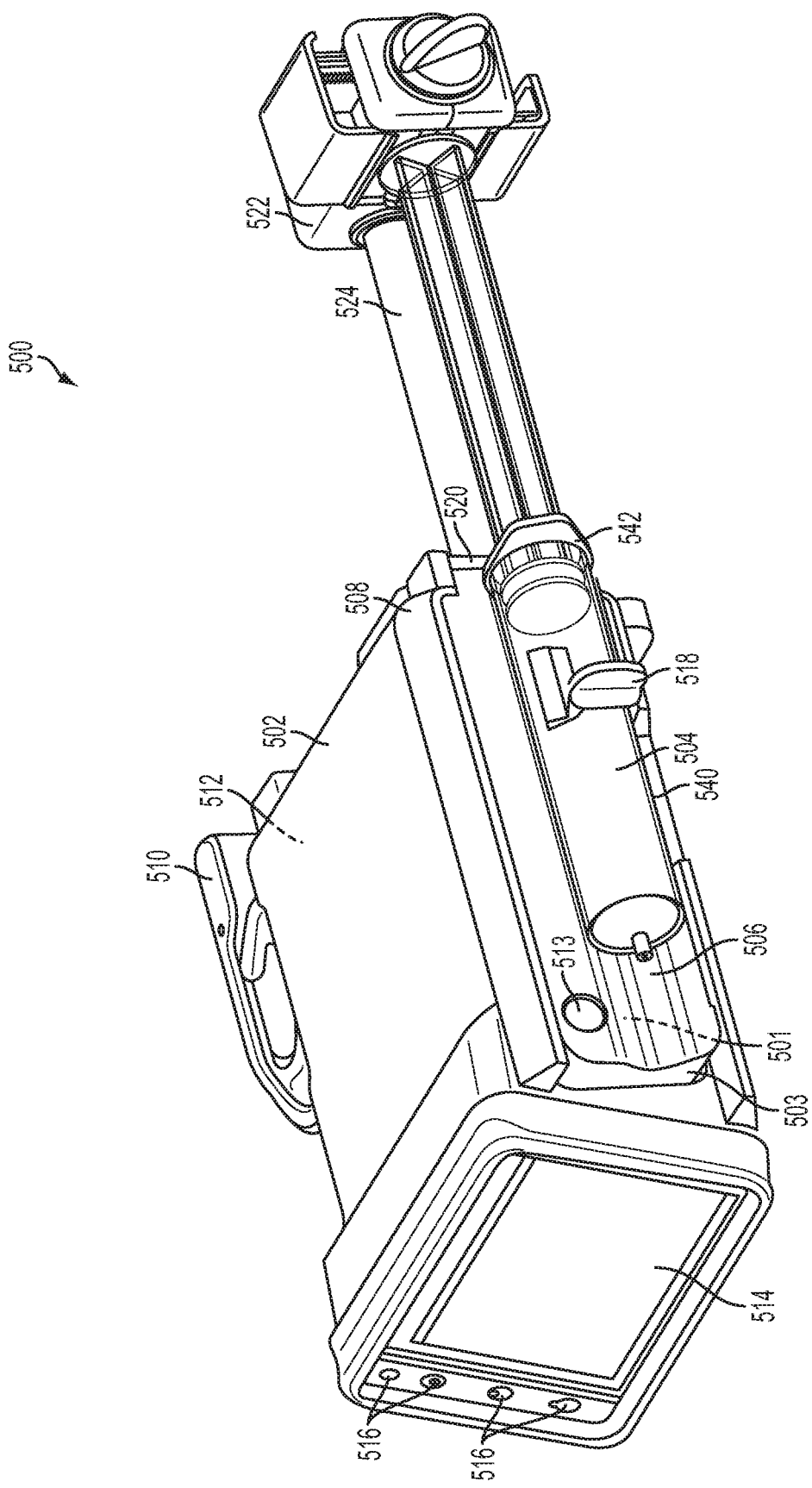
FIG. 28 shows a view of an exemplary embodiment of a syringe pump in accordance with an embodiment of the present disclosure.

In an example embodiment, as shown in FIG. 28, a syringe pump 500 is depicted. The syringe pump 500 may be used to deliver an agent, such as but not limited to, an analgesic, medicament, nutrient, chemotherapeutic agent, etc. to a patient. The syringe pump may be used to precisely delivery a quantity of an agent to a patient or deliver a precise quantity of an agent over a period of time. The syringe pump 500 may be used in any suitable application, such as though not limited to, intravenous deliver, intrathecal delivery, intra-arterial delivery, enteral delivery or feeding, etc.

The syringe pump 500 comprises a housing 502 and a syringe pump assembly 501. In the example embodiment in FIG. 28, the housing 502 is substantially a rectangular box. In alternative embodiments, the housing 502 may take any of a variety of other suitable shapes. The housing 502 may be made of any of a number of materials or combination of materials including, but not limited to, metal or plastic. The housing 502 may be extruded, injection molded, die cast, etc. In some embodiments, the housing 502 may be comprised of a number of separate parts which may be coupled together by any suitable means. In some embodiments, the housing 502 may be taken apart or comprise a removable panel to allow the syringe pump 500 to be easily serviced.

As shown in FIG. 28, a syringe 504 may be seated on the syringe pump assembly 501. The syringe 504 may be a glass, plastic, or any other type of syringe 504. The syringe 504 may be a syringe 504 of any capacity. In some embodiments, including the embodiment in FIG. 28, the syringe 504 may be seated on a syringe seat 506 comprising part of the syringe pump assembly 501. The syringe seat 506 may comprise a contour which allows the syringe 506 to be cradled by the syringe seat 506. The syringe seat 506 may be made of the same material as the rest of the housing 502, a different material, or may be made of several materials. The syringe seat 506 may be coupled to the housing 502 by a mount 508 which may also serve as a spill, splash, drip, fluid, or debris guard.

In some embodiments, the syringe seat 506 may comprise part of the housing 502. In the embodiment shown in FIG. 28, the syringe seat 506 is part of a syringe pump assembly housing 503 of the syringe pump assembly 501. In some embodiments the syringe pump assembly housing 503 may be at least partially formed as an extrusion. In such embodiments, the contours of the syringe seat 506 may be formed during extrusion.

The syringe pump assembly 501 may be inserted into the housing 502 or may be coupled thereto. In the example embodiment in FIG. 28, the syringe pump assembly 501 is mostly disposed inside the housing 502. The syringe seat 506, syringe barrel holder 518, barrel flange clip 520, plunger head assembly 522, and plunger tube 524, each a part of the syringe pump assembly 501, are not disposed inside the housing 502 in the exemplary embodiment shown in FIG. 28. In embodiments where the syringe seat 506 is not part of the housing 502, the mount 508 may comprise a gasket which functions as a seal to keep unwanted foreign material from entering the housing 502 and getting into portions of the syringe pump assembly 501, which are disposed inside the housing 502. In some embodiments, the mount 508 may overhang the syringe seat 506 and may function as a drip edge, splash guard, etc. which will shed liquid off and away from the syringe pump 500

In some embodiments, the syringe pump 500 may be converted into a different device such as, though not limited to, a peristaltic large volume pump. This may be accomplished by removing the syringe pump assembly 501 from the housing 502 and replacing the syringe pump assembly 501 with another desired assembly. Replacement assemblies may include for example, other infusion pumps assemblies such as a peristaltic infusion pump assembly.

In some embodiments, a clamp 510 may be coupled to the housing 502. The clamp 510 may be any type of clamp, for example, a standard pole clamp 510 or a quick release pole clamp 510 (shown). The clamp 510 may be used to keep the syringe pump 500 at a desired location on an object such as an I.V. pole. The clamp 510 may be removably coupled to the housing 502 through a clamp mount 512. In some embodiments, the clamp mount 512 may comprise any of a variety of fasteners such as screws, bolts, adhesive, hook and loop tape, snap fit, friction fit, magnets, etc. In some embodiments, the clamp 510 or a part of the clamp 510 may be formed as an integral part of the housing 502 during manufacture.

As shown in FIG. 28, the housing 502 may also include a display 514. The display 514 may function as a graphic user interface and allow a user to program and monitor pump operation. The display 514 may be an electronic visual display such as a, liquid crystal display, touch screen, L.E.D. display, plasma display, etc. In some embodiments, the display may be complimented by any number of data input means 516. In the example embodiment, the data input means 516 are several user depressible buttons. The buttons may have fixed functions such as "power", "stop", "silence", "emergency stop", "start therapy", or "lock". The lock function may lock all the user inputs to avoid inadvertent commands from being issued to the syringe pump 500, due to a touch screen display 514 being touched, buttons being depressed or touched, or any other inadvertent gesture. The data input means 516 of other embodiments may differ. In embodiments where the display 514 is a touch screen display, the data input means 516 may include a number of physically depressible buttons. The physically depressible button data input means 516 may be a back-up for the touch screen display 514 and may be used in the event that the touch screen display 514 is compromised or becomes otherwise non-functional.

In a non-limiting example embodiment, the data input means 516 may be built into the function of a touch screen display 514. The touch screen display may detect the position of a user's finger or fingers on the screen. The touch screen may be a capacitive touch screen or any other type of touch screen. The software may display virtual buttons, slides, and other controls. The software may also detect the user's touch or the touch of a stylus to control the machine and interact with remote computers that may communicate with the syringe pump 500. The software may also recognize multi-touch gestures which may control: the display, functioning of the syringe pump 500, interaction of the syringe pump 500 with one or more remote computers, etc. In some embodiments, the syringe pump 500 may include sensors that detect user gestures when the user is not in contact with the display. These motion detection sensors may comprise a device that transmits invisible near-infrared light, measuring its "time of flight" after it reflects off objects. Such a measurement may allow the syringe pump 500 to detect the location of objects and the distance from the syringe pump 500 to said objects. The syringe pump 500 may thus be able to monitor and take commands via a user's limbs, hands, and fingers or movements of a user's limbs, hands, and fingers. One example of a motion detector is the PrimeSense 3D sensor made by the company PrimeSense of Israel. In some embodiments, the display 514 and data input means may be mounted onto the housing 502 during manufacture of the syringe pump 500. The display 514 may be removed and replaced during servicing if necessary.

The syringe pump 500 may include a syringe barrel holder 518. The syringe barrel holder 518 may securely hold the syringe barrel 540 against the syringe seat 506. The syringe barrel holder 518 may easily be adjusted by a user to accommodate syringes 504 of various sizes. In some embodiments, the syringe barrel holder 518 may be biased so as to automatically adjust to the diameter of any size syringe 504 after the syringe barrel holder 518 is pulled out by a user. The syringe barrel holder 518 will be further elaborated upon later in the specification.

The syringe pump 500 may also include a barrel flange clip 520. The barrel flange clip 520 in the example embodiment depicted in FIG. 28 is disposed on an end of the syringe pump assembly housing 503 and is capable of holding the syringe barrel flange 542 in place against the end of the syringe pump assembly housing 503. The barrel flange clip 520 is also capable of retaining any of a variety of syringe barrel flange 542 types and sizes which may be available to a user. The barrel flange clip 520 will be further elaborated upon later in the specification. For a more detailed description of the barrel flange clip 520, see FIG. 61 and FIG. 62.

The syringe pump 500 may additionally include a plunger head assembly 522. The plunger head assembly 522 may be attached to the syringe pump assembly 501 by a plunger tube 524. In the example embodiment depicted in FIG. 28, the plunger head assembly 522 and plunger tube 524 extend out of the housing 502 toward the right of the page.

The syringe pump 500 may also comprise a downstream pressure sensor 513 as shown in FIG. 28. The downstream pressure sensor 513 may comprise part of the syringe pump assembly 501 or the housing 502. The downstream pressure sensor 513 may take pressure measurements from a fluid line i.e. tubing extending from the syringe 504 to a patient. In some embodiments, the fluid line may include a span of tubing which is different from the rest of the tubing. For example, a span of the fluid line may be made of a deformable PVC material. Such embodiments may make fluid line pressures easier to determine.

The downstream pressure sensor 513 may comprise a cradle with a pressure sensor, such as a force sensor. In such embodiments, the fluid line may be held against the cradle and pressure sensor of the downstream pressure sensor 513 by a non-deformable or deflectable structure. The downstream pressure sensor 513 may cause the syringe pump 500 to alarm if the detected pressure falls outside of an acceptable range. The measurement of the downstream pressure sensor 513 may be referenced against a look-up table to determine the pressure in the fluid line. If an abnormal pressure reading (e.g. a high pressure generated during an occlusion event beyond a predetermined threshold) is taken, a control system of the syringe pump 500 may stop delivering fluid. In some embodiments, the syringe pump 500 may be caused to back up and relieve some of the pressure in response to the detection of pressures suggestive of an occlusion.

Figure 29:
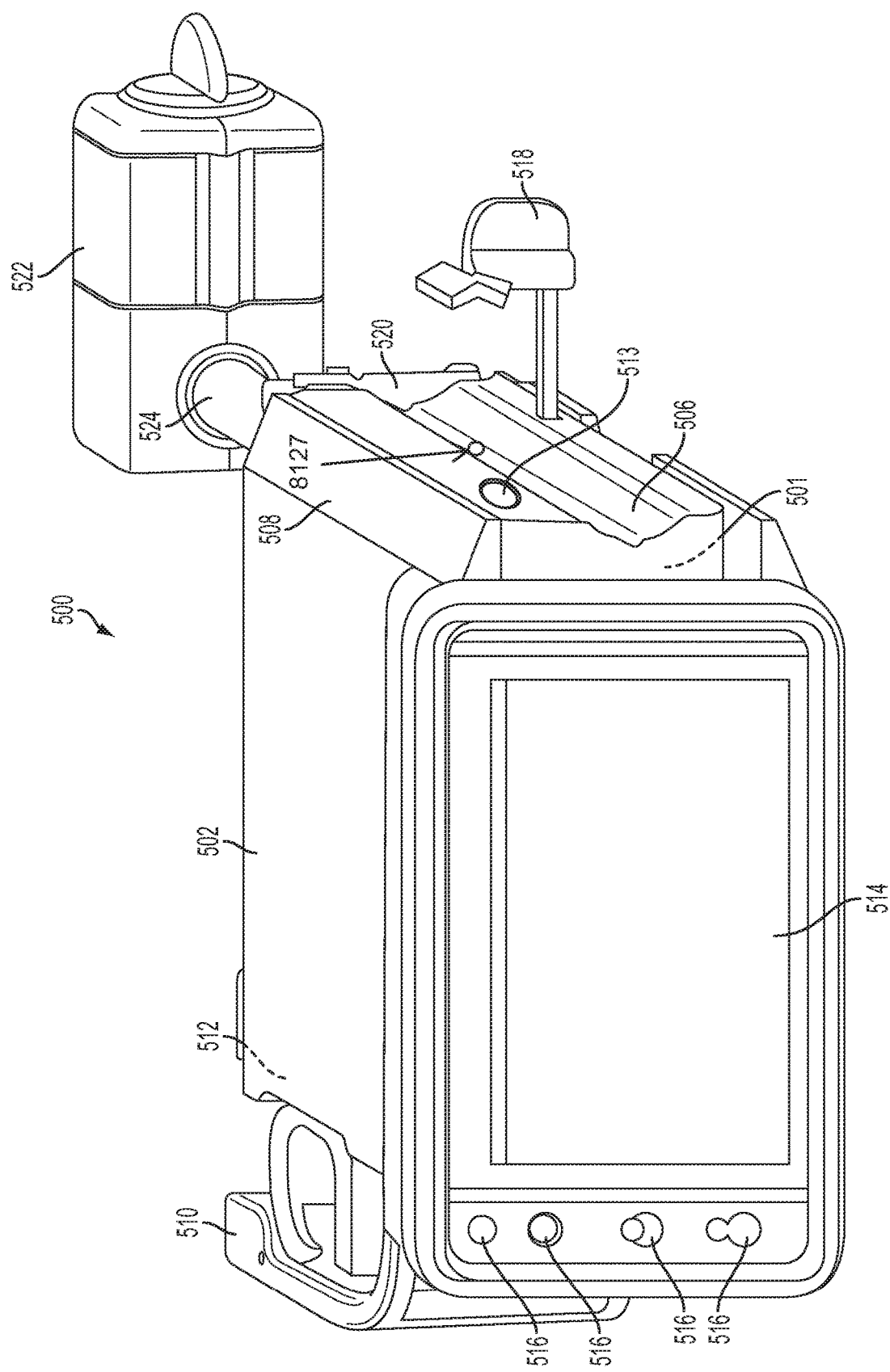
FIG. 29 shows a front view of an exemplary embodiment of a syringe pump in accordance with an embodiment of the present disclosure.

FIG. 29 shows the syringe pump 500 from another perspective. In this view, the display 514 and data input means 516 coupled to the housing 502 face the front of the page. The clamp 510 is coupled to the housing 502 by a clamp mount 512. The syringe pump assembly 501 is disposed mostly inside the housing 502. The syringe seat 506, which comprises part of the syringe pump assembly 501, forms a substantial part of one side of the housing 502. The mount 508 retains the syringe pump assembly 501 and helps seal the interior of the housing 502 from exposure to debris. In embodiments where the mount 508 functions as a drip edge the mount 508 may cover the syringe pump assembly 501 and help shed liquid away from the interior of the housing 502. The syringe barrel clamp 518 extends through the syringe seat 506. In the depicted position in FIG. 29, the syringe barrel clamp 518 has been pulled away from its resting position and is biased such that it may automatically retract back toward the housing 502. In some embodiments, the syringe barrel clamp 518 may be locked in a non-resting position, such as the position depicted in FIG. 31. The barrel flange clip 520 is visible and disposed on the end of the syringe pump assembly housing 503 closest to the plunger head assembly 522. The plunger tube 524 connects the plunger head assembly 522 to the rest of the syringe pump assembly 501 as described above. The downstream pressure sensor 513 is disposed on the syringe seat 506.

In some specific embodiments, a camera 8127 is positioned to view the syringe. The camera 8127 may be coupled to the RTP 3500 and/or to the processor 3600 of FIG. 59J to provide image data thereto. The camera 8127 may include a CCD image sensor, a CMOS image sensor, or any other type of imaging sensor. In some embodiment of the present disclosure, the camera 8127 includes an array of image sensors.

An image of the syringe loaded into the syringe seat 506 may be displayed on the display 514 as seen from the camera 8127. The processors 3500 and/or 3600 may use the images from the camera 8127 to: read QR codes on the syringe to identify the syringe, detect particulates or bubbles in the syringe, measure the location of the plunger to measure the volume delivered and thus the volume remaining, determine when the syringe state has changed, determine if the syringe is present, estimate bolus discharges, check the color of the fluid to determine if it is the correct fluid, and/or determine if syringe is missing or an improperly loaded.

By using frame differencing to detect motion and a Gaussian filter to help reduce camera's 8127 shot noise (which looks like an impurity, but smaller), the moving impurities can be detected. To locate the syringe's plunger, the fiducials on the syringe may be used, template matching (the plunger being the template) may use pattern recognition to locate the fiducials and thus the plunger.

FIGS. 30-34 illustrate how a user may place a syringe 504 into the syringe pump assembly 501. The syringe pump assembly 501 is shown by itself in FIG. 30. The syringe 504 is not seated against the syringe seat 506. As shown, the plunger head assembly 522 comprises two jaws, an upper plunger clamp jaw 526 and a lower plunger clamp jaw 528. The upper plunger clamp jaw 526 and lower plunger clamp jaw 528 are in the open position. The upper plunger clamp jaw 526 and lower plunger clamp jaw 528 are capable of clamping and retaining the plunger flange 548 on the plunger 544 of the syringe 504. The upper plunger clamp jaw 526 and lower plunger clamp jaw 528 may be actuated to open or closed positions via rotation of a dial 530 comprising part of the plunger head assembly 522. The plunger head assembly 522 may also comprise a plunger pressure sensor 532.

Figure 30:
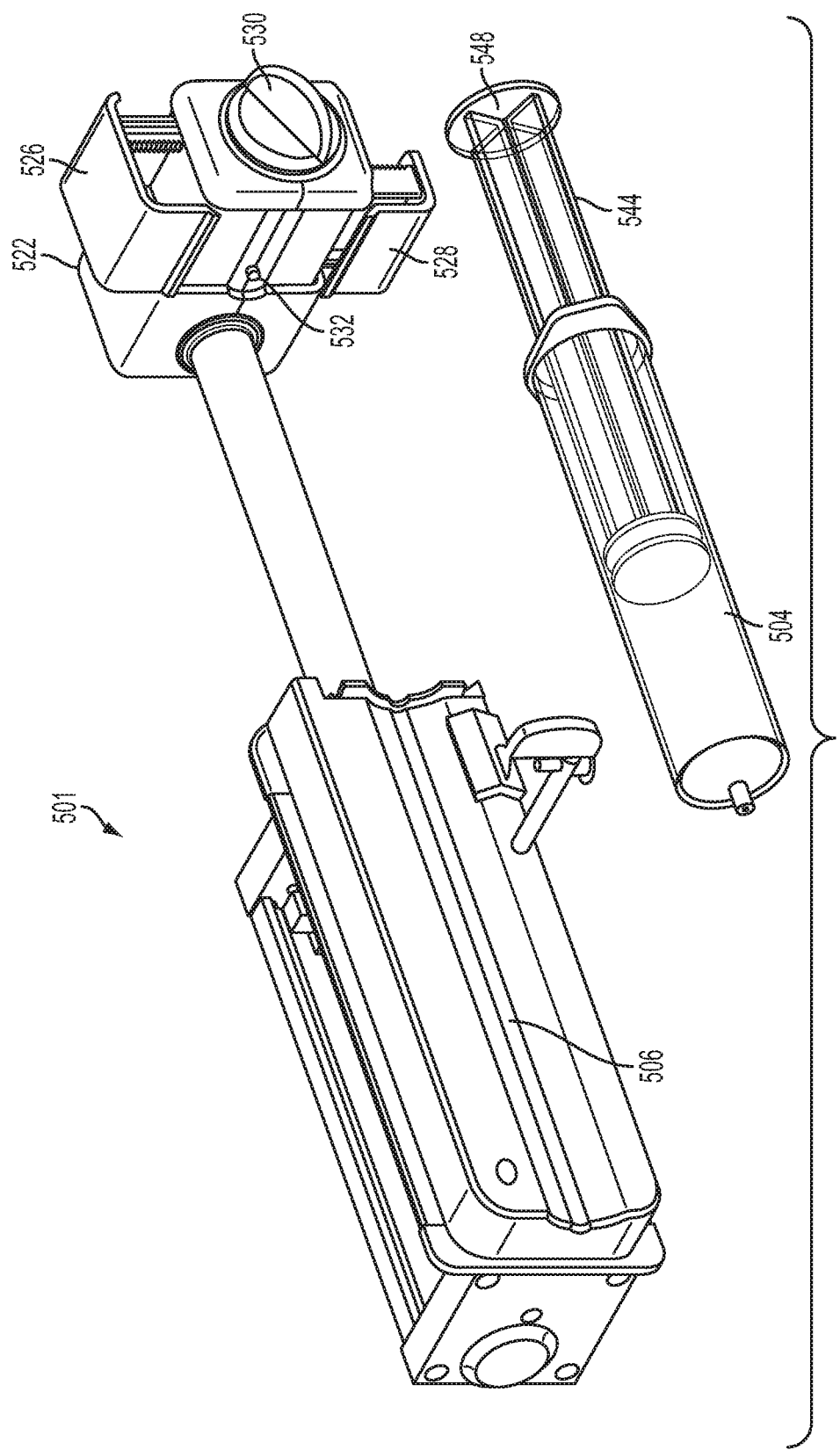
FIG. 30 is a view of an exemplary embodiment of the syringe pump assembly in accordance with an embodiment of the present disclosure.
Figure 31:
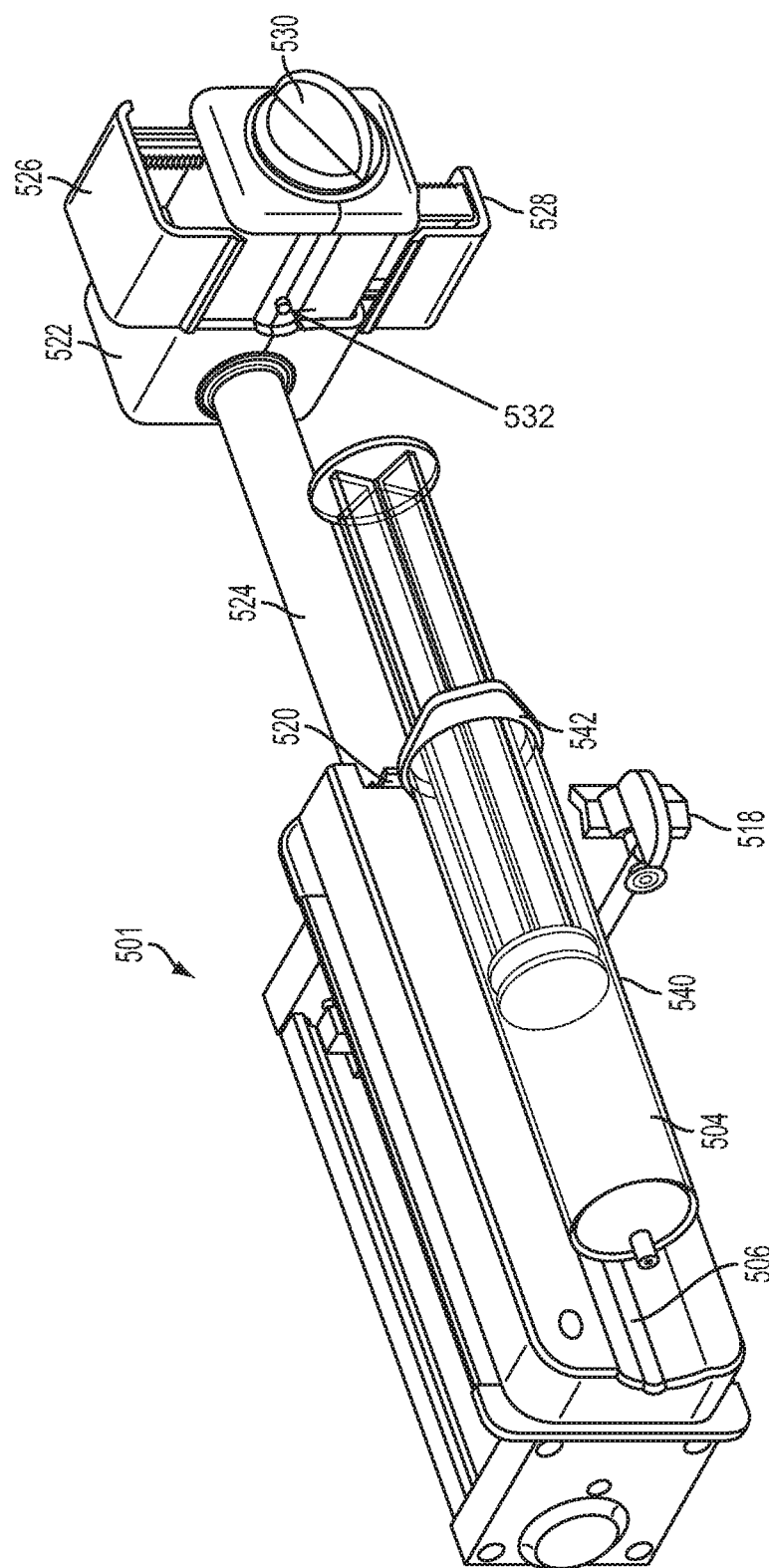
FIG. 31 is another view of an exemplary embodiment of the syringe pump assembly in accordance with an embodiment of the present disclosure.

In FIG. 31, the syringe pump assembly 501 is again shown by itself. The syringe 504 which had not been seated on the syringe seat 506 in FIG. 30 is seated in place on the syringe seat 506 in FIG. 31. The syringe barrel flange 542 is clipped in place by the barrel flange clip 520. The syringe barrel holder 518, has been pulled out so the syringe 504 may be placed into the syringe pump assembly 501, but has not yet been allowed to automatically adjust to the diameter of the syringe barrel 540. In the example embodiment shown in FIG. 31, the syringe barrel holder 518 has been rotated 90° clockwise from its orientation in FIG. 30 to lock it in position. Alternate embodiments may require counter-clockwise rotation, a different degree of rotation, or may not require rotation to lock the syringe barrel holder 518 in position. The plunger tube 524 and attached plunger head assembly 522 are fully extended away from the rest of the syringe pump assembly 501. Since the dial 530 has not been rotated from the orientation shown in FIG. 30, the upper plunger clamp jaw 526 and the lower plunger clamp jaw 528 are still in the open position.

Figure 32:
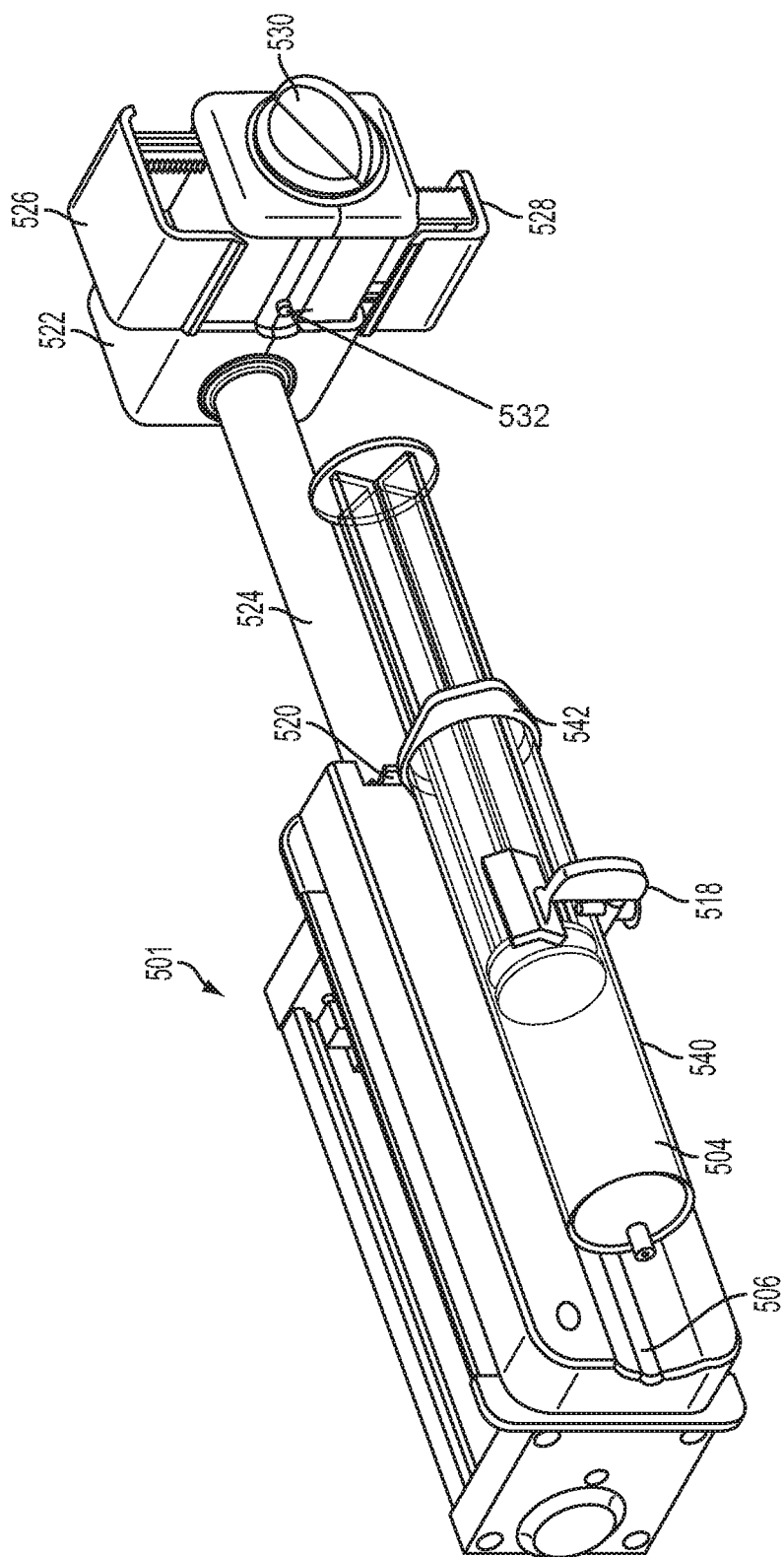
FIG. 32 is another view of an exemplary embodiment of the syringe pump assembly in accordance with an embodiment of the present disclosure.

In FIG. 32, the syringe pump assembly 501 is again shown by itself. The syringe 504 is seated against the syringe seat 506. The syringe barrel holder 518 has been rotated out of the locked position and has been allowed to automatically adjust to the diameter of the syringe barrel 540. The syringe barrel holder 518 is holding the syringe 504 in place on the syringe pump assembly 501. The syringe 504 is additionally held in place on the syringe pump assembly 501 by the barrel flange clip 520 which retains the syringe barrel flange 542. The plunger tube 524 and attached plunger head assembly 522 are fully extended away from the rest of the syringe pump assembly 501. Since the dial 530 has not been rotated from the orientation shown in FIG. 30, the upper plunger clamp jaw 526 and the lower plunger clamp jaw 528 are still in the open position.

Figure 33:
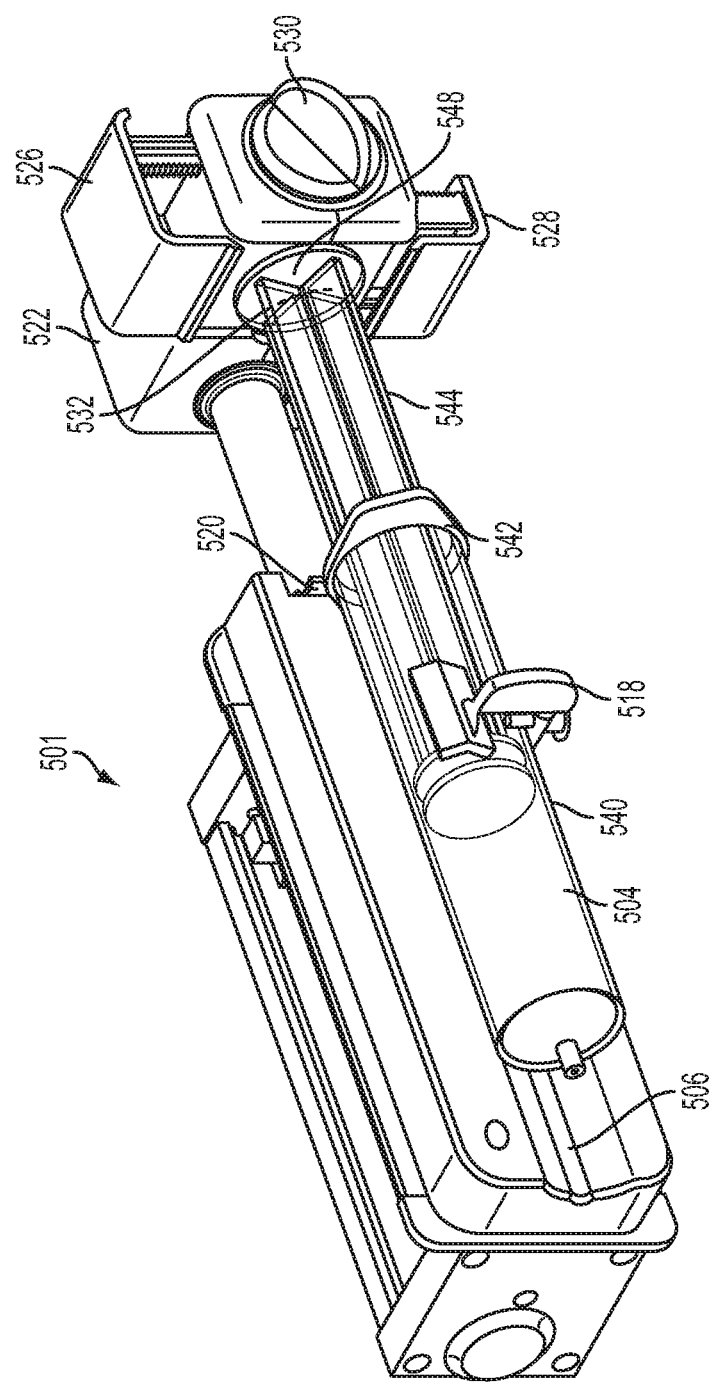
FIG. 33 is another view of an exemplary embodiment of the syringe pump assembly in accordance with an embodiment of the present disclosure.

In FIG. 33, the syringe pump assembly 501 is again shown by itself. The syringe 504 is seated against the syringe seat 506. The syringe barrel holder 518 is pressing against the syringe barrel 540 and holding the syringe 504 in place on the syringe pump assembly 501. The barrel flange clip 520 is holding the syringe barrel flange 542 and helping to the hold the syringe 504 in place on the syringe pump assembly 501. The amount that the plunger tube 524 extends away from the rest of the syringe pump assembly 501 has been adjusted such that the plunger head assembly 522 is in contact with the plunger flange 548 on the syringe plunger 544. Since the dial 530 has not been rotated from the orientation shown in FIG. 30, the upper plunger clamp jaw 526 and the lower plunger clamp jaw 528 are still in the open position. The plunger flange 548 is in contact with the plunger pressure sensor 532.

Figure 34:
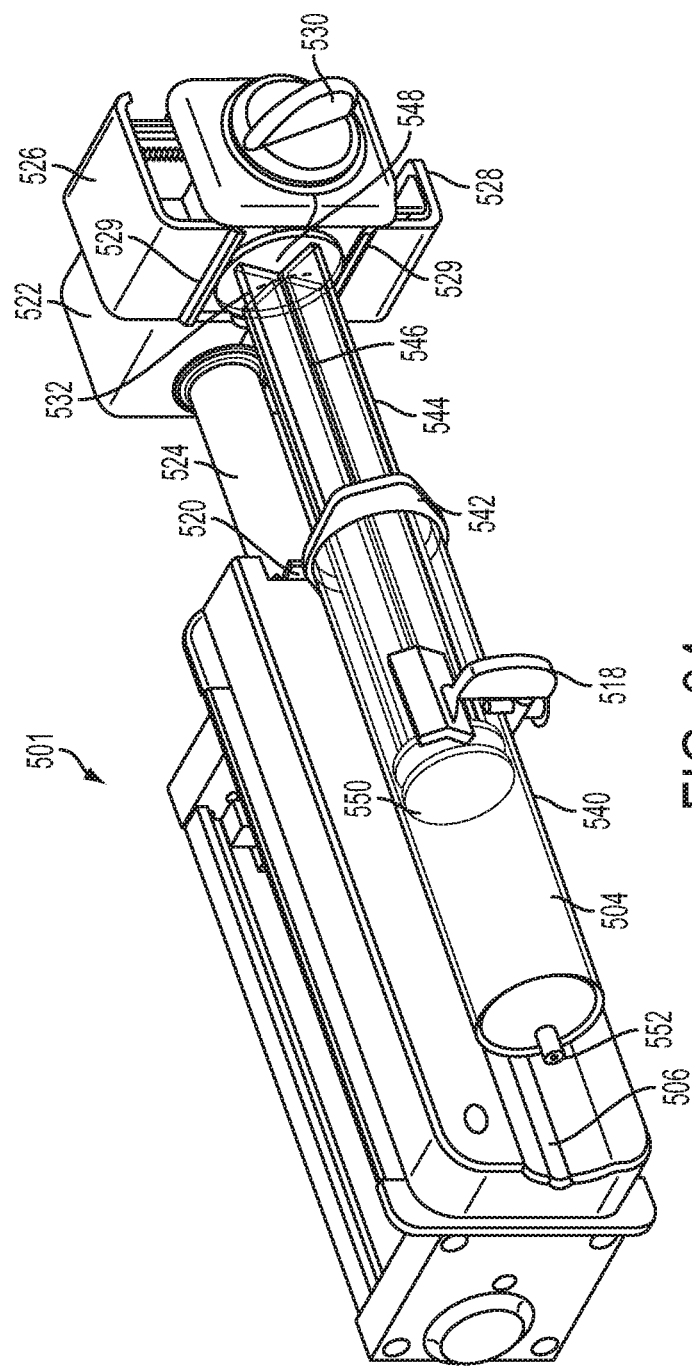
FIG. 34 is another view of an exemplary embodiment of the syringe pump assembly in accordance with an embodiment of the present disclosure.

In FIG. 34 the syringe pump assembly 501 is again shown by itself. The syringe 504 is seated against the syringe seat 506. The syringe barrel holder 518 is pressing against the syringe barrel 540 and holding the syringe 504 in place on the syringe pump assembly 501. The barrel flange clip 520 is clipping the syringe barrel flange 542 and helping to the hold the syringe 504 in place on the syringe pump assembly 501. The amount that the plunger tube 524 extends away from the rest of the syringe pump assembly 501 has been adjusted such that the plunger head assembly 522 is in contact with the plunger flange 548 on the syringe plunger 544. The dial 530 has been rotated from the orientation depicted in FIGS. 30-33. Consequentially, the upper plunger clamp jaw 526 and lower plunger clamp jaw 528 have moved to a closed position in which the plunger flange 548 of the syringe plunger 544 is retained by the plunger head assembly 522. Since the upper plunger clamp jaw 526 and lower plunger clamp jaw 528 close about the horizontal centerline of the plunger head assembly 522, the plunger flange 548 has been centered on the plunger head assembly 522.

In the preferred embodiment, the upper plunger clamp jaw 526 and lower plunger clamp jaw 528 each comprise a fin 529 as illustrated in FIG. 34. The fins 529 bow out away from the plunger head assembly 522 and toward the left of the page (relative to FIG. 34). The fins 529 are disposed about the upper plunger clamp jaw 526 and lower plunger clamp jaw 528 such that the fins 529 are the only part of the upper plunger clamp jaw 526 and lower plunger clamp jaw 528 to contact a plunger flange 548 when a syringe 504 is placed on the syringe pump assembly 501. As the upper plunger clamp jaw 526 and lower plunger clamp jaw 528 are closed down on a plunger flange 548 the thickness and diameter of the plunger flange 548 determine when the upper plunger clamp jaw 526 and lower plunger clamp jaw 528 stop moving. At least some part of the fins 529 will overhang the plunger flange 548 and ensure the plunger flange 548 is retained. Since the upper plunger clamp jaw 526 and lower plunger clamp jaw 528 do not deflect, this forces the plunger flange 548 against the rest of the plunger head assembly 522. That is, the angle of contact of the upper plunger clamp jaw 526 and lower plunger clamp jaw 528 on the plunger flange 548 results in a force with a component that pushes the plunger flange 548 against the plunger head assembly 522. This resultant force additionally has a component which centers the plunger flange 548 on the plunger head assembly 522. This is especially desirable because such an arrangement does not allow for any "play" of the plunger flange 548 between upper plunger clamp jaw 526 and lower plunger clamp jaw 528 and the rest of the plunger head assembly 522. Additionally, such an arrangement is desirable because it not only securely holds the plunger flange 548 in place against the plunger head assembly 522, but also doubles as an anti-siphon mechanism. Such an arrangement furthermore, ensures that the plunger flange 548 consistently contacts the plunger pressure sensor 532. Any force component generated by the upper plunger clamp jaw 526 and lower plunger clamp jaw 528 which may affect readings of the plunger pressure sensor 532 may be predictable and subtracted out or otherwise compensated for.

In other embodiments, the upper plunger clamp jaw 526 and lower plunger clamp jaw 528 may not comprise fins 529. Instead the upper plunger clamp jaw 526 and lower plunger clamp jaw 528 overhang a portion of the plunger flange 548 when in the clamped position. The upper plunger clamp jaw 526 and lower plunger clamp jaw 528 may stop moving when they abut the cruciform which comprises the plunger stem 546. In other embodiments, the upper plunger clamp jaw 526 and lower plunger clamp jaw 528 may clamp a plunger stem 546 that need not be a cruciform. In another embodiment, the upper plunger clamp jaw 526 and lower plunger clamp jaw 528 may include a wedge, ramp, or tapered rib feature on the surfaces of the jaws that faces the pump head assembly 522. The wedge, ramp or tapered rib serve to push the plunger flange 548 toward the pump head assembly 522 until the plunger flange 548 is securely held against the pump head assembly 522.

To dispense the contents of the syringe 504, the syringe pump 500 may actuate the plunger head assembly 522 to thereby push the plunger 544 into the syringe barrel 540. Since the contents of the syringe 504 may not flow through or past the plunger pusher 550, the contents of the syringe 504 are forced out of the syringe outlet 552 as the plunger 544 is advanced into the syringe barrel 540. Any pressure generated as the plunger 544 advances into the syringe barrel 540 is transmitted to the plunger pressure sensor 532. The plunger pressure sensor 532, may, in some embodiments, comprise a force sensor such as a strain beam. When an occlusion occurs, fluid within the syringe barrel 540 and/or the fluid lines prevents movement of the plunger 544. When the plunger head assembly 522 continues to advance, high forces are produced between the plunger 544 and the plunger head assembly 522. The pressure transmitted to the plunger pressure sensor 532 may have a programmed acceptable range so that possible occlusions may be identified. If the pressure applied to the plunger pressure sensor 532 exceeds a predetermined threshold, the syringe pump 500 may alarm or issue an alert.

FIG. 35 shows the plunger head assembly 522 with the upper plunger clamp jaw 526 and lower plunger clamp jaw 528 in the fully closed position. The dial 530 is oriented such that the raised part of the dial 530 is on a plane substantially parallel to the top and bottom faces of the plunger head assembly 522. The plunger tube 524 is shown extending from the plunger head assembly 522 to the sliding block assembly 800. One end of a flex connector 562 is attached to the sliding block assembly 800. A position indicator mark has been placed on the dial 530 for illustrative purposes in FIG. 35 and FIG. 36.

The view shown in FIG. 36 is similar to the view shown in FIG. 35. In FIG. 36, the dial 530 on the plunger head assembly 522 has been rotated approximately 135° clockwise. This rotation has in turn caused the upper plunger clamp jaw 526 and lower plunger clamp jaw 528 to separate and move to the fully open position. In alternate embodiments, the dial 530 may require more or less rotation than the approximately 135° shown in the example embodiment to transition the upper plunger clamp jaw 526 and lower plunger clamp jaw 528 from a fully open position to a fully closed position. The plunger head assembly may be capable of holding itself in this position (described later in the specification).

Figure 37:
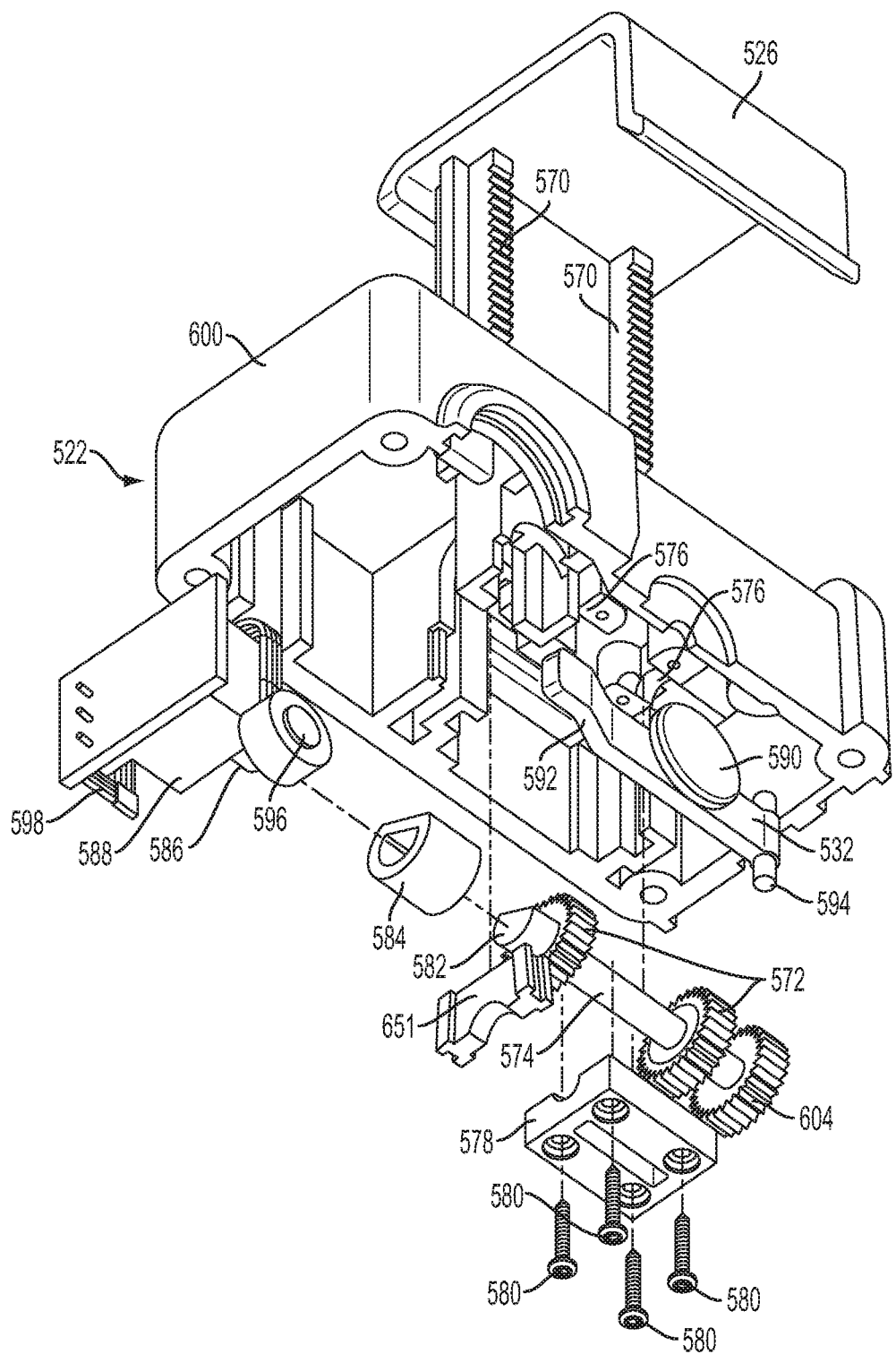
FIG. 37 is an exploded view of an exemplary embodiment of the top of the plunger head assembly with half of the plunger head assembly removed in accordance with an embodiment of the present disclosure.

An exploded view of the top half of the plunger head assembly 522 is shown in FIG. 37. As shown, the upper plunger clamp jaw 526 comprises two racks 570. In other embodiments, there may only be one rack 570. In some embodiments, there may be more than two racks 570. When the plunger head assembly 522 is fully assembled, the racks 570 may interdigitate with a corresponding number of upper jaw pinion gears 572. The upper jaw pinion gears 572 spin about the axis of an upper jaw drive shaft 574. The upper jaw drive shaft 574 may also comprise an upper jaw drive gear 604 which will be elaborated upon later.

The plunger head assembly 522 may comprise a number of bearing surfaces for the upper jaw drive shaft 574. In the example embodiment in FIG. 37, the plunger head assembly 522 comprises two upper bearing surfaces 576 and a lower bearing surface 578 for the upper jaw drive shaft 574. The upper bearing surfaces 576 may be coupled into the plunger head assembly housing top 600. The upper bearing surfaces 576 may be coupled to the plunger head assembly housing top 600 by any of a variety of means including, but not limited to, screws bolts, adhesive, snap fit, friction fit, welds, a tongue in groove arrangement, pins, or may be formed as a continuous part of the plunger head assembly housing top 600 (shown). The upper bearing surfaces 576 provide a bearing surface for at least a span of the top half of the upper jaw drive shaft 574.

The lower bearing surface 578 is coupled into the plunger head assembly housing top 600. The lower bearing surface 578 may be coupled to the plunger head assembly housing top 600 by any suitable means such as, but not limited to, screws 580 (shown), bolts, adhesive, snap fit, friction fit, magnets, welds, a tongue in groove arrangement, etc. In some embodiments, the lower bearing surface 578 may be formed as a continuous part of the plunger head assembly housing top 600. The lower bearing surface 578 provides a bearing surface for at least a span of the bottom half of the upper jaw drive shaft 574.

In some embodiments, there may also be an upper dial shaft bearing surface 651 which couples into the plunger head assembly housing top 600. The upper dial shaft bearing surface 651 may be coupled into the plunger head assembly housing top 600 by any of a variety of means including, but not limited to, screws, bolts, adhesive, snap fit, friction fit, welds, a tongue in groove arrangement (shown), pins, or may be formed as a continuous part of the plunger head assembly housing top 600. The upper dial shaft bearing surface 651 will be further elaborated upon later.

The upper jaw drive shaft 574 may also comprise a D-shaped span 582. The D-shaped span 582 may be located on an end of the upper jaw drive shaft 574 as shown in the example embodiment in FIG. 37. The D-shaped span 582 of the upper jaw drive shaft 574 may couple into a complimentary shaped orifice in one side of a D-shaped connector 584. The D-shaped span 582 of the upper jaw drive shaft 574 may not extend all the way through the D-shaped connector 584. In some embodiments, the orifice may run through the entire D-shaped connector 584. The other side of the D-shaped connector 584 may couple onto a D-shaped shaft 586 projecting out of a plunger clamp jaws position sensor 588. Any rotation of the upper jaw drive shaft 574 may cause the D-shaped connector 584 to rotate as well. In turn, this may cause rotation of the D-shaped shaft 586 projecting from the plunger clamp jaws position sensor 588. In some embodiments, the D-shaped span 582 of the upper jaw drive shaft 574 may extend directly into the plunger clamp jaws position sensor 588. In such embodiments, the D-shaped connector 584 and D-shaped shaft 586 may not be needed. In some embodiments, the D-shaped span 582, the D-shaped connector 584, and D-shaped shaft 586 need not be D-shaped. In some embodiments they may be have a triangular shape, square shape, star shape, etc.

In some embodiments, the plunger clamp jaws position sensor 588 may comprise a potentiometer. As the D-shaped shaft 586 projecting from the plunger clamp jaws position sensor 588 rotates, the wiper of the potentiometer is slid across the resistive element of the potentiometer thus varying the resistance measured by the potentiometer. The resistance value may then be interpreted to indicate the position of the upper plunger clamp jaw 526 and lower plunger clamp jaw 528. Alternatively, the plunger clamp jaws position sensor 588 may comprise a magnet on the end of the upper jaw drive shaft 574 and a rotary encoder such as the AS5030ATSU by Austrianmicrosytems of Austria. Alternatively, the position of the upper jaw 526 and or lower jaw 528 can be measured with a linear encoder or a linear potentiometer.

By obtaining a position from the plunger clamp jaws position sensor 588, the syringe pump 500 may be able to determine a number of things. The position may be used to indicate whether a plunger flange 548 has been clamped by the plunger head assembly 522. The position may indicate whether a plunger flange has been correctly clamped by the plunger head assembly 522. This may be accomplished by referencing the determined position against a position or a range of positions which may be acceptable for a specific syringe 504. The information about the specific syringe 504 being used may be input by a user or may be gathered by one or more other sensors comprising other parts of the syringe pump 500.

Since the position measured by the plunger clamp jaws position sensor 588 depends on the diameter and thickness of a clamped plunger flange 548, the positional information may also be used to determine information about the specific syringe 504 being used (for example, its type, brand, volume, etc.). This may be accomplished by referencing the measured position against a database of positions which would be expected for different syringes 504. In embodiments where there are a number of sensors gathering information about the syringe 504, the positional information generated by the plunger clamp jaws position sensor 588 may be checked against data from other sensors to make a more informed decision on which specific syringe 504 is being utilized. If the position measured by the plunger clamp jaws position sensor 588 does not correlate with data gathered by other sensors, the syringe pump 500 may alarm.

As shown in FIG. 37, the plunger head assembly housing top 600 may also house the plunger pressure sensor 532 mentioned earlier. The plunger pressure sensor 532 may comprise a plunger pressure sensor push plate 590. The plunger pressure sensor push plate 590 may be a nub, a disc, or any other suitable shape. The plunger pressure sensor push plate 590 may be flat or rounded. The plunger pressure sensor push plate 590 may extend out of the plunger head assembly 522 such that it may physically contact a plunger flange 548 clamped against the plunger head assembly 522. The plunger pressure sensor push plate 590 may directly transmit any force applied to it to a plunger pressure sensor input surface 596. In some embodiments, the plunger pressure sensor push plate 590 may be attached to a plunger pressure sensor lever 592. The plunger pressure sensor lever 592 may be pivotally coupled to a plunger pressure sensor pivot 594. The plunger pressure sensor pivot 594 may be disposed at any point along the length of the plunger pressure sensor lever 594. In the example embodiment in FIG. 37, any force applied to the plunger pressure sensor push plate 590 is transmitted through the plunger pressure sensor lever 592 to the plunger pressure sensor input surface 596. In some specific embodiments, the plunger pressure sensor lever 592 and plunger pressure sensor pivot 594 may serve to constrain the motion of the plunger pressure plate 590 to a plane perpendicular to the plunger flange 548 and minimize resistance to free movement of the plunger pressure plate 590. Although the location of the plunger pressure sensor pivot 594 in relation to the plunger pressure sensor push plate 590 does not multiply the force exerted against the plunger pressure sensor input surface 596 in FIG. 37, other embodiments may use different arrangements to create a mechanical advantage.

The force measurement which is read via the plunger pressure sensor 532 may be interpreted to determine the hydraulic pressure of the fluid being dispensed. This may contribute to safety of operation because the sensed fluid pressure may be useful in identifying possible occlusions so that they may be corrected. The pressure may be monitored such that if the pressure exceeds a predefined value, the syringe pump 500 may alarm. The pressure measurement from the plunger pressure sensor 532 may be checked against the pressure measurement from the downstream pressure sensor 513 (see FIG. 28) in embodiments including both a plunger pressure sensor 532 and a downstream pressure sensor 513. This may help to ensure greater accuracy. If the pressure measurements do not correlate, an alarm may be generated. Additionally, since the sensors are redundant, if one of the plunger pressure sensor 532 or downstream pressure sensor 513 fails during a therapy, the syringe pump 500 may function on only one of the sensors in a fail operative mode.

As shown in FIG. 37, a number of electrical conduits 598 run to and from the both the plunger pressure sensor 532 and the plunger clamp jaws position sensor 588. The conduits 598 provide power to the plunger pressure sensor 532 and plunger clamp jaws position sensor 588. The electrical conduits 598 also comprise the data communication pathways to and from the plunger pressure sensor 532 and the plunger clamp jaws position sensor 588.

Figure 38:
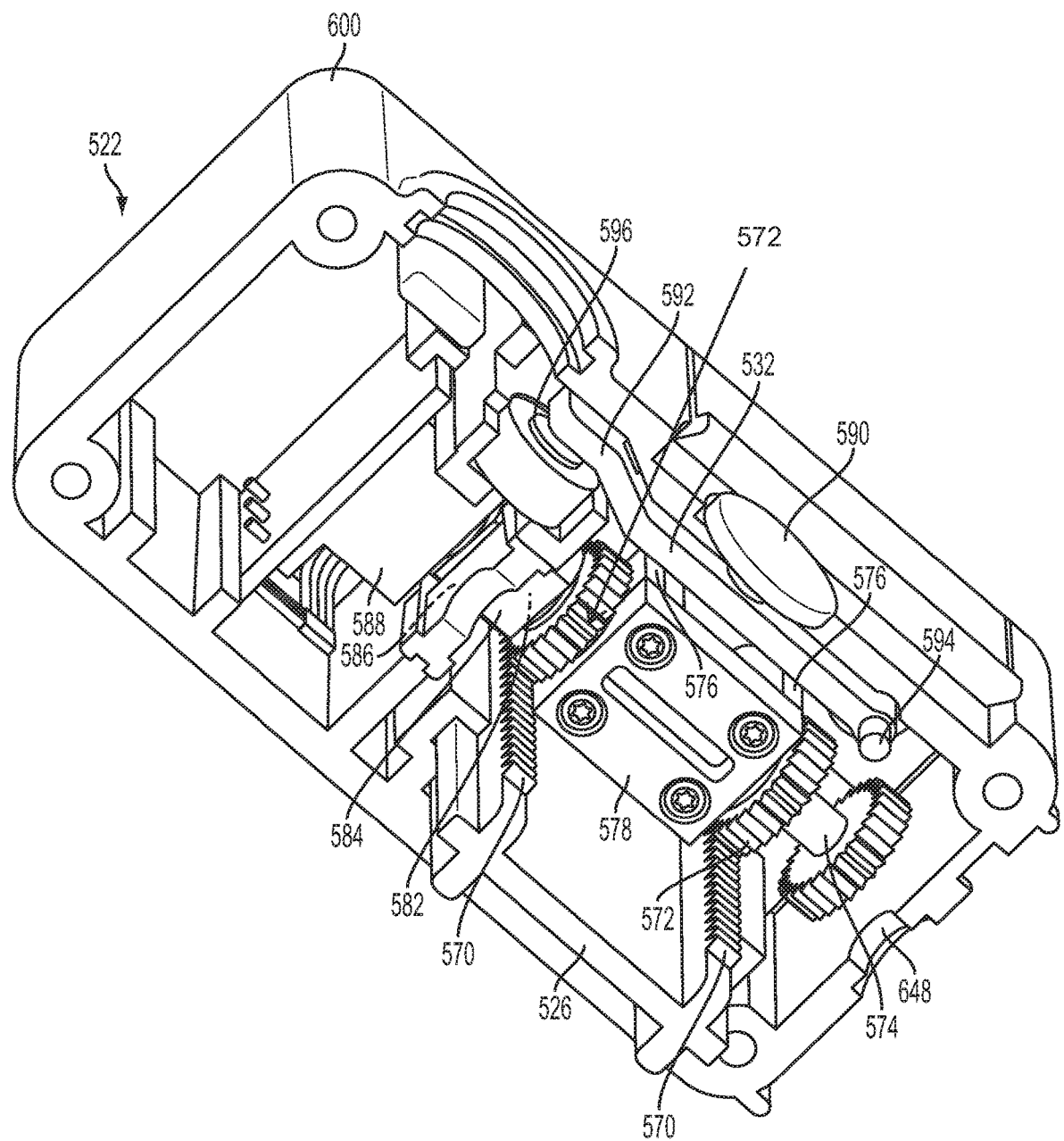
FIG. 38 is an assembled view of an exemplary embodiment of the top of the plunger head assembly with half of the plunger head assembly removed in accordance with an embodiment of the present disclosure.

FIG. 38 shows an assembled view of the top half of the plunger head assembly 522. In FIG. 38, the upper plunger clamp jaw 526 is in a closed position. The two racks 570 on the upper plunger clamp jaw 526 are engaged with the two pinion gears 572 on the upper jaw drive shaft 574 such that any rotation of the upper jaw drive shaft 574 translates into linear displacement of the upper plunger clamp jaw 526. The upper jaw drive shaft 574 is surrounded by the upper bearing surfaces 576 and the lower bearing surface 578.

The D-shaped span 582 of the upper jaw drive shaft 574 and the D-shaped shaft 586 of the plunger clamp jaws position sensor 588 are coupled together by the D-shaped connector 584. Any rotation of the upper jaw drive shaft 574 will cause rotation of the D-shaped span 582, D-shaped connector 584, and D-shaped shaft 586. As mentioned above this rotation may cause the wiper to slide across the resistive element of the plunger clamp jaws position sensor 588 in embodiments where the plunger clamp jaws position sensor 588 comprises a potentiometer.

The plunger pressure sensor 532 is also shown in FIG. 38. The plunger pressure sensor push plate 590 may extend out of the plunger head assembly 522 such that it may physically contact a plunger flange 548 (see FIG. 30) clamped against the plunger head assembly 522. The plunger pressure sensor push plate 590 may directly transmit any force applied to it to a plunger pressure sensor input surface 596. In some embodiments, including the one shown in FIG. 38, the plunger pressure sensor push plate 590 may be attached to a plunger pressure sensor lever 592. The plunger pressure sensor lever 592 may be pivotally coupled to a plunger pressure sensor pivot 594. The plunger pressure sensor pivot 594 may be disposed at any point along the length of the plunger pressure sensor lever 592. In the example embodiment in FIG. 38, any force applied to the plunger pressure sensor push plate 590 is transmitted through the plunger pressure sensor lever 592 to the plunger pressure sensor input surface 596. Although the location of the plunger pressure sensor pivot 594 in relation to the plunger pressure sensor push plate 590 does not multiply the force exerted against the plunger pressure sensor input surface 596 in FIG. 38, other embodiments may use different arrangements to create a mechanical advantage.

The plunger head assembly housing top 600 also includes the top half of a dial shaft passage 648 for a dial shaft 650 (not shown) which will be explained later in the specification. In the example embodiment shown in FIG. 38, the dial shaft passage 648 passes through the right face of the plunger head assembly housing top 600.

Figure 39:
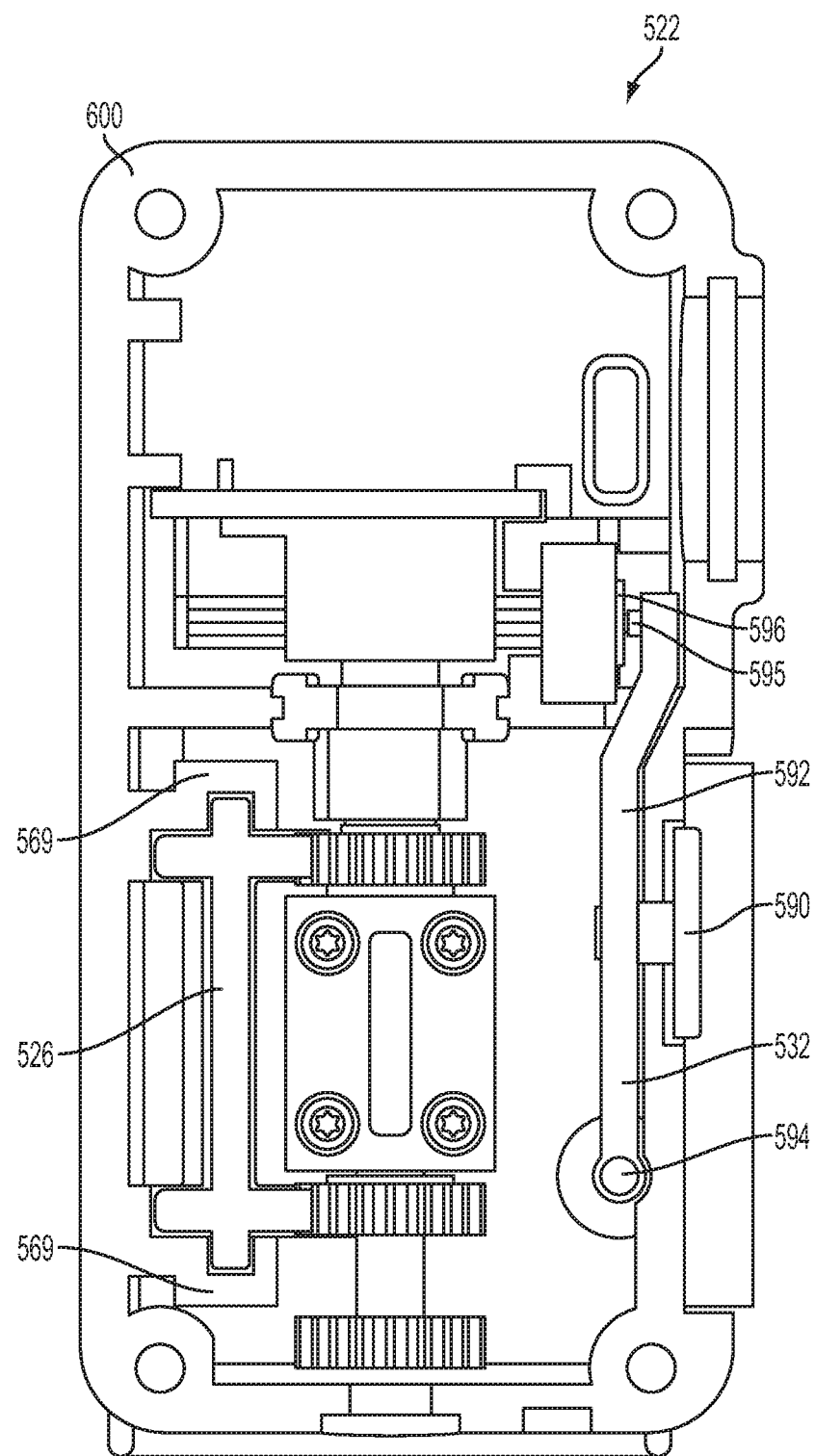
FIG. 39 is a bottom view of an exemplary embodiment of the top of the plunger head assembly in accordance with an embodiment of the present disclosure.

FIG. 39 shows another assembled view of the top half of the plunger head assembly 522. As shown in FIG. 39 the plunger head assembly housing top 600 may comprise upper jaw guides 569. The upper jaw guides 569 are sized and disposed such that they form a track-way in which the upper plunger clamp jaw 526 may move along. In the example embodiment, the upper jaw guides 569 are formed as a continuous part of the plunger head assembly housing top 600 and span the entire height of the side wall of the plunger head assembly housing top 600. In other embodiments, the upper jaw guides 569 may only span a part of the height of the side wall of plunger head assembly housing top 600.

As shown in FIG. 39, the plunger pressure sensor 532 may comprise a plunger pressure sensor force concentrator 595. In embodiments where the plunger pressure sensor push plate 590 transmits force directly to the plunger pressure sensor input surface 596, the plunger pressure sensor force concentrator 595 may help to concentrate the force applied to the plunger pressure sensor push plate 590 while exerting it against the plunger pressure sensor input surface 596. In embodiments where the plunger pressure sensor 532 comprises a plunger pressure sensor lever 592 on a plunger pressure sensor pivot 594, the plunger pressure sensor force concentrator 595 may be on the end and face of the plunger pressure sensor lever 592 which presses against the plunger pressure sensor input surface 596. This may help to concentrate the force exerted against the plunger pressure sensor input surface 596 which may increase accuracy. It may also help to concentrate the force at the center of the plunger pressure sensor input surface 596, making measurements more consistent and accurate.

Figure 40:
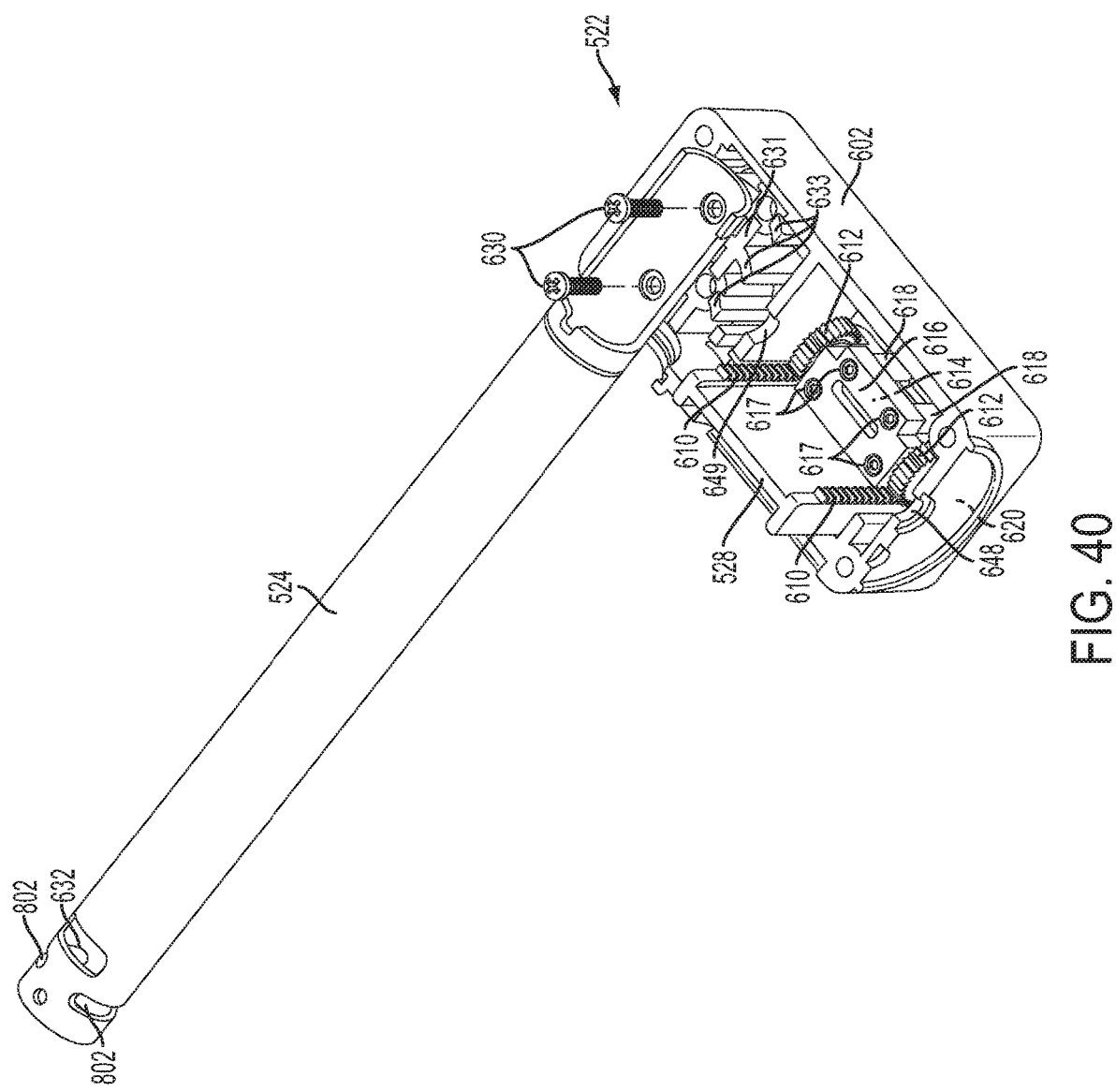
FIG. 40 is an assembled top view of an exemplary embodiment of the bottom of the plunger head assembly and plunger tube in accordance with an embodiment of the present disclosure.

The bottom half of the plunger head assembly 522 and the plunger tube 524 are shown in FIG. 40. As shown, the lower plunger clamp jaw 528 comprises two lower plunger clamp jaw racks 610. In other embodiments, there may only be one lower plunger clamp jaw rack 610. In some embodiments, there may be more than two lower plunger clamp jaw racks 610. Each lower plunger clamp jaw rack 610 interdigitates with a lower plunger clamp jaw pinion gear 612. The lower plunger clamp jaw pinion gears 612 are capable of rotating about the axis of a lower clamp jaw drive shaft 614. A lower jaw drive gear 620 is also disposed on the lower clamp jaw drive shaft 614. The lower jaw drive gear 620 will be elaborated upon later.

Similar to the upper half of the plunger head assembly 522 the lower half of the plunger head assembly 522 may comprise a number of bearing surfaces for the lower jaw drive shaft 614. In the example embodiment in FIG. 40, the plunger head assembly 522 comprises one upper bearing surface 616 and two lower bearing surfaces 618 for the lower jaw drive shaft 614. The upper bearing surface 616 is coupled into the plunger head assembly housing bottom 602. The upper bearing surface 616 may be coupled to the plunger head assembly housing bottom 602 by any of a variety of means including, but not limited to, screws 617 (shown), bolts, adhesive, snap fit, friction fit, welds, a tongue in groove arrangement, pins, or may be formed as a continuous part of the plunger head assembly housing bottom 602. The upper bearing surface 616 provide a bearing surface for at least a span of the top half of the lower jaw drive shaft 614.

The lower bearing surfaces 618 are coupled into the plunger head assembly housing bottom 602. The lower bearing surfaces 618 may be coupled to the plunger head assembly housing bottom 602 by any suitable means such as, but not limited to, screws, bolts, adhesive, snap fit, friction fit, magnets, welds, a tongue in groove arrangement, pin (shown), etc. In some embodiments, the lower bearing surfaces 618 may be formed as a continuous part of the plunger head assembly housing bottom 602. The lower bearing surfaces 618 provide a bearing surface for at least a span of the bottom half of the lower jaw drive shaft 614.

In some embodiments, there may also be a lower dial shaft bearing surface 649 which is coupled to the plunger head assembly housing bottom 602. The lower dial shaft bearing surface 649 may be coupled into the plunger head assembly housing bottom 602 by any of a variety of means including, but not limited to, screws, bolts, adhesive, snap fit, friction fit, welds, a tongue in groove arrangement, pins, or may be formed as a continuous part of the plunger head assembly housing bottom 602 as shown. The lower half of the dial shaft passage 648 mentioned above is cut through the right face of the plunger head assembly housing bottom 602 The lower dial shaft bearing surface 649 and dial shaft passage 648 will be further elaborated upon later.

As shown in FIG. 40, the plunger tube 524 may be coupled into the bottom half of the plunger head assembly 522. In the example embodiment shown in FIG. 40, the plunger tube 524 is coupled by two screws 630 onto a plunger tube cradle 631. In other embodiments, the number or type of fastener/coupling method may be different. For example, the plunger tube 524 may be coupled to the plunger tube cradle 631 by any other suitable means such as, but not limited to, bolts, adhesive, snap fit, friction fit, magnets, welds, a tongue in groove arrangement, pin, etc.

The plunger tube cradle 631 may comprise arcuated ribs 633 which are arced such that they are flush with the outside surface of the plunger tube 524 and support the plunger tube 524. In some embodiments, a portion of the arc of the plunger tube 524 may be eliminated on the span of the plunger tube 524 which is coupled inside of the plunger head assembly 522 when the syringe pump 500 is fully assembled. In the embodiment shown in FIG. 40, about a 180° segment, or the upper half of the plunger tube 524 has been eliminated. The end of the plunger tube 524 opposite the end of the plunger tube 524 coupled to the plunger tube cradle 631 may comprise a number of plunger tube cutouts 802 which will be explained later. There may also be a conduit opening 632 near the plunger tube cutouts 802.

Figure 41:
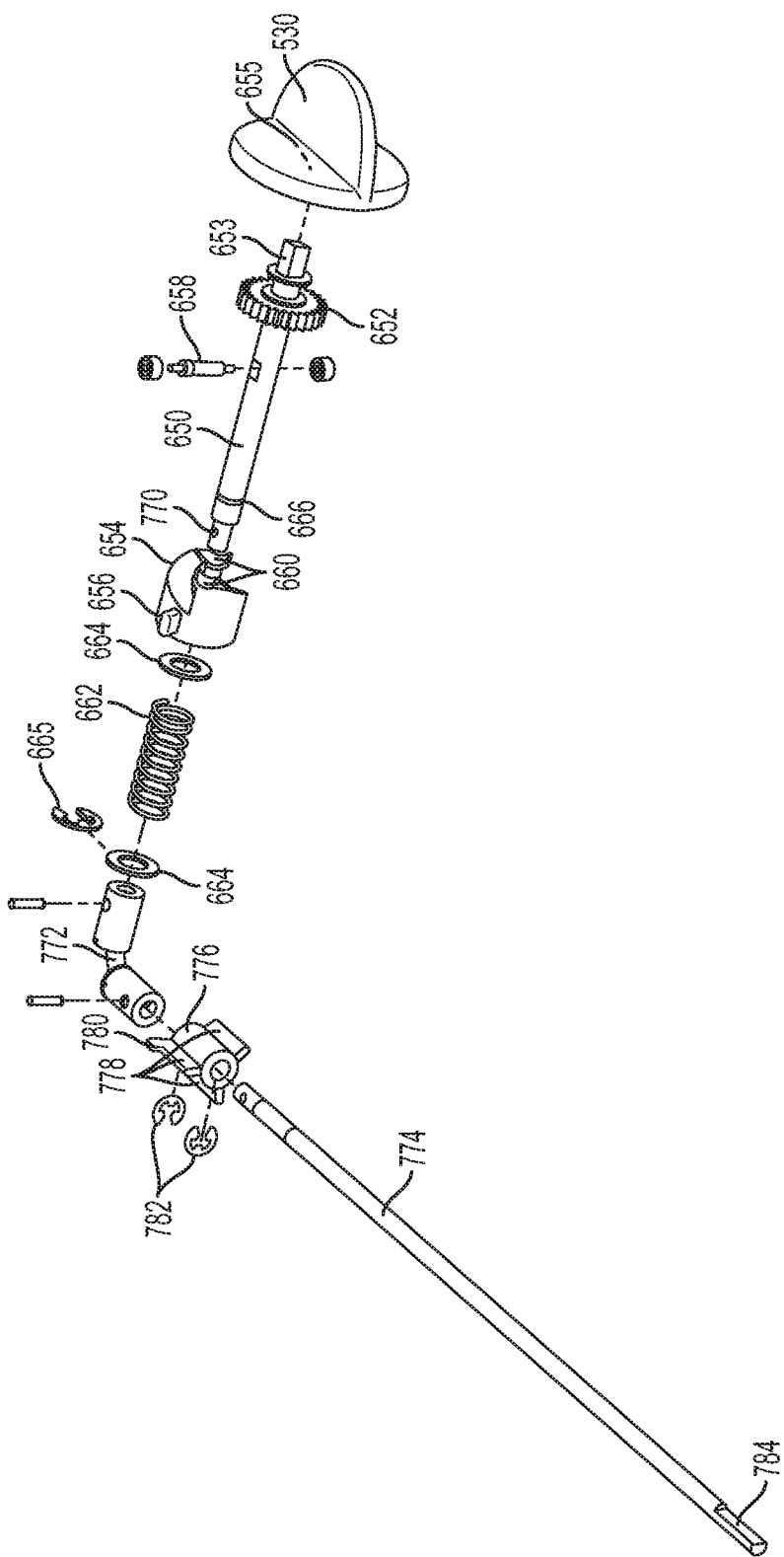
FIG. 41 is an exploded view of an exemplary embodiment of the dial shaft and related parts of the syringe pump in accordance with an embodiment of the present disclosure.

In FIG. 41, the dial 530 of the plunger head assembly 522 is shown exploded away from a dial shaft 650 to which it couples onto when assembled. As shown, the dial shaft 650 comprises a square shaped end 653. The square shaped end 653 of the dial shaft 650 fits into a square shaped orifice 655 in the dial 530 such that as the dial 530 is rotated, the dial shaft 650 is caused to rotate as well. In other embodiments, the square shaped end 653 of the dial shaft 650 and square shaped orifice 655 on the dial 530 need not necessarily be square shaped, but rather D-shaped, hexagonal, or any other suitable shape.

A dial shaft gear 652 may be disposed about the dial shaft 650. As the dial shaft 650 is rotated, the dial shaft gear 652 may be caused to rotate about the axis of the dial shaft 650. A dial shaft cam 654 may be slidably coupled to the dial shaft 650 such that the dial shaft cam 654 is capable of sliding along the axial direction of the dial shaft 650 and the dial shaft 650 freely rotates inside the dial shaft cam 654. The dial shaft cam 654 may comprise one or more dial shaft cam ears 656. The dial shaft cam ears 656 may also be referred to as dial shaft cam guides since they perform a guiding function. In the example embodiment, the dial shaft cam 654 comprises two dial shaft cam ears 656. In the example embodiment, the cam surface of the dial shaft cam 654 is substantially a section of a double helix. At the end of cam surface of the dial shaft cam 654 there may be one or more dial shaft cam detents 660. The end of the dial shaft cam 654 opposite the cam surface may be substantially flat.

A dial shaft cam follower 658 may be coupled into the dial shaft 650 such that it rotates with the dial shaft 650. In the example embodiment shown in FIG. 41 the dial shaft cam follower 658 runs through the dial shaft 650 such that at least a portion of the dial shaft cam follower 658 projects from the dial shaft 650 on each side of the dial shaft 650. This effectively creates two dial shaft cam followers 658 which are offset 180° from each other. Each end of the dial shaft cam follower 658 follows one helix of the double helix shaped cam surface of the dial shaft cam 654.

A bias member may also be placed on the dial shaft 650. In the example embodiment, a dial shaft compression spring 662 is placed on the dial shaft 650. The dial shaft compression spring 662 may have a coil diameter sized to fit concentrically around the dial shaft 650. In the example embodiment depicted in FIG. 41, the dial shaft compression spring 662 is retained on each end by dial shaft washers 664.

A dial shaft retaining ring 665 may fit in an annular groove 666 recessed into the dial shaft 650.

In FIG. 41, the end of the dial shaft 650 opposite the square shaped end 653 features a peg-like projection 770. The peg-like projection 770 may couple into a joint of a double universal joint 772. The peg-like projection 770 may couple into the double universal joint 772 by any suitable means such as, but not limited to, screws, bolts, adhesive, snap fit, friction fit, magnets, welds, a tongue in groove arrangement, pin (shown), etc. The other joint of the double universal joint 772 may also couple onto a driven shaft 774. The other joint of the double universal joint 772 may be coupled onto the driven shaft 774 by any suitable means such as, but not limited to, screws, bolts, adhesive, snap fit, friction fit, magnets, welds, a tongue in groove arrangement, pin (shown), etc. The dial shaft 650 and the driven shaft 774 may be oriented approximately perpendicular to each other.

In some embodiments, a driven shaft bushing 776 may be included on the driven shaft 774. In the example embodiment shown in FIG. 41 the driven shaft bushing 776 is a sleeve bushing. The inner surface of the driven shaft bushing 776 comprises the bearing surface for the driven shaft 774. The outer surface of the driven shaft bushing 776 may comprise a number of driven shaft bushing projections 778 which extend outwardly from the outer surface of the driven shaft bushing 776. In the example embodiment in FIG. 41, the driven shaft bushing projections 778 are spaced approximately 120° apart from each other along the arc of the outer surface of the driven shaft bushing 776. In the example embodiment shown in FIG. 41, the driven shaft bushing projection 778 which projects toward the top of the page comprises a nub 780 which extends from the top edge of the driven shaft bushing projection 778 toward the top of the page. The driven shaft bushing 776 is held in place on the drive shaft 774 by driven shaft retaining rings 782. One of the driven shaft retaining rings 782 may be clipped into place on the driven shaft 774 on each side of the driven shaft bushing 776. The end of the driven shaft 774 not coupled into the double universal joint 772 may comprise a driven shaft D-shaped segment 784.

Figure 42:
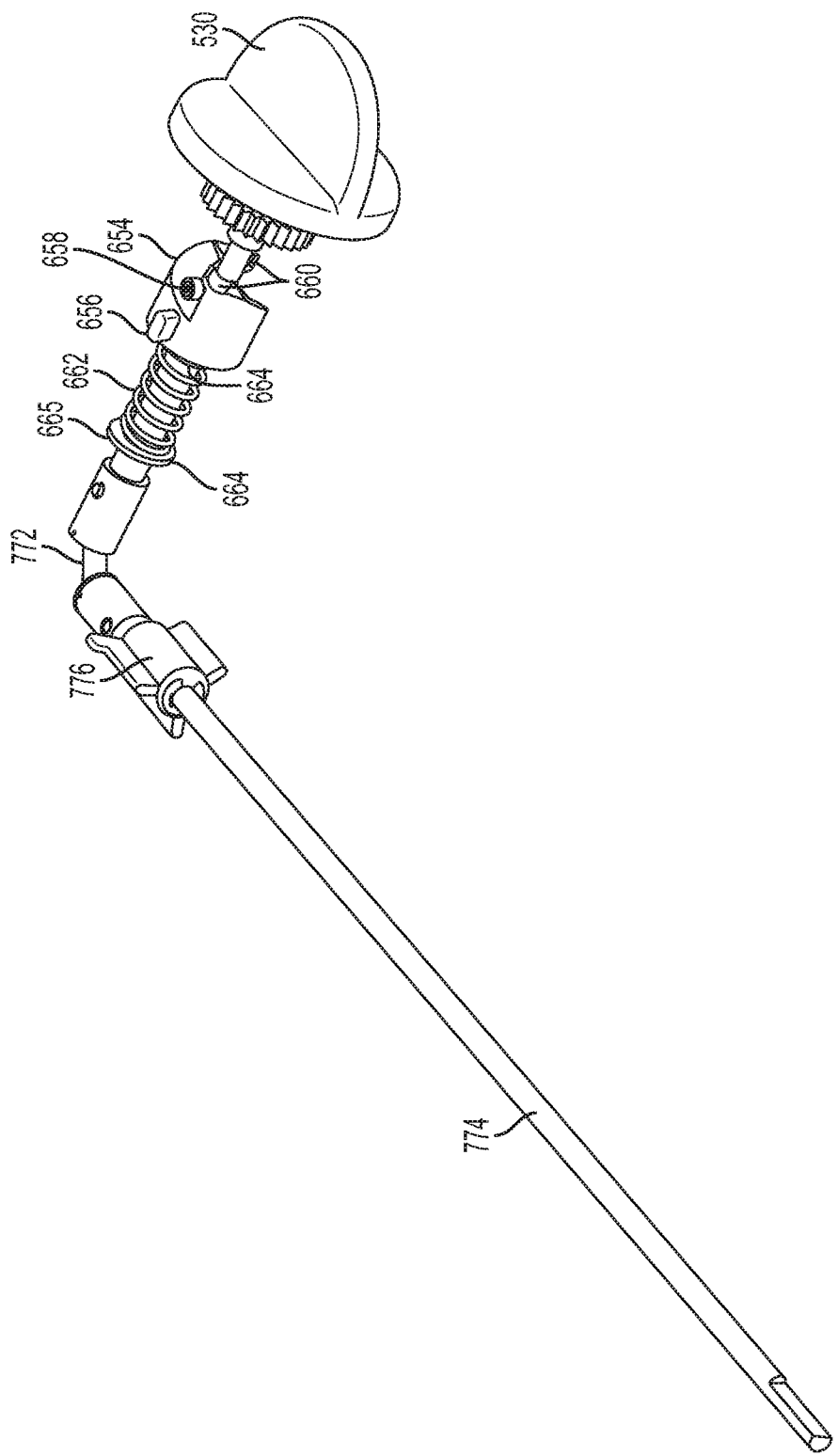
FIG. 42 is an assembled view of the exemplary embodiment of FIG. 41 in accordance with an embodiment of the present disclosure.

When assembled, as shown in FIG. 42, the dial shaft compression spring 662 biases the dial shaft cam 654 against the dial shaft cam follower 658 such that the ends of the dial shaft cam follower 658 are at the bottom of the cam surface of the dial shaft cam 654. One dial shaft washer 664 abuts the dial shaft retaining ring 665 and the other dial shaft washer 664 abuts the flat side of the dial shaft cam 654. Preferably, the distance between the dial shaft washers 664 is at no point greater than or equal to the resting length of the dial shaft compression spring 662. This ensures that there is no "slop" and that the dial shaft cam 654 is always biased against the ends of the dial shaft cam follower 658.

As shown, the double universal joint 772 connects dial shaft 650 to the driven shaft 774 when assembled. The driven shaft bushing 776 is clipped into place on the driven shaft 774 by driven shaft retaining rings 782 (see FIG. 41). In the embodiment depicted in FIG. 42 the dial shaft 650 functions as the drive shaft for the driven shaft 774. Any rotation of the dial shaft 650 generated through rotation of the dial 530 will be transmitted via the double universal joint 772 to the driven shaft 774.

Figure 43:
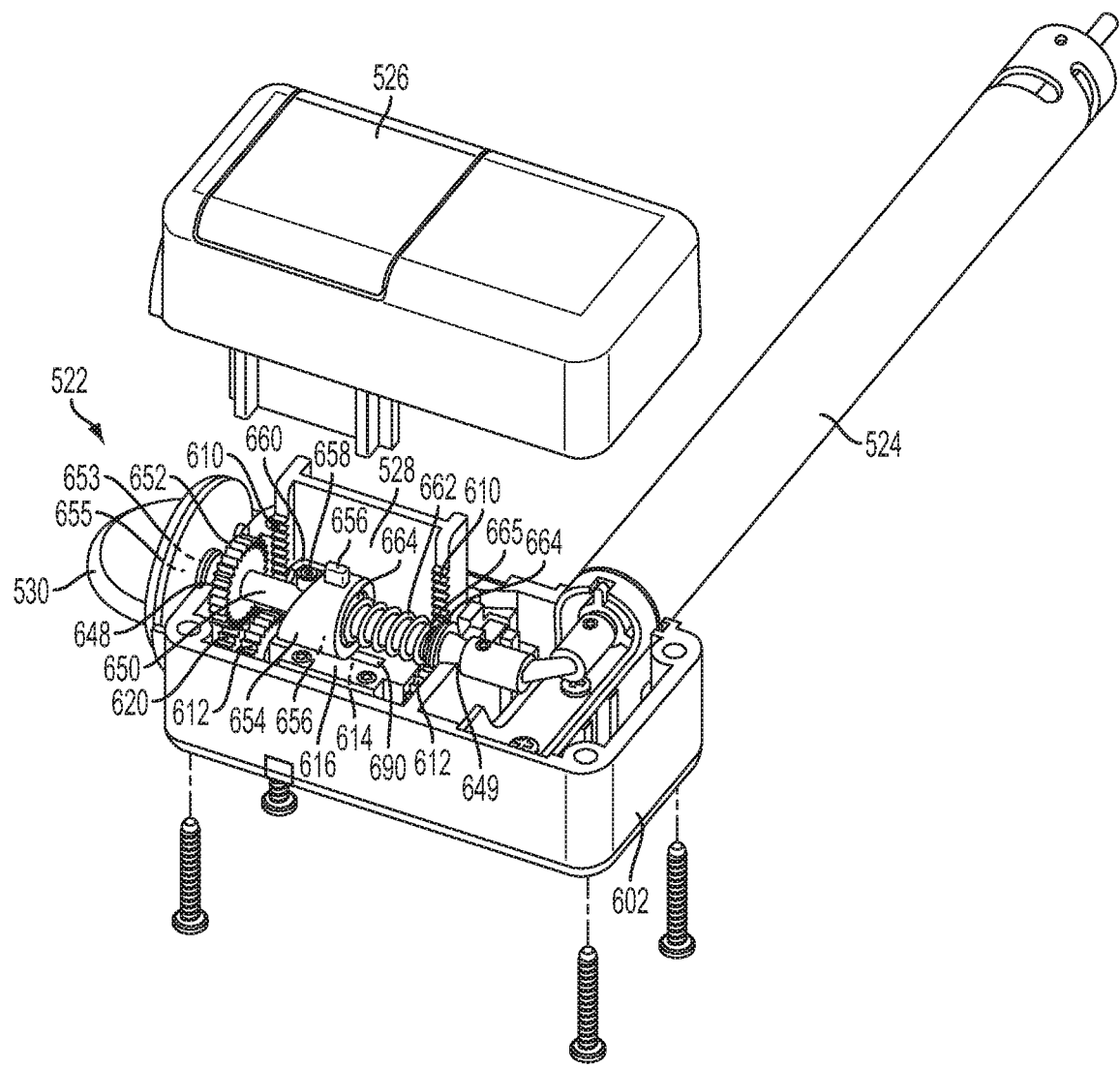
FIG. 43 is a partially assembled view of an exemplary embodiment of the plunger head assembly and plunger tube in accordance with an embodiment of the present disclosure.

FIG. 43 shows the whole plunger head assembly 522 with the plunger tube 524 coupled in place. The top half of the plunger head assembly 522 is exploded away from the bottom half of the plunger head assembly 522. The bottom half of the dial shaft 650 is sitting in the lower dial shaft bearing 649 on the plunger head assembly housing bottom 602. Another span of the bottom half of the dial shaft 650 is seated on the portion of the dial shaft passage 648 located on the plunger head assembly housing bottom 602. As shown, the dial shaft passage 648 functions as a second bearing surface for the dial shaft 650. The square shaped end 653 of the dial shaft 650 extends beyond the dial shaft passage 648 and couples into the square shaped orifice 655 on the dial 530.

As shown in FIG. 43, the dial shaft gear 652 on the dial shaft 650 interdigitates with the lower jaw drive gear 620. As the dial 530 is rotated, the dial shaft 650 and dial shaft gear 652 also rotate. Rotation is transmitted through the dial shaft gear 652 to the lower jaw drive gear 620. Rotation of the lower jaw drive gear 620 rotates the lower clamp jaw drive shaft 614 and the lower clamp jaw pinion gears 612 on the lower clamp jaw drive shaft 614. Since the lower clamp jaw pinion gears 612 interdigitate with the lower plunger clamp jaw racks 610, any rotation of the lower clamp jaw pinion gears 612 is translated into linear displacement of the lower plunger clamp jaw 528. Thus, in the shown embodiment, rotating the dial 530 is the means by which a user may actuate the lower plunger clamp jaw 528 to an open or clamped position.

In the embodiment shown in FIG. 43, rotation of the dial 530 also causes a linear displacement of the dial shaft cam 654 away from the dial 530 and in the axial direction of the dial shaft 650. As shown in the example embodiment, the upper bearing surface 616 for the lower clamp jaw drive shaft 614 comprises a dial shaft cam ear slit 690 which functions as a track for a dial shaft cam ear 656. One of the dial shaft cam ears 656 projects into the dial shaft cam ear slit 690. This ensures that the dial shaft cam 654 may not rotate with the dial 530 and dial shaft 650 because rotation of the dial shaft cam ear 656 is blocked by the rest of the upper bearing surface 616 for the lower clamp jaw drive shaft 614.

The dial shaft cam ear slit 690 does, however, allow the dial shaft cam 654 to displace linearly along the axial direction of the dial shaft 650. As the dial 530 and dial shaft 650 are rotated, the dial shaft cam follower 658 also rotates. The dial shaft cam follower's 658 location on the dial shaft 650 is fixed such that the dial shaft cam follower 658 is incapable of linear displacement. As the ends of the dial shaft cam follower 658 ride up the cam surface of the dial shaft cam 654, the dial shaft cam 654 is forced to displace toward the right face of the plunger head assembly housing bottom 602 (relative to FIG. 43). The dial shaft cam ears 656 also slide in this direction within the dial shaft cam ear slit 690. This causes the dial shaft compression spring 662 to compress between the dial shaft washer 664 abutting the dial shaft cam 654 and the dial shaft washer 664 abutting the dial shaft retaining ring 665. The restoring force of the dial shaft compression spring 662 serves to bias the dial 530, and all parts actuated by the dial 530 to their original positions prior to any dial 530 rotation. If the dial 530 is released, the dial 530 and all parts actuated by the dial 530 will be caused to automatically return to their original orientations prior to any dial 530 rotation due to the expansion of the compressed dial shaft compression spring 662. In the example embodiment, the original position prior to any dial 530 rotation, is the position depicted in FIG. 35 where the upper plunger clamp jaw 526 and lower plunger clamp jaw 528 are fully closed.

In some embodiments, including the embodiment shown in FIG. 43, the dial shaft cam 654 may comprise a dial shaft cam detent 660 along the cam surface of the dial shaft cam 654. The dial shaft cam detent 660 may allow a user to "park" the dial shaft cam follower 658 at a desired point along the cam surface of the dial shaft cam 654. In the example embodiment, the dial shaft cam detent 660 may be reached by the dial shaft cam follower 658 when the dial 530 has been fully rotated. When the dial shaft cam follower 658 is in the dial shaft cam detent 660, the dial shaft compression spring 662 may not automatically return the dial 530 and all parts actuated by the dial 530 to their orientation prior to any rotation of the dial 530. A user may need to rotate the dial 530 such that the dial shaft cam follower 658 moves out of the dial shaft cam detent 660 before the restoring force of the compressed dial shaft compression spring 662 may be allowed to expand the dial shaft compression spring 662 to a less compressed state.

Figure 44:
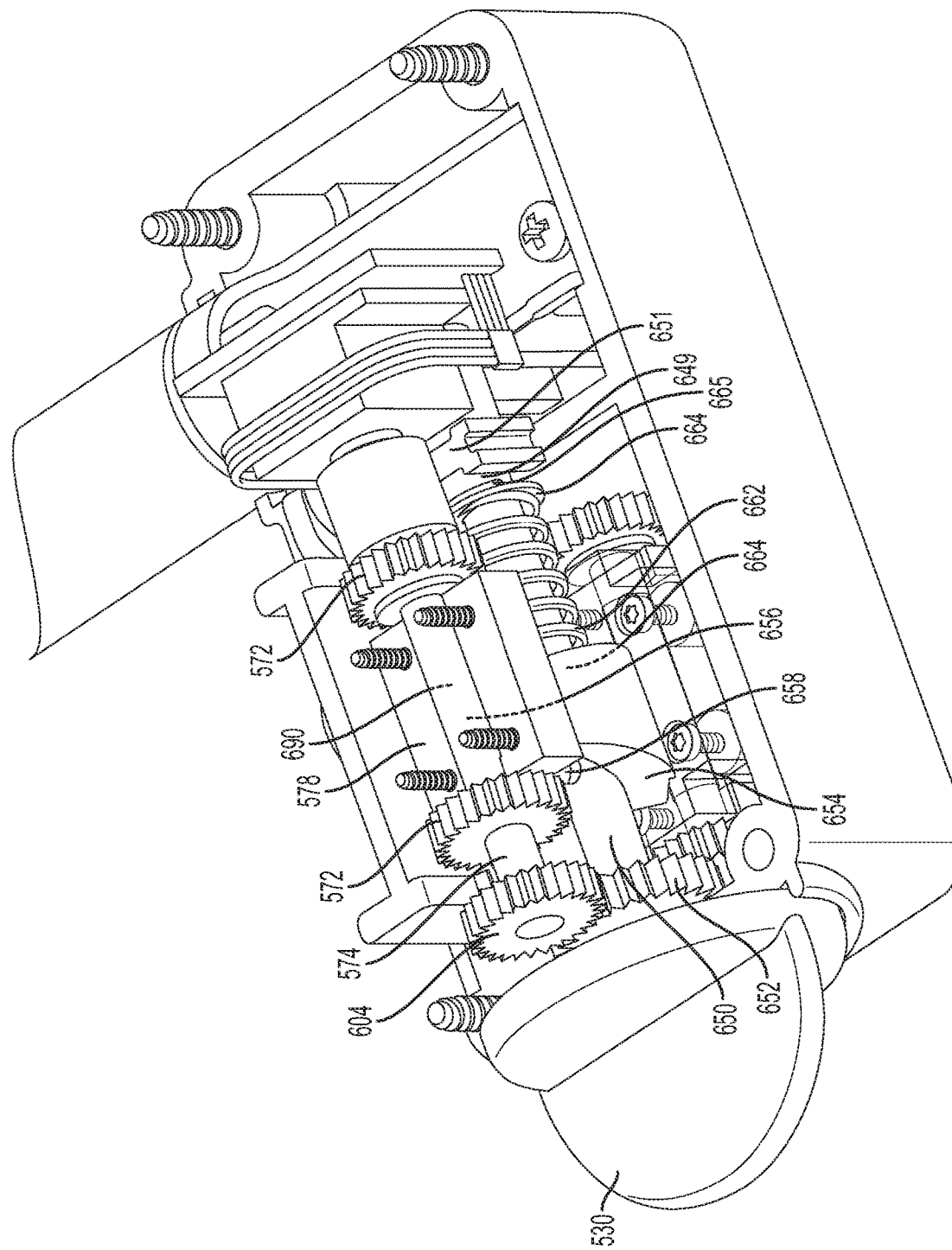
FIG. 44 is a view of an exemplary embodiment of the plunger head assembly with the plunger head assembly housing top removed in accordance with an embodiment of the present disclosure.

FIG. 44 shows a similar view to the view illustrated in FIG. 43. In FIG. 44, the plunger head assembly housing top 600 and some parts comprising the top half of the plunger head assembly 522 are not visible. Among the parts that are visible are the upper dial shaft bearing 651, upper clamp jaw drive shaft 574, the upper clamp jaw pinion gears 572, and the upper jaw drive gear 604. As shown in FIG. 44, when assembled the dial shaft 650 is sandwiched between the upper dial shaft bearing 651 and lower dial shaft bearing 649, the dial shaft gear 652 on the dial shaft 650 interdigitates with the upper jaw drive gear 604. As the dial 530 is rotated, the dial shaft 650 and dial shaft gear 652 also rotate. Rotation is transmitted through the dial shaft gear 652 to the upper jaw drive gear 604. Rotation of the upper jaw drive gear 604 rotates the upper clamp jaw drive shaft 574 and the upper clamp jaw pinion gears 572 on the upper clamp jaw drive shaft 574.

Referring back to FIG. 38, the upper clamp jaw pinion gears 572 interdigitate with the upper plunger clamp jaw racks 570. Any rotation of the upper clamp jaw pinion gears 572 is translated into linear displacement of the upper plunger clamp jaw 526. Thus rotation of the dial 530 is the means by which a user may actuate the upper plunger clamp jaw 526 (not shown in FIG. 44) to an open or clamped position.

The lower bearing surface 578 for the upper jaw drive shaft 574 is also visible in FIG. 44. The lower bearing surface 578 for the upper jaw drive shaft 574 may comprise a second dial shaft cam ear slit 690 in embodiments where the dial shaft cam 654 comprises more than one dial shaft cam ear 656. The second dial shaft cam ear slits 690 may functions as a track for a dial shaft cam ear 656. One of the dial shaft cam ears 656 projects into the second dial shaft cam ear slit 690. This ensures that the dial shaft cam 654 may not rotate with the dial 530 and dial shaft 650 because rotation of the dial shaft cam ear 656 is blocked by the rest of the lower bearing surface 578 for the upper clamp jaw drive shaft 574.

The second dial shaft cam ear slit 690 does, however, allow the dial shaft cam 654 to displace linearly along the axial direction of the dial shaft 650. As the dial 530 and dial shaft 650 are rotated, the dial shaft cam follower 658 also rotates. The dial shaft cam follower's 658 location on the dial shaft 650 is fixed such that the dial shaft cam follower 658 is incapable of linear displacement. As the ends of the dial shaft cam follower 658 ride up the cam surface of the dial shaft cam 654, the dial shaft cam 654 is forced to displace toward the right face of the plunger head assembly housing bottom 602 (relative to FIG. 44). A dial shaft cam ear 656 also slides in this direction within the second dial shaft cam ear slit 690. This causes the dial shaft compression spring 662 to compress between the dial shaft washer 664 abutting dial shaft cam 654 and the dial shaft washer 664 abutting the dial shaft retaining ring 665. The dial shaft compression spring 662, dial 530, and all parts actuated by the dial 530 may then behave per the above description.

In some embodiments, the upper jaw drive gear 604 (best shown in FIG. 37) and lower jaw drive gear 620 (best shown in FIG. 43) may be substantially identical gears. Additionally, the upper jaw pinion gears 572 (best shown in FIG. 37) and lower clamp jaw pinion gears 612 (best shown in FIG. 40) may be substantially identical gears. In such embodiments, the upper plunger clamp jaw 526 and lower plunger clamp jaw 528 (see FIGS. 30-34) will experience an equal amount of linear displacement per degree of rotation of the dial 530. Since the point of interdigitation of the upper jaw drive gear 604 on dial shaft gear 652 is opposite the point of interdigitation of the lower jaw drive gear 620 on the dial shaft gear 652, the upper plunger clamp jaw 526 and lower plunger clamp jaw 528 will linearly displace in opposite directions.

Figure 45:
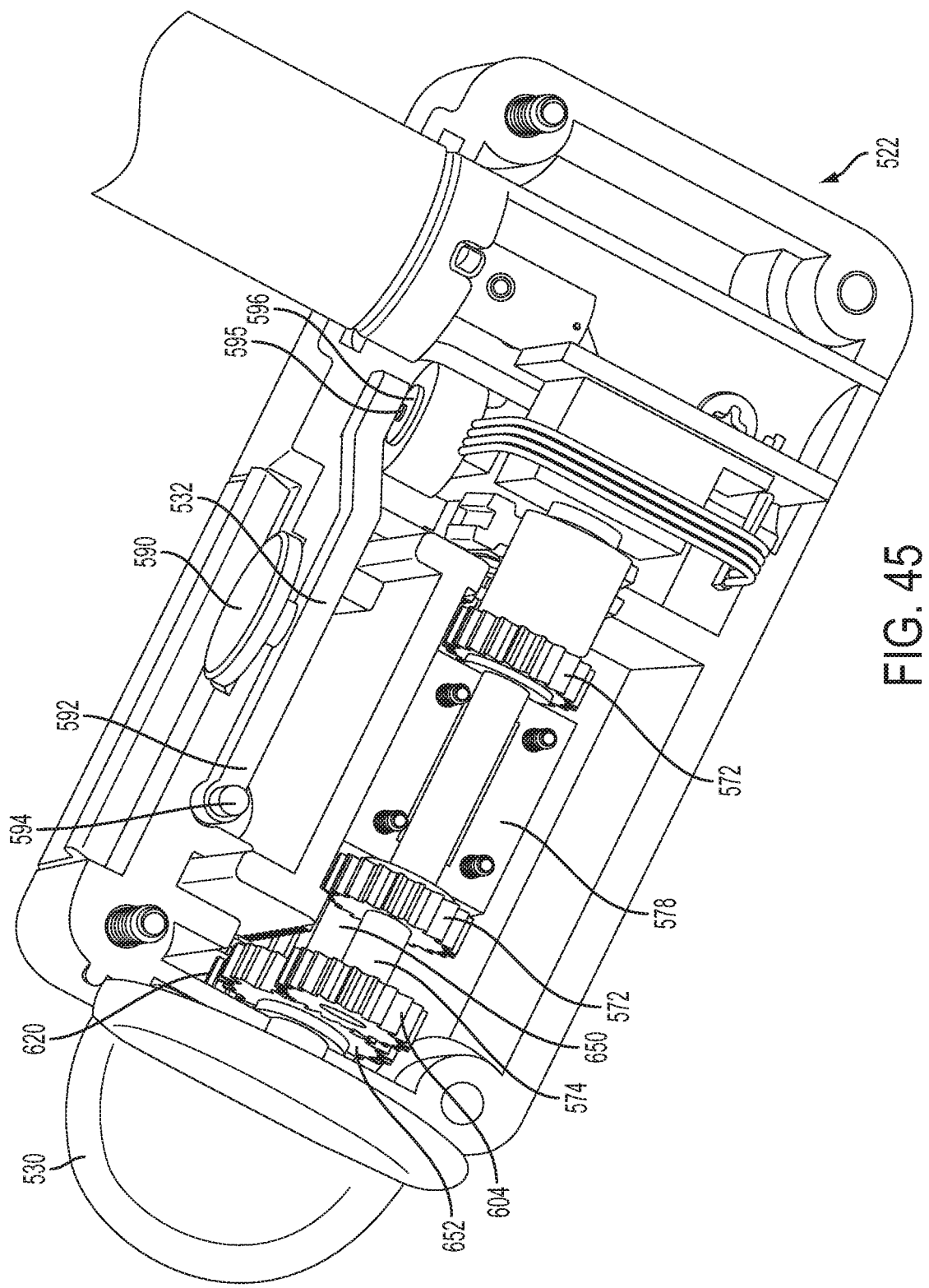
FIG. 45 is a top view of the exemplary embodiment of FIG. 44 in accordance with an embodiment of the present disclosure.

FIG. 45 shows a view similar to the view shown in FIG. 44. FIG. 45 depicts an assembled view of the plunger head assembly 522 from a slightly different perspective. As shown in FIG. 45, the dial 530 is coupled to the dial shaft 650. The dial shaft gear 652 is in an interdigitating relationship with both the upper jaw drive gear 604 and the lower jaw drive gear 620. The upper jaw drive gear 604 is disposed on the upper jaw drive shaft 574 along with two upper jaw pinion gears 572. The upper jaw pinion gears 572 may be spaced apart by the lower bearing surface 578 for the upper jaw drive shaft 574 as shown in FIG. 45.

The plunger pressure sensor 532 in the embodiment depicted in FIG. 45 comprises a plunger pressure sensor push plate 590 which extends out of the plunger head assembly 522 such that it may physically contact a plunger flange 548 (as shown in FIG. 34) clamped against the plunger head assembly 522. The plunger pressure sensor push plate 590 is attached to a plunger pressure sensor lever 592. The plunger pressure sensor lever 592 is pivotally coupled to a plunger pressure sensor pivot 594. The plunger pressure sensor pivot 594 is disposed at the left end of the plunger pressure sensor lever 594 (relative to FIG. 45). In the example embodiment in FIG. 45, any force applied to the plunger pressure sensor push plate 590 is transmitted through the plunger pressure sensor lever 594 to the plunger pressure sensor input surface 596. Although the location of the plunger pressure sensor pivot 594 in relation to the plunger pressure sensor push plate 590 does not multiply the force exerted against the plunger pressure sensor input surface 596 in FIG. 45, other embodiments may use different arrangements to create a mechanical advantage. The plunger pressure sensor 532 in FIG. 45 also comprises a plunger pressure sensor force concentrator 595 which is a small projection extending from the plunger pressure sensor lever 592 to the plunger pressure sensor input surface 596. The plunger pressure sensor force concentrator 595 concentrates force exerted against the plunger pressure sensor input surface 596 to help promote a more accurate pressure reading.

Figure 46:
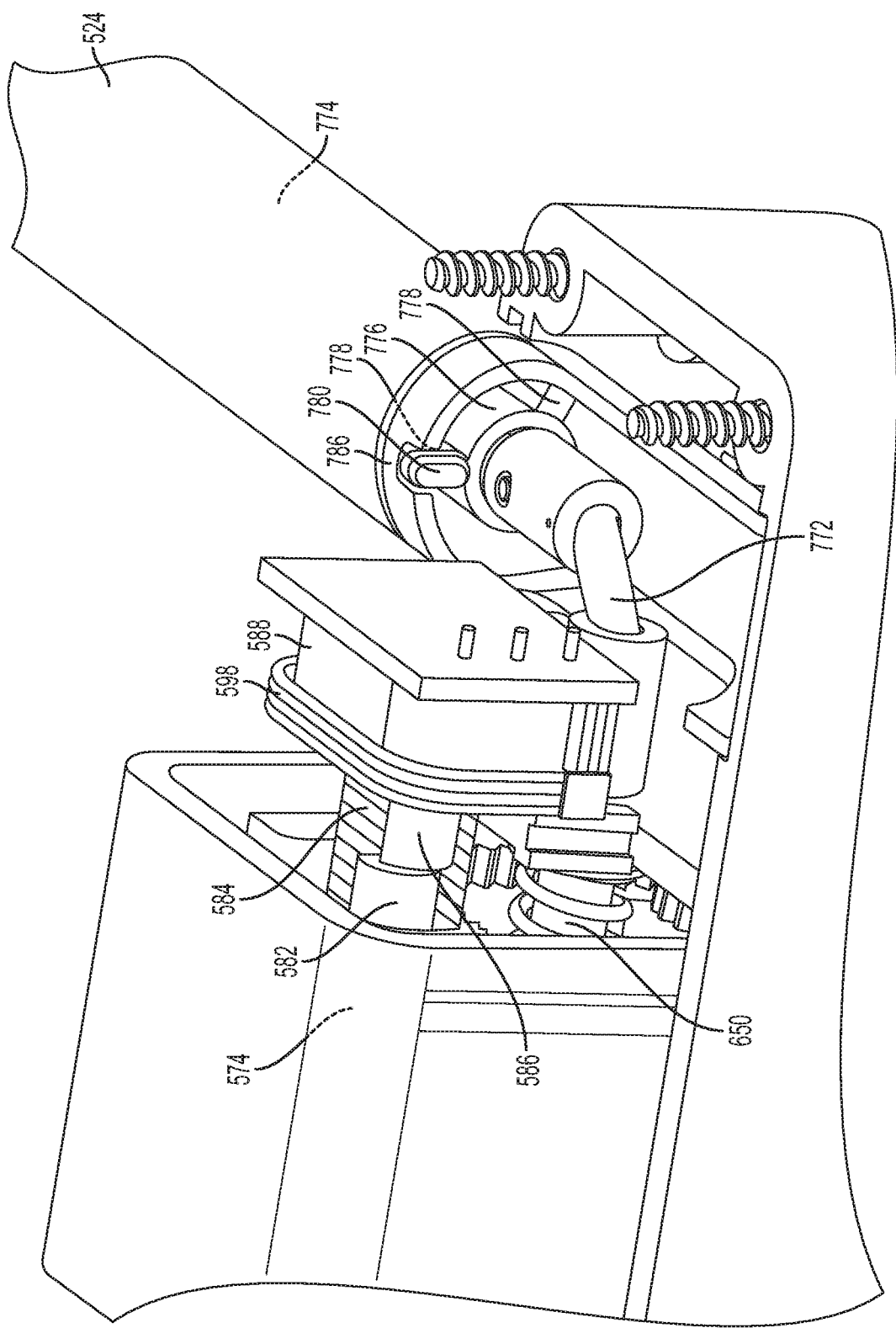
FIG. 46 is a partial view of an exemplary embodiment of the plunger head assembly in which the D-shaped connector is shown in cross section in accordance with an embodiment of the present disclosure.

FIG. 46 shows a close up of how the upper jaw drive shaft 574 is connected to the D-shaped shaft 586 projecting from the plunger clamp jaws position sensor 588. In the embodiment depicted in FIG. 46, the upper jaw drive shaft 574 comprises a D-shaped span 582. The D-shaped span 582 of the upper jaw drive shaft 574 projects into a complimentary shaped orifice in the D-shaped connector 584. The D-shaped connector 584 in FIG. 46 is shown in cross-section. A D-shaped shaft 586 projecting out of the plunger clamp jaws position sensor 588 also projects into the D-shaped connector 584. Any rotation of the upper jaw drive shaft 574 may cause the D-shaped connector 584 to rotate as well. In turn, this may cause rotation of the D-shaped shaft 586 projecting from the plunger clamp jaws position sensor 588. As mentioned above this rotation may cause the wiper to slide across the resistive element of the plunger clamp jaws position sensor 588 in embodiments where the plunger clamp jaws position sensor 588 comprises a potentiometer.

FIG. 46 also shows the dial shaft 650 connected to the double universal joint 772. As shown in the example embodiment in FIG. 46, the driven shaft 774 is also coupled to the double universal joint projects down the interior of the hollow plunger tube 524. The nub 780 on the driven shaft bushing projection 778 of the driven shaft bushing 776 is seated in a plunger tube notch 786 recessed into the edge of the plunger tube 524 to lock the nub 780 within the plunger tube notch 786. Seating the nub 780 in the plunger tube notch 786 restricts the driven shaft bushing 776 from rotation because the nub 780 may not rotate through the sides of the plunger tube notch 786. Each of the driven shaft bushing projection 778 abuts the interior surface of the plunger tube 524 which keeps the driven shaft bushing 776 centered in the plunger tube 524.

The plunger tube 524 may also serve as a channel for the electrical conduits 598 to and from the plunger clamp jaws position sensor 588 and the plunger pressure sensor 532. Since the plunger tube 524 is sealed to liquid when the syringe pump is fully assembled, the plunger tube 524 protects the electrical conduits 598 from exposure to liquid. The electrical conduits 598 exit the plunger tube 524 through the conduit opening 632 of the plunger tube 524 shown in FIG. 47.

Figure 47:
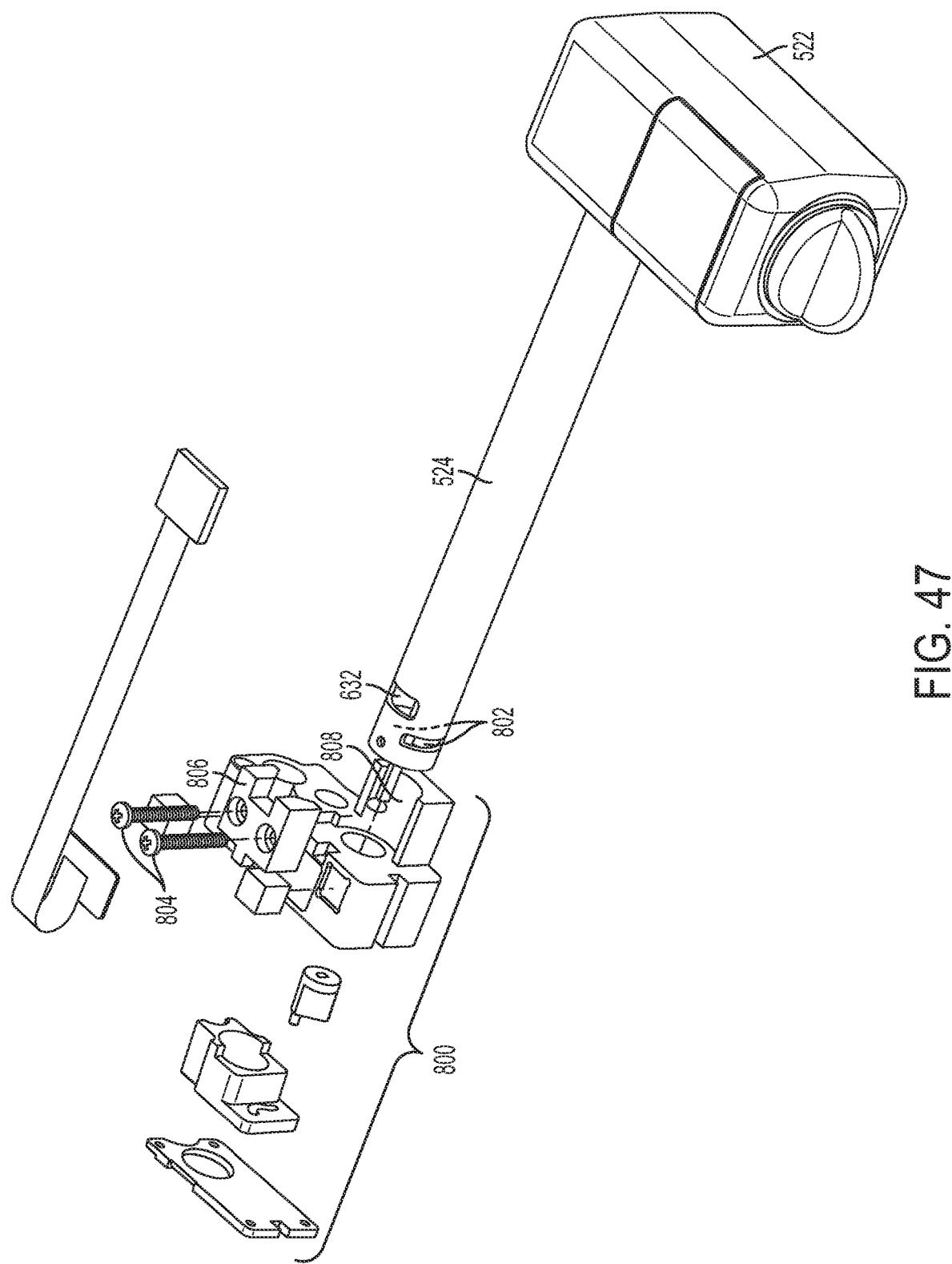
FIG. 47 is a view of an exemplary embodiment of the plunger head assembly, plunger tube, and sliding block assembly in which the sliding block assembly is exploded in accordance with an embodiment of the present disclosure.

FIG. 47 depicts an exploded view of a sliding block assembly 800. As shown, the plunger tube 524 which extends from the plunger head assembly 522 comprises two plunger tube cutouts 802. The plunger tube cutouts 802 are cut into the front and back sides of the plunger tube 524. In FIG. 47, only the front plunger tube cutout 802 is visible. The plunger tube cutouts 802 allow the plunger tube to be non-rotationally coupled to the sliding block assembly 800. In the example embodiment, two plunger tube coupling screws 804 run through a plunger tube bracket 806, down the plunger tube cutouts 802 and into a plunger tube support 808. The plunger tube 524, is thus tightly sandwiched between the plunger tube bracket 806 and the plunger tube support 808. Any rotation of the plunger tube 524 is obstructed by plunger tube coupling screws 804 which abut the top and bottom edges of the plunger tube cutouts 802. Similarly, any axial displacement of the plunger tube 524 is obstructed by the plunger tube coupling screws 804 which abut the sides of the plunger tube cutouts 802. In other embodiments, the plunger tube 524 may be coupled to the sliding block assembly 800 by any other suitable means such as, but not limited to, bolts, adhesive, snap fit, friction fit, magnets, welds, a tongue in groove arrangement, pin, etc.

Figure 48A:
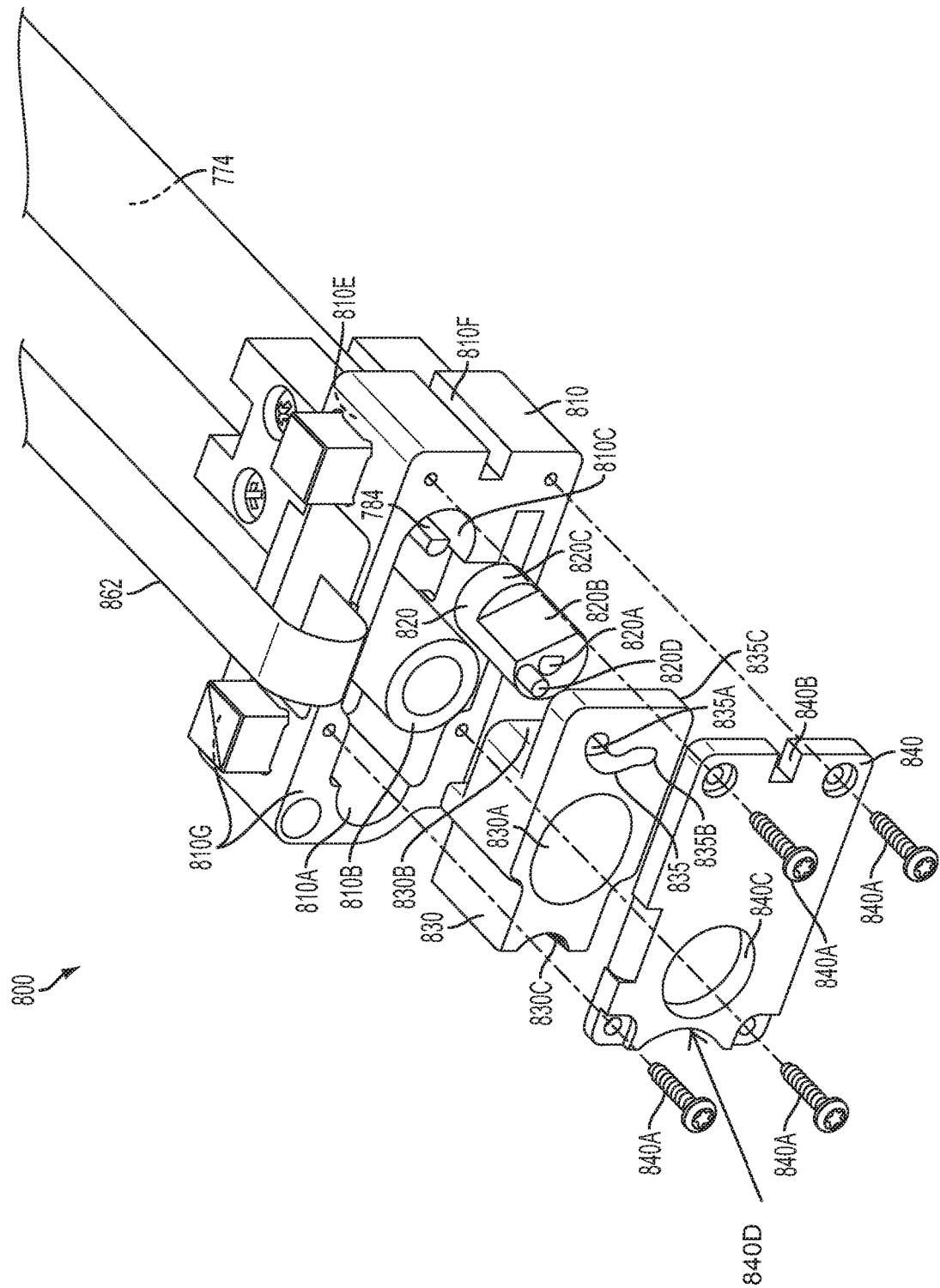
FIG. 48A is an exploded view of an exemplary embodiment of the sliding block assembly in accordance with an embodiment of the present disclosure.

A closer exploded view of the sliding block assembly 800 is shown in FIG. 48A. The sliding block assembly 800 comprises a number of parts. The sliding block assembly 800 comprises a half nut housing 810, a barrel cam 820, a half nut 830, and a half nut cover plate 840. The half nut housing 810 may be manufactured from any suitable strong material will not significantly deform under the applied loads such as, metal, nylon, glass-filled plastics, molded plastic, a polyoxymethylene plastic such as Delrin, etc. The half-nut 830 is preferably fabricated from bearing metals such as brass, bronze etc that interact well with stainless steel surfaces typical of lead screws. The barrel-cam 820 is preferably fabricated from a hard metal such as stainless to form a good bearing pair with the half nut 830. The half nut housing 810 comprises a lead screw void 810A. The lead screw void 810A allows the lead screw 850 (not shown, see FIG. 48B) to pass through the half nut housing 810. The lead screw void 810A has a diameter larger than the lead screw 850 which ensures that the lead screw 850 passes uninhibited through the lead screw void 810A irrespective of the point on the lead screw 850 at which sliding block assembly 800 is located. The sliding block assembly 800 includes a ribbon cable 562 to receive power from and for communications with the circuit board 1150 (refer to FIG. 58A).

Figure 48B:
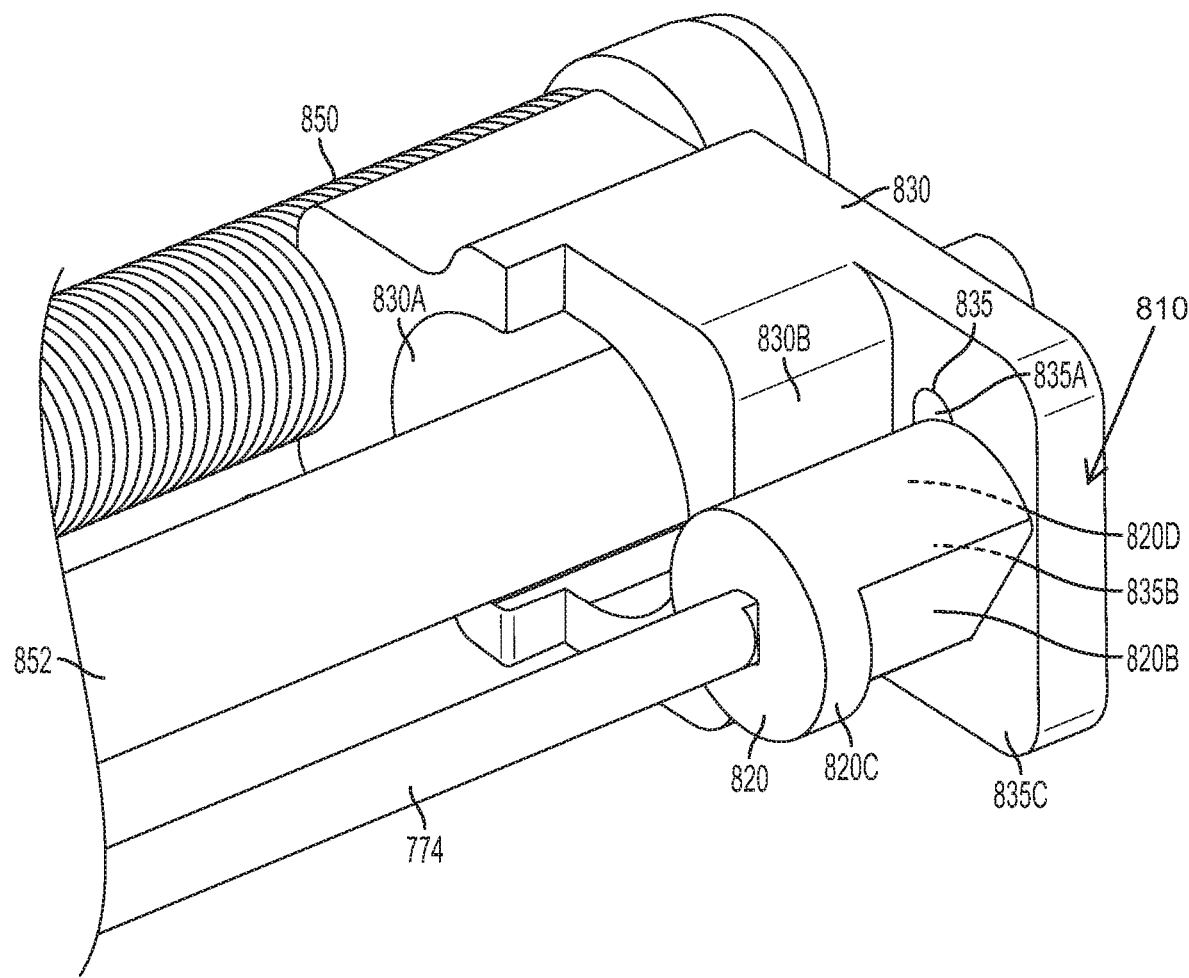
FIG. 48B is a view an exemplary embodiment of the lead screw, half nut, barrel cam, and drive shaft in accordance with an embodiment of the present disclosure.

The half nut housing 810 may also comprise a guide rod bushing 810B. The guide rod bushing 810B in the example embodiment depicted in FIG. 48A is formed as continuous piece of the half nut housing. The guide rod 852 (not shown, see FIG. 48B) extends through the guide rod bushing 810B in the half nut housing 810 with the interior surface of the guide rod bushing 810B serving as a bearing surface for the guide rod 852. In some embodiments, the guide rod bushing 810B may not be formed as a continuous part of the half nut housing 810 but rather coupled to the half nut housing 810 in any number of suitable ways. The guide rod bushing 810B may be made from a lubricious material such as bronze, brass, PTFE, delrin etc., which provides a low friction surface to mate with a hard surface of a guide rod 852 (FIG. 48B).

The half nut housing 810 may also comprise a barrel cam void 810C. The barrel cam void 810C may be sized such that it has a diameter slightly larger than the diameter of the barrel cam 820. When the sliding block assembly 800 is fully assembled, the barrel cam 820 may fit into the barrel cam void 810C on the half nut housing 810. In some embodiments, the barrel cam void 810C may extend all the way through the half nut housing 810. In the example embodiment shown in FIG. 48A, the barrel cam void 810C does not extend all the way through the half nut housing 810. The barrel cam void 810C may function as a bushing for the barrel cam 820 when the sliding block assembly 800 is fully assembled. The barrel cam void 810C and barrel cam 820 may be manufactured with a clearance fit. In one example the diametrical clearance between the barrel cam void 810C and the barrel cam 820 is 0.001 to 0.005 inches.

In some embodiments, including the embodiment depicted in FIG. 48A, the half nut housing 810 may include a half nut void 810D. The half nut void 810D, may be recessed into the half nut housing 810 such that the half nut 830 may fit in the half nut void 810D when the sliding block assembly 800 is fully assembled. In some embodiments, the lead screw void 810A, barrel cam void 810C, and half nut void 810D may all be part of a single void recessed into the half nut housing 810.

The half nut housing 810 may comprise a driven shaft aperture 810E. The driven shaft aperture 810E extends through the half nut housing 810 and into the barrel cam void 810C. In FIG. 48A the driven shaft D-shaped segment or shaft collar 784 is shown protruding into the barrel cam void 810C through the driven shaft aperture 810E.

The half nut housing 810 may additionally comprise a half nut housing groove 810F. In the example embodiment in FIG. 48A, the half nut housing groove 810F is recessed into the half nut housing 810. The half nut housing groove 810F is recessed along the entire side of the half nut housing 810. The half nut housing groove 810F extends in a direction parallel to the direction of elongation of the plunger tube 524, lead screw 850, and guide rod 852 (shown, e.g., in FIG. 48B).

In some embodiments, the half nut housing 810 may comprise at least one limit switch 810G (not shown). In the example embodiment depicted in FIG. 48A, the half nut housing 810 may comprise two limit switches 810G (not shown). One limit switch 810G is located on the front of the half nut housing 810 and the other limit switch 810G is located on the back of the half nut housing 810. The limit switch(es) 810G may be used to limit the range of movement of the sliding block assembly along the lead screw 850 (FIG. 48B). The limit switches 810G will be further elaborated upon later.

As previously mentioned, the barrel cam 820 fits into the barrel cam void 810C in the half nut housing 810 when the sliding block assembly 800 is fully assembled. As shown, the barrel cam 820 comprises a D-shaped orifice 820A which extends through the entire barrel cam 820 along the axial direction of the barrel cam 820. The D-shaped orifice 820A is sized and shaped to allow the barrel cam 820 to be coupled onto the driven shaft D-shaped segment 784. When the D-shaped orifice 820A of the barrel cam 820 is coupled onto the driven shaft D-shaped segment 784 any rotation of the driven shaft 774 and driven shaft D-shaped segment 784 causes the barrel cam 820 to rotate as well. The barrel cam 820 may be joined to the driven shaft 774 in any of the standard methods including but not limited to set screws, pins, adhesive, friction fit, welds, etc.

As shown in FIG. 48A the barrel cam 820 is generally a truncated cylinder, and comprises a barrel cam flat 820B which is cut into the barrel cam 820 along a chord of the front facing base of the cylinder of the barrel cam 820. The barrel cam flat 820B may be cut such that some distance from the barrel cam center-line so that the full diameter of the barrel cam 820 remains. The remaining material of barrel cam 820 on the far side of the centerline relative to the half-nut 830B bearing surface provides a bearing surface to transfer forces from the half-nut 820 to the barrel cam void 820C along the entire length of the barrel cam 820.

The barrel cam flat 820B may not extend along the entire barrel cam 820 leaving some of the cylinder of the barrel cam 820 to have an unadulterated, classic cylindrical shape. This is desirable because the classic cylindrically shaped portion of the barrel cam 820 may act as a journal within the barrel cam void 810C which may act as a bushing. In the example embodiment depicted in FIG. 48A, the barrel cam flat 820B extends along the barrel cam 820 until a barrel cam shoulder 820C begins. The barrel cam shoulder 820C may extend perpendicularly from the surface of the barrel cam flat 820B. In the example embodiment in FIG. 48A, the expanse of the barrel cam 820 with the unadulterated, classic cylindrical shape is the barrel cam shoulder 820C.

As shown, the barrel cam 820 may also comprise a barrel cam pin 820D. The barrel cam pin 820D in the example embodiment in FIG. 48A projects perpendicularly from the front facing base of the cylinder of the barrel cam 820. The barrel cam pin 820D projects from the front facing base of the barrel cam 820 near the chord from which the barrel cam flat 820B has been extended into the cylinder of the barrel cam 820.

The sliding block assembly 800 may also comprise a half nut 830 as mentioned above. In the example embodiment in FIG. 48A, the half nut 830 comprises a half nut slot 835. The half nut slot 835 is sized such that it may act as a track-way for the barrel cam pin 820D. The half nut slot 835 comprises an arcuate section 835A and an end section 835B which is not curved or arced. The half nut slot 835 may be cut into a half nut slot plate 835C which extends perpendicularly from a half nut cam follower surface 830B. The half nut cam follower surface 830B and the half nut slot 835 will be further elaborated on in the following paragraphs.

The half nut 830 may comprise a guide rod bushing void 830A. The guide rod bushing void 830A of the half nut 830 allows the guide rod bushing 810B to pass through the half nut 830. In the example embodiment shown in FIG. 48A, the guide rod bushing void 830A is substantially larger than the diameter of the guide rod bushing 810B. Additionally, the guide rod bushing void 830A in the half nut 830 may have an elliptical shape or stadium shape. Such a shape allows the guide rod bushing 810B to fit comfortably within the guide rod bushing void 830A when the half nut 830 is engaged, disengaged, or in transition between either position.

The half nut 830 may also comprise a span of half nut threads 830C. The half nut threads 830C are capable of engaging the threads of the lead screw 850 (not shown, see FIG. 48B). In the example embodiment shown in FIG. 48A, the half nut threads 830C are V-shaped threads. V-shaped threads may be desirable because such a shape may help to self align the half nut threads 830C on the lead screw 850.

As mentioned above, the sliding block assembly 800 may also comprise a sliding block cover plate 840. The sliding-block, cover plate 840 may be coupled onto the half nut housing 810 such that the barrel cam 820 and half nut 830 are kept in place within the sliding block assembly 800 when the sliding block assembly 800 is fully assembled. In the example embodiment shown in FIG. 48A the sliding block cover plate 840 may be coupled onto the half nut housing 810 by sliding block cover plate screws 840A as shown, or by any suitable means such as, but not limited to, bolts, adhesive, snap fit, friction fit, magnets, welds, a tongue in groove arrangement, pin, etc. The sliding block cover plate 840 may comprise a cover plate groove 840B to assist in guiding the half nut housing 810. The cover plate groove 840B may be recessed into the sliding block cover plate 840. In the example embodiment shown in FIG. 48A the cover plate groove 840B is recessed along an entire side edge of the sliding block cover plate 840. The cover plate groove 840B may sized and disposed such that it lines up with the half nut housing groove 810F on the half nut housing 810.

The sliding block cover plate 840 may comprise a guide rod bushing aperture 840C. The guide rod bushing aperture 840C is sized and disposed such that the guide rod bushing 810B may project through the guide rod bushing aperture 840C. The guide rod bushing aperture 840C may have a diameter substantially equal to, or slightly larger than, the outer diameter of the guide rod bushing 810B.

The edge of the sliding block cover plate 840 opposite the cover plate groove 840B, may comprise a lead screw trough 840D. The lead screw trough 840D may be an arced section recessed into the edge of the sliding block cover plate 840. The lead screw trough 840D, in conjunction with the lead screw void 810A of the half nut housing 810 allows the sliding block assembly 800 to be placed on the lead screw 850.

In operation, the sliding block assembly 800 may be caused to move along the axial direction of the lead screw 850 and guide rod 852 as a result of lead screw 850 rotation. The sliding block assembly 800 may also be moved along the axial direction of the lead screw 850 and guide rod 852 by a user. For a user to move the sliding block assembly 800 along the axial direction of the lead screw 850 the user may need to adjust the location of the plunger head assembly 522 relative to the rest of the syringe pump assembly 501 as shown and described in relation to FIGS. 32-33. This may only be done by a user when the half nut 830 is not engaged with the lead screw 850

FIG. 48B shows the half nut 830 in an engaged position on the lead screw 850. The half nut housing 810, and half nut cover plate 840 visible in FIG. 48A have been removed in FIG. 48B. When the half nut 830 is in engagement with the lead screw 850, the half nut threads 830C may operatively be engaged with the threads of the lead screw 850. Any rotation of the lead screw 850 may cause the half nut 830 to move in the axial direction of the lead screw 850.

To move the half nut 830 between an engaged and disengaged position on the lead screw 850, the barrel cam 820 must be rotated. As the barrel cam 820 is rotated, the barrel cam pin 820D may move along the half nut slot 835 in the half nut slot plate 835C. In the example embodiment shown in FIG. 48B, when the barrel cam pin 820D is located in the arcuate section 835A of the half nut slot 835, the half nut 830 is engaged with the lead screw 850. The arcuate section 835A of the half nut slot 835 may be shaped such that any movement of the barrel cam pin 820D within the arcuate section 835A of the half nut slot 835 does not result in any movement of the half nut 830.

When the barrel cam 820 is rotated such that the barrel cam pin 820D enters the straight, end section 835B of the half nut slot 835, further rotation of the barrel cam 820 may cause the half nut 830 to disengage from the lead screw 850. The straight nature of the end section 835B ensures that the further rotation of the barrel cam 820 causes the barrel cam pin 820D to pull the half nut 830 away from the lead screw 850 until the barrel cam pin 820D reaches the end of the end section 835B. Rotation of the barrel cam 820 in the opposite direction will cause the barrel cam pin 820D to push the half nut 830 back into engagement with the lead screw 850.

In the example embodiment in FIG. 48B, when the barrel cam 820 has disengaged the half nut 830 from the lead screw 850, the half nut cam follower surface 830B rests in the void created by the barrel cam flat 820B. When the half nut 830 is disengaged, the distance between the half nut threads 830C and their point of full engagement on the lead screw 850 is less than or equal to the length of the sagitta of the cylindrical segment removed from the barrel cam 820 to create the barrel cam flat 820B. As the barrel cam 820 is rotated to engage the half nut 830 with the lead screw 850, the pin 820D in the straight, end section 835B moves the half-nut toward the lead screw 850 until the half-nut 830 is at least partial engaged with the lead screw 850. As the pin 820D exits the end section 835B, the untruncated arc of barrel cam 820 rotates onto the half nut cam follower surface 830B of the half nut 830. The untruncated arc of the barrel may push the half nut 830 into full engagement with the lead screw 850 and supplements the action of the barrel cam pin 820D in the half nut slot 835.

Referring back to the example embodiment shown in FIG. 48A, the driven shaft 774 to which the barrel cam 820 is coupled may not deflect when the barrel cam 820 has engaged, disengaged, or is transitioning the half nut 830 from an engaged or disengaged position on the lead screw 850. As shown, the barrel cam void 810C in the half nut housing 810 supports the barrel cam 820 when the sliding block assembly 800 is fully assembled. Consequently, any force promoting deflection of the driven shaft 774 is checked by the barrel cam 820 abutting the sides of the barrel cam void 810C. This ensures that the half nut threads 830C may not skip on the threads of the lead screw 850 under high axial loads. It also creates minimal drag as the sliding block assembly 800 travels along the lead screw 850 with rotation of the lead screw 850.

In some embodiments, the fit of the half nut 830 and the barrel cam 820 may be adjustable. In such embodiments, a portion of the barrel cam housing 810 that defines the barrel cam void 810C may have an adjustable position relative to the guide rod that can be adjusted for example by rotation of a set screw or other adjustment means. This may also allow a user to adjust the barrel cam 820 to an optimal or near optimal position. Alternatively, inserts may be added to the barrel cam void 810C or the barrel cam 820 may be replaced with different sized barrel cam 820 to position the half-nut 830D/barrel cam 820 interface at the optimal location. In such a position, the barrel cam 820 may engage the half nut threads 830C on the lead screw 850 such that there is zero or minimal backlash without loading the half nut threads 830C against the lead screw 850 and creating excessive drag.

In alternate embodiments, the barrel cam pin 820D may be optional. In some alternate embodiments, the barrel cam pin 820D may be replaced by one or more bias members. The bias members may bias the half nut 830 to the disengaged position. In such embodiments, rotation of the barrel cam 820 may cause the half nut 830 engage or disengage with the lead screw 850. When the barrel cam flat 820B is not contacting the half nut cam follower surface 830B the one or more bias members may be overcome and the half nut threads 830C may be engaged with the threads of the lead screw 850. As the barrel cam flat 820B rotates onto the half nut cam follower surface 830B, the bias member(s) may act as a spring return which automatically biases the half nut 830 out of engagement with the lead screw 850 and against the barrel cam flat 820B. The barrel cam 820 may include a transitional cam surface between the barrel cam flat 820 B and the untruncated arc of barrel cam 820 to facilitate displacing the half nut 830 toward the lead screw 850. Use of the barrel cam pin 820D may be desirable because such an arrangement requires less torque to engage or disengage the half nut 830 than embodiments which may employ one or more bias members as a substitute. Some embodiments may use both the barrel cam pin 820D and one or more bias members to effect engagement or disengagement of the half nut 830.

In some embodiments, the bias member may bias the half nut 830 towards the engaged position, in which case, the barrel cam pin 820 may be configured to lift the half nut threads 830C off the lead screw 850.

In another alternative embodiment, the barrel cam 820 may not comprise a barrel cam pin 820D and the half nut 830 may not comprise a half nut slot 835. In such embodiments, the barrel cam flat 820B may comprise a magnet and the half nut cam follower surface 830B may also comprise a magnet. Instead of using the barrel cam pin 820D to pull the half nut 830 away from the lead screw 850, the magnet on the half nut cam follower surface 830B may be attracted to the magnet on the barrel cam flat 820B and be pulled off the lead screw 850 toward the barrel cam flat 820B when the barrel cam 820 has been rotated the appropriate amount. In some embodiments, the barrel cam 820 may be a simple two pole magnet. In such embodiments, the barrel cam 820 may be disposed such that it may repel or attract a magnet on the half nut cam follower surface 830B. When like poles of the magnets face each other, the half nut is forced into engagement with the lead screw 850. By rotating the driven shaft 774 and therefore the magnetic barrel cam 820, opposite poles may be made to face each other. In turn, this may cause the half nut 830 to disengage from the lead screw 850 as it is attracted to the magnetic barrel cam 820.

In some embodiments, a magnet may be configured to bias the half nut 830 towards the engaged position, in which case, the barrel cam pin 820 may be configured to lift the half nut threads 830C off of the lead screw 850.

The guide rod 852 is also visible in FIG. 48B. In FIG. 48B the guide rod 852 extends in an axial direction parallel to that of the lead screw 850. The guide rod passes through the guide rod bushing void 830A in the half nut 830. In the example embodiment, the guide rod 852 is made of a hard and durable material. For example, in some embodiments, the guide rod 852 may be made of a material such as stainless steel. In other embodiments, the guide rod 852 may be chromium plated.

Figure 49:
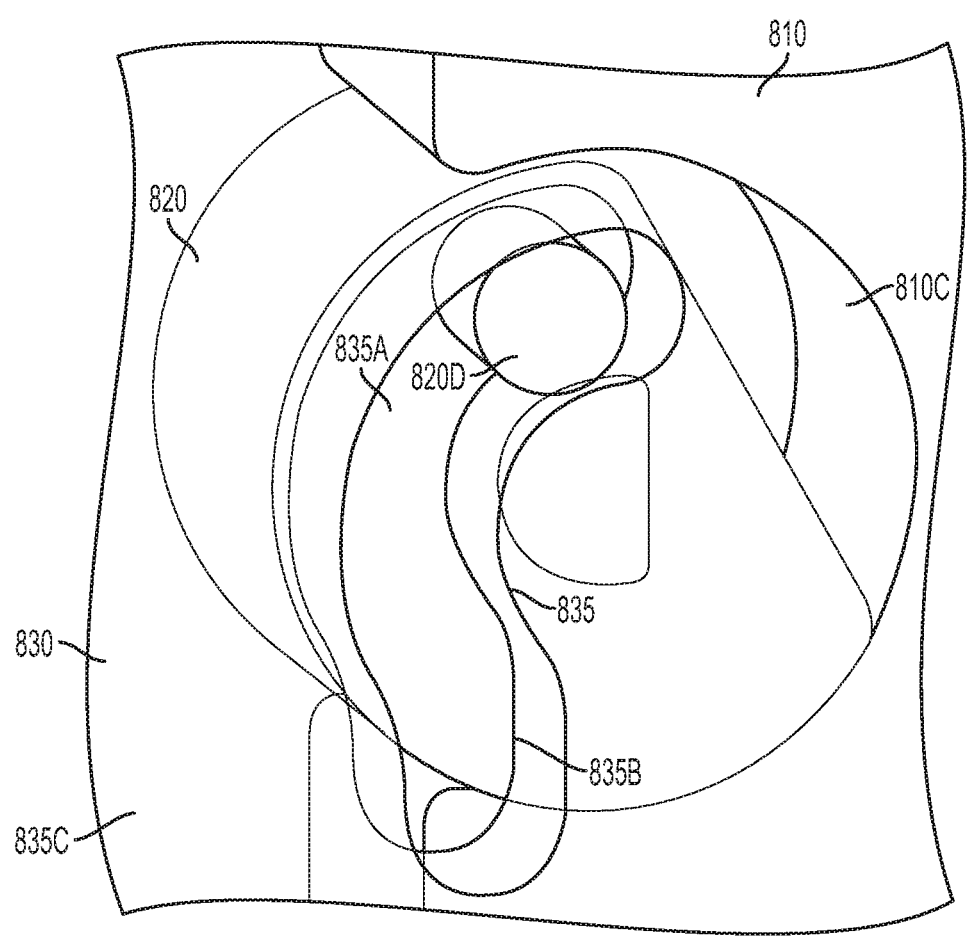
FIG. 49 is a partial front view of an exemplary embodiment of the half nut and barrel cam in which the half nut is shown as transparent in accordance with an embodiment of the present disclosure.

FIG. 49 shows a close up view of the half nut slot plate 835C. The half nut slot plate 835C is transparent in the FIG. 49. The half nut slot 835 is shown in the half nut slot plate 835C. As described above, the half nut slot 835 comprises an arcuate section 835A and a straight, end section 835B. The barrel cam 820 is shown behind the transparent half nut slot plate 835C. As shown, the barrel cam pin 820D is located in the arcuate section 835A of the half nut slot 835. As mentioned above, when the barrel cam pin 820D is in the arcuate section 835A of the half nut slot 835 the half nut 830 is engaged with the lead screw 850 as shown in FIG. 48B. The barrel cam 820 is disposed in the barrel cam void 810C in the half nut housing 810. The barrel cam void 810C acts as a bushing for the barrel cam 820 and supports the barrel cam 820.

Figure 50:
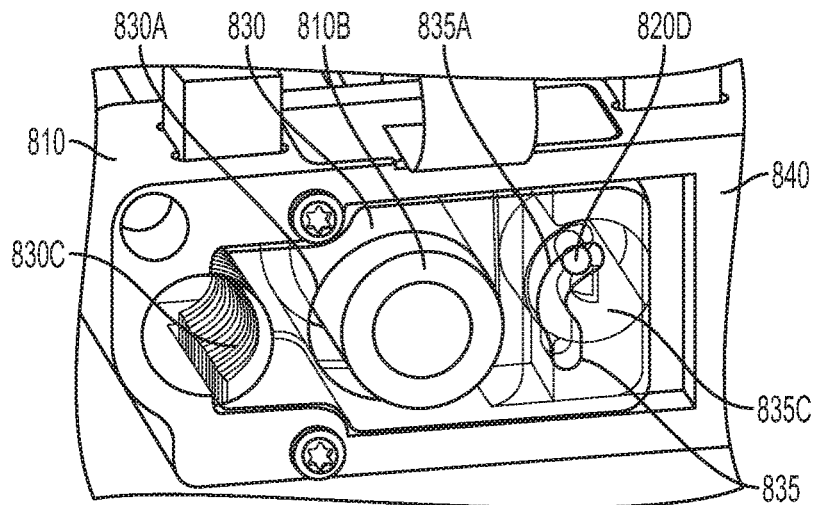
FIG. 50 is a front view of an exemplary embodiment of the sliding block assembly in which the half nut is in an engaged position in accordance with an embodiment of the present disclosure.
Figure 51:
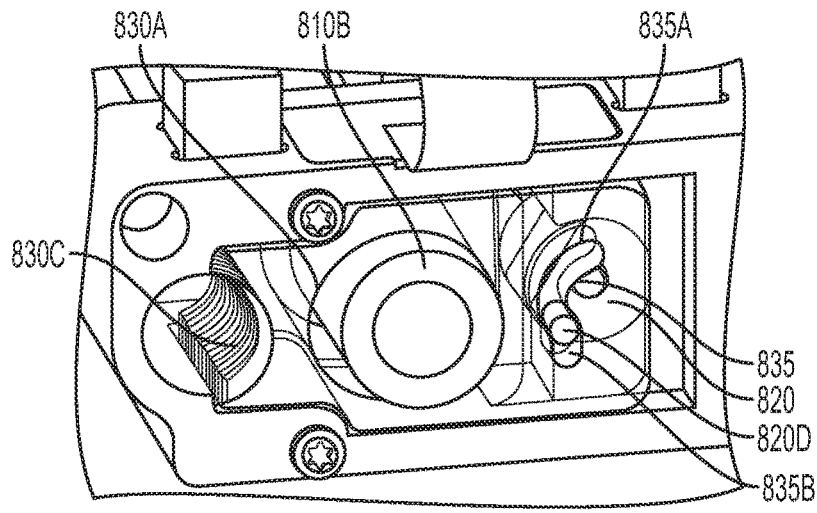
FIG. 51 is a front view of an exemplary embodiment of the sliding block assembly in which the half nut is in the engaged position in accordance with an embodiment of the present disclosure.
Figure 52:
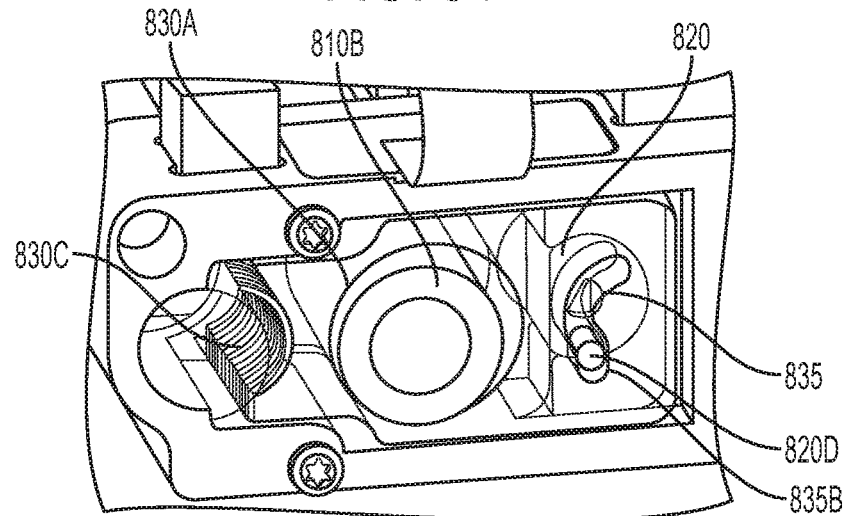
FIG. 52 is a front view of an exemplary embodiment of the sliding block assembly in which the half nut is in the disengaged position in accordance with an embodiment of the present disclosure.

FIGS. 50-52 show sliding block assembly 800 with the half nut cover plate 840 and half nut 830 shown as transparent. In FIGS. 50-52, the half nut 830 transitions from an engaged position (FIG. 50) to a disengaged position (FIG. 52). As shown in FIG. 50 the half nut 830 is in the engaged position. The barrel cam pin 820D is located in arcuate section 835A of the half nut slot 835. The half nut threads 830C are at the far left extent (relative to FIGS. 50-52) of their range of movement. The guide rod bushing 810B of the half nut housing 810 projects through the guide rod bushing void 830A of the half nut 830. As shown, the guide rod bushing 810B is located at the far right end of the guide rod bushing void 830A. In the example embodiment shown in FIGS. 50-52 the guide rod bushing void 830A in the half nut 830 is roughly stadium shaped.

The barrel cam 820 has been rotated such that the barrel cam pin 820D is about to cross from the arcuate section 835A of the half nut slot 835 and into the end section 835B of the half nut slot 835 in FIG. 51. As shown, the half nut threads 830C have not moved from the engaged position and are still at the far left extent (relative to FIGS. 50-52) of their range of movement. Similarly, the half nut 830 may not have moved relative to the guide rod bushing 810B from the position depicted and described in relation to FIG. 50.

In FIG. 52 the barrel cam 820 has been rotated such that the barrel cam pin 820D has moved into the straight, end section 835B of the half nut slot 835. As described above, further rotation of the barrel cam 820 once the barrel cam pin 820D enters the end section 835B of the half nut slot 835 causes the half nut 830 to disengage. As shown, the half nut 830, and consequentially the half nut threads 830C, have moved from the far left extent (relative to FIGS. 50-52) of their range of movement and toward the right of the page. The half nut 830 has moved in relation to the guide rod bushing 810B, such that the guide rod bushing 810B is now near the far left end of the guide rod bushing void 830A.

Figure 53:
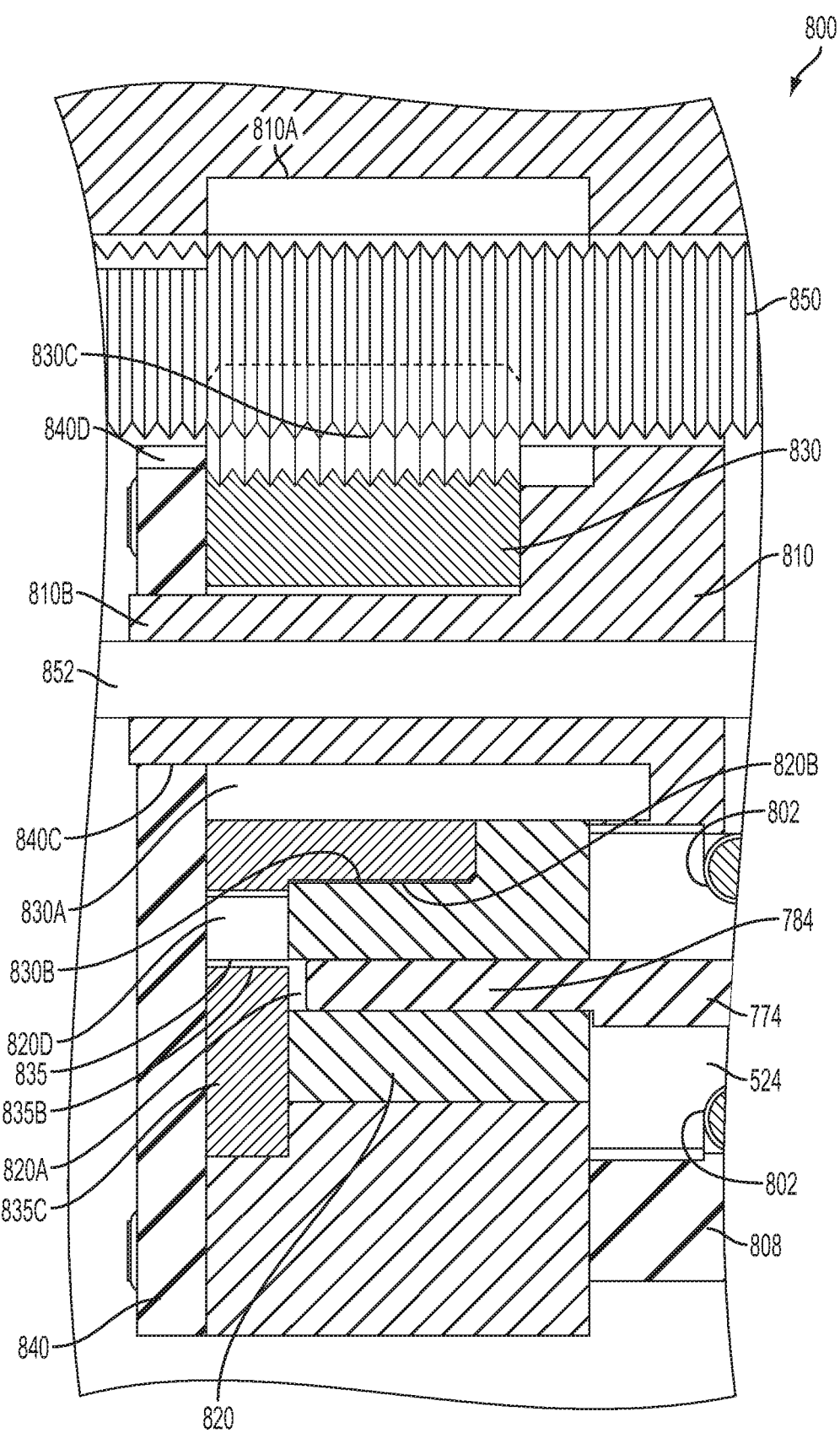
FIG. 53 is a cross sectional view of an exemplary embodiment of the sliding block assembly on the lead screw and guide rod in accordance with an embodiment of the present disclosure.

FIG. 53 shows a cross section of most of the components comprising an embodiment of the sliding block assembly 800. The sliding block assembly 800 is depicted fully assembled in FIG. 53. The lead screw 850 and guide rod 852 are not depicted in cross section in FIG. 53. As shown, the lead screw 850 extends through the lead screw void 810A in the half nut housing 810 and over the lead screw trough 840D in the half nut cover plate 840. The guide rod extends through the guide rod bushing 810B. The guide rod bushing 810B extends through both the guide rod bushing void 830A in the half nut 830 and the guide rod bushing aperture 840C in the half nut cover plate 840.

In the example embodiment shown in FIG. 53, the half nut 830 is in the disengaged position. The half nut threads 830C are not operatively interdigitated with the threads of the lead screw 850. The guide rod bushing 810B is near the top of the guide rod bushing void 830A in the half nut 830. The half nut cam follower surface 830B is near or is abbuting (depending on the embodiment) the barrel cam flat 820B on the barrel cam 820. Additionally, the barrel cam pin 820D is at the end of the straight, end section 835B of the half nut slot 835 which is cut into the half nut slot plate 835C.

FIG. 53 also shows the D-shaped orifice 820A of the barrel cam 820 coupled onto the driven shaft D-shaped segment 784 of the driven shaft 774. The plunger tube 524 through which the driven shaft 774 is disposed can be seen coupled onto the sliding block assembly 800 by means of screws running through the plunger tube cutouts 802 and into the plunger tube support 808.

Figure 54:
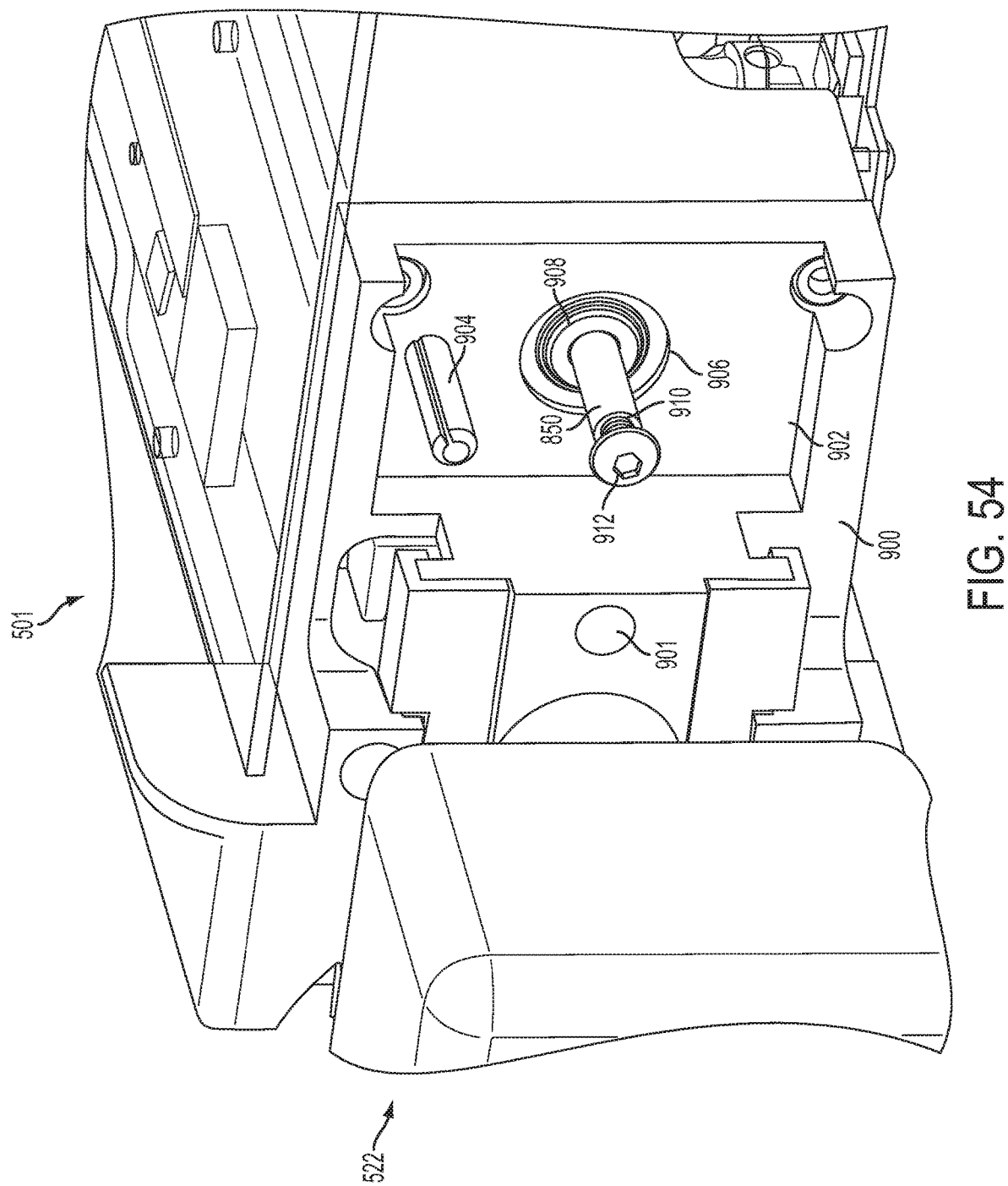
FIG. 54 is a view of an exemplary embodiment of the rear face of the syringe pump assembly in accordance with an embodiment of the present disclosure.

FIG. 54 shows a view of a portion of an embodiment of the syringe pump assembly 501. At the left side of FIG. 54, a section of the plunger head assembly 522 is visible. As shown in FIG. 54, the rear face 900 of the syringe pump assembly 501 may comprise a rear face guide rod hole 901. The rear face guide rod hole 901 may run through the entire rear face 900 of the syringe pump assembly 501 at an angle perpendicular to the rear face 900 of the syringe pump assembly 501. As shown, the guide rod hole 901 may be substantially cylindrical.

The rear face 900 of the syringe pump assembly 501 may comprise a gearbox depression 902. As shown, the gearbox depression 902 is recessed into the rear face 900 of the syringe pump assembly 501. In the example embodiment, the gearbox depression 902 is a roughly rectangular shaped depression. In other embodiments, the gearbox depression 902 may have alternative shapes.

As shown in FIG. 54, an anti-rotation pin 904 projects out of the gearbox depression 902. The anti-rotation pin 904 in the example embodiment shown in FIG. 54 is cylindrical. In alternate embodiments, the anti-rotation pin 904 may take any other suitable shape. As shown in FIG. 54, the gearbox depression 902 in the rear face 900 of the syringe pump assembly 501 may also comprise a lead screw void 906. The lead screw void 906 may be cut all the way through the rear face 900 of the syringe pump assembly 501 and allow at least a portion of the lead screw 850 to project beyond of the rear face 900 of the syringe pump assembly 501. As shown in the example embodiment, the section of the lead screw 850 which projects beyond the rear face 900 of the syringe pump assembly 501 is not threaded.

In the example embodiment shown in FIG. 54, the section of the lead screw 850 that is visible is smaller in diameter than the lead screw void 906. This is desirable because it may allow a rear face lead screw bearing 908 to be placed in the lead screw void 906 to provide a bearing surface for the lead screw 850. In the example embodiment in FIG. 54 a lead screw bearing is disposed in the lead screw void 906 to provide a bearing surface for the lead screw 850.

As shown, the end of the of the section of the lead screw 850 which projects out of the rear face 900 may comprise a threaded bore 910. In the example embodiment shown in FIG. 54, a gearbox attachment fastener 912 is coupled into the threaded bore 910 on the end of the lead screw 850. In the example embodiment, the gearbox attachment fastener 912 is a screw with a hex socket head. In other embodiments, any other suitable fastener, or fastener head may be used.

Figure 55:
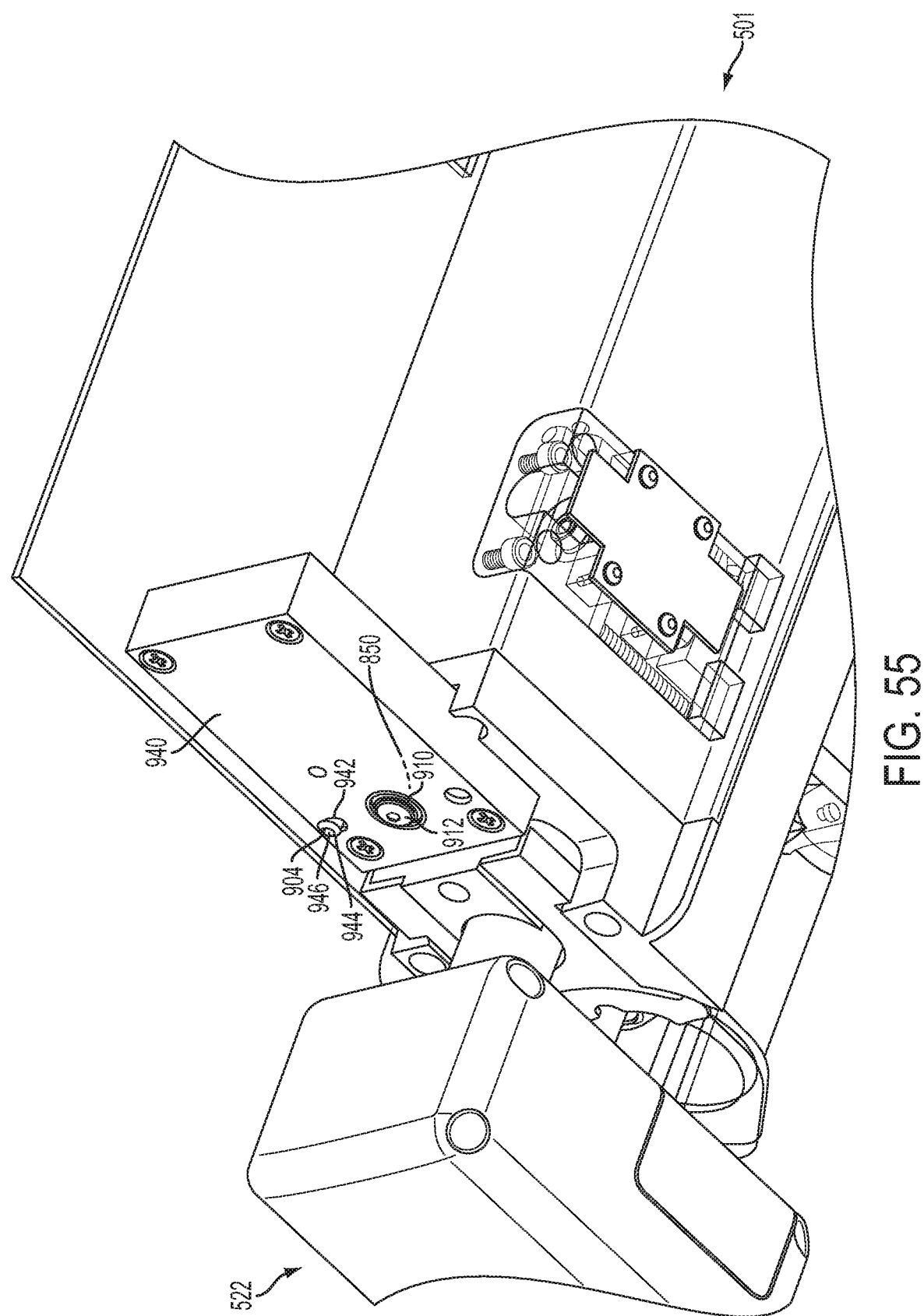
FIG. 55 is another view of an exemplary embodiment of the rear face of the syringe pump assembly with the gearbox in place in accordance with an embodiment of the present disclosure.

In FIG. 55, another view of a portion of an embodiment of the syringe pump assembly 501 is shown. At the left side of FIG. 55, part of the plunger head assembly 522 is also visible. The gearbox 940 is shown in place in the gearbox depression 902 on the rear face 900 of the syringe pump assembly 501. As shown, the anti-rotation pin 904 may project through an anti-rotation pin hole 942 in the gearbox 940. The anti-rotation pin 904 ensures that the gearbox 940 causes rotation of the lead screw 850 and that the gearbox 940 may not rotate around the axis of the lead screw 850. As shown, the anti-rotation pin 942 does not help to hold the gearbox 940 against the rear face 900 of the syringe pump assembly 501. In alternate embodiments, the anti-rotation pin 904 may have a threaded anti-rotation pin bore 944 (not shown) similar to that of the end of the lead screw 850 described in above in relation to FIG. 54. An anti-rotation pin gearbox fastener 946 may be threaded into the thread anti-rotation pin bore 944 to help hold the gearbox 940 against the back face 900 of the syringe pump assembly 501. The gearbox 940 may be friction locked onto the lead screw 850 to ensure that rotation of the gears in the gearbox 940 is transmitted to the lead screw 850 with zero or minimal backlash.

In embodiments where the syringe pump assembly 501 may be removed from the housing 502 (see FIG. 28) and replaced with another assembly such as a peristaltic large volume pump assembly, the gearbox 940 may be compatible with a replacement assembly.

Figure 56:
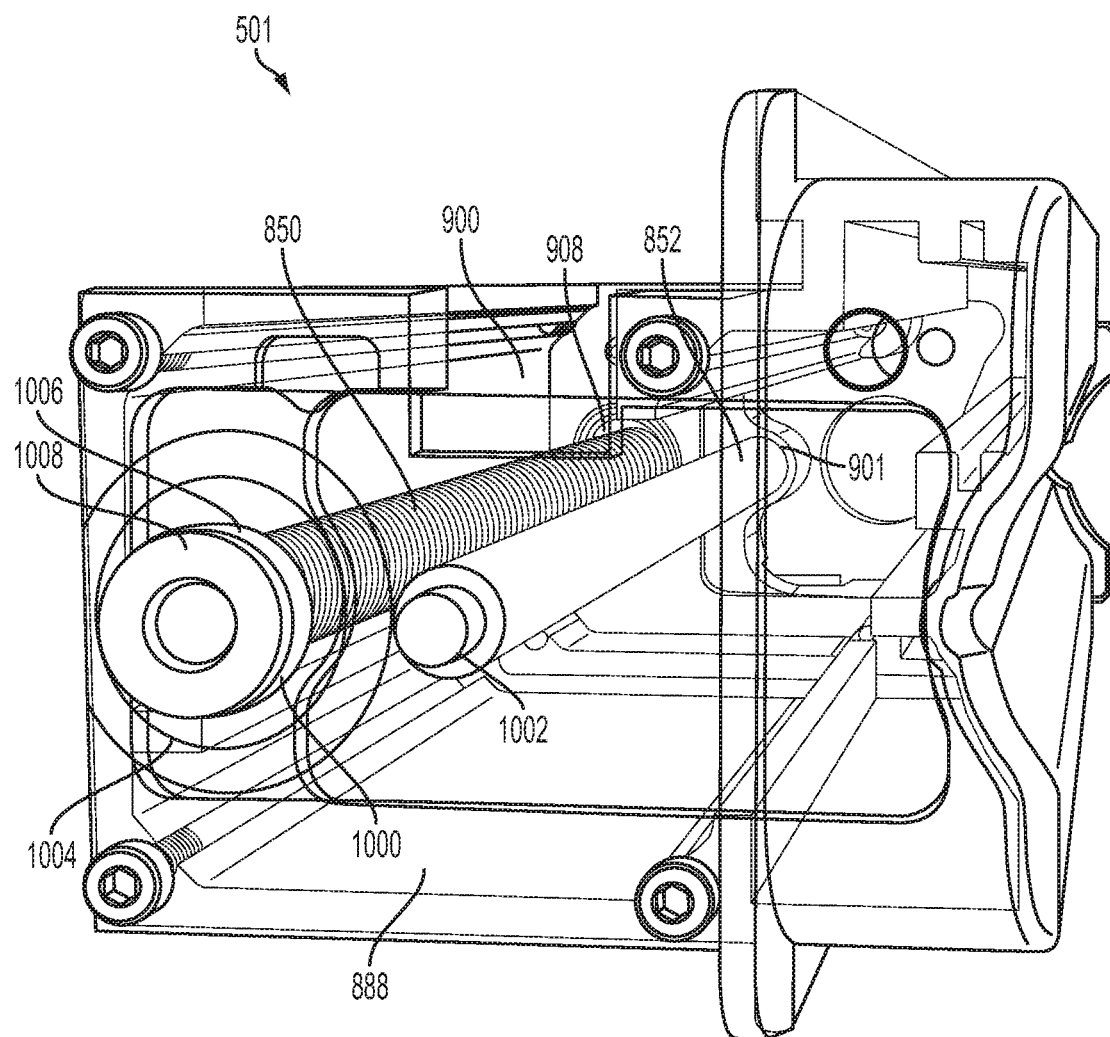
FIG. 56 is an interior view of an exemplary embodiment of the syringe pump assembly in accordance with an embodiment of the present disclosure.

FIG. 56 shows an embodiment of the interior of the syringe pump assembly 501. As shown, the front face 888 of the syringe pump assembly 501 is shown as transparent. As shown, the guide rod 852 projects perpendicularly from the interior of the rear face 900 of the syringe pump assembly 501 and toward the front of the page. The lead screw 850 may similarly project into the interior of the syringe pump assembly 501 through the rear face lead screw bearing 908 at an angle perpendicular to the interior of the rear face 900 of the syringe pump assembly 501. The guide rod 852 and lead screw 850 may run parallel to each other. In the example embodiment in FIG. 56, the lead screw 850 is offset toward the left of the page from the guide rod 852.

As shown, one end of the guide rod 852 is seated in the rear face guide rod hole 901. The other end of the guide rod 852 is seated in the front face 888 of the syringe pump assembly 501. In the example embodiment depicted in FIG. 56, the end of the guide rod 852 facing the front of the page is smaller in diameter than the rest of the guide rod 852. This section of the guide rod 852 may be placed in a guide rod hole 1002 in the front face 888 of the syringe pump assembly 501 when the syringe pump assembly 501 is fully assembled. The guide rod hole 1002 may extend through the entire front face 888 of the syringe pump assembly 501 at an angle substantially perpendicular to the front face 888. The smaller diameter section of the guide rod 852 may have a diameter slightly though not substantially smaller than the diameter of the guide rod hole 1002 such that the guide rod 852 may fit snuggly in the guide rod hole 1002 when the syringe pump assembly 501 is assembled. The end of the guide rod 852 may be flush with the plane of the front face 888 of the syringe pump assembly 501. Though both the guide rod hole 1002 and the section of the guide rod 852 seated in the guide rod hole 1002 are cylindrical in the example embodiment shown in FIG. 56, their shape may differ in alternate embodiments.

The lead screw 850 is seated in a lead screw depression 1000 in the front face 888 of the syringe pump assembly 501. In the example embodiment shown in FIG. 56, the depth of the lead screw depression 1000 is substantially the thickness of the front face 888 of the syringe pump assembly 501. In embodiments where the depth of the lead screw depression 1000 is substantially the depth of the front face 888, a circular plateau 1004 may be raised off the front face 888 of the syringe pump assembly 501 to accommodate the depth of the lead screw depression 1000. The center of the circular plateau 1004 may be concentric with the center of a cylindrical lead screw depression 1000 as shown in FIG. 56. In some embodiments, the edges of the circular plateau 1004 may extend perpendicularly from the front face 888 of the syringe pump assembly 501 to the raised circular plateau. In the example embodiment illustrated in FIG. 56, the edges of the circular plateau 1004 curve up from the front face 888 of the syringe pump assembly 501 to the circular plateau 1004.

As shown, the lead screw depression 1000 may house a front face lead screw bearing 1006 which surrounds the end of the lead screw 850 and provides a bearing surface for the lead screw 850. In some embodiments, such as the embodiment depicted in FIG. 56, a Belleville washer 1008 may be seated against the bottom of the lead screw depression 1000. The Belleville washer 1008 may ensure that there is no "play" of the lead screw 850 when the lead screw 850 is seated in the lead screw depression 1000.

In some embodiments, the Belleville washer 1008 may be replaced by non-compliant end cap which loads the front face lead screw bearing 1006 against the lead screw 850. In such embodiments, the end cap may be threaded on its out diameter. The lead screw depression 1000 may feature complimentary threads to which the end cap may screw into. Again the end cap may also ensure that there is no "play" of the lead screw 850 when the lead screw 850 is seated in the lead screw depression 1000.

FIG. 57 shows a view of the interior of the syringe pump assembly 501. The front face 888 which is shown as transparent in FIG. 56, is not present in FIG. 57. As shown, the sliding block assembly 800 described above is in place within the syringe pump assembly 501. The guide rod 852 extends through the guide rod bushing 810B in the half nut housing 810. The when the half nut 830 is disengaged from the lead screw 850, the sliding block assembly 800 may be free to slide about the axial direction of the guide rod 852.

Movement of the sliding block assembly 800 is also guided by a syringe pump assembly guide rail 1010. In the example embodiment shown in FIG. 57, the syringe pump assembly guide rail 1010 extends from the interior face of the syringe seat 506. The syringe pump assembly guide rail 1010 is shaped such that the half nut housing groove 810F and cover plate groove 840B on the sliding block assembly 800 may fit on the syringe pump assembly guide rail 1010 and slide along the syringe pump assembly guide rail 1010. The syringe pump assembly guide rail 1010 also ensures that the sliding block assembly 800 may not rotate within the syringe pump assembly 501. The syringe pump assembly guide rail 1010 may be formed as part of the extrusion in embodiments where the syringe pump assembly housing 503 is formed by extrusion.

As shown in FIG. 57, when half nut 830 of the sliding block assembly 800 is engaged with the lead screw 850, the lead screw 850 may cause linear movement of the sliding block assembly 800 along the axial direction of the lead screw 850. To cause linear movement of the sliding block assembly 800, the lead screw 850 must be rotated. In the example embodiment in FIG. 57, the rotational motion of the lead screw 850 causes the half nut 830 and consequently the sliding block assembly 800 to move along the lead screw 850 due to the pitch of the threads of the lead screw 850. The amount of linear movement per 360° rotation of the lead screw 850 may vary depending on the pitch of the threads of the lead screw 850 which may differ in various embodiments.

As mentioned above, the half nut housing 810 of the sliding block assembly 800 may comprise one or more limit switches 810G. In the example embodiment in FIG. 57, a limit switch 810G is not shown, although it is indicated that a limit switch 810G may be located on the front of the half nut housing 810. In other embodiments, there may be multiple limit switches 810G which may be disposed about other portions of the sliding block assembly 800. In embodiments where a limit switch may be disposed on the front of the half nut housing 810, the limit switch 810G may prevent the sliding block assembly 800 from being driven into the front face 888 (shown in FIG. 56) of the syringe pump assembly 501.

In embodiments comprising a limit switch 810G, the limit switch 810G may be a micro switch, although hall sensors and magnets, optical sensors, etc. could also be used. In embodiments where the limit switch 810G comprises a micro switch, the micro switch may be actuated when the sliding block assembly 800 nears a predefined location along the lead screw 850. In some embodiments, when the limit switch 810G is in the actuated position, the lead screw 850 may not be further rotated to advance the sliding block assembly 800 in the direction of the predefined location.

As shown in FIG. 57, the syringe pump assembly 501 may additionally comprise a sliding block linear position sensor 1050 to determine the sliding block assembly's 800 location on the lead screw 850. In some embodiments, the sliding block linear position sensor 1050 may be used to determine the amount of contents left in a syringe 504 which may be in place on the syringe pump assembly 501. In such embodiments, the sliding block linear position sensor 1050 may be used to determine a quantified volume of syringe 504 contents or may be used as a "gas gauge" which generates a more general syringe 504 contents volume reading.

In some embodiments, the sliding block linear position sensor 1050 may comprise a linear potentiometer. In such embodiments, the wiper of the sliding block linear position sensor 1050 may be disposed such that it slides across the resistive element of the potentiometer with movement of the sliding block assembly 800 along the lead screw 850. The resistance measured by the sliding block linear position sensor 1050 may be used to determine the location of the sliding block assembly 800 along the lead screw 850.

In some embodiments, including the example embodiment shown in FIG. 57, the sliding block linear position sensor 1050 may comprise an array of sliding block magnetic linear position sensors 1054. The sliding block magnetic linear position sensors 1054 may be any suitable magnetic linear position sensor. An example of a suitable magnetic linear position sensor is the "AS5410 Absolute Linear 3D Hall Encoder" available from Austriamicrosystems of Austria. As shown, the sliding block assembly 800 may include a sliding block assembly magnet 1056 which is mounted a suitable distance away from the sliding block magnetic linear position sensors 1054 and may be used in conjunction with the array of sliding block magnetic linear position sensors 1054 in order to determine the location of the sliding block assembly 800 on the lead screw 850. In some embodiments, the location of the sliding block magnetic linear position sensors 1054 may differ. As shown, the sliding block 800 includes a second magnet 1057 disposed such that it may interact with the sliding block magnetic linear position sensors 1054 when they are placed in an alternate location.

Figure 57A:
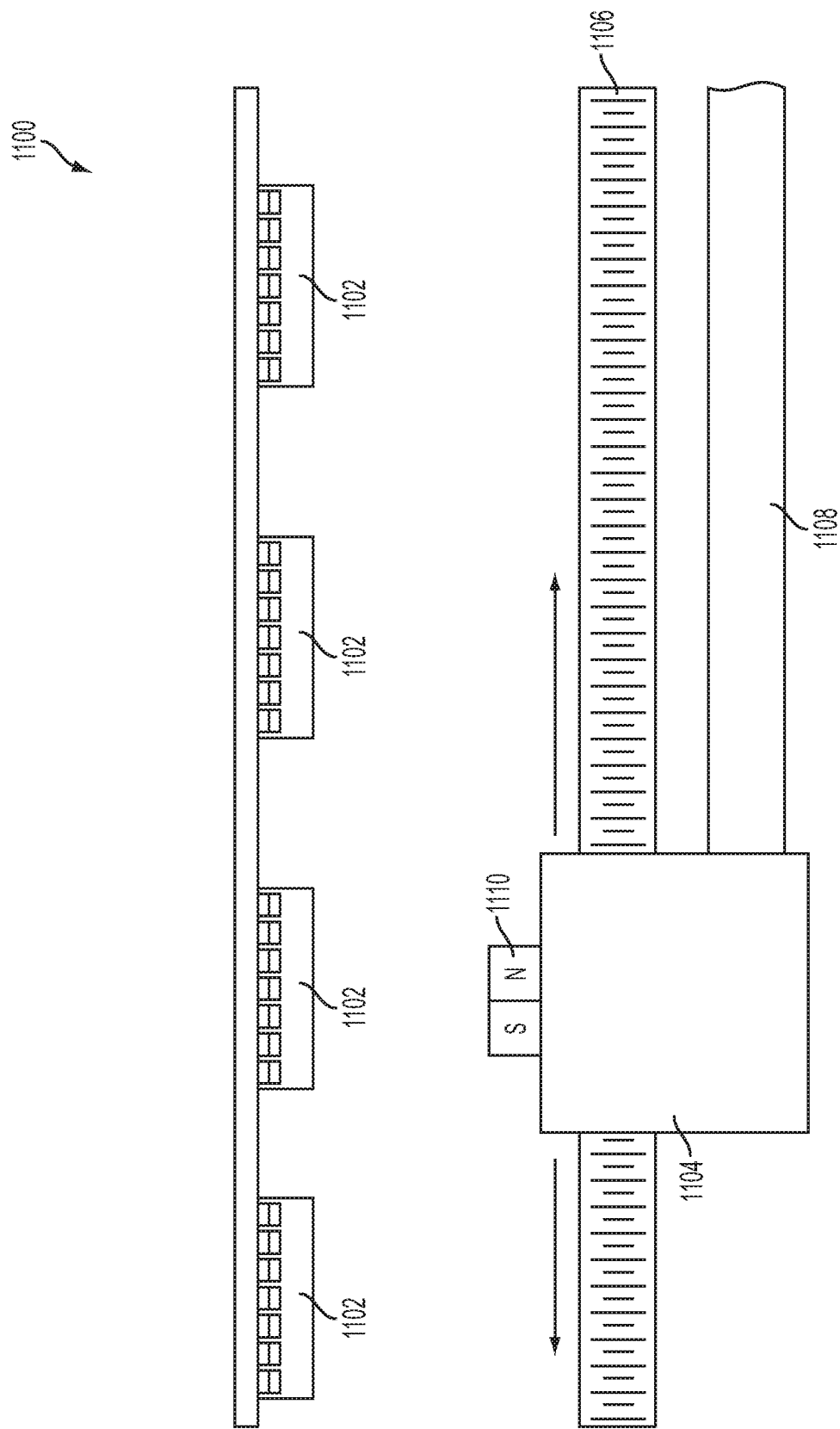
FIG. 57A is a top view of an embodiment of a magnetic linear position sensor in accordance with an embodiment of the present disclosure.

FIG. 57A shows an example of a possible linear position sensor 1100 arrangement to estimate the position of a sliding block assembly 800. In the example linear position sensor 1100 arrangement, the linear position sensor 1100 comprises an array of magnetic linear position sensors 1102 such as the "AS5410 Absolute Linear 3D Hall Encoder" available from Austriamicrosystems of Austria mentioned above. A position changing block 1104 (e.g., the sliding block assembly 800) is depicted at a position along a position changing block lead screw 1106. A position changing block arm 1108 projects off the page as indicated by the broken line defining its rightmost edge. An object attached to the position changing block arm 1108 may be caused to move with the position changing block 1104 as the position changing block 1104 moves along the lead screw 1106. The position changing block 1104 in FIG. 57A may be considered the sliding block assembly 800 in FIG. 57.

In the example linear position sensor 1100 arrangement shown in FIG. 57A, the position changing block 1104 comprises a position changing block magnet 1110. As shown, the position changing block magnet is located on the face of the position changing block closest to the array of magnetic linear position sensors 1102. The position changing block magnet 1110 is a dipole magnet. The north pole of the position changing block magnet 1110 is oriented to face toward the right of the page while the south pole faces the left of the page. As the position changing block 1104 moves along the position changing block lead screw 1106, the position changing block magnet 1110 also moves. This movement may be measured by the array of magnetic linear position sensors 1102 and analyzed to determine an absolute location of the position changing block 1104 along the position changing block lead screw 1106. In some embodiments, the array of magnetic linear position sensors 1102 may be used to determine differential movements of the position changing block 1104.

Figure 58:
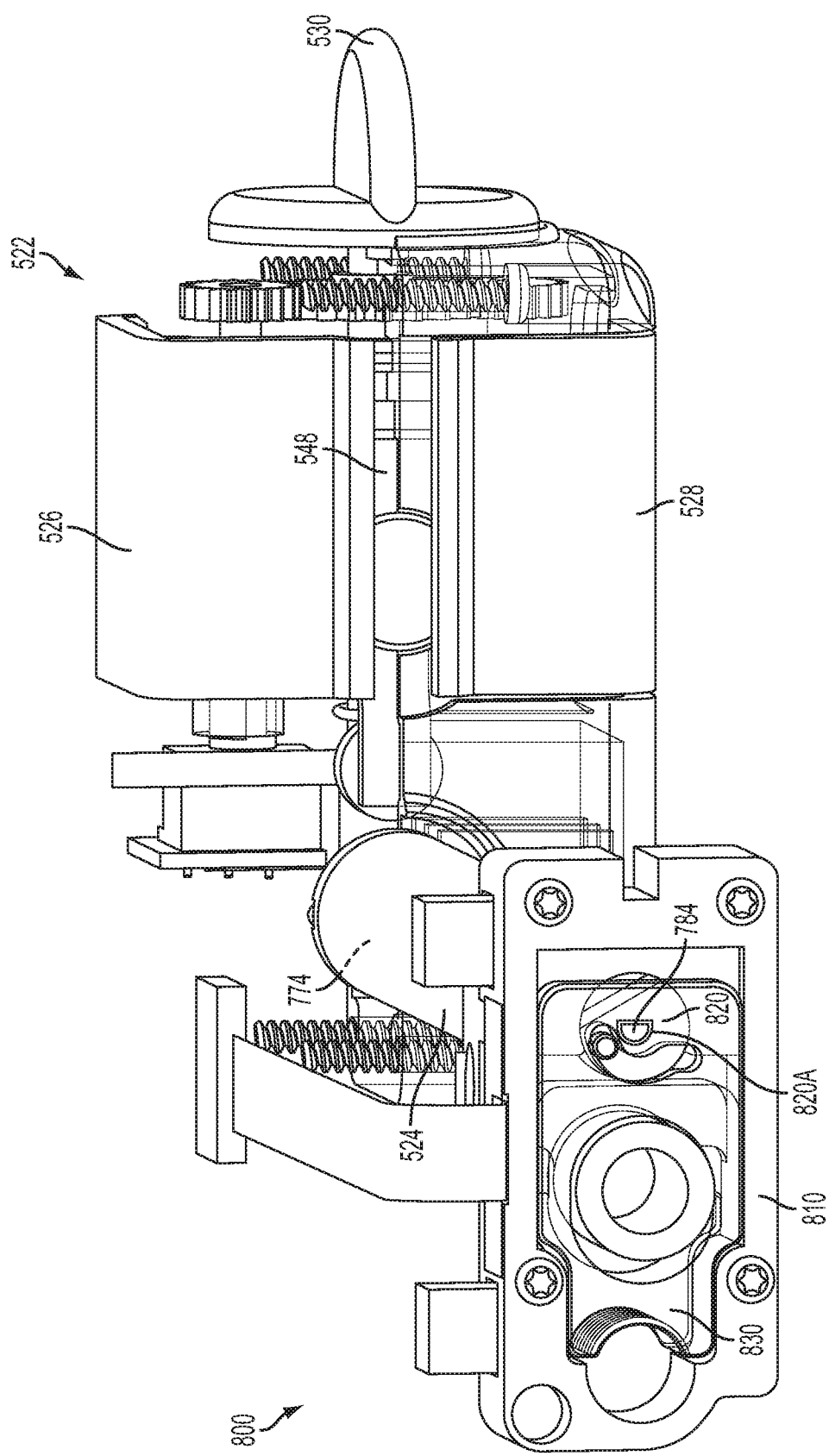
FIG. 58 is a partially assembled front view of an exemplary embodiment of the sliding block assembly, plunger tube, and plunger head assembly in accordance with an embodiment of the present disclosure.

As shown in FIG. 58 an embodiment of the sliding block assembly 800 is shown assembled with the half nut cover plate 840 (see FIG. 48) removed. The half nut 830 is depicted in the engaged position and is shown as transparent so that the half nut housing 810 and the barrel cam 820 may be seen behind it. The driven shaft D-shaped segment 784 of the driven shaft 774 is shown in the D-shaped orifice 820A of the barrel cam 820. The driven shaft 774 extends through the plunger tube 524 which couples the sliding block assembly 800 and plunger head assembly 522 together.

Referring back to FIG. 42, the driven shaft 774 couples into a double universal joint 772. The double universal joint 772 translates any rotational motion from the dial 530 which rotates the dial shaft 650 to rotational motion of the driven shaft 774. Rotational motion of the driven shaft 774 in turn causes rotation of the barrel cam 820. Rotation of the barrel cam 820 engages or disengages the half nut 830 as described above.

As also detailed above, rotation of the dial 530 causes linear displacement of the upper plunger clamp jaw 526 and lower plunger clamp jaw 528. The dial 530 is thus multifunctional. When rotated, the dial 530 both engages or disengages the half nut 830 and opens or closes the upper plunger clamp jaw 526 and lower plunger clamp jaw 528. It should be noted that the arcuate section 835A of the half nut slot 835 is shaped such that the half nut 830 does not begin to disengage until the largest plunger flange 548 (not shown) which can be accepted by the upper plunger clamp jaw 526 and lower plunger clamp jaw 528 has been released by the upper plunger clamp jaw 526 and lower plunger clamp jaw 528. When the plunger flange 548 (not shown) has been released and the half nut 830 has disengaged, the dial shaft cam follower 658 on the dial shaft 650 may sit in the dial shaft cam detents 660 of the dial shaft cam 654 as described in relation to FIG. 43. As put forth in the detailed description of FIG. 43, this would allow a user to "park" the dial 530 in the fully rotated position where the half nut 830 is disengaged and the upper plunger clamp jaw 526 and lower plunger clamp jaw 528 are in the open position. In the example embodiment depicted in FIG. 58, when the dial 530 is in the "parked" position, a user may remove their hand from the dial 530 and easily adjust the plunger head assembly 522 so that a syringe 504 (not shown) may be inserted onto the syringe pump assembly 501 (see FIGS. 30-34 for example illustrations and discussion of syringe 504 placement onto the syringe pump assembly 501).

Figure 59A:
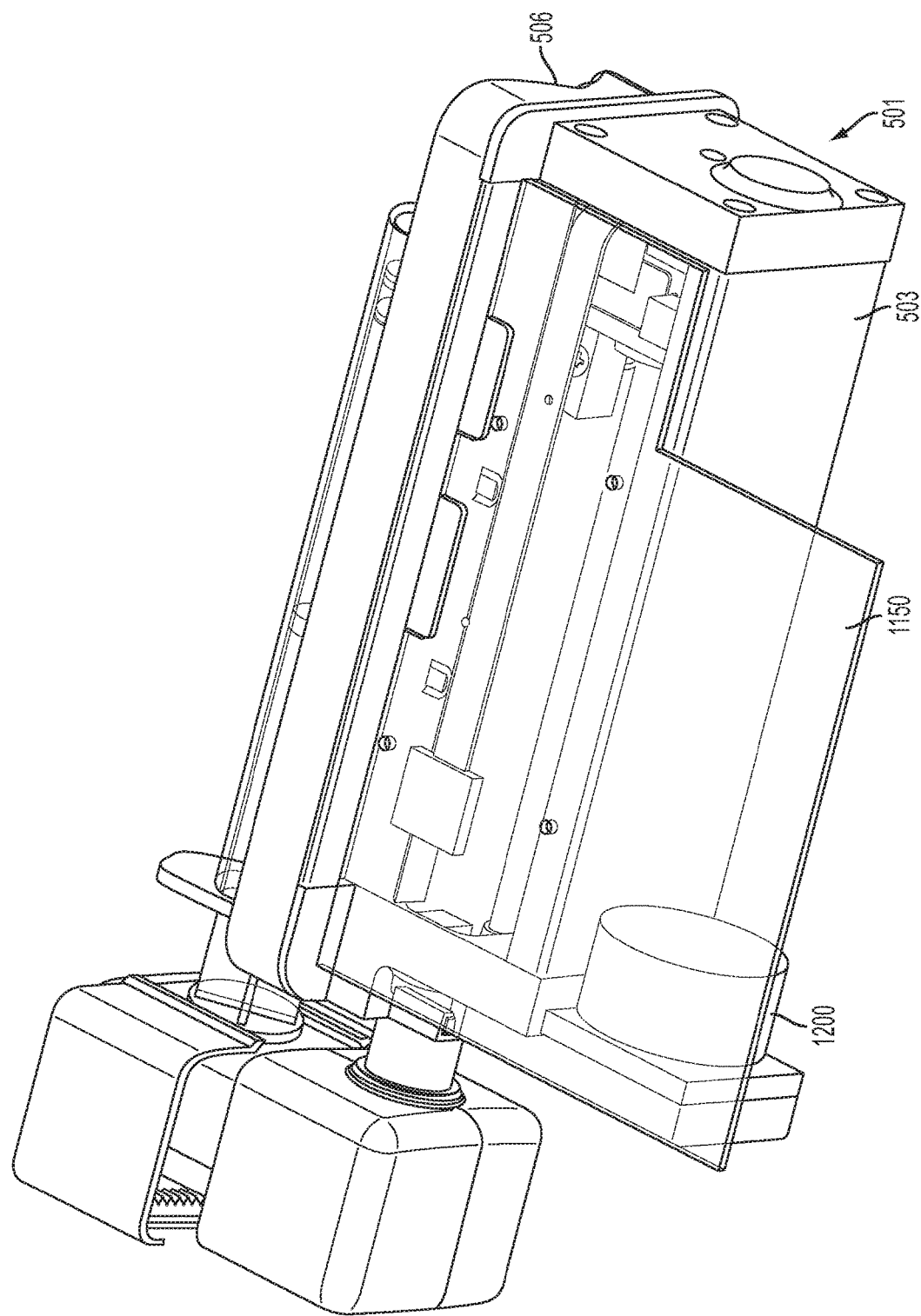
FIG. 59A is a view of an exemplary embodiment of the syringe pump assembly in accordance with an embodiment of the present disclosure.

FIG. 59A shows an embodiment of the syringe pump assembly 501. As shown, the syringe pump assembly 501 is fully assembled. A syringe 504 is seated on the syringe seat 506 of the syringe pump assembly housing 503. The gearbox 940 is shown in place on the syringe pump assembly 501. The motor 1200 which drives the gearbox 940 is also shown coupled to the gearbox 940. A main printed circuit board (PCB) 1150 is shown transparently on the syringe pump assembly 501. The main PCB 1150 is coupled to the top of the syringe pump assembly housing 503. In the example embodiment, the flex connector 562 extending from the sliding block assembly 800 is connected to the main PCB 1150. The electrical system comprising the main PCB will be described in FIGS. 59A-59J.

The electrical system 4000 of the syringe pump 500 (see FIG. 28) is described in a block schematic in FIGS. 59B-59J. The electrical system 4000 controls the operation of the syringe pump 500 based on inputs from the user interface 3700 and sensors 3501. The electrical system 4000 includes a power system comprised of a rechargeable main battery 3420 and battery charger 3422 that plugs into the AC mains. The electrical system 4000 is architected to provide safe operation with redundant safety checks, and allow the syringe pump 500 to operate in fail operative modes for some errors and fail safe for the rest.

Figure 59B:
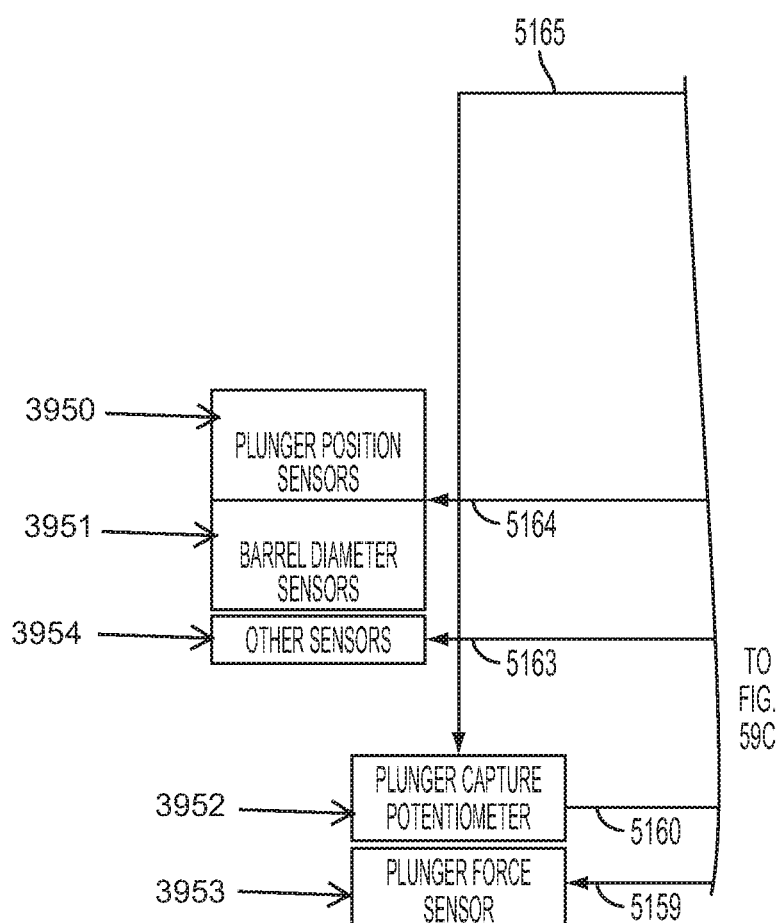
FIGS. 59B-59J are electrical schematics of the syringe pump in accordance with an embodiment of the present disclosure.
Figure 59C:
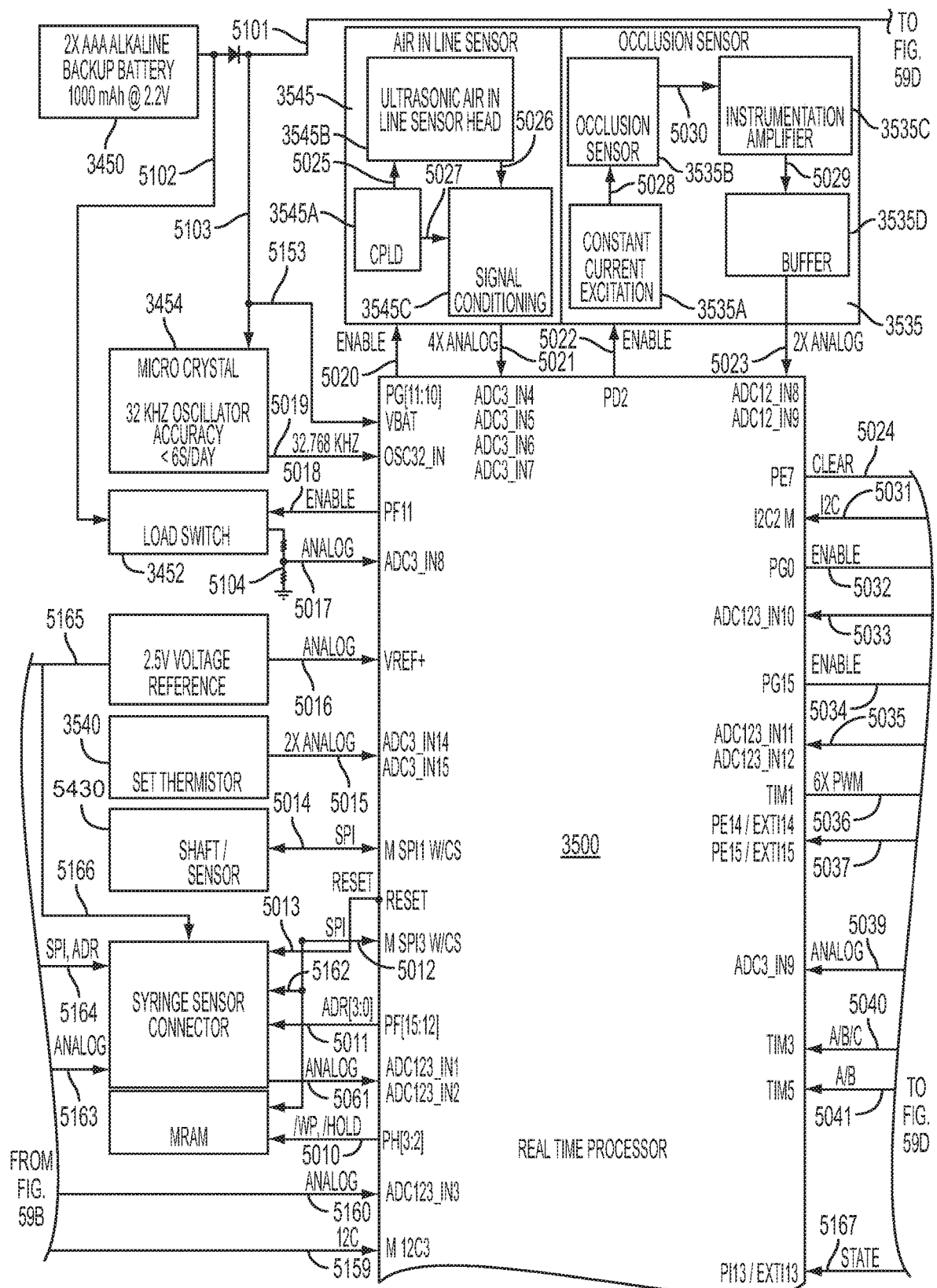
Figure 59D:
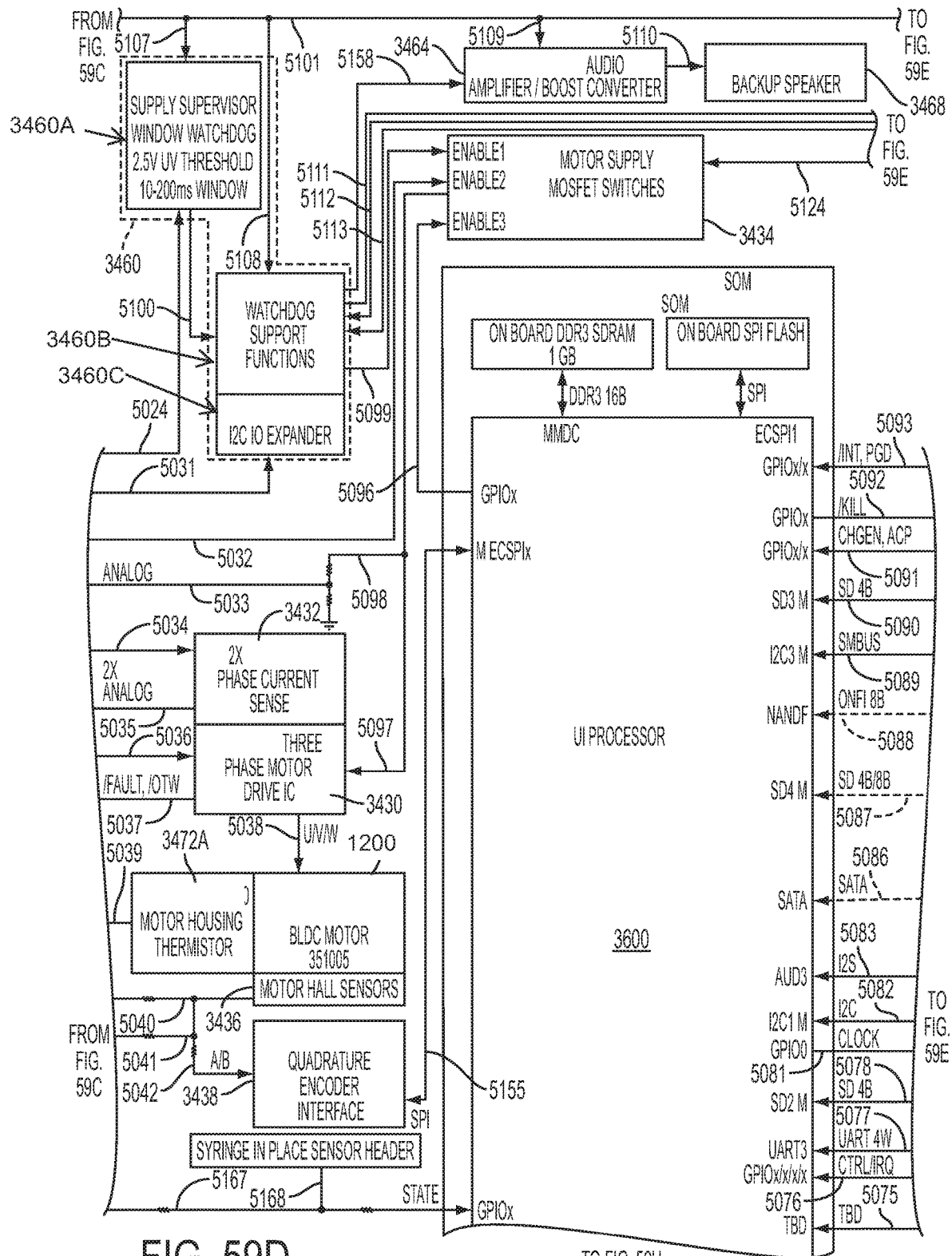
Figure 59E:
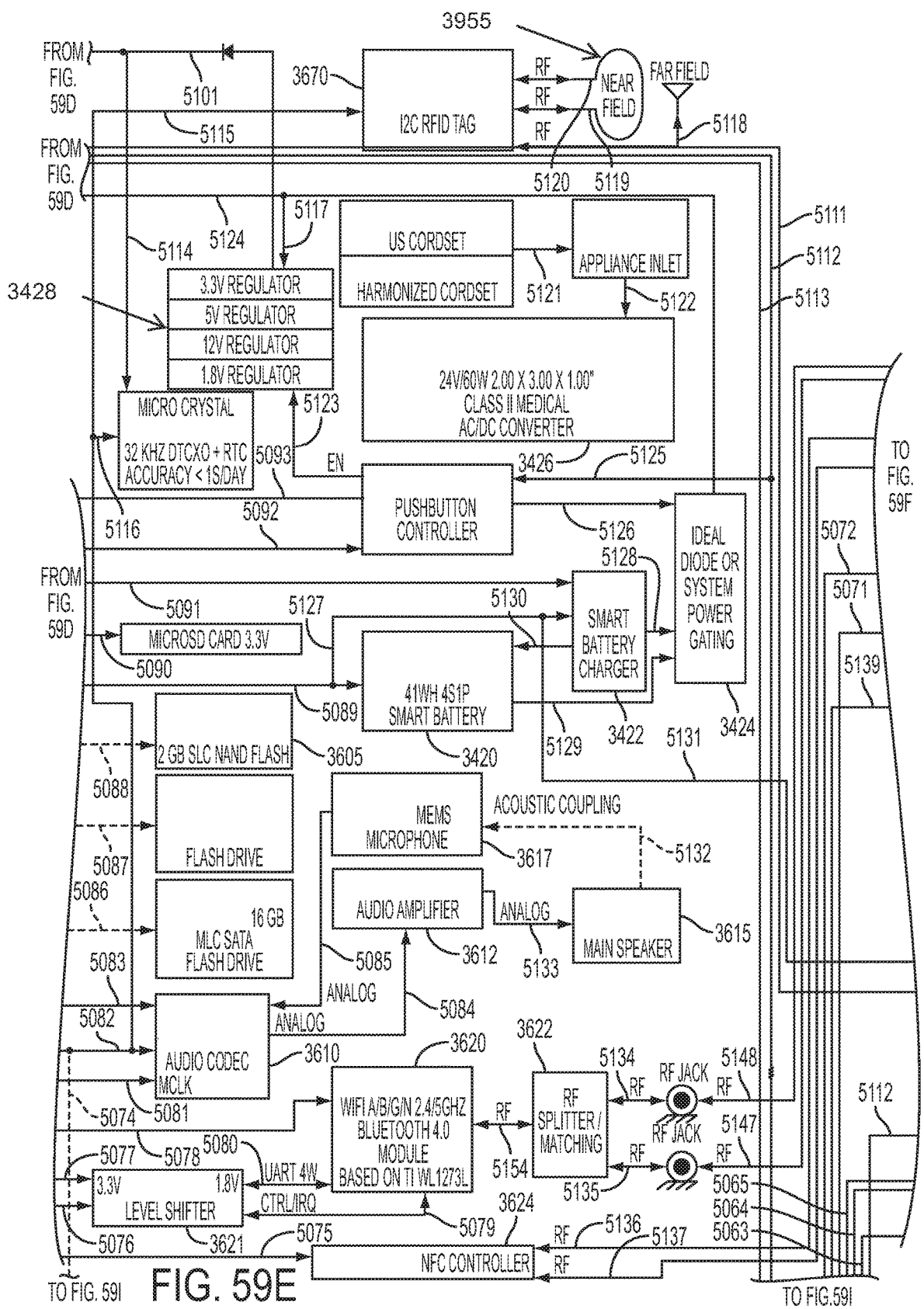
Figure 59F:
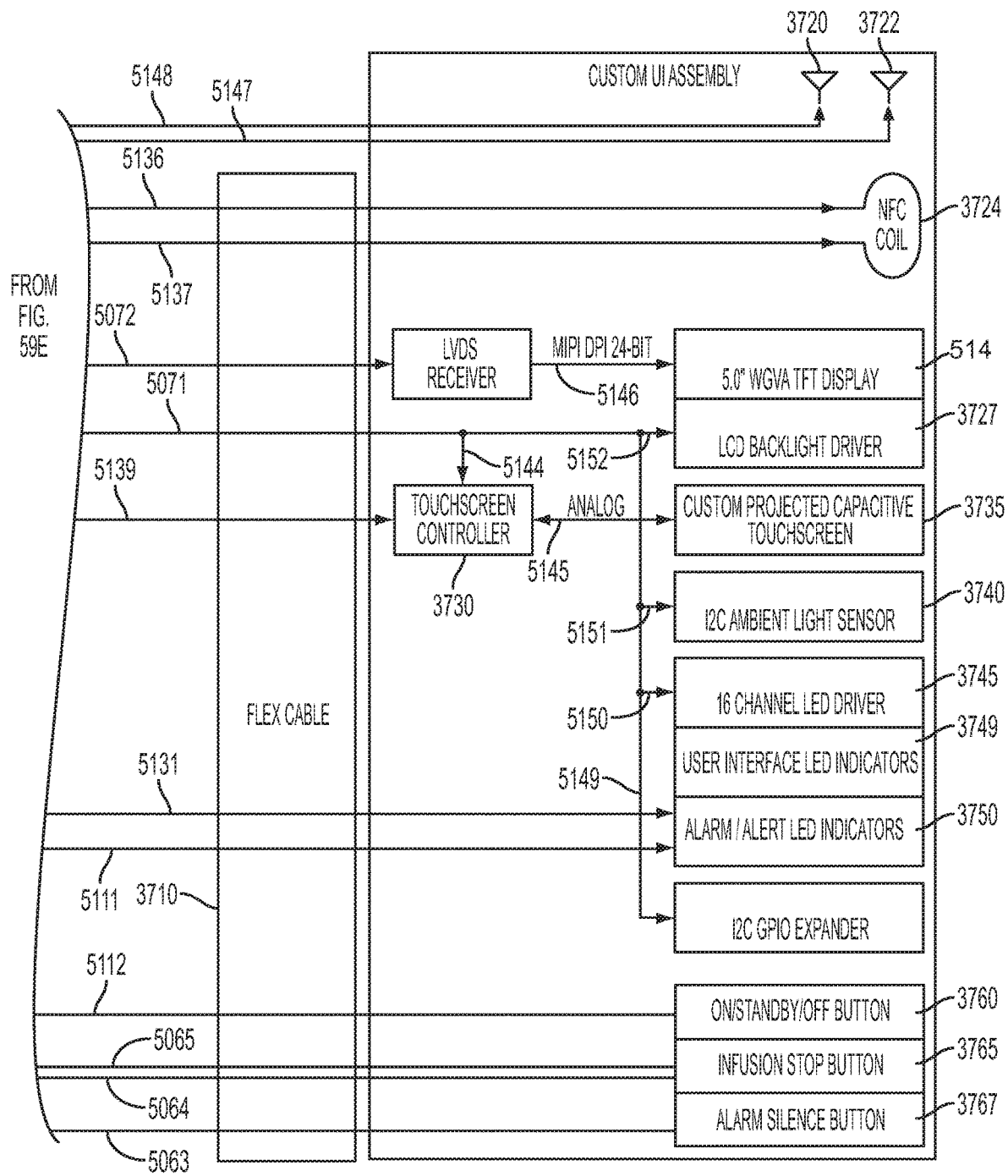
Figure 59G:
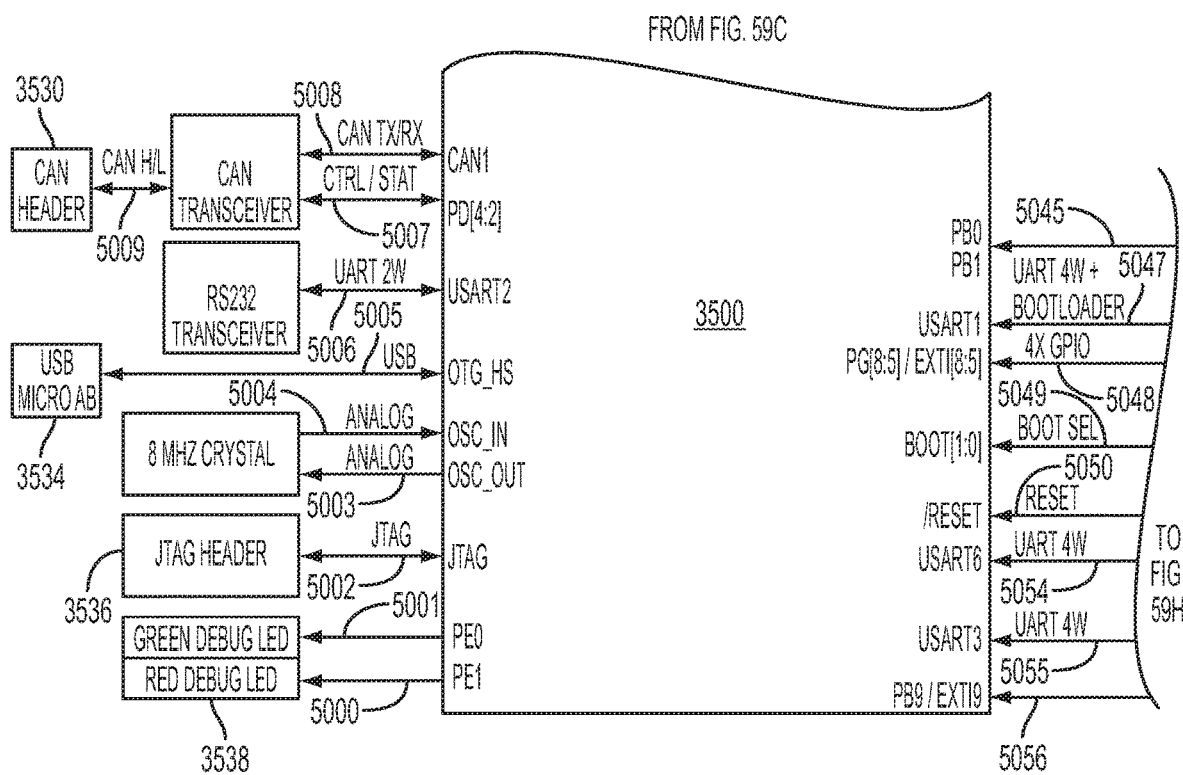
Figure 59H:
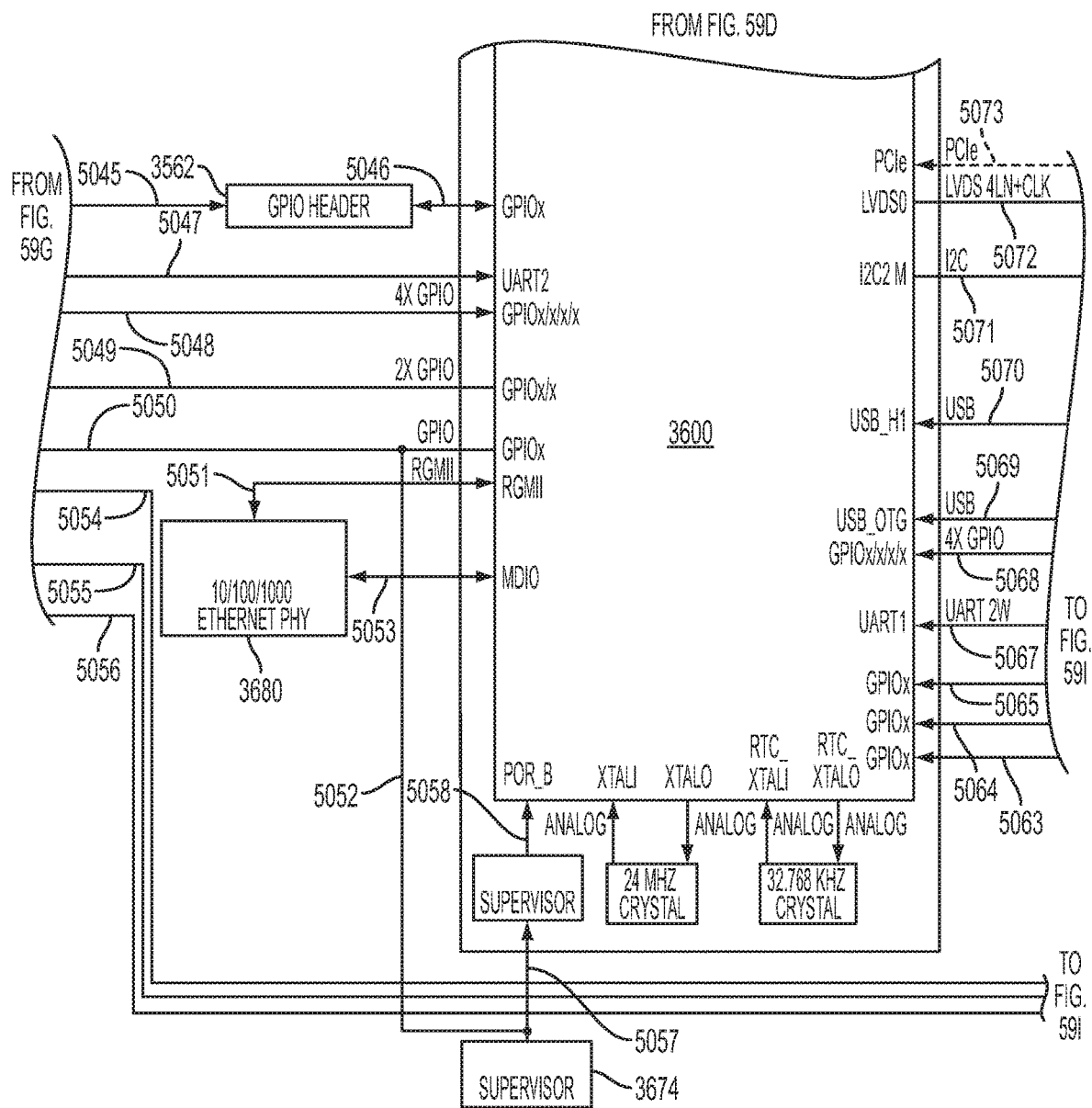
Figure 59I:
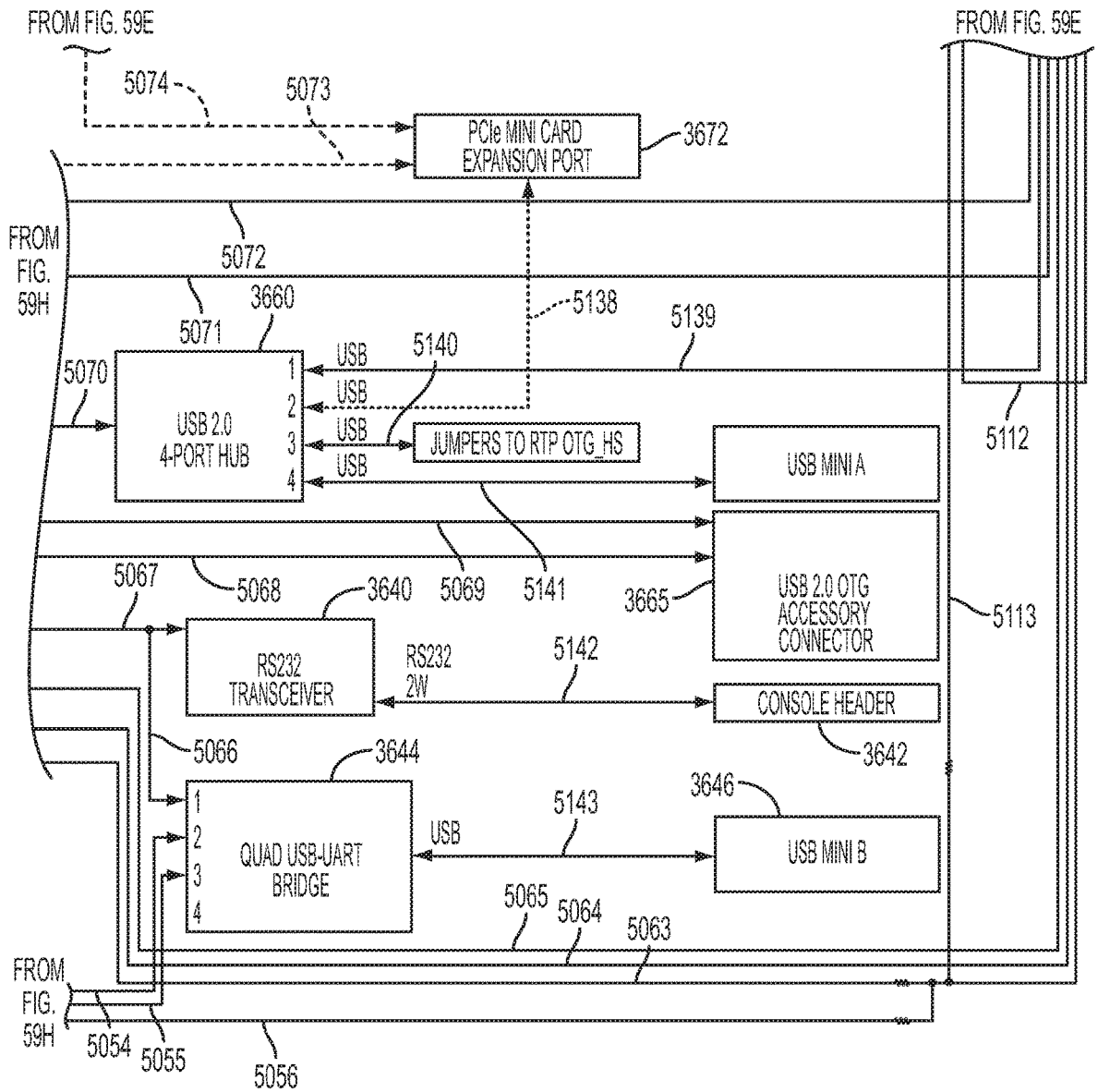
Figure 59J:
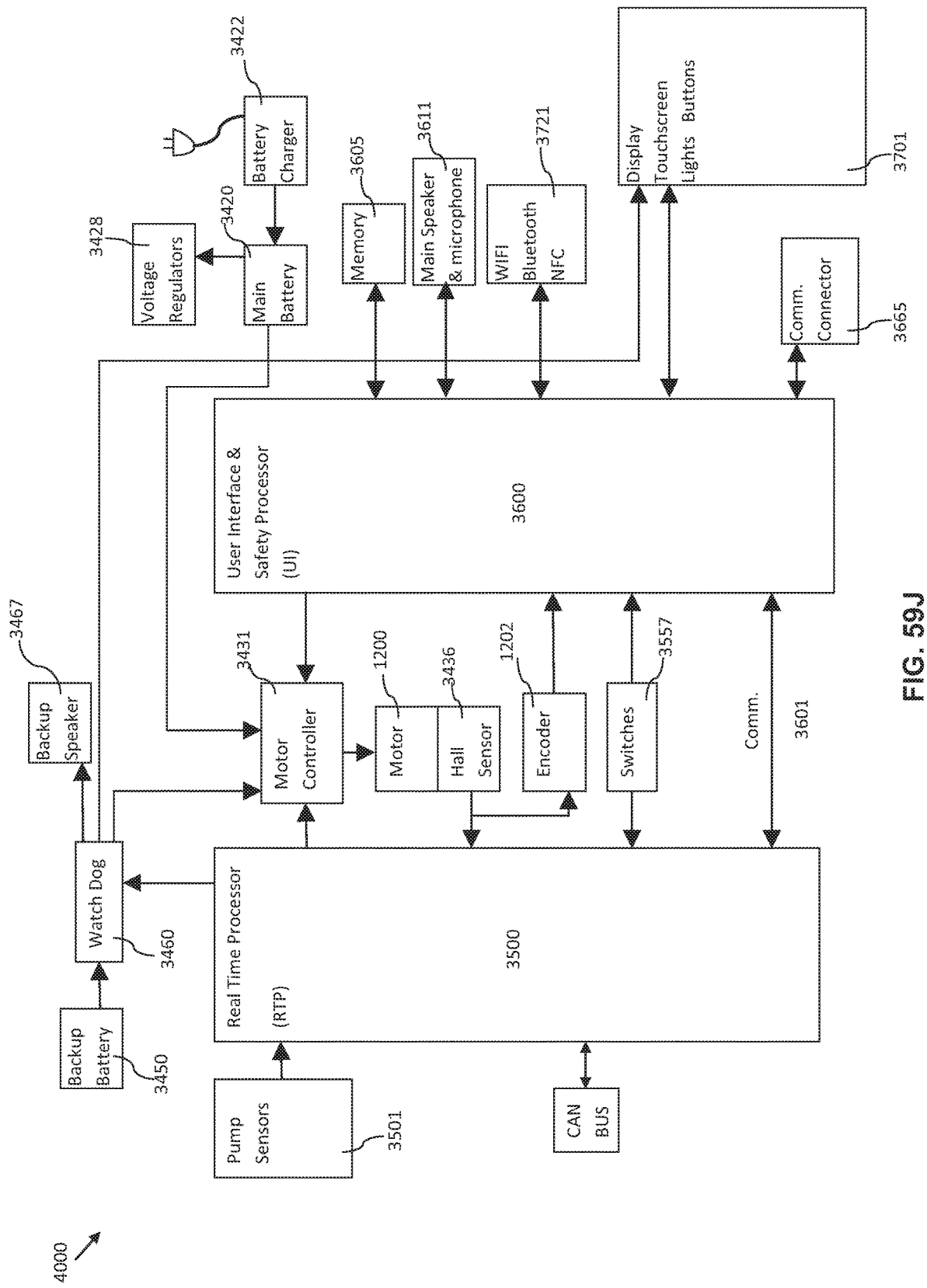

The high level architecture of multiple processors is shown in the last block diagram detailing the electrical system 4000, FIG. 59J. In one example the electrical system 4000 is comprised of two main processors, a real time processor 3500 and a User Interface/Safety Processor 3600. The electrical system 4000 may also comprise a watch-dog circuit 3460, motor control elements 3431, sensors 3501, and input/output elements. One main processor referred to as the Real Time Processor (hereafter RTP) 3500 may control the speed and position of the motor 1200 that rotates the lead screw 850 (see FIG. 48B). The RTP 3500 may control the motor 1200 based on input from the sensors 3501 and commands from the User Interface & Safety Processor (hereafter UIP) 3600. The UIP 3600 may manage telecommunications, manage the user interface 3701, and provide safety checks on the RTP 3500. The UIP 3600 may estimate the volume pumped based on the output of a motor encoder 1202 and may signal an alarm or alert when the estimated volume differs by more than a specified amount from a desired volume or the volume reported by the RTP 3500.

The watch dog circuit 3460 monitors the functioning of the RTP 3500. If the RTP 3500 fails to clear the watch dog circuit 3460 on schedule, the watch dog 3460 may disable the motor controller 3431, sound an alarm and turn on one or a number of failure lights at the user interface 3701. The RTP 3500 uses the sensor inputs to control the motor 1200 position and speed in a closed-loop controller (further described below). The telecommunications may include a WIFI driver and antenna to communicate with a central computer or accessories, a Bluetooth driver and antenna to communicate with accessories, tablets, cell-phones etc. and a Near Field Communication (NFC) driver and antenna for RFID tasks and a Bluetooth. In FIG. 59J these components are collectively referred to with the reference number 3721. The user interface 3701 may include a display 514 (see FIG. 28). In some embodiments, the display 514 may be a touch screen. In some embodiments the user interface 3701 may comprise one or more buttons or data input means 516 (see FIG. 28) via which a user may communicate with the syringe pump 500.

The detailed electrical connections and components of the electrical system 4000 are shown in FIGS. 59B-59I. FIGS. 59B-59I also depict a number of line traces 5000-5169 running to and from various components. A number of sensors of the syringe pump 500 are shown in FIG. 59B. As shown, plunger position sensors 3950, a barrel diameter sensor 3951, a plunger capture potentiometer sensor 3952, a plunger force sensor 3953, and other sensors 3954 are shown. The plunger position sensors 3950 may be any of the plunger position sensors described herein. The barrel diameter sensor 3951 may be the syringe barrel holder linear position sensors 1540 to be described herein. The plunger capture potentiometer sensor 3952 may not necessarily be a potentiometer sensor in all embodiments. In some embodiments, the plunger capture potentiometer sensor 3952 may be the plunger clamp jaws position sensor 588 described herein. The plunger force sensor 3953 may be the plunger pressure sensor 532 described herein. The plunger capture potentiometer 3952 may be a switch to detect a syringe 504 loaded into the syringe seat 506. The above sensors may communicate signals respective of and indicative of what they are sensing to the RTP 3500 or another component.

As shown in FIG. 59C, a thermistor 3540 may provide a signal to the RTP 3500 indicative of the temperature of the infusate in an infusion line. Alternatively the thermistor 3540 may measure a temperature in the syringe pump 500 or the temperature of the circuit 4000. In different embodiments, suitable replacement components may be used in place of the specific parts listed in the FIGS. 59B-59I. In some embodiments, the electrical system 4000 may comprise additional components. In some embodiments the electrical system 4000 may comprises fewer components than the number of components shown in FIGS. 59B-59J.

Two sensors which may be located downstream of the syringe pump 500 are shown in FIG. 59C. One sensor is an air-in-line sensor 3545. The other is an occlusion sensor 3535. Both are connected to the RTP 3500. These sensors are optional. The air-in-line sensor 3545 may detect the presence of air in the section of an infusion line in near the air-in-line sensor 3545. In an example embodiment, the air-in-line sensor 3545 may comprise an ultra-sonic sensor 3545B, a logic unit 3545A and a signal conditioning unit 3545C. In some embodiments, the syringe pump 500 may not comprise an air-in-line sensor 3545.

The occlusion sensor 3535 may measure the internal pressure of an infusate in an infusion line. In some embodiments, the occlusion sensor 3535 may be the downstream pressure sensor 513 described herein. In an example embodiment, the occlusion sensor 3535 may comprise a force sensor 3535B, an amplifier 3535A, a signal amplifier 3535C and a buffer 3535D. The buffer 3535D may protect the RTP 3500 from over-voltages due to high forces generated from pressures applied to the force sensor 3535B. In alternative embodiments, the occlusion sensor 3535 may differ.

The watch dog circuit 3460 is shown in FIGS. 59D. The watch dog circuit 3460 may enabled by an I2C command from the RTP 3500. The watch dog circuit 3460 may signal an error and disable the motor controller 3430 (e.g., via chip 3434) if it does not receive a signal from the RTP 3500 at a specified frequency. The watch dog circuit 3460 may signal the user via an audible alarm. The audible alarm may be issued via an amplifier 3464 and/or backup speaker 3468. The watch dog circuit 3460 may signal the user with visual alarm LEDs 3750 (shown in FIG. 59F) if an abnormal condition is detected. In one embodiment, the RTP 3500 must "clear" the watchdog 3460 between 10 ms and 200 ms after the watch dog circuit's 3460 last clear. In some embodiments, the watch dog circuit 3460 is comprised of a window watchdog 3460A, a logic circuit 3460B (which may include one or more flip-flop switches) and an 10 expander 3460C that communicates with the RTP 3500 over an I2C bus. A backup battery 3450 (see FIG. 59C) may provide power to the watch dog circuit 3460 and backup speaker system (which may comprise an audio amplifier 3464, and a backup speaker 3468) in case the main battery 3420 (see FIG. 59E) fails. The backup battery 3450 may provide power to the RTP 3500 and UIP 3600 to maintain the internal timekeeping, which may be especially desirable when the main battery 3420 is changed. The RTP 3500 may also monitor the voltage of the backup battery 3450 with a switch such as the "FAIRCHILD FPF1005 LOAD SWITCH" 3452 shown in FIG. 59C.

The RTP 3500 directly controls the speed and position of the motor 1200. The motor 1200 may be any of a number of types of motors 1200 including a brushed DC motor, a stepper motor, or a brushless DC motor. In the embodiment illustrated in FIGS. 59B-59J, the syringe pump 500 is driven by a brushless direct current (BLDC) servo motor 1200. In one example embodiment, the RTP 3500 receives signals from the hall-sensors 3436 of a brushless DC motor 1200 and does the calculations to commutate power to the winding of the motor 1200 to achieve a desired speed or position. The commutation signals may be sent to the motor controller 3430 which selectively connects the windings to the motor power supply 3434. The motor 1200 may be monitored for damaging or dangerous operation via current sensors 3432 and a temperature sensor 1200A.

The signals from the hall sensors 3436 may be supplied to both the RTP 3500 and to an encoder 1202. In one embodiment, three hall signals are generated. Any two of the three hall signals may be sent to the encoder 1202. The encoder 1202 may use these signals to provide a position signal to the UIP 3600. The UIP 3600 estimates the total volume of fluid dispensed by the syringe pump 500 from the position signal of the encoder 1202. In some specific embodiments, each syringe pump 500 may be calibrated during assembly to establish the nominal volume/stroke that may be stored in memory. The UIP 3600 estimated volume may then be compared at regular intervals to the volume which would be expected for a commanded therapy. In some embodiments, the interval between comparisons may be shorter for different infusates, for example short half-life infusates. The therapy may specify, among other parameters, a flow rate, duration, and a total volume to be infused (VTBI). In any case, the expected volume based on the programmed therapy at a given time during that therapy may be calculated and compared to the volume estimated by the UIP 3600. The UIP 3600 may signal an alert or alarm if the difference between UIP 3600 estimated volume and the expected volume for therapy is outside of a predefined threshold. The UIP 3600 may signal an alarm if the difference between UIP 3600 estimated volume and the expected volume for the therapy is outside another predefined threshold.

The UIP 3600 may also compare the estimated volume to the volume reported by the RTP 3500. The UIP 3600 may signal an alert if the difference between UIP 3600 estimated volume and the RTP 3500 reported volume is outside a predefined threshold. The UIP 3600 may signal an alarm if the difference between UIP 3600 estimated volume and the RTP 3500 reported volume is outside a second threshold.

In some embodiments, the UIP 3600 may compare the RTP 3500 reported volume to the expected volume for the therapy and signal an alert if the two values differ by more than a predefined threshold. The UIP 3600 may signal an alarm if the difference between the RTP 3500 reported volume and the expected volume for the therapy differ by more than another predefined threshold. The values of the alert and alarm thresholds may be different for comparisons between different sets of volumes. The thresholds may be stored memory. The thresholds may vary depending on a number of different parameters, such as, but not limited to, medication, medication concentration, clinical usage, patient, therapy type, or location. The thresholds may be predefined in a DERS (Drug Error Reduction System) database and downloaded from the device gateway server.

Optionally, in some embodiments, a rotary encoder 5430 may be used to estimate the rotation of the motor threaded screw 1200. The motor sensor 5430 may be formed by a magnet on the motor's 1200 shaft with a Hall Effect sensor nearby to estimate the position of the threaded shaft.

An RFID tag 3670 (see FIG. 59E) may be connected by an I2C bus to the UIP 3600 and to a near field antenna 3955. The RFID tag 3670 may be used by med-techs or other users or personnel to acquire or store information when the syringe pump 500 is in an unpowered state. The UIP 3600 may store service logs, error codes, etc. in the RFID tag 3670. The service logs, error codes, etc. may be accessible by an RFID reader. A med-tech, for example, could inspect unpowered syringe pumps 500 in storage or evaluate non-functioning syringe pumps 500 by using an RFID reader to interrogate the RFID tag 3670. In another example, a med-tech or other personnel may perform service on the syringe pump 500 and store any related service information in the RFID tag 3670. The UIP 3600 may then cull the latest service information from the RFID tag 3670 and store it in memory 3605 (see FIG. 59E).

The main battery 3420 may supply all the power to the syringe pump 500. The main battery 3420 may be connected via a system power gating element 3424 to the motor power supply 3434. All of the sensors and processors described herein may be powered by one of the several voltage regulators 3428 (see FIG. 59E). The main battery 3420 may be charged from AC power via a battery charger 3422 and an AC/DC converter 3426. The UIP 3600 be connected to one or more memory chips 3605.

The UIP 3600 controls the main audio system which comprises a main speaker 3615 and the audio-chips 3610 (audio codec), 3612 (audio amplifier) (see FIG. 59E). The main audio system may be capable of producing a range of sounds indicating, for example, alerts and alarms. The audio system may also provide confirmatory sounds to facilitate and improve user interaction with the display 514 and/or data input means 516 (see FIG. 28). The main audio system may include a microphone 3617 which may be used to confirm the operation of the main speaker 3615 as well as the backup speaker 3468. The main audio system may produce one or more tones, modulation sequences and/or patterns of sound and the audio codec chip 3610 may compare the signal received from the microphone 3617 to the signal sent to the main speaker 3615. The use of one or more tones and comparison of signals may allow the system to confirm main speaker 3615 function independently of any ambient noise. Alternatively the UIP 3600 or the audio codec 3610 may confirm that the microphone 3617 produces a signal at the same time a signal is sent to the speaker amplifier 3612.

The UIP 3600 may provide a range of different wireless signals for different uses. The UIP 3600 may communicate with the hospital wireless network via a dual band WiFi using chips 3621, 3620, and 3622 and antennas 3720 and 3722. The spatially diverse dual antenna may be desirable because in may be capable of overcoming dead spots within a room due to multiple paths and cancellation. A hospital device gateway may communicate DERS, CQI (Continuous Quality Improvement), prescriptions, patient data, etc. to the syringe pump 500 via the WiFi system.

The Bluetooth system using, the same chips 3621, 3620 and 3622 (see FIG. 59E) and antennas 3720 and 3722 (see FIG. 59F), may provide a convenient method to connect auxiliaries to the syringe pump 500 that may include pulse-oximeters, blood pressure readers, bar-code readers, tablets, phones, etc. The Bluetooth may include version 4.0 to allow low power auxiliaries which may communicate with the syringe pump 500 periodically such as, for example, a continuous glucose meter that sends an update once a minute.

The NFC system may be comprised of an NFC controller 3624 (see FIG. 59E) and an antenna 3724 (see FIG. 59F). The NFC controller 3624 may also be referred to as an RFID reader. The NFC system may be used to read RFID chips identifying drugs or other inventory information. The RFID chips may also be used to identify patients and caregivers. The NFC controller 3624 may also interact with a similar RFID reader on, for example, a phone or tablet computer to input information including prescriptions, bar-code information, patient, care-giver identities, etc. The NFC controller 3624 may also provide information to phone or tablet computers such as the syringe pump 500 history or service conditions. The RFID antennas 3720 and 3722 and/or NFC antenna 3724 may preferably be located around or near the display 514 screen, so all interaction with the syringe pump 500 occurs on or near the display 514 whether reading an RFID chip or interacting with a touch screen display 514 or other data input means 516 near the display.

The UIP 3600 may include a medical grade connector 3665 (see FIG. 59I) so that other medical devices may plug into the syringe pump 500 and provide additional capabilities. The connector 3665 may implement a USB interface.

The display 514 may include the RFID antennas 3720, 3722, the NFC antenna 3724, the display 514, the touch screen 3735, an LCD backlight driver 3727, a light sensor 3740, a 16 channel LED driver 3745, LED indicator lights 3747 and 3749, and three buttons 3760, 3765, 3767. The buttons may collectively be referred to herein as data input means 516. The display 514 may include a backlight 3727 and an ambient light sensor 3740 to allow the display 514 brightness to automatically respond and/or adjust to ambient light. The first button 3760 may be the "Power" button, while another button 3765 may be an infusion stop button. These buttons 3760, 3765 may not provide direct control of the syringe pump 500, but rather provide a signal to the UIP 3600 to either initiate or terminate infusion. The third button 3767 may silence an alarm or alert at the main speaker 3615 and at the backup speaker 3468. Silencing the alarm or alert will not clear the fault, but may end the audible alarm or alert. The electrical system 4000 described above, or an alternative embodiment of the electrical system 4000 described above may be used with the syringe pump 500 described herein.

Figure 60:
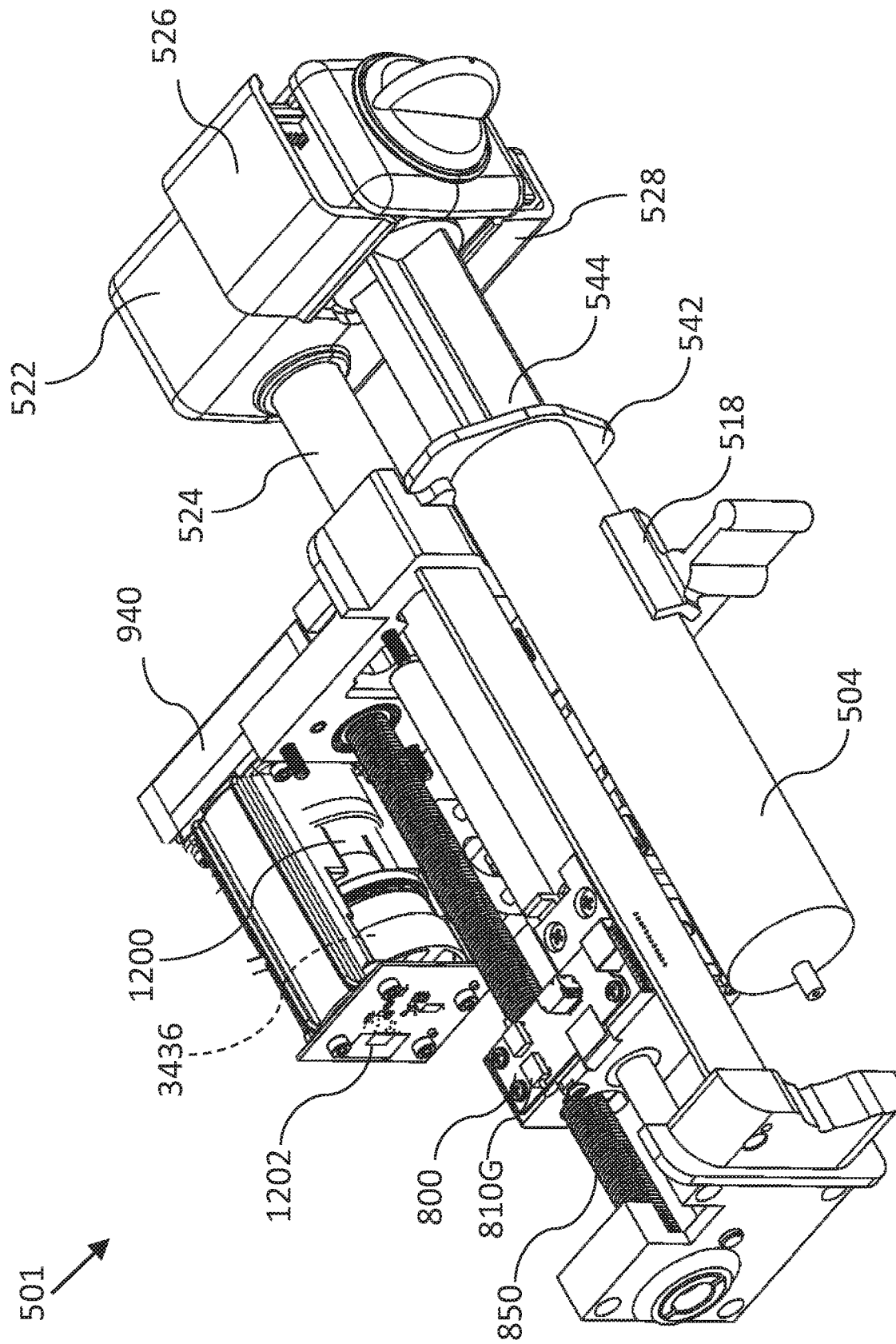
FIG. 60 is a bottom partial view of an exemplary embodiment of the syringe pump assembly in accordance with an embodiment of the present disclosure.

FIG. 60 shows an exemplary embodiment of the syringe pump assembly 501. In FIG. 60 the syringe pump assembly housing 503 which is shown in FIG. 59A has been removed. As shown, a syringe 504 is in place on the syringe pump assembly 501 and is being held by the syringe barrel holder 518. The sliding block assembly 800 is located approximately in the middle of the axial length of the lead screw 850. Since the plunger tube 524 connects the sliding block assembly 800 to the plunger head assembly 522, the plunger head assembly 522 is at location where it has caused the syringe plunger 544 to dispense about half of the content of the syringe 504.

As shown, a motor 1200 is operatively coupled to the gearbox 940 in FIG. 60. Rotation of the motor 1200 is transmitted through the gearbox 940 to drive the rotation of the lead screw 850. As described above, since the upper plunger clamp jaw 526 and lower plunger clamp jaw 528 are closed on the plunger flange 548, the half nut 830 is engaged with the lead screw 850. Consequently, in the embodiment depicted in FIG. 60 as the motor 1200 causes the lead screw 850 to rotate, the sliding block assembly 800 will travel along the axial length of the lead screw 850. As motor 1200 rotates the lead screw 850 such that the sliding block assembly 800 moves toward the left of the page (relative to FIG. 60), the sliding block assembly's 800 movement will additionally cause the plunger tube 524 and plunger head assembly 522 to displace toward the left of the page. As the plunger head assembly 522 displaces toward the left of the page, the syringe plunger 544 is advanced into the syringe barrel 540 of the syringe 504 and the contents of the syringe are dispensed.

The motor 1200 may be any suitable motor 1200. As shown in FIG. 59A a small profile pancake motor 1200 may be used to drive the rotation of the lead screw 850. The embodiment shown in FIG. 60 does not use a pancake motor 1200. The motor 1200 shown in FIG. 60 is an alternative motor that also has hall sensors 3436 to inform commutation of the motor 1200. As shown in FIG. 60, the motor 1200 may comprise a magnet on the rotor that is detected by a rotary encoder 1202. The rotary encoder 1202 may be any of a variety of suitable rotary encoders 1202 such as the AS5055 by Austrianmicrosystems of Austria. In some embodiments, the rotary encoder 1202 may be a magnetic. The rotary encoder 1202 may be used to monitor rotation of the lead screw 850. Information from the rotary encoder 1202 may be used to determine when a given amount of the contents of the syringe 504 has been dispensed. Additionally, the rotary encoder 1202 may be used to determine the location of the sliding block assembly 800 on the lead screw 850.

To ensure that the rotary encoder 1202 is functioning properly, a self test may be preformed. The motor 1200 may be powered to move the sliding block assembly 800 back and forth along a distance of the lead screw 850. Measurements from the rotary encoder 1202 may be confirmed against the measurements of the sliding block assembly linear position sensor 1050. The same self test may also be used to confirm the hall sensors 3436 of the brushless motor 1200 are functioning properly.

As previously indicated, the syringe pump 500 includes a number of sensor redundancies. This allows the syringe pump 500 to function in a fail operative mode if deemed appropriate. In the event that the rotary encoder 1202 fails, the hall sensors 3436 of the brushless motor 1200 may be used in a fail operative mode to measure the dispensation of syringe 504 contents via the rotation of the motor 1200 and provide a feed-back signal for the motor controller. Alternatively the location of the sliding block assembly 800 along the lead screw 850 may be used in a fail operative mode to measure the dispensation of syringe 504 contents via position of the sliding block assembly 800 and provide a feed-back signal for the controller. Alternatively the sliding block assembly linear position sensor 1050, may be used to monitor the dispensation of syringe 504 contents via position of the sliding block assembly 800 on the lead screw and to provide a feed-back signal for the controller. In some embodiments, the motor hall sensors 3436 or the linear sliding block assembly linear position sensor 1050 may be used to monitor the position of the sliding block assembly 800 on the lead screw 850 to avoid driving the sliding block assembly 800 against the pump frame.

In the event of a failure of the rotary encoder 1202, the syringe pump 500 may finish a therapy if a therapy is in progress and disallow a user from commencing another therapy until the syringe pump 500 has been serviced. In the event of a failure of the rotary encoder 1202 the syringe pump 500 may alarm. In some embodiments, if the rotary encoder 1202 fails and the motor 1200 is being used to deliver at a low flow rate, the syringe pump 500 may not finish the therapy. If such a failure occurs, the syringe pump 500 may alarm and the syringe pump 500 may finish a therapy if a therapy is in progress and disallow a user from commencing another therapy until the syringe pump 500 has been serviced. The controller of the syringe pump 500 may base its decision to continue a therapy based on the risk level of the infusate being delivered to a patient. If the risk of non-delivery to a user is higher than the risk of delivering with reduced accuracy, the syringe pump 500 will deliver in a fail operative mode.

Figure 61:
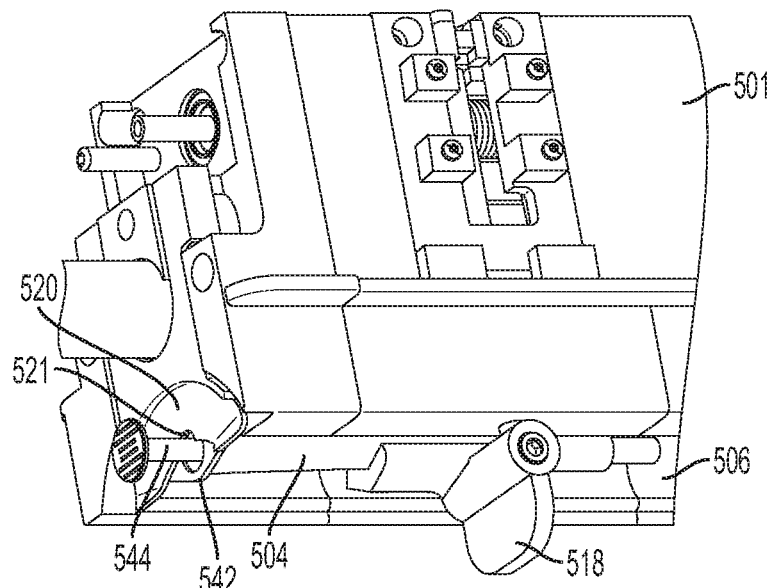
FIG. 61 is a partial view of an exemplary embodiment of the syringe pump assembly in which a barrel flange of a small syringe has been clipped by the barrel flange clip in accordance with an embodiment of the present disclosure.

FIG. 61 shows a small volume syringe 504 in place on the syringe pump assembly 501. Only a small portion of the syringe pump assembly 501 is visible in FIG. 61. As shown, the syringe 504 is held in place against the syringe seat 506 by the syringe barrel clamp 518. The syringe barrel flange 542 is clipped in place against the syringe pump assembly 501 by the barrel flange clip 520. The barrel flange clip 520 is slightly offset from the rest of the syringe pump assembly 501 such that there is small gap between the syringe pump assembly 501 and the barrel flange clip 520. When a user places the syringe 504 on the syringe seat 506, the user may also place the syringe barrel flange 542 into the small gap between the syringe pump assembly 501 and the barrel flange clip 520.

As shown in FIG. 61, the outward edge of the barrel flange clip 520 bows out toward the left of the page. This helps to guide the syringe barrel flange 542 into the gap between the barrel flange clip 520 and the syringe pump assembly 501. The barrel flange clip 520 may also include one or a number of cutouts 521. In the example embodiment in FIG. 61, the cutouts 521 of the barrel flange clip comprise two valleys. The first valley is recessed into the center span of the outward edge of the barrel flange clip 520. The second valley, which is recessed into the lowest span of the first valley, is considerably smaller and shallower. In other embodiments, the cutouts 521 may be different in shape, size, etc. The plunger 544 of the small syringe 504 in FIG. 61 is located entirely within the cutouts 521 in the barrel flange clip 520. Without the cutouts 521 in the barrel flange clip 520, the plunger 544 of the syringe 504 would contact the outward edge of the barrel flange clip 520 and obstruct user placement of the syringe barrel flange 542 into the gap between the barrel flange clip 520 and the syringe pump assembly 501.

Figure 62:
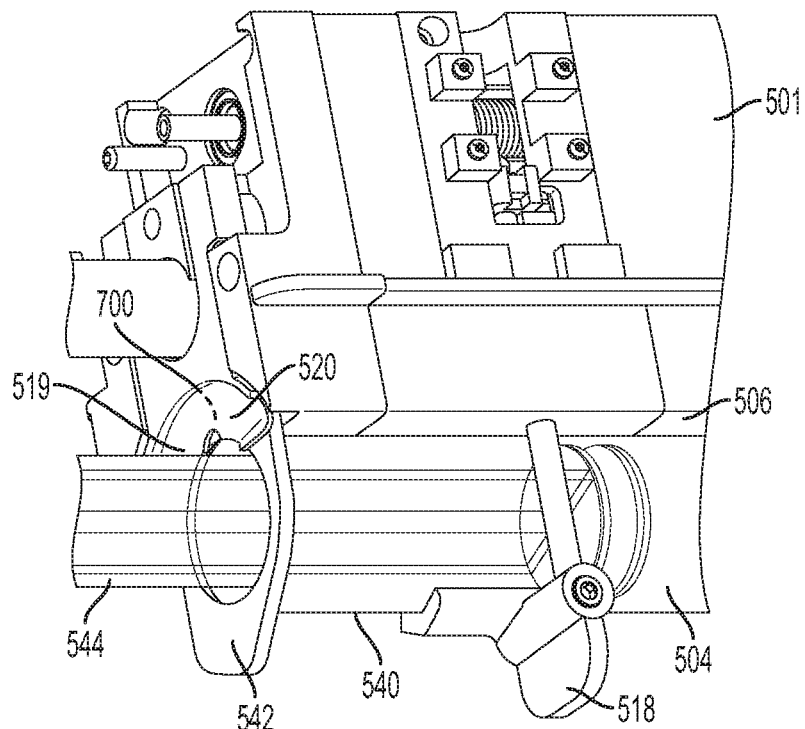
FIG. 62 is a partial view of an exemplary embodiment of the syringe pump assembly in which a barrel flange of a large syringe has been clipped by the barrel flange clip in accordance with an embodiment of the present disclosure.

FIG. 62 shows a large volume syringe 504 in place on the syringe pump assembly 501. Only a small portion of the syringe pump assembly 501 is visible in FIG. 62. As shown, the syringe 504 is held in place against the syringe seat 506 by the syringe barrel clamp 518. The syringe barrel flange 542 is clipped in place against the syringe pump assembly 501 by the barrel flange clip 520. The barrel flange clip 520 is slightly offset from the rest of the syringe pump assembly 501 such that there is small gap between the syringe pump assembly 501 and the barrel flange clip 520. When a user places the syringe 504 on the syringe seat 506, the user may also place the syringe barrel flange 542 into the small gap between the syringe pump assembly 501 and the barrel flange clip 520.

As shown in FIG. 62, the barrel flange clip 520 may also include a roughly semi-circular depression 519 which thins the barrel flange clip 520. The roughly semi-circular depression 519 may be included to accommodate the plunger flange 548 (not shown) of a syringe 504. In embodiments where the barrel flange clip 520 includes the roughly semi-circular depression 519, the plunger 544 may be advanced a distance equal to the depth of the semi-circular depression 519 further into the syringe barrel 540. This is desirable because it allows more of the contents of the syringe 504 to be administered to a patient.

As shown in FIG. 62, the barrel flange clip 520 may include a barrel flange sensor 700. The barrel flange sensor 700 may be comprised of any number of suitable sensors. In some embodiments, the barrel flange sensor 700 may function in a binary (yes/no) manner to indicate whether a syringe barrel flange 542 is clipped by the barrel flange clip 520. In some embodiments, the barrel flange sensor 700 may comprise a micro switch which is actuated as the syringe barrel flange 524 is placed in the gap between the syringe pump assembly 501 and the barrel flange clip 520. In other embodiments, the barrel flange sensor 700 may comprise a photosensor. Insertion of the syringe barrel flange 542 into the gap between the syringe pump assembly and the barrel flange clip 520 may block a light source for the barrel flange sensor 700 in embodiments where the barrel flange sensor 700 comprises a photosensor. In such embodiments, the barrel flange sensor 700 may indicate a syringe barrel flange 542 is clipped in place when the light source is blocked. In other embodiments, the barrel flange sensor 700 may be comprised of a different sensor than those described above. The barrel flange sensor 700 may be caused generate an alarm in the event that other sensors, such as the plunger clamp jaws position sensor 588 (mentioned above) or the syringe barrel holder linear position sensor 1540 (see FIG. 66), detect a syringe 504 in place of the syringe pump assembly 501 when the barrel flange sensor 700 does not detect a syringe 504 in place and an initiation of a therapy is attempted.

Figure 63:
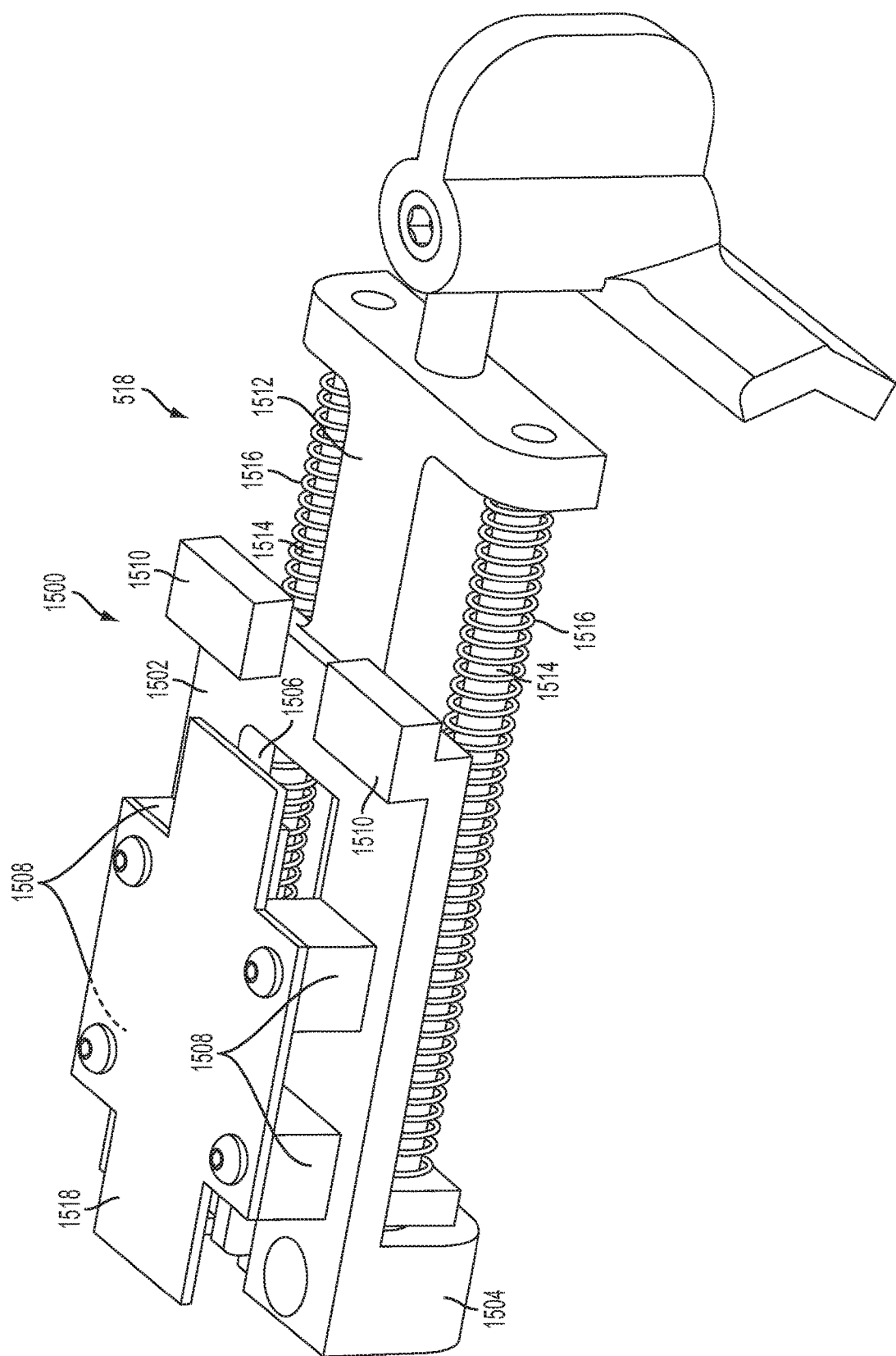
FIG. 63 is a view of an exemplary embodiment of the syringe barrel holder in accordance with an embodiment of the present disclosure.

FIG. 63 shows an embodiment of part of the syringe barrel holder 518. As shown in FIG. 63, the syringe barrel holder 518 comprises a syringe barrel holder housing 1500. In the example embodiment, the syringe barrel holder housing 1500 has a planate base plate 1502. The planate base plate 1502 comprises a syringe barrel holder housing member 1504 at its left end (relative to FIG. 63). The syringe barrel holder housing member 1504 projects off the bottom of the syringe barrel holder housing 1500 at an angle substantially perpendicular to the plane of the planate base plate 1502. The syringe barrel holder housing member 1504 may extend substantially perpendicularly from the entire length of the left end of the planate base plate 1502. In some embodiments, the syringe barrel holder housing member 1504 may take the form of a rectangular prism. In the example embodiment shown in FIG. 63, the syringe barrel holder housing member 1504 has a form close to a rectangular prism, but the bottom edges of the syringe barrel holder housing member 1504 have been rounded off.

As shown in FIG. 63, the planate base plate 1502 may have a base plate slot 1506 cut into it. The base plate slot 1506 may be cut into the planate base plate 1502 from the left edge (relative to FIG. 63) of the planate base plate 1502. The base plate slot 1506 may extend into the planate base plate 1502 at an angle substantially perpendicular to the left edge of the planate base plate 1502. The base plate slot does not extend all the way across the planate base plate 1502 and stops short of the right edge.

On the flanks of the base plate slot 1506, one or more syringe barrel holder housing posts 1508 may be disposed. In the example embodiment shown in FIG. 63, four syringe barrel holder housing posts 1508 flank the base plate slot 1506. The four syringe barrel holder housing posts 1508 are divided up such that there are two syringe barrel holder housing posts 1508 on each flank of the base plate slot 1506. The syringe barrel holder housing posts 1508 extend substantially perpendicularly from the top face of the planate base plate 1502 toward the top of the page. The syringe barrel holder housing posts 1508 in the example embodiment shown in FIG. 63 have the form of rectangular prisms. In alternate embodiment, the syringe barrel housing posts 1508 may be cylindrical or have any other suitable shape.

The planate base plate 1502 may also comprise one or more syringe barrel holder housing bodies 1510. In the example embodiment shown in FIG. 63, there are two syringe barrel holder housing bodies 1510. The syringe barrel holder housing bodies 1510 projects perpendicularly from the top of the planate base plate 1502 toward the top of the page. The syringe barrel holder housing bodies 1510 have the form of rectangular prisms. As shown, the syringe barrel holder housing bodies 1510 may overhang the right edge of the planate base plate 1502. The syringe barrel holder housing bodies 1510 may comprise one side which is flush with the front edge or back edge (relative to FIG. 63) of the planate base plate 1502.

In some embodiments, the syringe barrel holder housing 1500 may comprise a "T" shaped member 1512. In the example embodiment shown in FIG. 63, the stem portion of the "T" shaped member extends toward the right of the page from the right edge of the planate base plate 1502. The "T" shaped member 1512 may extend on a plane substantially parallel to the plane of the planate base plate 1502. In the example embodiment, the "T" shaped member 1512 projects from roughly the center of the right edge of the planate base plate 1502. The cross portion of the "T" shaped member 1512 is roughly parallel with the right edge of the planate base plate 1502. The cross portion of the "T" shaped member 1512 overhangs the stem equally on both sides of the stem.

As shown in FIG. 63, syringe barrel holder guide rails 1514 may extend substantially perpendicularly from the right face of the syringe barrel holder housing member 1504 and into the left faces of the overhanging cross portions of the "T" shaped member 1512. The syringe barrel holder guide rails 1514 may extend substantially parallel to each other. In the example embodiment shown in FIG. 63, a coil spring 1516 surrounds each syringe barrel holder guide rail 1514. One end of each coil spring 1516 may abut the left face of the cross portion of the "T" shaped member 1512. In the example embodiment, the coil springs 1516 are compression springs. In alternate embodiments, other bias members or bias member arrangements may be utilized.

As shown in the embodiment in FIG. 63, a syringe barrel holder printed circuit board (PCB) 1518 may be held in place on the syringe barrel holder housing posts 1508. The syringe barrel holder PCB may be coupled in place on the syringe barrel holder housing posts 1508 by any suitable means. In the example embodiment shown in FIG. 63, the syringe barrel holder PCB is coupled to the syringe barrel holder housing posts 1508 by screws.

Figure 64:
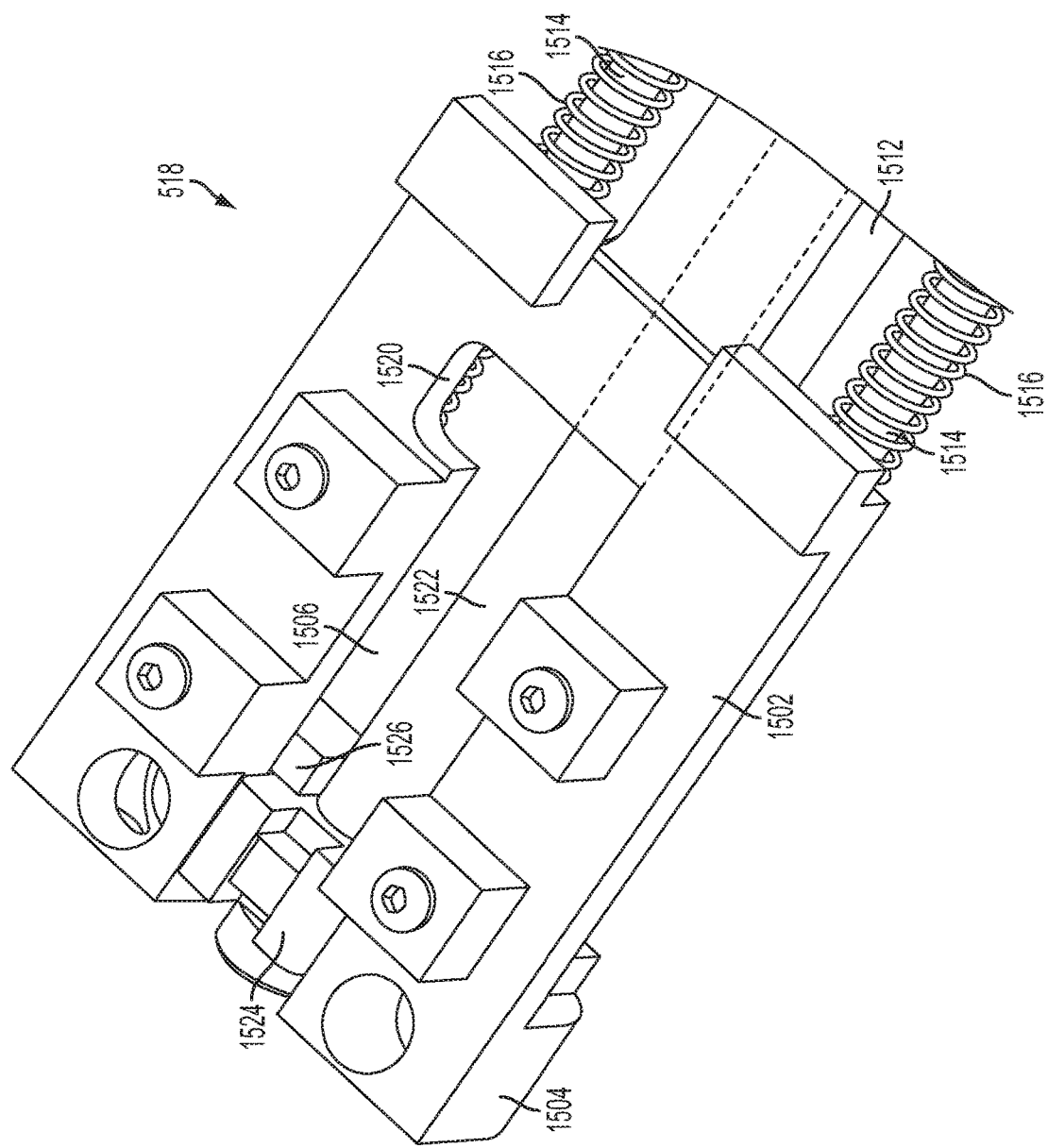
FIG. 64 is a partial view of an exemplary embodiment of the syringe barrel holder in accordance with an embodiment of the present disclosure.

FIG. 64 shows an embodiment of part of the syringe barrel holder 518. In the embodiment shown in FIG. 64, the syringe barrel holder PCB 1518 shown in FIG. 63 has been removed. As shown in FIG. 64 the base plate slot 1506 may extend down into the syringe barrel holder housing member 1504. The base plate slot 1508 may comprise a base plate notch catch 1520. In embodiments where the base plate slot 1508 comprises a base plate notch catch 1520 the base plate notch catch 1520 may be a void in the planate base plate 1502 of the syringe barrel holder housing 1500. In the example embodiment, the void of the base plate notch catch 1520 extends out from the right end section of the base plate slot 1508 at an angle substantially perpendicular to the side of the base plate slot 1508.

The syringe barrel holder 518 may also comprise a syringe barrel holder arm rod 1522. In the example embodiment shown in FIG. 64, the syringe barrel holder arm rod 1522 extends through an appropriately sized bore in the approximate center of the "T" shaped member 1512 (only the stem of the "T" shaped member 1512 is visible in FIG. 64). The syringe barrel holder arm rod 1522 may be movably coupled to the syringe barrel holder 518. In embodiments where the syringe barrel holder arm rod 1522 is movably coupled to the syringe barrel holder 518, the syringe barrel holder arm rod 1522 may move along a direction parallel to the edges of the stem of the "T" shaped member 1512. In the example embodiment in FIG. 64, the syringe barrel holder arm rod 1522 is able to slide along the bore in the "T" shaped member 1512 and uses the bore in the "T" shaped member 1512 as a linear motion bearing. In the example embodiment, the syringe barrel holder arm rod 1522 is longer than the length of the stem of the "T" shaped member 1512.

As shown in FIG. 64, one end of the syringe barrel holder arm rod 1522 may comprise a collar which may be a "U" shaped member 1524. The "U" shaped member 1524 may be fixedly coupled to the syringe barrel holder arm rod 1522. In the example embodiment, the bottom span of the "U" shaped member 1524 is thicker than the uprights of the "U" shaped member 1524. The thick bottom span of the "U" shaped member 1524 comprises a hole which allows the "U" shaped member 1524 to be coupled onto the syringe barrel holder arm rod 1522 when the syringe barrel holder 518 is assembled. In the example embodiment, the uprights of the "U" shaped member 1524 extend up through the base plate slot 1506 and are substantially flush with the plane of the top face of the planate base plate 1502. The uprights of the "U" shaped member 1524 may constrain the syringe barrel holder arm rod 1522 from rotation since any rotation is blocked by the uprights of the "U" shaped member 1524 abutting the edges of the base plate slot 1506.

In the example embodiment shown in FIG. 64, the syringe barrel holder 518 comprises a bias bar 1526. The bias bar 1526 in the example embodiment, is roughly rectangular in shape. The bias bar 1526 may comprise two holes which allow the bias bar 1526 to be placed on the syringe barrel holder guide rails 1514. The bias bar 1526 may be capable of guided movement along the axial direction of the syringe barrel holder guide rails 1514. In the example embodiment, the end of the coil springs 1516 on the syringe barrel holder guide rails 1514 not abutting the cross portion of the "T" shaped member 1512 abuts the front face of the bias bar 1526. In the example embodiment shown in FIG. 64 the maximum distance between the face of the bias bar 1526 which one end of the coil springs 1516 abut and the face of the "T" shaped member 1512 which the other end of the coil springs 1516 abut is shorter than the uncompressed length of the coil springs 1516. This ensures that the bias bar 1526 will always be biased toward the position shown in FIG. 64.

As shown in FIG. 64, the bias bar 1526 may comprise a cutout which allows the bias bar 1526 to fit around at least part of the syringe barrel holder arm rod 1522. The "U" shaped member 1524 may abut the face of the bias bar 1526 opposite the side which the coil springs 1516 abut. In such embodiments, the action of the coil springs 1516 biasing the bias bar 1526 toward the position depicted in FIG. 64, additionally biases the syringe barrel holder arm rod 1522 to the position depicted in FIG. 64.

Figure 65:
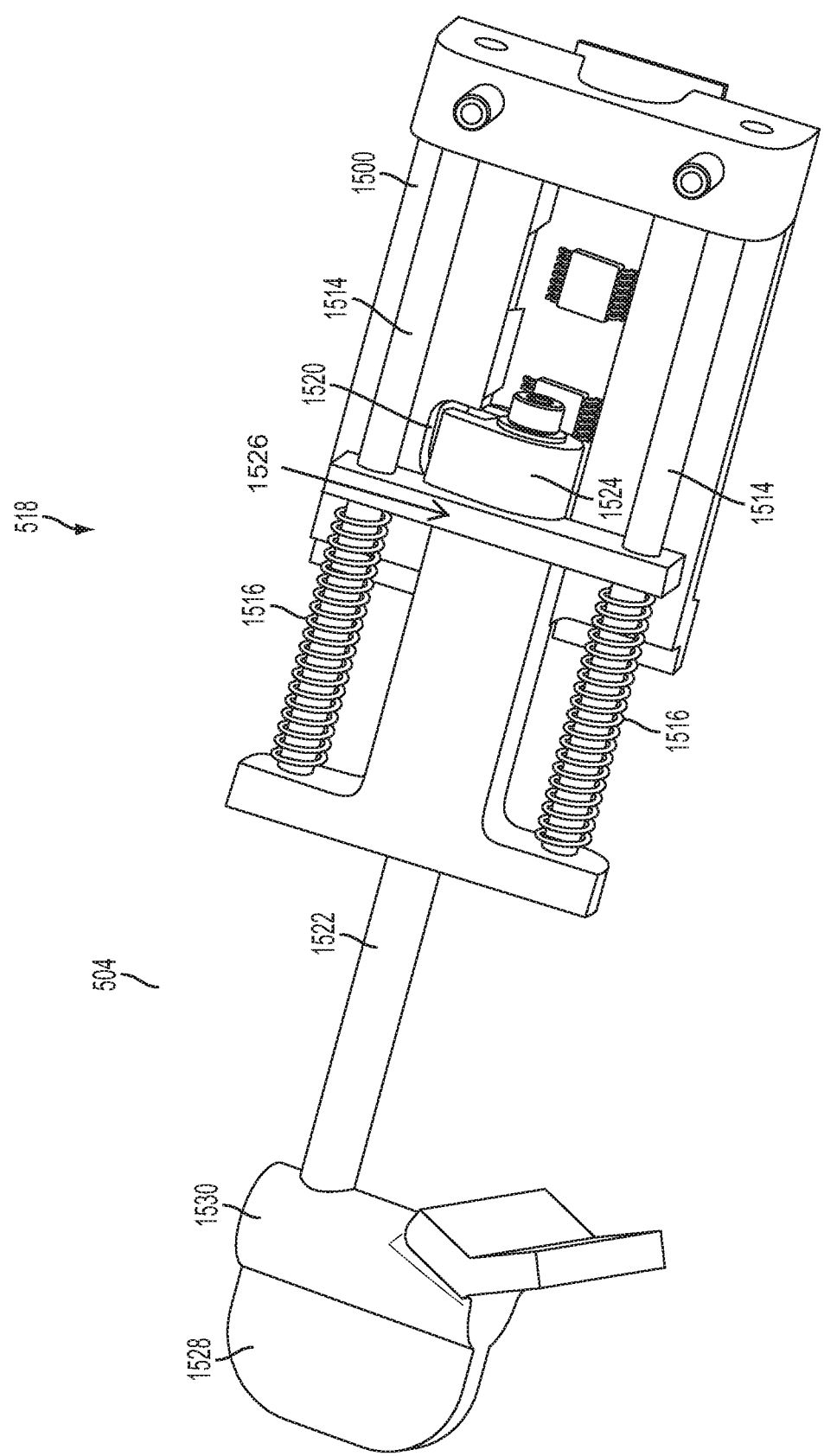
FIG. 65 is a view of an exemplary embodiment of the syringe barrel holder in which the syringe barrel holder is locked in the fully open position in accordance with an embodiment of the present disclosure.

In the example embodiment in FIG. 65, the syringe barrel holder 518 is shown in the fully open position. To move the syringe barrel holder 518 to the open fully open position, a user may grasp the syringe barrel holder grip 1528. In the example embodiment shown in FIG. 65, the syringe barrel holder grip 1528 is a projection which extends from the barrel contacting structure 1530 of the syringe barrel holder 518 which is fixedly coupled to the syringe barrel holder arm rod 1522. After grasping the syringe barrel holder grip 1528, a user may pull the syringe barrel holder arm rod 1522 away from the syringe barrel holder housing 1500. This action causes the "U" shaped member 1524 which is fixedly attached to the syringe barrel holder arm rod 1522 to move as well. Since the "U" shaped member 1524 may not pass through the bias bar 1526, the bias bar 1526 moves with the "U" shaped member 1524 and syringe barrel holder arm rod 1522. As the bias bar 1526 moves along the syringe barrel holder guide rails 1514, the coil springs become compressed such that if a user releases the syringe barrel holder grip 1528, the restoring force of the coil springs will automatically return the bias bar 1526, "U" shaped member 1524, and syringe barrel holder arm rod 1522 to the positions shown in FIG. 64.

To hold the syringe barrel holder 518 in the fully open position against the bias of the coil springs 1516, the syringe barrel holder 518 may be locked in the open position. As shown, the syringe barrel holder 518 may be locked in the open position by rotating the syringe barrel holder arm rod 1522 and all parts fixedly coupled to the syringe barrel holder arm rod 1522. In FIG. 65, the syringe barrel holder arm rod 1522 has been rotated substantially 90° such that the bottom span of the "U" shaped member 1524 is disposed within the base plate notch catch 1520. When the "U" shaped member is rotated into the base plate notch catch 1520, the restoring force of the coil springs 1516 is not capable of returning the syringe barrel holder 518 to the position shown in FIG. 64 because travel of the "U" shaped member 1524 is blocked by the base plate notch catch 1520.

After rotating the syringe barrel holder arm rod 1522 such that the syringe barrel holder 518 is locked in the open position, a user may release the syringe barrel holder grip 1528 to grasp a syringe 504 (not shown) and put it in place. As mentioned above, the syringe barrel holder 518 will remain in the fully open position. A user may then rotate the syringe barrel holder arm rod 1522 90° back to its original, unlocked position and allow the syringe barrel holder 518 to hold the syringe 504 in place.

Referring back to FIG. 31 the syringe barrel holder 518 is shown fully open and rotated into the locked position. In the fully open position, the syringe barrel contacting structure 1530 and syringe barrel holder grip 1528 are at their furthest possible distance from the syringe seat 506 of the syringe pump assembly 501. In some embodiments, this distance may be substantially larger than the diameter of the largest syringe 504 which may be accepted by the syringe pump 500. In FIG. 31, a syringe 504 has been put in place against the syringe seat 506 while the syringe barrel holder 518 has be locked in the open position. In FIG. 32, the syringe barrel holder has been rotated out of the locked position and has been allowed to automatically adjust to the size of the syringe barrel 540. As mentioned in the discussion of FIG. 65, this automatic adjustment is a result of the restoring force of the coil springs 1516 automatically pushing the bias bar 1526, "U" shaped member 1524, and the syringe barrel holder arm rod 1522 toward the position depicted in FIG. 64.

Figure 66:
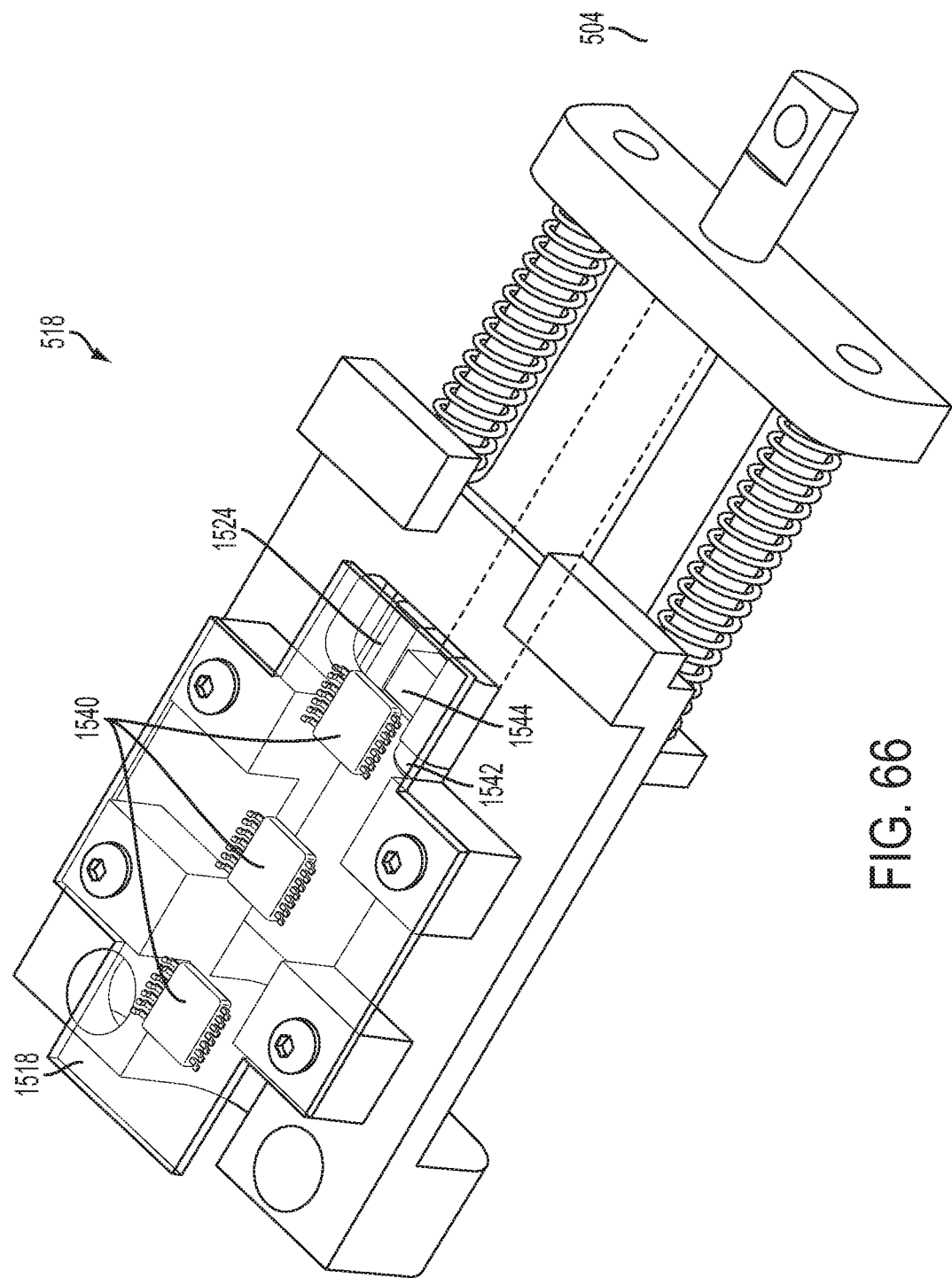
FIG. 66 is a view of an exemplary embodiment the syringe barrel holder linear position sensor in which the linear position sensor printed circuit board is shown as transparent in accordance with an embodiment of the present disclosure.

In FIG. 66, an example embodiment of the syringe barrel holder 518 is shown. In the embodiment depicted in FIG. 66 the syringe barrel holder PCB 1518 is shown as transparent. The syringe barrel holder PCB 1518 may comprise one or a number of syringe barrel holder linear position sensors 1540. In the example embodiment, there are three syringe barrel holder linear position sensors 1540. The syringe barrel holder linear position sensors 1518 may be used to determine the size of the syringe 504 (not shown) which the syringe barrel holder 518 is holding in place.

In some embodiments, there may only be a single syringe barrel holder linear position sensor 1540. In such embodiments, the syringe barrel holder linear position sensor 1540 may be a linear potentiometer. In embodiments where the syringe barrel holder linear position sensor 1540 is a linear potentiometer, the syringe barrel holder linear position sensor 1540 may comprise a barrel sizing wiper 1542 which may slide across the resistive element of the potentiometer with movement of the syringe barrel holder arm rod 1522. When a syringe 504 (not shown) is held by the syringe barrel holder 518, the size of the syringe 504 (not shown) will determine the position of the barrel sizing wiper 1542 along the linear potentiometer type syringe barrel holder linear position sensor 1540. Since the location of the wiper 1542 will vary the resistance measured by the linear position sensor 1540, the resistance measured may be used to establish information (size, volume, brand, etc.) about the syringe 504 (not shown) being used. In some embodiments, the resistance measurement may be referenced with a database or resistance measurements which would be expected from different syringes 504 to determine information about the syringe 504. The resistance measurement may additionally be used to determine whether a syringe 504 is properly held by the syringe barrel holder 518. For example, if the resistance measurement indicates that the syringe barrel holder 518 is in the fully open position (as it is in FIG. 66), an alarm may be generated and a therapy may not be initiated.

In some embodiments, including the example embodiment shown in FIG. 66, the syringe barrel holder linear position sensors 1540 may be magnetic linear position sensors. Any suitable magnetic linear position sensor may be used for the syringe barrel holder linear position sensor 1540. The syringe barrel holder linear position sensors 1540 may be the same type of sensors as the sliding block assembly linear position sensors 1050. An example of a suitable magnetic linear position sensor is the "AS5410 Absolute Linear 3D Hall Encoder" available from Austria-microsystems of Austria. The syringe barrel holder linear position sensors 1540 gather their positional data from a syringe barrel holder magnet 1544 placed at a suitable distance from the syringe barrel holder linear position sensors 1540. In the example embodiment shown in FIG. 66, the syringe barrel holder magnet 1544 rests on the bottom span of the "U" shaped member 1524 between the two uprights of the "U" shaped member 1524. The absolute location of the syringe barrel holder magnet may be measured by the syringe barrel holder linear position sensors 1540. Since the measured absolute location of the syringe barrel holder magnet 1544 may vary depending on the syringe 504 (not shown) being held by the syringe barrel holder 518, the absolute location of the syringe barrel holder magnet 1544 can be used to determine specific information (for example, size, volume, brand, etc.) about the syringe 504 (not shown) being held. In some embodiments, the absolute location of the syringe barrel holder magnet 1544 may be referenced with a database to determine information about the syringe 504 being utilized. In such embodiments, the database may be a database of absolute locations which would be expected with different syringes 504. The absolute position measurement may also be used to determine whether a syringe 504 is correctly held in place by the syringe barrel holder 518. For example, if the absolute position measurement indicates that the syringe barrel holder 518 is in the fully open position (as it is in FIG. 66), an alarm may be generated and a therapy may not be initiated.

In some embodiments, the data gathered by the syringe barrel holder linear position sensor 1540 may be compared to data gathered by other sensors to make a more informed decision on the specific syringe 504 being used. For example, in embodiments where a plunger clamp jaws position sensor 588 may make a determination on the type of syringe 504 being used (see discussion of FIG. 37) the data from the plunger clamp jaws position sensor 588 and linear position sensor 1540 may be compared. If the data gathered by the syringe barrel holder linear position sensor 1540 does not correlate with data gathered by other sensors, an alarm may be generated.

In some embodiments, data from the plunger clamp jaws position sensor 588 may be first referenced against a syringe 504 database to narrow down acceptable syringe barrel 540 measurements. In some embodiments, data from the syringe barrel holder linear position sensor may be referenced against a syringe 504 database to set a range of acceptable plunger flange 548 measurements.

Figure 67:
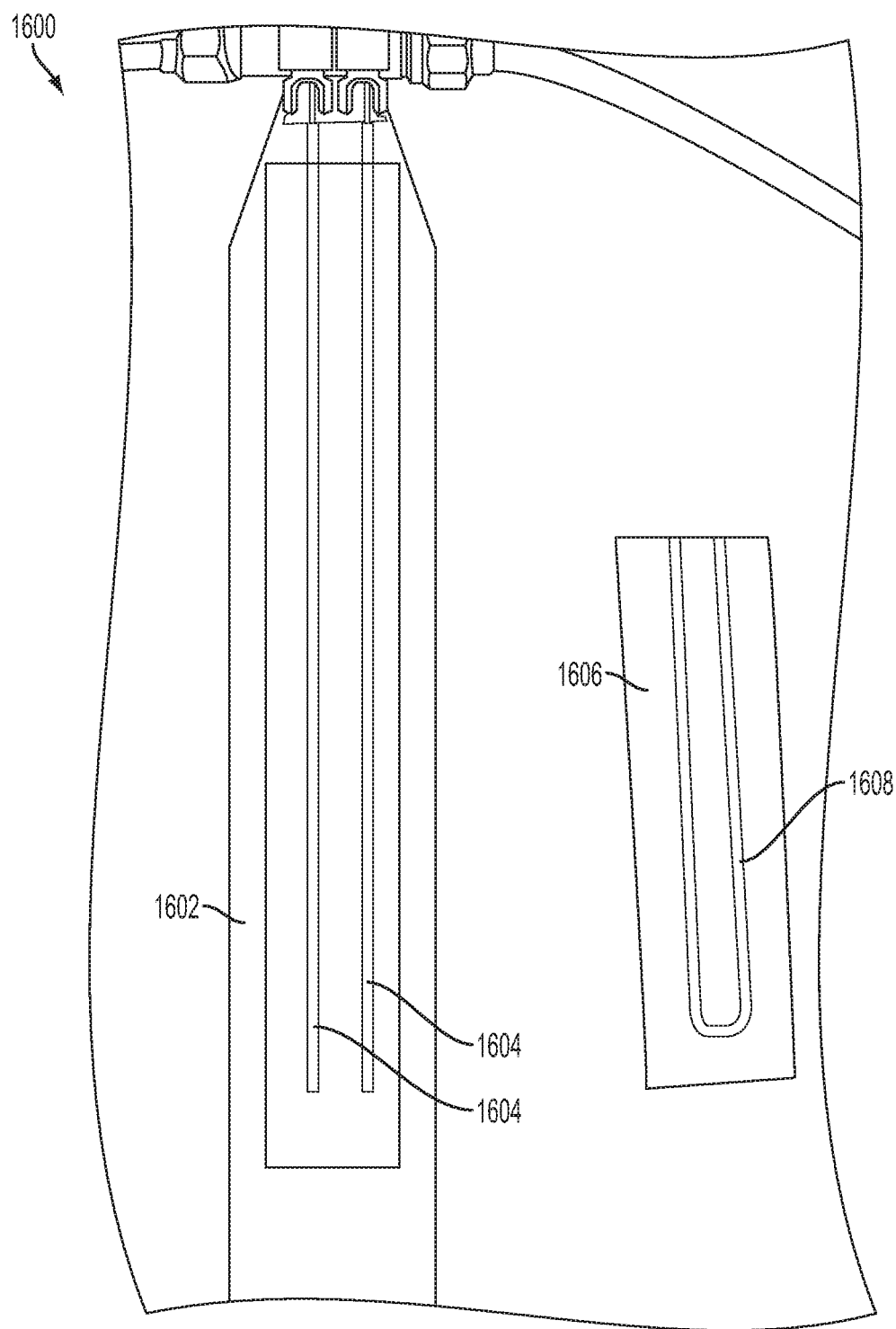
FIG. 67 is a view of an exemplary embodiment of a phase change detector linear position sensor in accordance with an embodiment of the present disclosure.

FIG. 67 shows a basic example of part of an alternative linear position sensor. The part of the alternative linear position sensor in FIG. 67 is a line stretcher 1600. In the example embodiment, the line stretcher 1600 comprises a stationary portion and a moving portion. The stationary portion comprises an FR-4 PCB substrate 1602. On the substrate 1602 there are two microstrips 1604. As shown, the microstrips 1604 extend parallel to each other. The microstrips 1604 act as transmission lines for a signal at a known frequency. The microstrips 1604 do not allow the signal to propagate into the ambient environment. The width of the microstrips 1604 is chosen so that it is suitable for the desired impedance. In an example embodiment, the desired impedance is 50Ω.

The moving portion in the example embodiment comprises a moving portion FR-4 PCB substrate 1606. As shown, the moving portion FR-4 PCB substrate comprises a moving portion microstrip 1608. The moving portion microstrip 1608 may be substantially "U" shaped. The uprights of the "U" shaped moving portion microstrip 1608 extend parallel to each other and are spaced such that when the line stretcher 1600 is assembled they may contact the two microstips 1604 on the stationary portion. The moveable portion microstrips 1608 have a width chosen so that it is suitable for desired amount of impedance (50Ω in the example embodiment). The bottom span of the "U" shaped movable portion microstrip 1608 connects the two uprights of the "U" shaped movable portion microstrip 1608 and is substantially perpendicular to the two uprights. When fully assembled, the bottom span of the "U" shaped movable portion microstrip 1604 forms a bridge between the two microstrips 1604 on the stationary portion of the line stretcher 1600. Any signal sent through one of the microstrips 1604 on the stationary portion may cross via the moving portion microstrip 1608 to the other microstrip 1604 on the stationary portion. By sliding the moving portion along the direction of extension of the stationary portion microstrips 1604 the signal must travel a greater or shorter distance before crossing from one stationary portion microstrip 1604 to the other. By manipulating the amount of travel of the signal, a user may predictably create a phase change of the signal. To reduce wear on the metal microstrips 1604 and 1608 a thin sheet of insulation 1609 may be placed between the microstrips 1604 and 1608, creating a capacitive coupling.

Figure 68:
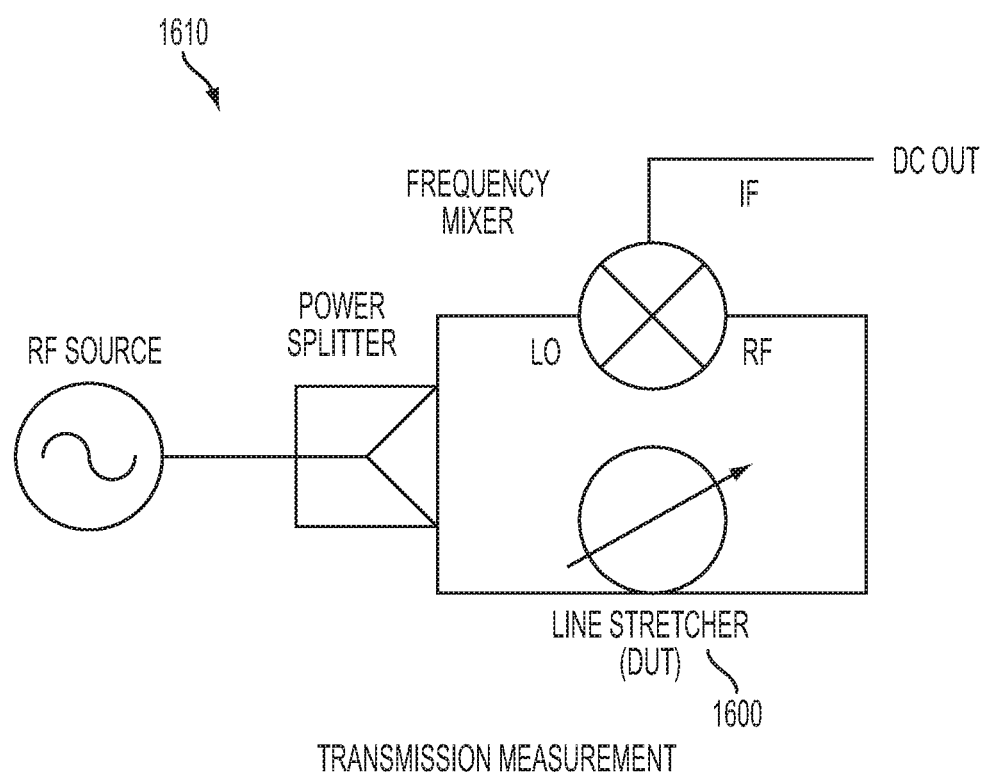
FIG. 68 shows a schematic of the exemplary view of a phase change detector linear position sensor in accordance with an embodiment of the present disclosure.

FIG. 68 shows an example of the line stretcher 1600 being incorporated into a phase change detector 1610. As shown, the phase change detector 1610 comprises a signal source shown as "RF SOURCE" in the example shown in FIG. 68. The source signal in the example shown in FIG. 68 travels from the "RF SOURCE" to a "POWER SPLITTER". The "POWER SPLITTER" splits the signal, keeping the two output signals in a constant phase relationship with one another. One of the signals travels directly to a "FREQUENCY MIXER". The other signal is delayed before it is allowed to reach the "FREQUENCY MIXER". In FIG. 68, the signal is delayed by the line stretcher 1600 (see FIG. 67). Delaying the signal causes the delayed signal to be predictably out of phase with the non-delayed signal which travels directly to the "FREQUENCY MIXER". The delayed signal travels from line stretcher 1600 to the "FREQUENCY MIXER". In the example embodiment shown in FIG. 68 the "FREQUENCY MIXER" is a double balanced frequency mixer. As is well known in the art, two identical frequency, constant-amplitude signals sent to a mixer will result in a DC output which is proportional to the phase difference between the two signals.

Figure 69:
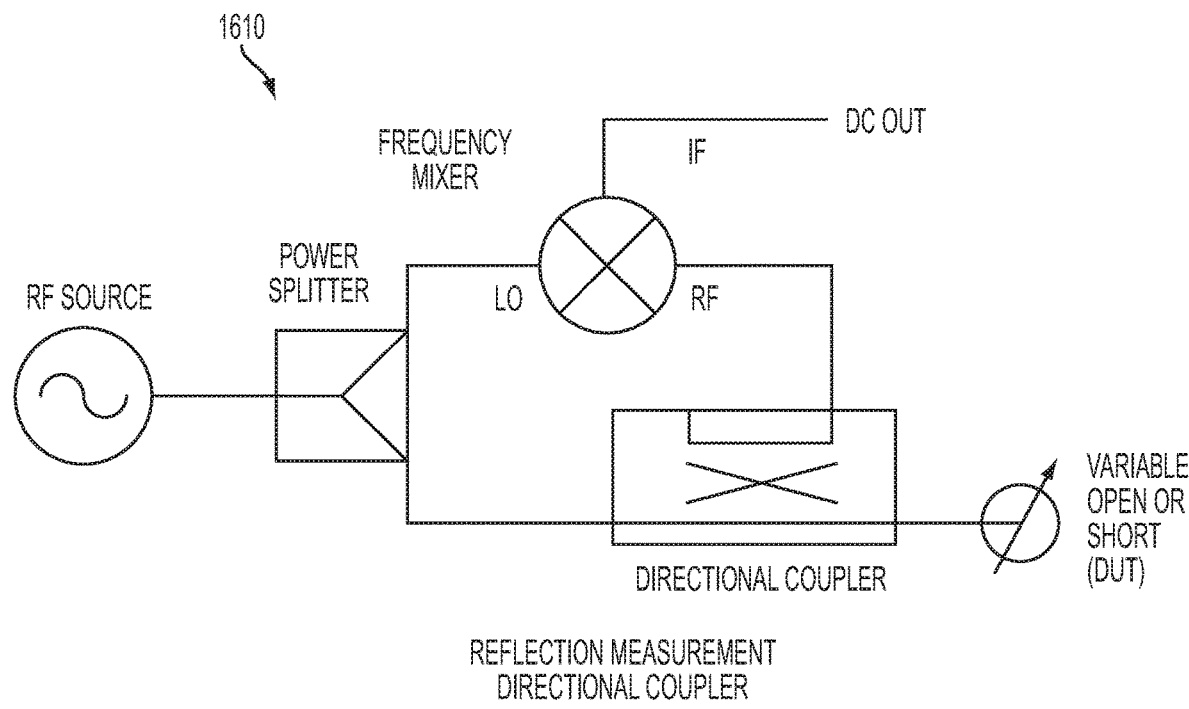
FIG. 69 shows a schematic of the exemplary view of a phase change detector linear position sensor in accordance with an embodiment of the present disclosure.

FIG. 69 depicts a slightly different embodiment of the phase change detector 1610. In FIG. 69 the delay means is not a line stretcher 1600 such as the one described in FIG. 67. The delay means is a variable open or short. As the object whose linear position is to be measured linearly displaces, the short or open's location on a transmission line may be caused to move proportionally. As shown, the signal travels through a "DIRECTIONAL COUPLER" which may be any suitable directional coupler. As one of the two signals the signal enters the "DIRECTIONAL COUPLER" from the "POWER SPLITTER" the signal is sent out of another port of the "DIRECTIONAL COUPLER to an open or short. The open or short causes the signal to reflect back to the port from which it traveled to reach the open or short. The signal reflected back into the port is then directed by the "DIRECTIONAL COUPLER" to travel into the "FREQUENCY MIXER". The delay of the signal caused by the distance traveled to and from the point of reflection causes a phase shift in the signal. The amount of phase shift of the signal is dependent on the distance from the port from which the signal exits the "DIRECTIONAL COUPLER" to the open or short. This distance may be caused to change in consequence to movement of the object whose linear position is to be measured. The second signal output of the "POWER SPLITTER" travels directly to the "FREQUENCY MIXER". As is well known in the art, two identical frequency, constant-amplitude signals sent to a mixer will result in a DC output which is proportional to the phase difference between the two signals.

Figure 70:
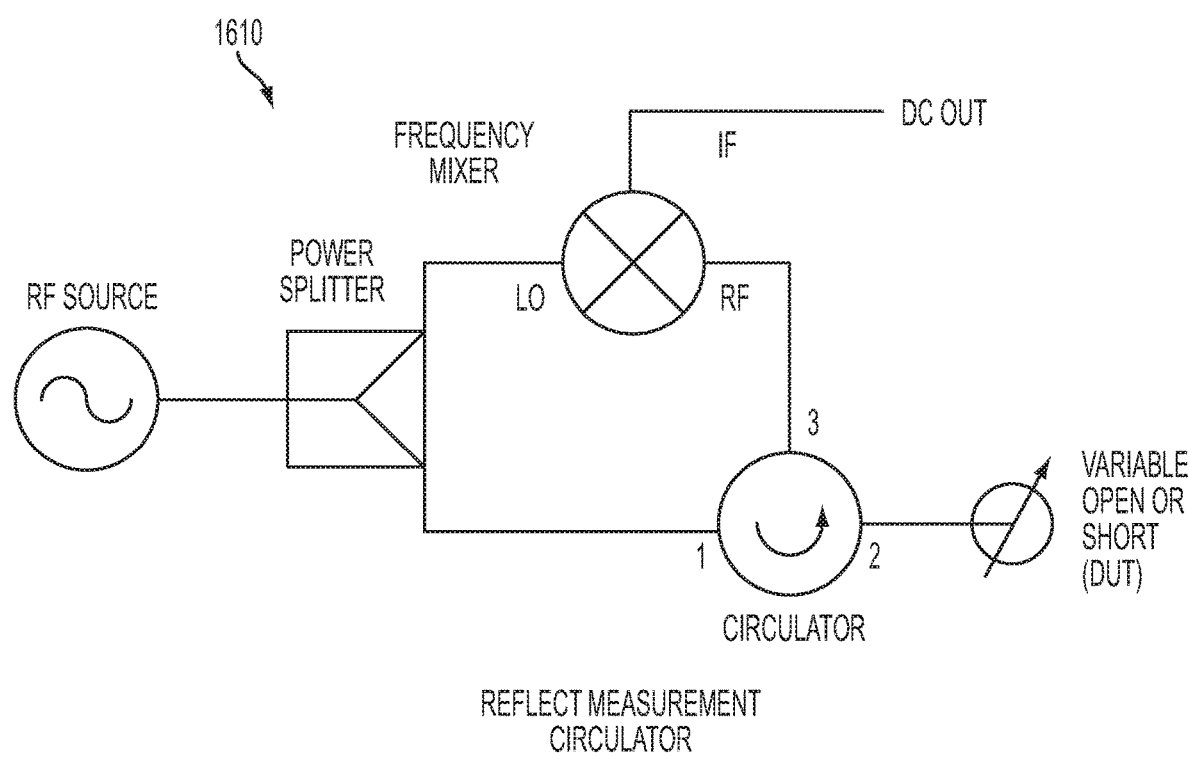
FIG. 70 shows a schematic of the exemplary view of a phase change detector linear position sensor in accordance with an embodiment of the present disclosure.

As shown in FIG. 70, the "DIRECTIONAL COUPLER" may be replaced with another piece of equipment such as a circulator. The phase change detector 1610 in FIG. 70 functions very similarly to the phase change detector 1610 in FIG. 69. One signal from the power splitter travels directly to the "FREQUENCY MIXER". The other signal is delayed. The delay is caused in the same manner as described above. Instead of using a "DIRECTIONAL COUPLER", however, a "CIRCULATOR" may be used to direct the signal. As the signal enters the "CIRCULATOR" at port 1 the signal is circulated to port 2. The signal travels from port 2 to the short or open and is reflected back into port 2. The reflected, phase shifted signal entering port 2 of the "CIRCULATOR" is circulated to port 3. The signal exits port 3 and travels to the "FREQUENCY MIXER" As is well known in the art, two identical frequency, constant-amplitude signals sent to a mixer will result in a DC output which is proportional to the phase difference between the two signals. Since the phase difference is dependent on the distance of the short or open from port 2 of the "CIRCULATOR" and the distances varies in proportion to the location of the object whose linear location is to be found the DC output of the mixer may be used to determine the objects location.

In some embodiments, the phase change detector 1610 may be used to substitute for the syringe barrel holder linear position sensors 1540 (see FIG. 66) or the sliding block magnetic linear position sensors 1054 (see FIG. 57). In some embodiments, only one of the syringe barrel holder linear position sensors 1540 or the sliding block magnetic linear position sensors 1054 may be substituted for with the phase change detector 1610. In some embodiments, a phase change detector 1610 may be used in conjunction with one or both the syringe barrel holder linear position sensors 1540 or the sliding block magnetic linear position sensors 1054 and function as a cross check or backup.

In embodiments where the sliding block assembly linear position sensor 1054 (see FIG. 57) is substituted for with a phase change detector 1610, the phase change detector 1610 may be used to detect the position of the sliding block assembly 800 along the lead screw 850 (see FIG. 57). If the phase shift detector 1610 uses a line stretcher 1600 (see FIG. 67) the moveable portion of the line stretcher 1600 may be caused to move along the stationary portion of the line stretcher 1600 with movement of the sliding block assembly 800 along the lead screw 850. In turn this would cause the degree of phase change to reflect the position of the sliding block assembly 800 on the lead screw 850. Consequently, the DC output voltage of the mixer (see FIG. 68) may be used to determine the position of the sliding block assembly 800. The positional data generated by the phase change detector 1610 may be used in the same manner as described above in relation to the prior discussion of sliding block assembly 800 linear position sensing.

In embodiments where the phase change detector 1610 uses a variable short or open (see FIG. 69 and FIG. 70), movement of the sliding block assembly 800 along the lead screw 850 may cause the short or open to change its location along the transmission line. In turn this would cause the degree of phase change to specify the position of the sliding block assembly 800 along the lead screw 850. Consequently, the DC output voltage of the mixer (see FIG. 69 and FIG. 70) may be used to determine the position of the sliding block assembly 800.

In embodiments where the syringe barrel holder linear position sensors 1540 (see FIG. 66) is substituted for by the phase change detector 1610, the phase change detector 1610 may be used to may be used to determine the size of the syringe 504 (see FIG. 28). If the phase change detector 1610 uses a line stretcher 1600 (see FIG. 67) the moveable portion of the line stretcher 1600 may be caused to move along the stationary portion of the line stretcher 1600 with movement of the syringe barrel holder arm rod 1522. In turn this would cause the degree of phase change to reflect the position of the syringe barrel holder arm rod 1522. Since the position of the syringe barrel holder arm rod 1522 is dependent upon various characteristics of the syringe 504, the DC output voltage of the mixer (see FIG. 68) may be used to determine the position of the of the syringe barrel holder arm rod 1522 and therefore a number of characteristics of the syringe 504.

In embodiments where the phase change detector 1610 uses a variable short or open (see FIG. 69 and FIG. 70), movement of the syringe barrel holder arm rod 1522 may cause the short or open to change its location along a transmission line. In turn this would cause the degree of phase change to specify the position of the syringe barrel holder arm rod 1522. Since the position of the syringe barrel holder arm rod 1522 is dependent upon various characteristics of the syringe 504, the DC output voltage of the mixer (see FIG. 69 and FIG. 70) may be used to determine the position of the syringe barrel holder arm rod 1522 and therefore a number of characteristics of the syringe 504. The positional data generated by the phase change detector 1610 may be used in the same manner as described above in relation to the prior discussion of syringe barrel holder linear position sensing.

Figure 71:
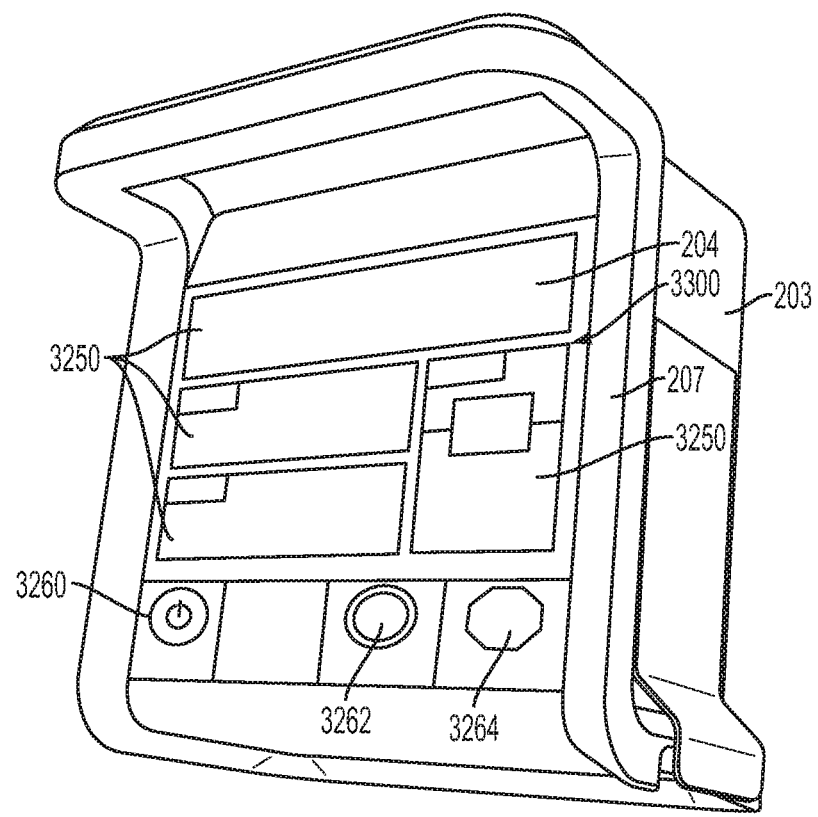
FIG. 71 shows a perspective view of a pump with the graphic user interface shown on the screen in accordance with an embodiment of the present disclosure.

An example embodiment of the graphic user interface (hereafter GUI) 3300 is shown in FIG. 71. The GUI 3300 enables a user to modify the way that an agent may be infused by the syringe pump 500 by customizing various programming options. Though the following discussion mostly details the use of the GUI 3300 with the syringe pump 500, it should be appreciated that the GUI 3300 may be used with other pumps, including the other pumps mentioned in this specification. For example, the GUI 3300 may be used with the pump 201, 202, or 203 (as shown in FIG. 71) detailed in the discussion of FIGS. 2-9. For purposes of example, the GUI 3300 detailed as follows uses a screen 3204 which is a touch screen display 514 (see FIG. 28) as a means of interaction with a user. In other embodiments, the means of interaction with a user may be different. For instance, alternate embodiments may comprise user depressible buttons or rotatable dials, audible commands, etc. In other embodiments, the screen 3204 may be any electronic visual display such as a, liquid crystal display, L.E.D. display, plasma display, etc.

As detailed in the preceding paragraph, the GUI 3300 is displayed on the display 514 of the syringe pump 500. Each syringe pump 500 may have its own individual screen 3204. In arrangements where there are multiple syringe pumps 500 or a syringe pump 500 and one or more other pumps, the GUI 3300 may be used to control multiple pumps. Only the master pump may require a screen 3204. As shown in FIG. 71, the pump 203 is seated in a Z-frame 3207. As shown, the GUI 3300 may display a number of interface fields 3250. The interface fields 3250 may display various information about the pump 203, infusion status, and/or the medication, etc. In some embodiments, the interface fields 3250 on the GUI 3300 may be touched, tapped, etc. to navigate to different menus, expand an interface field 3250, input data, and the like. The interface fields 3250 displayed on the GUI 3300 may change from menu to menu.

The GUI 3300 may also have a number of virtual buttons. In the non-limiting example embodiment in FIG. 71 the display has a virtual power button 3260, a virtual start button 3262, and a virtual stop button 3264. The virtual power button 3260 may turn the syringe pump 500 on or off. The virtual start button 3262 may start an infusion. The virtual stop button 3264 may pause or stop an infusion. The virtual buttons may be activated by a user's touch, tap, double tap, or the like. Different menus of the GUI 3300 may comprise other virtual buttons. The virtual buttons may be skeuomorphic to make their functions more immediately understandable or recognizable. For example, the virtual stop button 3264 may resemble a stop sign as shown in FIG. 71. In alternate embodiments, the names, shapes, functions, number, etc. of the virtual buttons may differ.

Figure 72:
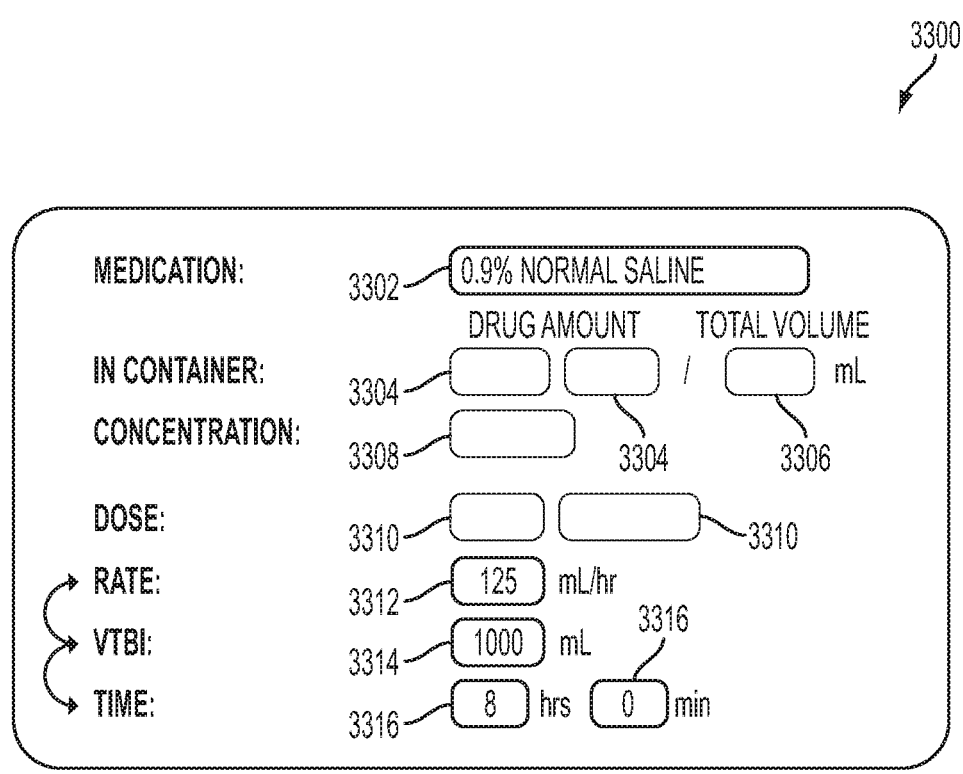
FIG. 72 shows an example infusion programming screen of the graphic user interface in accordance with an embodiment of the present disclosure.

As shown in the example embodiment in FIG. 72, the interface fields 3250 of the GUI 3300 (see FIG. 71) may display a number of different programming parameter input fields. For the GUI 3300 to display the parameter input fields, a user may be required to navigate through one or a number of menus. Additionally, it may be necessary for the user to enter a password before the user may manipulate any of the parameter input fields.

In FIG. 72, a medication parameter input field 3302, in container drug amount parameter input field 3304, total volume in container parameter input field 3306, concentration parameter input field 3308, dose parameter input field 3310, volume flow rate (hereafter abbreviated as rate) parameter input field 3312, volume to be infused (hereafter VTBI) parameter input field 3314, and time parameter input field 3316 are displayed. The parameters, number of parameters, names of the parameters, etc. may differ in alternate embodiments. In the example embodiment, the parameter input fields are graphically displayed boxes which are substantially rectangular with rounded corners. In other embodiments, the shape and size of the parameter input fields may differ.

In the example embodiment, the GUI 3300 is designed to be intuitive and flexible. A user may choose to populate a combination of parameter input fields which are simplest or most convenient for the user. In some embodiments, the parameter input fields left vacant by the user may be calculated automatically and displayed by the GUI 3300 as long as the vacant fields do not operate independently of populated parameter input fields and enough information can be gleaned from the populated fields to calculate the vacant field or fields. Throughout FIGS. 72-76, fields dependent upon on another are tied together by curved double-tipped arrows.

The medication parameter input field 3302 may be the parameter input field in which a user sets the type of infusate agent to be infused. In the example embodiment, the medication parameter input field 3302 has been populated and the infusate agent has been defined as "0.9% NORMAL SALINE". As shown, after the specific infusate has been set, the GUI 3300 may populate the medication parameter input field 3302 by displaying the name of the specific infusate in the medication parameter input field 3302.

To set the specific infusate agent to be infused, a user may touch the medication parameter input field 3302 on the GUI 3300. In some embodiments, this may cull up a list of different possible infusates. The user may browse through the list until the desired infusate is located. In other embodiments, touching the in medication parameter input field 3302 may cull up a virtual keyboard. The user may then type the correct infusate on the virtual keyboard. In some embodiments, the user may only need to type only a few letters of the infusate on the virtual keyboard before the GUI 3300 displays a number of suggestions. For example, after typing "NORE" the GUI 3300 may suggest "NOREPINEPHRINE". After locating the correct infusate, the user may be required to perform an action such as, but not limited to, tapping, double tapping, or touching and dragging the infusate. After the required action has been completed by the user, the infusate may be displayed by the GUI 3300 in the medication parameter input field 3302. For another detailed description of another example means of infusate selection see FIG. 82.

In the example embodiment in FIG. 72, the parameter input fields have been arranged by a user to perform a volume based infusion (for instance mL, mL/hr, etc.). Consequentially, the in container drug amount parameter input field 3304 and total volume in container parameter input field 3306 have been left unpopulated. The concentration parameter input field 3308 and dose parameter input field 3310 have also been left unpopulated. In some embodiments, the in container drug amount parameter input field 3304, total volume in container parameter input field 3306, concentration parameter input field 3308, and dose parameter input field 3310 may be locked, grayed out, or not displayed on the GUI 3300 when such an infusion has been selected. The in container drug amount parameter input field 3304, total volume in container parameter input field 3306, concentration parameter input field 3308, and dose parameter input field 3310 will be further elaborated upon in subsequent paragraphs.

When the GUI 3300 is being used to program a volume base infusion, the rate parameter input field 3312, VTBI parameter input field 3314, and time parameter input field 3316 do not operate independent of one another. A user may only be required to define any two of the rate parameter input field 3312, VTBI parameter input field 3314, and time parameter input field 3316. The two parameters defined by a user may be the most convenient parameters for a user to set. The parameter left vacant by the user may be calculated automatically and displayed by the GUI 3300. For instance, if a user populates the rate parameter input field 3312 with a value of 125 mL/hr (as shown), and populates the VTBI parameter input field 3314 with a value of 1000 mL (as shown) the time parameter input field 3316 value may be calculated by dividing the value in the VTBI parameter input field 3314 by the value in the rate parameter input field 3312. In the example embodiment shown in FIG. 72, the quotient of the above calculation, 8 hrs and 0 min, is correctly populated by the GUI 3300 into the time parameter input field 3316.

For a user to populate the rate parameter input field 3312, VTBI parameter input field 3314, and time parameter input field 3316 the user may touch or tap the desired parameter input field on the GUI 3300. In some embodiments, this may cull up a number pad with a range or number, such as 0-9 displayed as individual selectable virtual buttons. A user may be required to input the parameter by individually tapping, double tapping, touching and dragging, etc. the desired numbers. Once the desired value has been input by a user, a user may be required to tap, double tap, etc. a virtual "confirm", "enter", etc. button to populate the field. For another detailed description of another example way of defining numerical values see FIG. 82.

Figure 73:
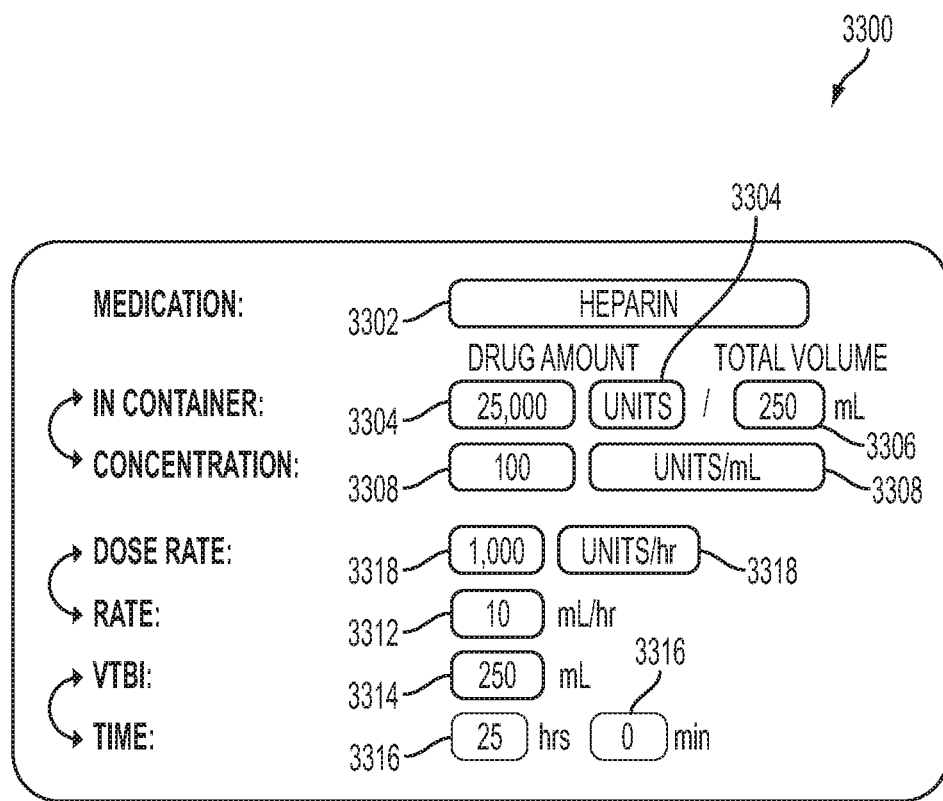
FIG. 73 shows an example infusion programming screen of the graphic user interface in accordance with an embodiment of the present disclosure.

FIG. 73 shows a scenario in which the infusion parameters being programmed are not those of a volume based infusion. In FIG. 73, the infusion profile is that of a continuous volume/time dose rate. In the example embodiment shown in FIG. 73, all of the parameter input fields have been populated. As shown, the medication parameter input field 3302 on the GUI 3300 has been populated with "HEPARIN" as the defined infusate. As shown, the in container drug amount parameter input field 3304, total volume in container input field 3306, and concentration parameter input field 3308 are populated in FIG. 73. Additionally, since a volume/time infusion is being programmed the dose parameter input field 3310 shown in FIG. 72 has been replaced with a dose rate parameter input field 3318.

The in container drug amount parameter input field 3304 is a two part field in the example embodiment shown in FIG. 73. In the example embodiment in FIG. 73 the left field of the in container drug amount parameter input field 3304 is a field which may be populated with a numeric value. The numeric value may defined by the user in the same manner as a user may define values in the rate parameter input field 3312, VTBI parameter input field 3314, and time parameter input field 3316. In the example embodiment shown in FIG. 73, the numeric value displayed by the GUI 3300 in the in left field of the in container drug amount parameter input field 3304 is "25,000".

The parameter defined by the right field of the in container drug amount parameter input field 3304 is the unit of measure. To define the right of the in container drug amount parameter input field 3304, a user may touch the in container drug amount parameter input field 3304 on the GUI 3300. In some embodiments, this may cull up a list of acceptable possible units of measure. In such embodiments, the desired unit of measure may be defined by a user in the same manner as a user may define the correct infusate. In other embodiments, touching the in container drug amount parameter input field 3304 may cull up a virtual keyboard. The user may then type the correct unit of measure on the virtual keyboard. In some embodiments the user may be required to tap, double tap, etc. a virtual "confirm", "enter", etc. button to populate the left field of the in container drug amount parameter input field 3304.

The total volume in container parameter input field 3306 may be populated by a numeric value which defines the total volume of a container. In some embodiments, the GUI 3300 may automatically populate the total volume in container parameter input field 3306 based on data generated by one or more sensors. In other embodiments, the total volume in container parameter input field 3306 may be manually input by a user. The numeric value may defined by the user in the same manner as a user may define values in the rate parameter input field 3312, VTBI parameter input field 3314, and time parameter input field 3316. In the example embodiment shown in FIG. 73 the total volume in container parameter input field 3306 has been populated with the value "250" mL. The total volume in container parameter input field 3306 may be restricted to a unit of measure such as mL as shown.

The concentration parameter input field 3308 is a two part field similar to the in container drug amount parameter input field 3304. In the example embodiment in FIG. 73 the left field of the concentration parameter input field 3308 is a field which may be populated with a numeric value. The numeric value may defined by the user in the same manner as a user may define values in the rate parameter input field 3312, VTBI parameter input field 3314, and time parameter input field 3316. In the example embodiment shown in FIG. 73, the numeric value displayed by the GUI 3300 in the in left field of the concentration parameter input field 3308 is "100".

The parameter defined by the right field of the concentration parameter input field 3308 is a unit of measure/volume. To define the right field of the concentration parameter input field 3308, a user may touch the concentration parameter input field 3308 on the GUI 3300. In some embodiments, this may cull up a list of acceptable possible units of measure. In such embodiments, the desired unit of measure may be defined by a user in the same manner as a user may define the correct infusate. In other embodiments, touching the concentration parameter input field 3308 may cull up a virtual keyboard. The user may then type the correct unit of measure on the virtual keyboard. In some embodiments the user may be required to tap, double tap, etc. a virtual "confirm", "enter", etc. button to store the selection and move on to a list of acceptable volume measurements. The desired volume measurement may be defined by a user in the same manner as a user may define the correct infusate. In the example embodiment shown in FIG. 73 the right field of the concentration parameter input field 3308 is populated with the unit of measure/volume "UNITS/mL".

The in container drug amount parameter input field 3304, total volume in container input field 3306, and concentration parameter input field 3308 are not independent of one another. As such, a user may only be required to define any two of the in container drug amount parameter input field 3304, total volume in container input field 3306, and concentration parameter input field 3308. For instance, if a user were to populate the concentration parameter input field 3308 and the total volume in container parameter input field 3306, the in container drug amount parameter input field may be automatically calculated and populated on the GUI 3300.

Since the GUI 3300 in FIG. 73 is being programmed for a continuous volume/time dose, the dose rate parameter input field 3318 has been populated. The user may define the rate at which the infusate is infused by populating the dose rate parameter input field 3318. In the example embodiment in FIG. 73, the dose rate parameter input field 3318 is a two part field similar to the in container drug amount parameter input field 3304 and concentration parameter input field 3308 described above. A numeric value may defined in the left field of the dose rate parameter input field 3318 by the user in the same manner as a user may define values in the rate parameter input field 3312. In the example embodiment in FIG. 73, the left field of the dose rate parameter input field 3318 has been populated with the value "1000".

The right field of the dose rate parameter input field 3318 may define a unit of measure/time. To define the right field of the dose rate parameter input field 3318, a user may touch the dose rate parameter input field 3318 on the GUI 3300. In some embodiments, this may cull up a list of acceptable possible units of measure. In such embodiments, the desired unit of measure may be defined by a user in the same manner as a user may define the correct infusate. In other embodiments, touching the dose rate parameter input field 3304 may cull up a virtual keyboard. The user may then type the correct unit of measure on the virtual keyboard. In some embodiments the user may be required to tap, double tap, etc. a virtual "confirm", "enter", etc. button to store the selection and move on to a list of acceptable time measurements. The desired time measurement may be defined by a user in the same manner as a user may define the correct infusate. In the example embodiment shown in FIG. 73 the right field of the dose rate parameter input field 3318 is populated with the unit of measure/time "UNITS/hr".

In the example embodiment, the dose rate parameter input field 3318 and the rate parameter input field 3312 are not independent of one another. After a user populates the dose rate parameter input field 3318 or the rate parameter input field 3312, the parameter input field left vacant by the user may be calculated automatically and displayed by the GUI 3300 as long as the concentration parameter input field 3308 has been defined. In the example embodiment shown in FIG. 73, the rate parameter input field 3312 has been populated with an infusate flow rate of "10 mL/hr". The dose rate parameter input field 3318 has been populated with "1000" "UNITS/hr".

In the example embodiment shown in FIG. 73 the VTBI parameter input field 3314 and time parameter input field 3316 have also been populated. The VTBI parameter input field 3314 and time parameter input field 3316 may be populated by a user in the same manner described in relation to FIG. 72. When the GUI 3300 is being programmed to a continuous volume/time dose rate infusion, the VTBI parameter input field 3314 and the time parameter input field 3316 are dependent on one another. A user may only need to populate one of the VTBI parameter input field 3314 or the time parameter input field 3316. The field left vacant by the user may be calculated automatically and displayed on the GUI 3300.

Figure 74:
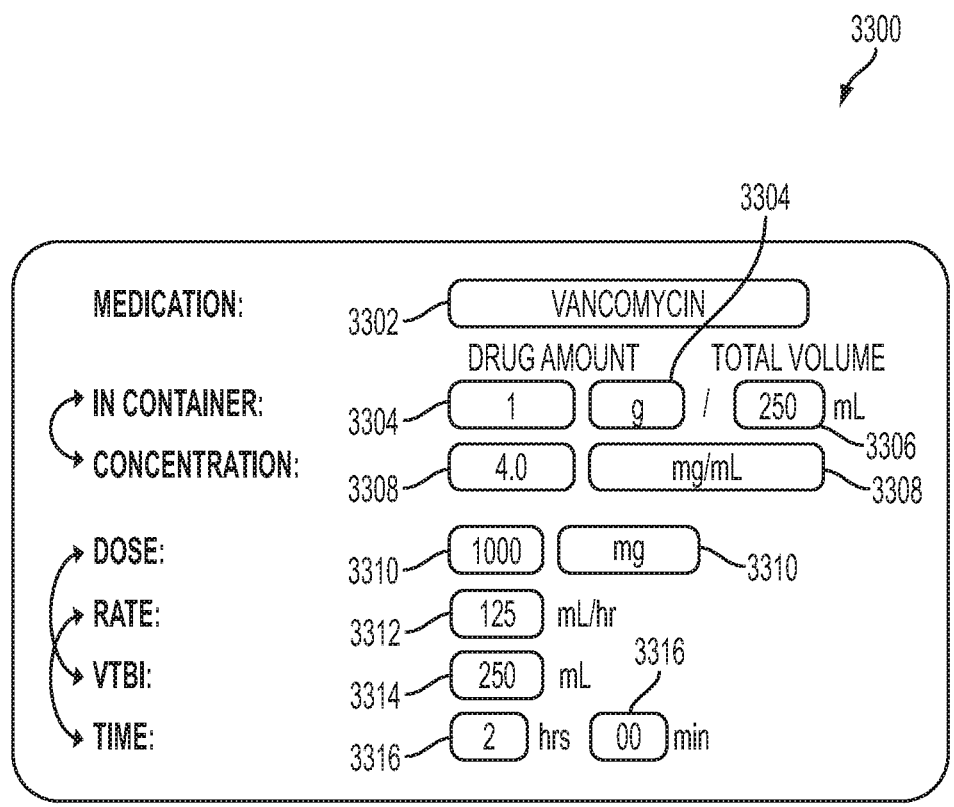
FIG. 74 shows an example infusion programming screen of the graphic user interface in accordance with an embodiment of the present disclosure.

FIG. 74 shows a scenario in which the infusion parameters being programmed are those of a drug amount based infusion herein referred to as an intermittent infusion. In the example embodiment shown in FIG. 74, all of the parameter input fields have been populated. As shown, the medication parameter input field 3302 on the GUI 3300 has been populated with the antibiotic "VANCOMYCIN" as the defined infusate.

As shown, the in container drug amount parameter input field 3304, total volume in container input field 3306, and concentration parameter input field 3308 are laid out the same as in FIG. 73. In the example embodiment in FIG. 74, the left field of the in container drug amount parameter input field 3304 has been populated with "1". The right field of the in container drug amount parameter input field 3304 has been populated with "g". Thus the total amount of Vancomycin in the container has been defined as one gram. The total volume in container parameter input field 3306 has been populated with "250" ml. The left field of the concentration parameter input field 3308 has been populated with "4.0". The right field of the concentration parameter input field has been populated with "mg/mL".

As mentioned in relation to other possible types of infusions which a user may be capable of programming through the GUI 3300, the in container drug amount parameter input field 3304, total volume in container input field 3306, and concentration parameter input field 3308 are dependent upon each other. As above, this is indicated by the curved double arrows connecting the parameter input field names. By populating any two of these parameters, the third parameter may be automatically calculated and displayed on the correct parameter input field on the GUI 3300.

In the example embodiment in FIG. 74, the dose parameter input field 3310 has been populated. As shown, the dose parameter input field 3310 comprises a right and left field. A numeric value may defined in the right field of the dose parameter input field 3310 by the user in the same manner as a user may define values for other parameter input fields which define numeric values. In the example embodiment in FIG. 74, the left field of the dose parameter input field 3310 has been populated with the value "1000".

The right field of the dose parameter input field 3310 may define a unit of mass measurement. To define the right field of the dose parameter input field 3310, a user may touch the dose parameter input field 3310 on the GUI 3300. In some embodiments, this may cull up a list of acceptable possible units of measure. In such embodiments, the desired unit of measure may be defined by a user in the same manner as a user may define the correct infusate. In other embodiments, touching the dose parameter input field 3310 may cull up a virtual keyboard. The user may then type the correct unit of measure on the virtual keyboard. In some embodiments the user may be required to tap, double tap, slide, etc. a virtual "confirm", "enter", etc. button to store the selection and move on to a list of acceptable mass measurements. The desired mass measurement may be defined by a user in the same manner as a user may define the correct infusate. In the example embodiment shown in FIG. 74 the right field of the dose parameter input field 3310 is populated with the unit of measurement "mg".

As shown, the rate parameter input field 3312, VTBI parameter input field 3314, and the time parameter input field 3316 have been populated. As shown, the rate parameter input field 3312 has been populated with "125" mL/hr. The VTBI parameter input field 3314 has been defined as "250" mL. The time parameter input field 3316 has been defined as "2" hrs "00" min.

The user may not need to individually define each of the dose parameter input field 3310, rate parameter input field 3312, VTBI parameter input field 3314, and the time parameter input field 3316. As indicated by the curved double arrows, the dose parameter input field 3310 and the VTBI parameter input field 3314 are dependent upon each other. Input of one value may allow the other value to be automatically calculated and displayed by the GUI 3300. The rate parameter input field 3312 and the time parameter input field 3316 are also dependent upon each other. The user may need to only define one value and then allow the non-defined value to be automatically calculated and displayed on the GUI 3300. In some embodiments, the rate parameter input field 3312, VTBI parameter input field 3314, and the time parameter input field 3316 may be locked on the GUI 3300 until the in container drug amount parameter input field 3304, total volume in container parameter input field 3306 and concentration parameter input field 3308 have been defined. These fields may be locked because automatic calculation of the rate parameter input field 3312, VTBI parameter input field 3314, and the time parameter input field 3316 is dependent upon values in the in container drug amount parameter input field 3304, total volume in container parameter input field 3306 and concentration parameter input field 3308.

In scenarios where an infusate may require a body weight based dosage, a weight parameter input field 3320 may also be displayed on the GUI 3300. The example GUI 3300 shown on FIG. 75 has been arranged such that a user may program a body weight based dosage. The parameter input fields may be defined by a user as detailed in the above discussion. In the example embodiment, the infusate in the medication parameter input field 3302 has been defined as "DOPAMINE". The left field of the in container drug amount parameter input field 3304 has been defined as "400". The right field of the in container drug amount parameter input field 3304 has been defined as "mg". The total volume in container parameter input field 3306 has been defined as "250" ml. The left field of the concentration parameter input field 3308 has been defined as "1.6". The right field of the concentration parameter input field 3308 has been defined as "mg/mL". The weight parameter input field 3320 has been defined as "90" kg. The left field of the dose rater parameter input field 3318 has been defined as "5.0". The right field of the dose rate parameter input field 3318 has been defined as "mcg/kg/min". The rate parameter input field 3312 has been defined as "16.9" mL/hr. The VTBI parameter input field 3314 has been defined as "250" mL. The time parameter input field 3316 has been defined as "14" hrs "48" min.

To define the weight parameter input field 3320, a user may touch or tap the weight parameter input field 3320 on the GUI 3300. In some embodiments, this may cull up a number pad with a range of numbers, such as 0-9 displayed as individual selectable virtual buttons. A user may be required to input the parameter by individually tapping, double tapping, touching and dragging, etc. the desired numbers. Once the desired value has been input by a user, a user may be required to tap, double tap, etc. a virtual "confirm", "enter", etc. button to populate the field.

Figure 75:
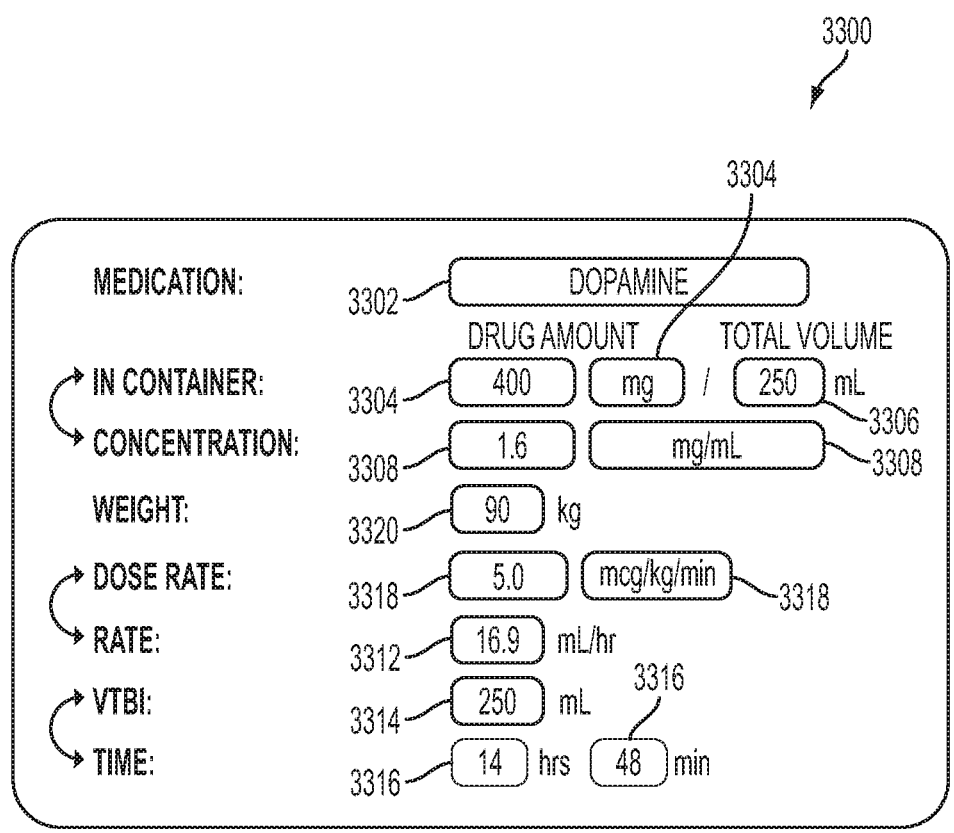
FIG. 75 shows an example infusion programming screen of the graphic user interface in accordance with an embodiment of the present disclosure.

As indicated by the curved double arrows, some parameter input fields displayed on the GUI 3300 may be dependent upon each other. As in previous examples, the in container drug amount parameter input field 3304, total volume in container parameter input field 3306, and concentration parameter input field 3308 may be dependent upon each other. In FIG. 75, the weight parameter input field 3320, dose rater parameter input field 3318, rate parameter input field 3312, VTBI parameter input field 3314, and the time parameter input field 3316 are all dependent upon each other. When enough information has been defined by the user in these parameter input fields, the parameter input fields not populated by the user may be automatically calculated and displayed on the GUI 3300.

In some embodiments, a user may be required to define a specific parameter input field even if enough information has been defined to automatically calculate the field. This may improve safety of use by presenting more opportunities for user input errors to be caught. If a value entered by a user is not compatible with already defined values, the GUI 3300 may display an alert or alarm message soliciting the user to double check values that the user has entered.

Figure 76:
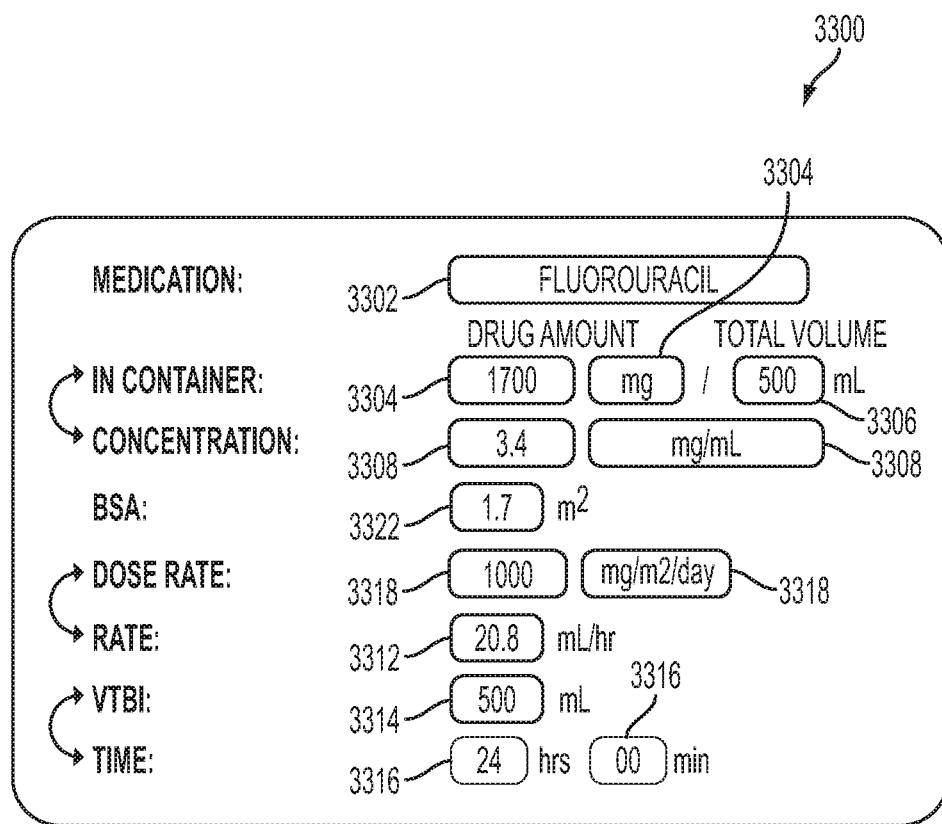
FIG. 76 shows an example infusion programming screen of the graphic user interface in accordance with an embodiment of the present disclosure.

In some scenarios the delivery of infusate may be informed by the body surface area (BSA) of a patient. In FIG. 76, the GUI 3300 has been set up for a body surface area based infusion. As shown, a BSA parameter input field 3322 may be displayed on the GUI 3300. The parameter input fields may be defined by a user as detailed in the above discussion. In the example embodiment, the infusate in the medication parameter input field 3302 has been defined as "FLUOROURACIL". The left field of the in container drug amount parameter input field 3304 has been defined as "1700". The right field of the in container drug amount parameter input field 3304 has been defined as "mg". The total volume in container parameter input field 3306 has been defined as "500" ml. The left field of the concentration parameter input field 3308 has been defined as "3.4". The right field of the concentration parameter input field 3308 has been defined as "mg/mL". The BSA parameter input field 3320 has been defined as "1.7" $m^2$. The left field of the dose rate parameter input field 3318 has been defined as "1000". The right field of the dose rate parameter input field 3318 has been defined as "mg/m2/day". The rate parameter input field 3312 has been defined as "20.8" mL/hr. The VTBI parameter input field 3314 has been defined as "500" mL. The time parameter input field 3316 has been defined as "24" hrs "00" min. The dependent parameter input fields are the same as in FIG. 75 with the exception that the BSA parameter input field 3322 has taken the place of the weight parameter input field 3320.

To populate the BSA parameter input field 3322, the user may touch or tap the BSA parameter input field 3322 on the GUI 3300. In some embodiments, this may cull up a number pad with a range of numbers, such as 0-9 displayed as individual selectable virtual buttons. In some embodiments, the number pad and any of the number pads detailed above may also feature symbols such as a decimal point. A user may be required to input the parameter by individually tapping, double tapping, touching and dragging, etc. the desired numbers. Once the desired value has been input by a user, a user may be required to tap, double tap, etc. a virtual "confirm", "enter", etc. button to populate the field.

In some embodiments, a patient's BSA may be automatically calculated and displayed on the GUI 3300. In such embodiments, the GUI 3300 may query the user for information about the patient when a user touches, taps, etc. the BSA parameter input field 3322. For example, the user may be asked to define a patient's height and body weight. After the user defines these values they may be run through a suitable formula to find the patient's BSA. The calculated BSA may then be used to populate the BSA parameter input field 3322 on the GUI 3300.

In operation, the values displayed in the parameter input fields may change throughout the course of a programmed infusion to reflect the current state of the infusion. For example, as the infusate is infused to a patient, the values displayed by the GUI 3300 in the in container drug amount parameter input field 3304 and total volume in container parameter input field 3306 may decline to reflect the volume of the remaining contents of the container. Additionally, the values in the VTBI parameter input field 3314 and time parameter input field 3316 may also decline as infusate is infused to the patient.

Figure 77:
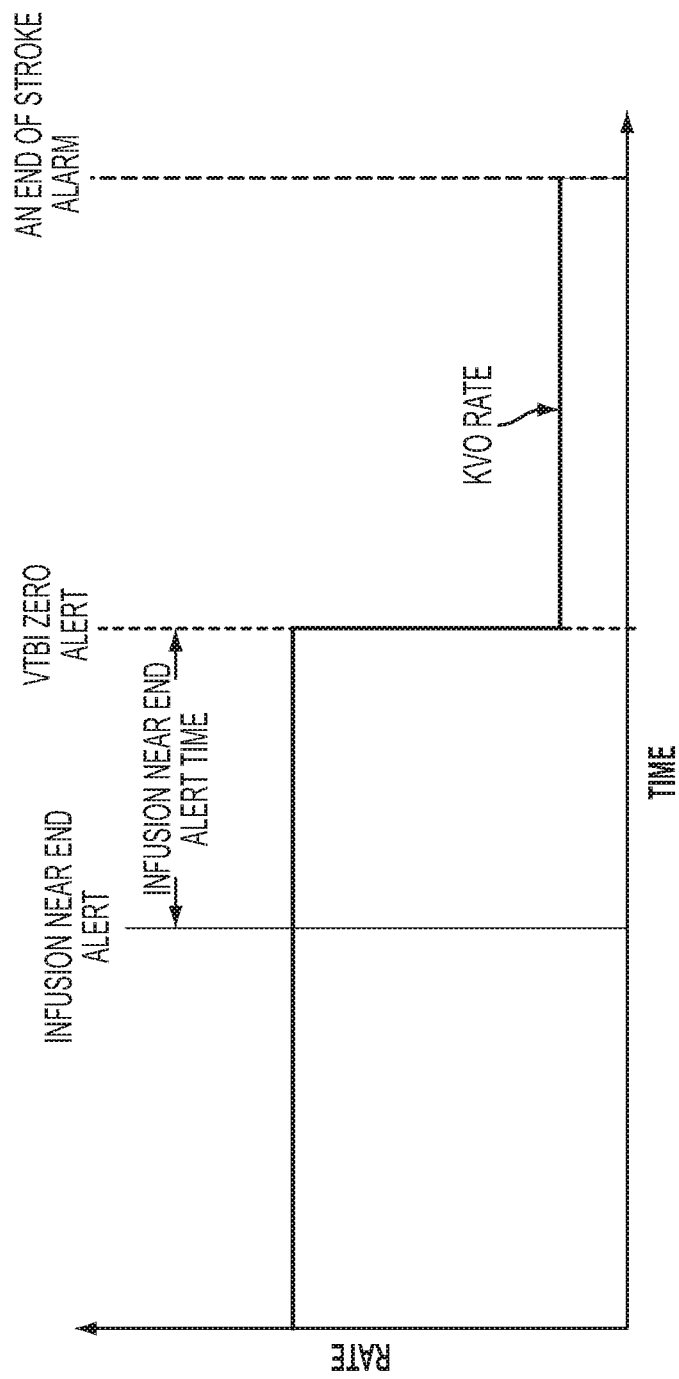
FIG. 77 shows an infusion rate over time graphical representation of an example infusion in accordance with an embodiment of the present disclosure.

FIG. 77 is an example rate over time graph detailing one behavioral configuration of a syringe pump 500 (see FIG. 28) over the course of an infusion. Though the following discussion mostly details behavioral configurations of a syringe pump 500, it should be appreciated that the graphs shown in FIG. 77-81 may also detail the behavioral configurations of other pumps, including the other pumps mentioned in this specification. The graph in FIG. 77 details an example behavioral configuration of the syringe pump 500 where the infusion is a continuous infusion (an infusion with a dose rate). As shown, the graph in FIG. 77 begins at the initiation of infusion. As shown, the infusion is administered at a constant rate for a period of time. As the infusion progresses, the amount of infusate remaining is depleted.

When the amount of infusate remaining reaches a predetermined threshold, an "INFUSION NEAR END ALERT" may be triggered. The point at which "INFUSION NEAR END ALERT" is issued may be configured by the user. The "INFUSION NEAR END ALERT" may also be configured to be triggered sooner on short-half life drugs. The "INFUSION NEAR END ALERT" may be in the form of a message on the GUI 3300 and may be accompanied by flashing lights, and audible noises such as a series of beeps. The "INFUSION NEAR END ALERT" allows time for the care giver and pharmacy to prepare materials to continue the infusion if necessary. As shown, the infusion rate may not change over the "INFUSION NEAR END ALERT TIME".

When the syringe pump 500 (see FIG. 28) has infused the VTBI to a patient a "VTBI ZERO ALERT" may be triggered. The "VTBI ZERO ALERT" may be in the form of a message on the GUI 3300 and may be accompanied by flashing lights and audible noises such as beeps. As shown, the "VTBI ZERO ALERT" causes the pump to switch to a keep-vein-open (hereafter KVO) rate until a new infusate container may be put in place. The KVO rate is a low infusion rate (for example 5-25 mL/hr). The rate is set to keep the infusion site patent until a new infusion may be started. The KVO rate may be configurable by the group (elaborated upon later) or medication and can be modified on the syringe pump 500. The KVO rate is not allowed to exceed the continuous infusion rate. When the KVO rate can no longer be sustained and the syringe has reached the end of its stoke, an "END OF STROKE ALARM" may be triggered. When the "END OF STROKE ALARM" is triggered, all infusion may stop. The "END OF STROKE ALARM" may be in the form of a message on the GUI 3300 and may be accompanied by flashing lights and audible noises such as beeps.

Figure 78:
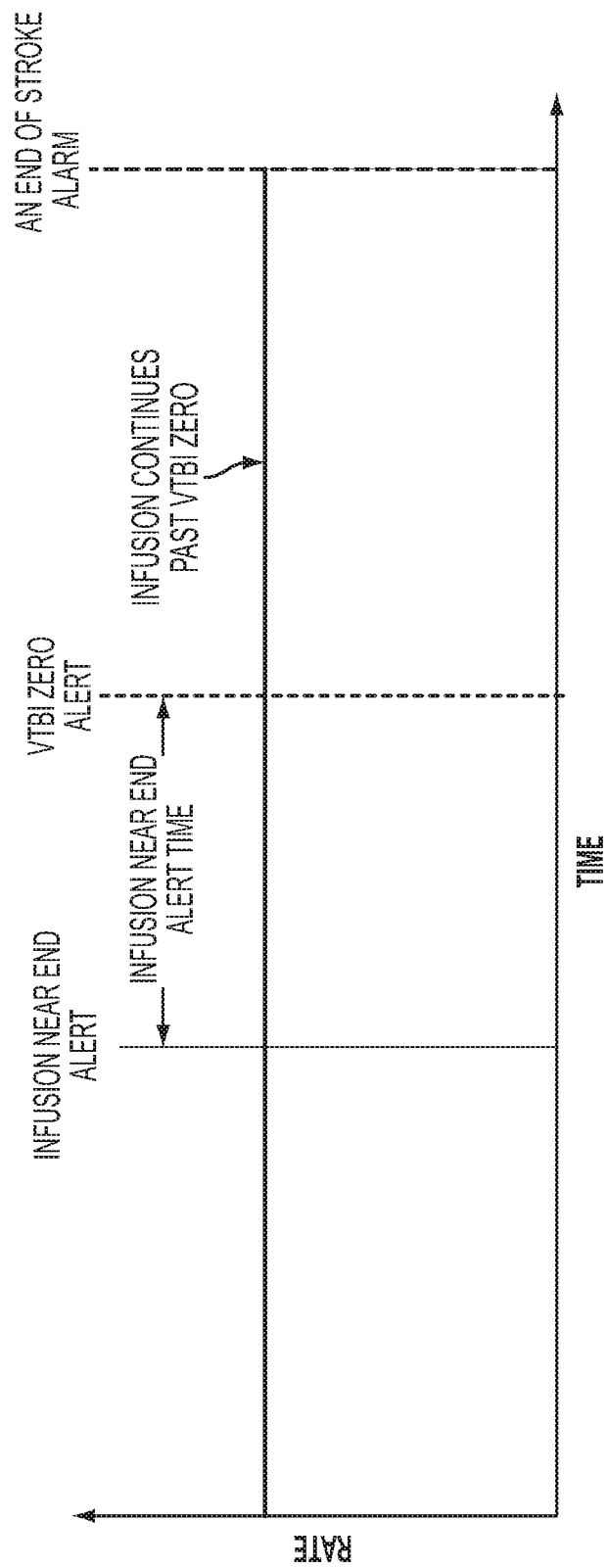
FIG. 78 shows an infusion rate over time graphical representation of an example infusion in accordance with an embodiment of the present disclosure.

FIG. 78 shows another example rate over time graph detailing one behavioral configuration of a syringe pump 500 (see FIG. 28) over the course of an infusion. The graph in FIG. 78 details an example behavioral configuration of a syringe pump 500 where the infusion is a continuous infusion (an infusion with a dose rate). The alerts in the graph shown in FIG. 78 are the same as the alerts shown in the graph in FIG. 77. The conditions which propagate the alerts are also the same. The rate, however, remains constant throughout the entire graph until the "END OF STROKE ALERT" is triggered and the infusion is stopped. By continuing infusion at a constant rate, it is ensured that the blood plasma concentration of the drug remains at therapeutically effective levels. Configuring the pump to continue infusion at a constant rate may be especially desirable in situations where the infusate is a drug with a short half-life. In some embodiments, the end of infusion behavior of the syringe pump 500 may be restricted depending on the defined infusate. For example, when the defined infusate is a short half-life drug the end of infusion behavior of the syringe pump 500 may be limited only to continuing to infuse at the rate of the finished infusion.

The syringe pump 500 (see FIG. 28) may also be used to deliver a primary or secondary intermittent infusion. During an intermittent infusion, an amount of a drug (dose) is administered to a patient as opposed to a continuous infusion where the drug is given at a specified dose rate (amount/time). An intermittent infusion is also delivered over a defined period of time, however, the time period and dose are independent of one another. The previously described FIG. 73 shows a setup of the GUI 3300 for a continuous infusion. The previously described FIG. 74 shows a setup of the GUI 3300 for an intermittent infusion.

Figure 79:
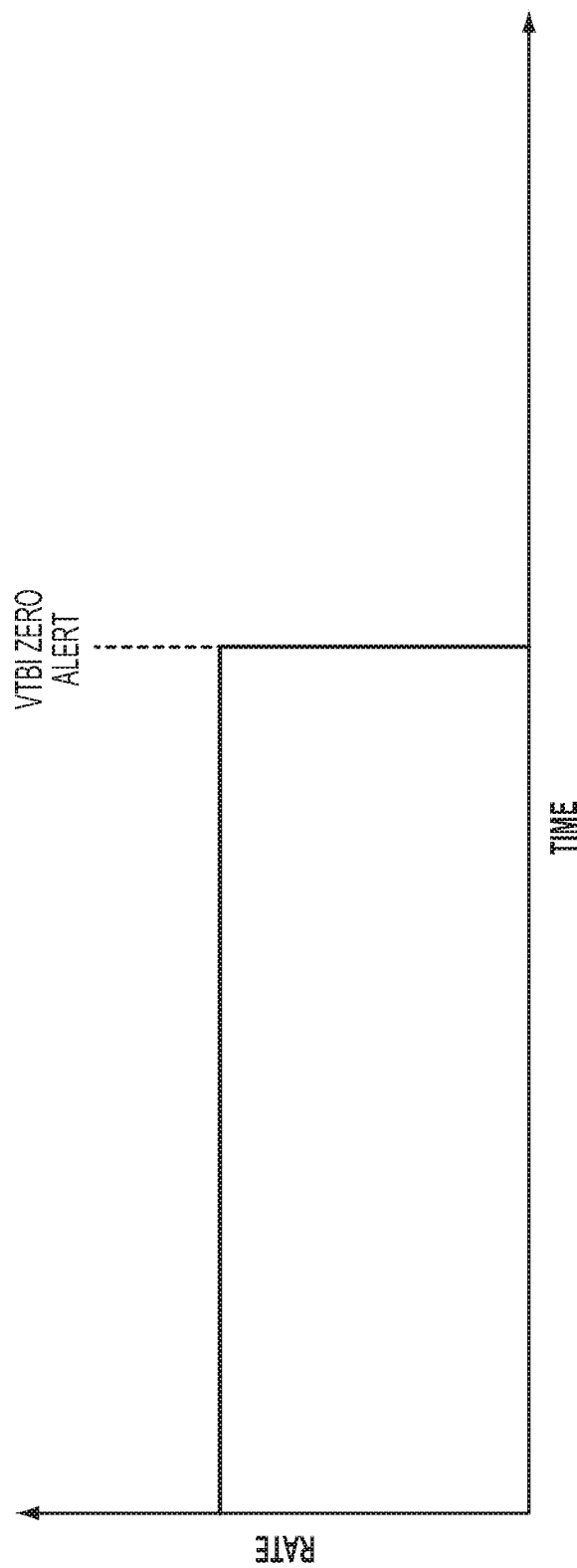
FIG. 79 shows an infusion rate over time graphical representation of an example infusion in accordance with an embodiment of the present disclosure.

FIG. 79 is an example rate over time graph detailing the one behavioral configuration of a syringe pump 500 (see FIG. 28) over the course of an intermittent infusion. As shown, the intermittent infusion is given at a constant rate until all infusate programmed for the intermittent infusion has been depleted. In the example behavioral configuration, the syringe pump 500 has been programmed to issue a "VTBI ZERO ALERT" and stop the infusion when all the infusate has been dispensed. In this configuration, the user may be required to manually clear the alert before another infusion may be started or resumed.

Depending on the group (further elaborated upon later) or the medication, it may be desirable to configure the syringe pump 500 to behave differently at the end of an intermittent infusion. Other configurations may cause a syringe pump 500 (see FIG. 28) to behave differently. For example, in scenarios where the intermittent infusion is a secondary infusion, the pump 201, 202, 203 (see FIG. 2) may be configured to automatically switch back to the primary infusion after issuing a notification that the secondary intermittent infusion has been completed. In alternate configurations, the a syringe pump 500 may be configured issue a "VTBI ZERO ALERT" and drop the infusion rate to a KVO rate after completing the intermittent infusion. In such configurations, the user may be required to manually clear the alert before a primary infusion is resumed.

A bolus may also be delivered as a primary intermittent infusion when it may be necessary or desirable to achieve a higher blood plasma drug concentration or manifest a more immediate therapeutic effect. In such cases, the bolus may be delivered by a pump 201, 202, 203 (see FIG. 2) executing the primary infusion. The bolus may be delivered from the same container which the primary infusion is being delivered from. A bolus may be performed at any point during an infusion providing there is enough infusate to deliver the bolus. Any volume delivered via a bolus to a patient is included in the value displayed by the VTBI parameter input field 3314 of the primary infusion.

Depending on the infusate, a user may be forbidden from performing a bolus. The dosage of a bolus may be pre-set depending on the specific infusate or infusate concentration being used. Additionally, the period of time over which the bolus occurs may be pre-defined depending on the infusate being used. After performing a bolus, the bolus function may be locked for a pre-defined period of time. In some embodiments, a user may be capable of adjusting these pre-sets by adjusting various setting on the GUI 3300. In some situations, such as those where the drug being infused has a long half-life (vancomycin, teicoplanin, etc.), a bolus may be given as a loading dose to more quickly reach a therapeutically effective blood plasma drug concentration.

Figure 80:
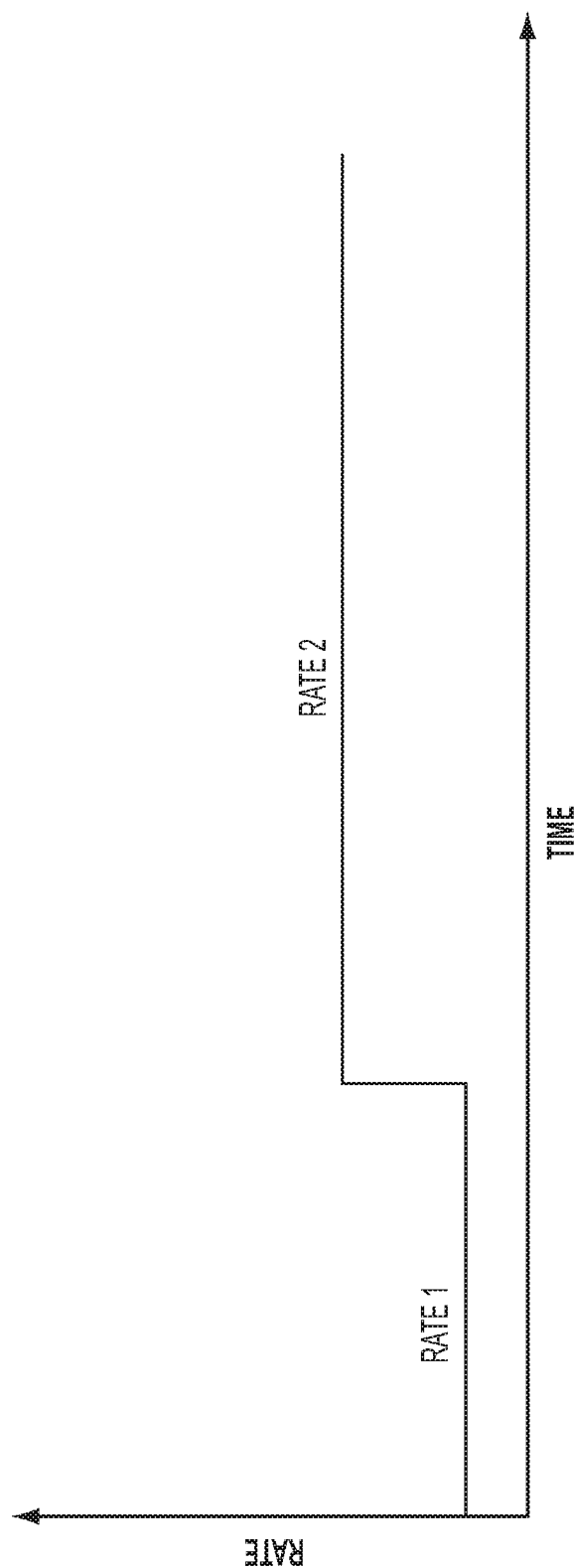
FIG. 80 shows an infusion rate over time graphical representation of an example infusion in accordance with an embodiment of the present disclosure.

FIG. 80 shows another rate over time graph in which the flow rate of the infusate has been titrated to "ramp" the patient up on the infusate. Titration is often used with drugs which register a fast therapeutic effect, but have a short half life (such as norepinephrine). When titrating, the user may adjust the delivery rate of the infusate until the desired therapeutic effect is manifested. Every adjustment may be checked against a series of limits defined for the specific infusate being administered to the patient. If an infusion is changed by more than a pre-defined percentage, an alert may be issued. In the exemplary graph shown in FIG. 80, the rate has been up-titrated once. If necessary, the rate may be up-titrated more than one time. Additionally, in cases where titration is being used to "wean" a patient off of a drug, the rate may be down-titrated any suitable number of times.

Figure 81:
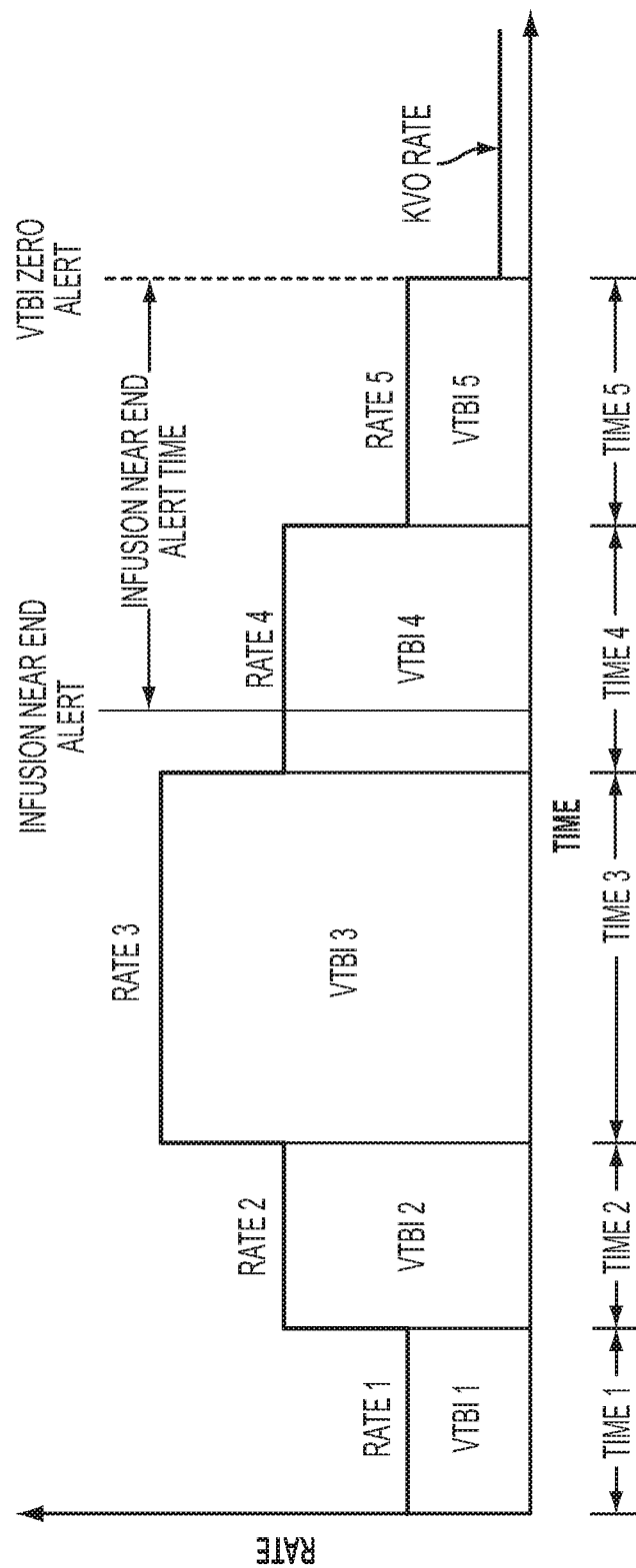
FIG. 81 shows an infusion rate over time graphical representation of an example infusion in accordance with an embodiment of the present disclosure.

FIG. 81 is another rate over time graph in which the infusion has been configured as a multi-step infusion. A multi-step infusion may be programmed in a number of different steps. Each step may be defined by a VTBI, time, and a dose rate. Multi-step infusions may be useful for certain types of infusates such as those used for parenteral nutrition applications. In the example graph shown in FIG. 81, the infusion has been configured as a five step infusion. The first step infuses a "VTBI 1" for a length of time, "Time 1", at a constant rate, "Rate 1". When the time interval for the first step has elapsed, the pump moves on to the second step of the multi-step infusion. The second step infuses a "VTBI 2" for a length of time, "Time 2", at a constant rate, "Rate 2". As shown, "Rate 2" is higher than "Rate 1". When the time interval for the second step has elapsed, the pump moves on to the third step of the multi-step infusion. The third step infuses a "VTBI 3" for a length of time, "Time 3", at a constant rate, "Rate 3". As shown "Rate 3" is the highest rate of any steps in the multi-step infusion. "Time 3" is also the longest duration of any step of the multi-step infusion. When the time interval for the third step has elapsed, the pump move on to the fourth step of the multi-step infusion. The fourth step infuses a "VTBI 4" for a length of time, "Time 4", at a constant rate, "Rate 4". As shown, "Rate 4" has been down-titrated from "Rate 3". "Rate 4" is approximately the same as "Rate 2". When the time interval for the fourth step of the multi-step infusion has elapsed, the pump move on to the fifth step. The fifth step infuses a "VTBI 5" for a length of time, "Time 5", at a constant rate, "Rate 5". As shown, "Rate 5" has been down-titrated from "Rate 4" and is approximately the same as "Rate 1".

The "INFUSION NEAR END ALERT" is triggered during the fourth step of the example infusion shown in FIG. 81. At the end of the fifth and final step of the multi-step infusion, the "VTBI ZERO ALERT" is triggered. In the example configuration shown in the graph in FIG. 81, the rate is dropped to a KVO rate after the multi-step infusion has been concluded and the "VTBI ZERO ALERT" has been issued. Other configurations may differ.

Each rate change in a multi-step infusion may be handled in a variety of different ways. In some configurations, the syringe pump 500 (see FIG. 2) may display a notification and automatically adjust the rate to move on to the next step. In other configurations, the syringe pump 500 may issue an alert before changing the rate and wait for confirmation from the user before adjusting the rate and moving on to the next step. In such configurations, the pump 500 may stop the infusion or drop to a KVO rate until user confirmation has been received.

In some embodiments, the user may be capable of pre-programming infusions. The user may pre-program an infusion to automatically being after a fixed interval of time has elapsed (e.g. 2 hours). The infusion may also be programmed to automatically being at a specific time of day (e.g. 12:30 pm). In some embodiments, the user may be capable of programming the syringe pump 500 (see FIG. 28) to alert the user with a callback function when it is time to being the pre-programmed infusion. The user may need to confirm the start of the pre-programmed infusion. The callback function may be a series of audible beeps, flashing lights, or the like.

In arrangements where there is more than one pump 201, 202, 203 (see FIG. 2), the user may be able to program a relay infusion. The relay infusion may be programmed such that after a first pump 201, 202, 203 has completed its infusion, a second pump 201, 202, 203 may automatically being a second infusion and so on. The user may also program a relay infusion such that the user is alerted via the callback function before the relay occurs. In such a programmed arrangement, the relay infusion may not being until confirmation from a user has been received. A pump 201, 202, 203 may continue at a KVO rate until user confirmation has been received.

Figure 82:
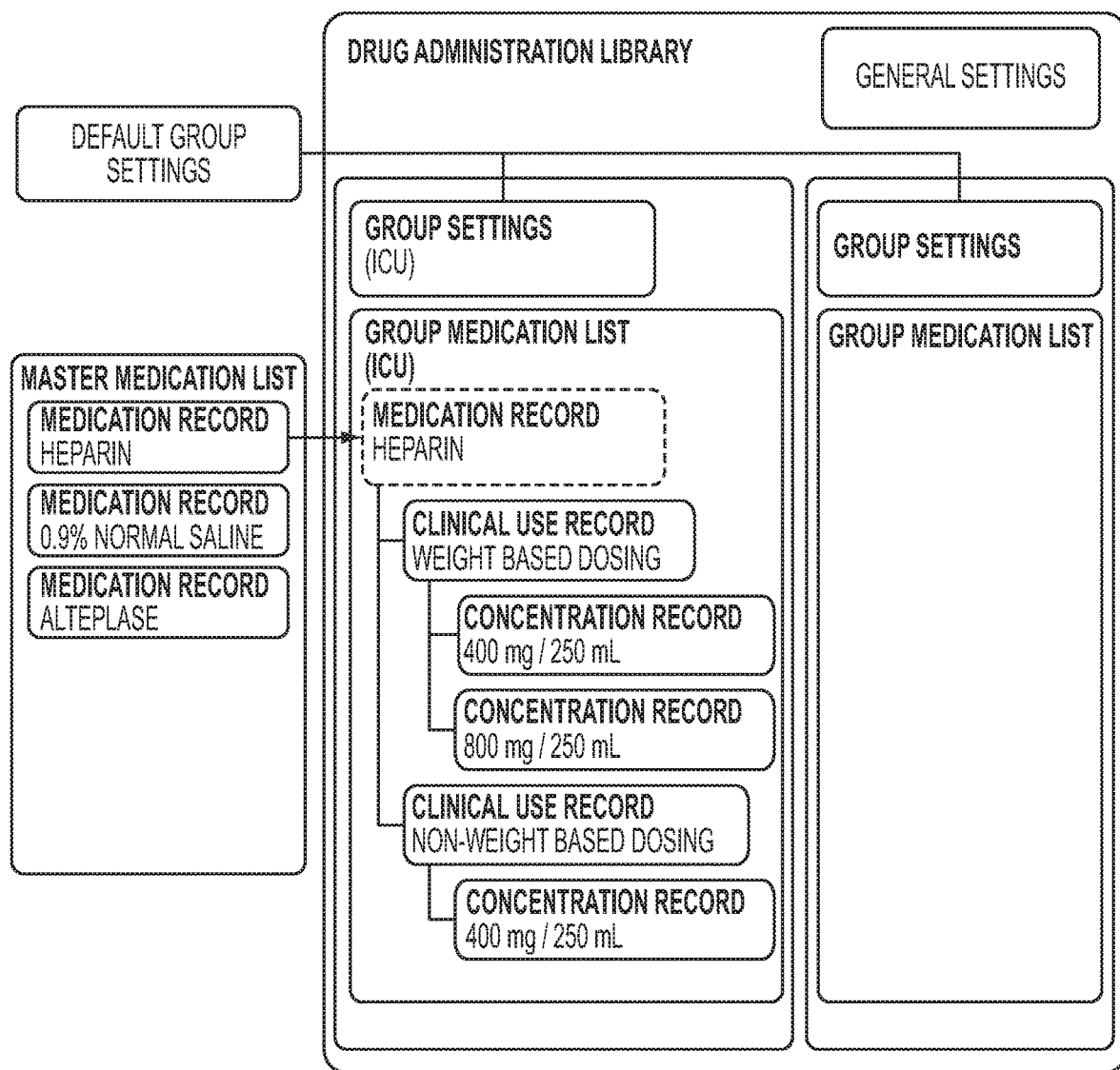
FIG. 82 shows an example drug administration library screen of the graphic user interface in accordance with an embodiment of the present disclosure.

FIG. 82 shows an example block diagram of a "Drug Administration Library" data structure. The data structure may be stored in any file format or in any database (e.g., an SQL database). In the upper right hand corner there is a box which is substantially rectangular, though its edges are rounded. The box is associated with the name "General Settings". The "General Settings" may include settings which would be common to all devices in a facility such as, site name (e.g. XZY Hospital), language, common passwords, and the like.

In FIG. 82, the "Drug Administration Library" has two boxes which are associated with the names "Group Settings (ICU)" and "Group Settings". These boxes form the headings for their own columns. These boxes may be used to define a group in within a facility (e.g. pediatric intensive care unit, emergency room, sub-acute care, etc.) in which the device is stationed. Groups may also be areas outside a parent facility, for example, a patient's home or an inter-hospital transport such as an ambulance. Each group may be used to set specific settings for various groups within a facility (weight, titration limits, etc.). These groups may alternatively be defined in other manners. For example, the groups may be defined by user training level. The group may be defined by a prior designated individual or any of a number of prior designated individuals and changed if the associated patient or device is moved from one specific group within a facility to another.

In the example embodiment, the left column is "Group Settings (ICU)" which indicates that the syringe pump 500 (see FIG. 28) is stationed in the intensive care unit of the facility. The right column is "Group Settings" and has not been further defined. In some embodiments, this column may be used to designate a sub group, for example operator training level. As indicated by lines extending to the box off to the left of the block diagram from the "Group settings (ICU)" and "Group Settings" columns, the settings for these groups may include a preset number of default settings.

The group settings may include limits on patient weight, limits on patient BSA, air alarm sensitivity, occlusion sensitivity, default KVO rates, VTBI limits, etc. The group settings may also include parameters such as whether or not a review of a programmed infusion is necessary for high risk infusates, whether the user must identify themselves before initiating an infusion, whether the user must enter a text comment after a limit has been overridden, etc. A user may also define the defaults for various attributes like screen brightness, or speaker volume. In some embodiments, a user may be capable of programming the screen to automatically adjust screen brightness in relation to one or more conditions such as but not limited to time of day.

As also shown to the left of the block diagram in FIG. 82, each facility may have a "Master Medication List" defining all of the infusates which may be used in the facility. The "Master Medication List" may comprise a number of medications which a qualified individual may update or maintain. In the example embodiment, the "Master Medication List" only has three medications: Heparin, 0.9% Normal Saline, and Alteplase. Each group within a facility may have its own list of medications used in the group. In the example embodiment, the "Group Medication List (ICU)" only includes a single medication, Heparin.

As shown, each medication may be associated with one or a number of clinical uses. In FIG. 82 the "Clinical Use Records" are defined for each medication in a group medication list and appear as an expanded sub-heading for each infusate. The clinical uses may be used to tailor limits and pre-defined settings for each clinical use of the infusate. For Heparin, weight based dosing and non-weight based dosing are shown in FIG. 82 as possible clinical uses. In some embodiments, there may be a "Clinical Use Record" setting requiring the user to review or re-enter a patient's weight (or BSA) before beginning an infusion.

Clinical uses may also be defined for the different medical uses of each infusate (e.g. stroke, heart attack, etc.) instead of or in addition to the infusate' s dose mode. The clinical use may also be used to define whether the infusate is given as a primary continuous infusion, primary intermittent infusion, secondary infusion, etc. They may also be use to provide appropriate limits on the dose, rate, VTBI, time duration, etc. Clinical uses may also provide titration change limits, the availability of boluses, the availability of loading doses, and many other infusion specific parameters. In some embodiments, it may be necessary to provide at least one clinical use for each infusate in the group medication list.

Each clinical use may additionally comprise another expanded sub-heading in which the concentration may also be defined. In some cases, there may be more than one possible concentration of an infusate. In the example embodiment in FIG. 82, the weight base dosing clinical use has a 400 mg/250 mL concentration and an 800 mg/250 mL concentration. The non-weight based dosing clinical use only has one concentration, 400 mg/mL. The concentrations may also be used to define an acceptable range for instances where the user may customize the concentration of the infusate. The concentration setting may include information on the drug concentration (as shown), the diluents volume, or other related information.

In some embodiments, the user may navigate to the "Drug Administration Library" to populate some of the parameter input fields shown in FIGS. 72-76. The user may also navigate to the "Drug Administration Library" to choose from the clinical uses for each infusate what type of infusion the syringe pump 500 (see FIG. 28) will administer. For example, if a user were to select weight based Heparin dosing on FIG. 82, the GUI 3300 might display the infusion programming screen shown on FIG. 75 with "Heparin" populated into the medication parameter input field 3302. Selecting a clinical use of a drug may also prompt a user to select a drug concentration. This concentration may then be used to populate the concentration parameter input field 3308 (see FIGS. 72-76). In some embodiments, the "Drug Administration Library" may be updated and maintained external to the syringe pump 500 and communicated to the syringe pump 500 via any suitable means. In such embodiments, the "Drug Administration Library" may not be changeable on the syringe pump 500 but may only place limits and/or constraints on programming options for a user populating the parameter input fields shown in FIG. 72-76.

As mentioned above, by choosing a medication and clinical use from the group medication list, a user may also be setting limits on other parameter input fields for infusion programming screens. For example, by defining a medication in the "Drug Administration Library" a user may also be defining limits for the dose parameter input field 3310, dose rate parameter input field 3318, rate parameter input field 3312, VTBI parameter input field 3314, time parameter input field 3316, etc. These limits may be pre-defined for each clinical use of an infusate prior to the programming of an infusion by a user. In some embodiments, limits may have both a soft limit and a hard limit with the hard limit being the ceiling for the soft limit. In some embodiments, the group settings may include limits for all of the medications available to the group. In such cases, clinical use limits may be defined to further tailor the group limits for each clinical usage of a particular medication.

Figure 83:
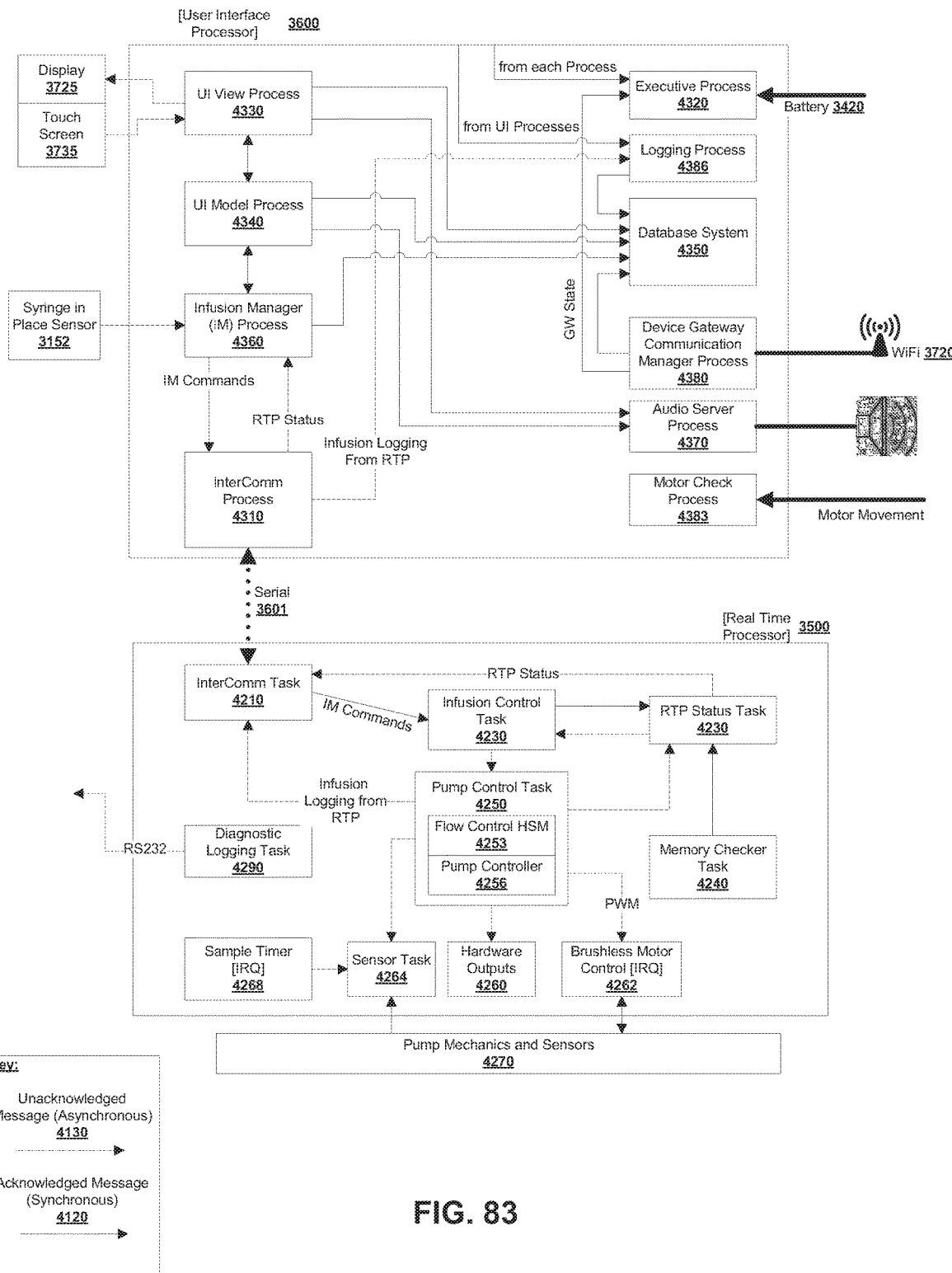
FIG. 83 shows a block software diagram in accordance with an embodiment of the present disclosure.

The software architecture of the syringe pump 500 is shown schematically in FIG. 83. The software architecture divides the software into cooperating subsystems that interact to carry out the required pumping action. The software is equally applicable to all the embodiments described herein. It is also possible to apply the software to other pumps not described herein. Each subsystem may be composed of one or more execution streams controlled by the underlying operating system. Useful terms used in the art include operating system, subsystem, process, thread and task.

Asynchronous messages 4130 are used to 'push' information to the destination task or process. The sender process or task does not get confirmation of message delivery. Data delivered in this manner is typically repetitive in nature. If messages are expected on a consistent schedule, the receiver process or task can detect a failure if a message does not arrive on time.

Synchronous messages 4120 may be used to send a command to a task or process, or to request ('pull') information from a process or task. After sending the command (or request), the originating task or process suspends execution while awaiting a response. The response may contain the requested information, or may acknowledge the receipt of the sent message. If a response is not received in a timely manner, the sending process or task may time out. In such an event, the sending process or task may resume execution and/or may signal a error condition.

An operating system (OS) is a collection of software that manages computer hardware resources and provides common services for computer programs. The operating system may act as an intermediary between programs and the computer hardware. Although some application code may be executed directly by the hardware, the application code may frequently make a system call to an OS function or be interrupted by it.

The RTP 3500 may run on a Real Time Operating System (RTOS) that has been certified to a safety level for medical devices. An RTOS is a multitasking operating system that aims at executing real-time applications. Real-time operating systems often use specialized scheduling algorithms so that they can achieve a deterministic nature of behavior. The UIP 3600 may run on a Linux operating system. The Linux operating system is a Unix-like computer operating system.

A subsystem is a collection of software (and perhaps hardware) assigned a specific set of (related) system functionality or functionalities. A subsystem has clearly defined responsibilities and a clearly defined interface to other subsystems. A subsystem is an architectural division of the software that uses one or more processes, threads or tasks.

A process is an independent executable running on a Linux operating system which runs in its own virtual address space. The memory management hardware on the CPU is used to enforce the integrity and isolation of this memory, by write protecting code-space, and disallowing data access outside of the process' memory region. Processes can only pass data to other processes using inter-process communication facilities.

In Linux, a thread is a separately scheduled, concurrent path of program execution. On Linux, a thread is always associated with a process (which must have at least one thread and can have multiple threads). Threads share the same memory space as its 'parent' process. Data can be directly shared among all of the threads belonging to a process but care must be taken to properly synchronize access to shared items. Each thread has an assigned execution priority.

A Task on an RTOS (Real Time Operating System) is a separately scheduled, concurrent path of program execution, analogous to a Linux 'thread'. All tasks share the same memory address space which consists of the entire CPU memory map. When using an RTOS that provides memory protection, each task's effective memory map is restricted by the Memory Protection Unit (MPU) hardware to the common code space and the task's private data and stack space.

The processes on the UIP 3600, communicate via IPC calls as shown by the one-way arrows in FIG. 83. Each solid-lined arrow represents a synchronous message 4120 call and response, and dotted-line arrows are asynchronous messages 4130. The tasks on the RTP 3500 similarly communicate with each other. The RTP 3500 and UIP 3600 may be bridged by an asynchronous serial line 3601, with one of an InterComm Process 4110 or InterComm Task 4210 on each side. The InterComm Process 4110 presents the same communications API (Application Programming Interface) on both sides of the bridge, so all processes and tasks can use the same method calls to interact.

The Executive Process 4320 may invoked by the Linux system startup scripts after all of the operating system services have started. The Executive Process 4320 then starts the various executable files that comprise the software on the UIP 3600. If any of the software components should exit or fail unexpectedly, the Executive Process 4320 may be notified, and may generate the appropriate alarm.

While the system is running, the Executive Process 4320 may act as a software 'watchdog' for various system components. After registering with the Executive Process 4320, a process is required to 'check in' or send a signal periodically to the Executive Process 4320. Failure to 'check in' at the required interval may be detected by the Executive Process 4320. Upon detection of a failed subsystem, the Executive Process 4320 may take remedial action of either: do nothing, declaring an alarm, or restarting the failed process. The remedial action taken is predetermined by a table entry compiled into the Executive Process 4320. The 'check-in' interval may vary from process to process. The amount of variance between 'check-in' times for different processes may be based in part on the importance of the process. The check-in interval may also vary during syringe pump 500 operation to optimize the pump controller response by minimizing computer processes. In one example embodiment, during syringe 504 loading, the pump controller may check-in less frequently than during active pumping.

In response to the required check-in message, the Executive Process 4320 may return various system status items to processes that checked-in. The system status items may be the status of one or more components on the syringe pump 500 and/or errors. The System Status items may include: battery status, WiFi connection status, device gateway connection status, device status (Idle, Infusion Running, Diagnostic Mode, Error, Etc.), technical error indications, and engineering log levels.

A thread running in the Executive Process 4320 may be used to read the state of the battery 3420 from an internal monitor chip in the battery 3420. This may be done at a relatively infrequent interval such as every 10 seconds.

The UI View 4330 implements the graphical user interface (GUI 3300 see FIG. 71), rendering the display graphics on the display 514, and responding to inputs on the touch screen in embodiments comprising a touch screen or to inputs communicated via other data input means 516. The UI View 4330 design is stateless. The graphic being displayed may be commanded by the UI Model Process 4340, along with any variable data to be displayed. The commanded graphic may be refreshed periodically regardless of data changes.

The style and appearance of user input dialogs (Virtual keyboard, drop down selection list, check box etc.) may be specified by the screen design, and implemented entirely by the UI View 4330. User input may be collected by the UI View 4330, and sent to the UI Model 4340 for interpretation. The UI View 4330 may provide for multi-region, multi-lingual support with facilities for the following list including but not limited to: virtual keyboards, unicode strings, loadable fonts, right to left entry, translation facility (loadable translation files), and configurable numbers and date formats.

The UI Model 4340 implements the screen flows, and so controls the user experience. The US Model 4340 interacts with the UI View 4330, specifying the screen to display, and supplies any transient values to be displayed on the screen. Here screen refers the image displayed on the physical display 514 and the defined interactive areas or user dialogs i.e. buttons, sliders, keypads etc, on the touch screen 3735. The UI Model 4340 interprets any user inputs sent from the UI View 4330, and may either update the values on the current screen, command a new screen, or pass the request to the appropriate system service (i.e. 'start pumping' is passed to the RTP 3500).

When selecting a medication to infuse from the Drug Administration Library, the UI Model 4340 interacts with the Drug Administration Library stored in the local data base which is part of the Database System 4350. The user's selections setup the run time configurations for programming and administering the desired medication.

While the operator is entering an infusion program, The UI Model 4340 may relay the user's input values to the Infusion Manager 4360 for validation and interpretation. Therapeutic decisions may not be made by the UI Model 4340. The treatment values may be passed from the Infusion Manager 4360 to the UI Model 4340 to the UI View 4330 to be displayed for the user.

The UI Model 4340 may continuously monitor the device status gathered from the Infusion Manager 4360 (current infusion progress, alerts, etc.) for possible display by the UI View 4330. Alerts/Alarms and other changes in system state may provoke a screen change by the UI Model 4340.

The Infusion Manager Process (IM) 4360 may validate and controls the infusion delivered by the syringe pump 500. To start an infusion, the user may interact with the UI View/Model 4330/4340 to select a specific medication and clinical use. This specification selects one specific Drug Administration Library (DAL) entry for use. The IM 4360 loads this DAL entry from the database 4350, for use in validating and running the infusion.

Once a Drug Administration Library entry is selected, the IM 4340 may pass the dose mode, limits for all user enterable parameters, and the default values (if set) up to the UI Model 4340. Using this data, the UI Model 4340 may guide the user in entering the infusion program.

As each parameter is entered by the user, the value may sent from the UI View/Model 4330/4340 to the IM 4360 for verification. The IM 4360 echoes the parameters back to the UI View/Model 4330/4340, along with an indication of the parameter's conformance to the DAL limits. This allows the UI View/Model 4330/4340 to notify the user of any values that are out of bounds.

When a complete set of valid parameters has been entered, the IM 4360 also may return a valid infusion indicator, allowing the UI View/Model 4330/4340 to present a 'Start' control to the user.

The IM 4360 may simultaneously make the infusion/pump status available to the UI View/Model 4330/4340 upon request. If the UI View/Model 4330/4340 is displaying a 'status' screen, it may request this data to populate it. The data may be a composite of the infusion state, and the pump state.

When requested to run the (valid) infusion, the IM 4360 may pass the 'Infusion Worksheet' containing user specified data and the 'Infusion Template' containing the read-only limits from the DAL as a CRC'd binary block to the Infusion Control Task 4220 running on the RTP 3500. The Infusion Control Task 4220 on the RTP 3500 takes the same user inputs, conversions and DERS inputs and recalculates the Infusion Worksheet. The Infusion Control Task 4220 calculated results may be stored in a second CRC'd binary block and compared to the first binary block from the UIP 3600. The infusion calculations performed on the UIP 3600 may be recalculated and double checked on the RTP 3500 before the infusion is run.

Coefficients to convert the input values (ie. □1, grams, %, etc.) to a standard unit such as ml may be stored in the UIP 3600 memory or database system 4350. The coefficients may be stored in a lookup table or at specific memory locations. The lookup table may contain 10's of conversion values. In order to reduce the chance that flipping a single bit will resulting in the wrong conversion factor being used, the addresses for the conversion values may be distributed among the values from zero to 4294967296 or $2^{32}$. The addresses may be selected so that the binary form of one address is never just one bit different from a second address.

While an infusion is running, the IM 4360 may monitor its progress, sequences, pauses, restarts, secondary infusions, boluses, and KVO (keep vein open) scenarios as needed. Any user alerts requested during the infusion (Infusion near complete, KVO callback, Secondary complete callback, etc) may be tracked and triggered by the IM 4360.

Processes on the UIP 3600 may communicate with each other via a proprietary messaging scheme based on a message queue library that is available with Linux. The system provides for both acknowledged (synchronous message 4120) and unacknowledged (asynchronous message 4130) message passing.

Messages destined for the Real-time Processor (RTP) 3500 may be passed to the InterComm Process 4310 which forwards the messages to the RTP 3500 over a serial link 3601. A similar InterComm Task 4210 on the RTP 3500 may relay the message to its intended destination via the RTP 3500 messaging system.

The messaging scheme used on this serial link 3601 may provide for error detection and retransmission of flawed messages. This may be needed to allow the system to be less susceptible to electrical disturbances that may occasionally 'garble' inter-processor communications.

To maintain a consistent interface across all tasks, the message payloads used with the messaging system may be data classes derived from a common baseclass (MessageBase). This class adds both data identity (message type) and data integrity (CRC) to messages.

The Audio Server Process 4370 may be used to render sounds on the system. All user feedback sounds (key press beeps) and alarm or alert tones may be produced by playing pre-recorded sound files. The sound system may also be used to play music or speech if desired.

Sound requests may be symbolic (such as "Play High Priority Alarm Sound"), with the actual sound file selection built into the Audio Server process 4370. The ability to switch to an alternative soundscape may be provided. This ability may be used to customize the sounds for regional or linguistic differences.

The Device Gateway Communication Manager Process (DGCM) 4380 may manage communications with the Device Gateway Server over a Wi-Fi network 3620, 3622, 3720. The DGCM 4380 may be started and monitored by the Executive Process 4320. If the DGCM 4380 exits unexpectedly, it may be restarted by the Executive Process 4320 but if the failures are persistent the system may continue to function without the gateway running.

It may be the function of the DGCM 4380 to establish and maintain the Wi-Fi connection and to then establish a connection to the Device Gateway. All interactions between the DGCM 4380 and the Device Gateway use a system such as the system described in the cross referenced nonprovisional application for System, Method, and Apparatus for Electronic Patient Care.

If the connection to the gateway is unavailable or becomes unavailable, the DGCM 4380 may discontinue any transfers in progress, and attempt to reconnect the link. Transfers may be resumed when the link is reestablished. Network and Gateway operational states are reported periodically to the Executive Process 4320. The Executive Process 4320 distributes this information for display to the user.

The DGCM 4380 may function as an autonomous subsystem, polling the Device Gateway Server for updates, and downloading newer items when available. In addition the DGCM 4380 may monitor the logging tables in the database, uploading new log events as soon as they are available. Events that are successfully uploaded may be flagged as such in the database. After a reconnection to the Device Gateway Server, the DGCM 4380 may 'catch up' with the log uploads, sending all items that were entered during the communications disruption. Firmware and Drug Administration Library updates received from the Gateway may be staged in the UIP's 3600 file system for subsequent installation. Infusion programs, clinical advisories, patient identification and other data items destined for the device may be staged in the database.

The DGCM 4380 may report connection status and date/time updates to the Executive Process 4320. There may not be other direct connections between the DGCM 4380 and any of the other operational software. Such a design decouples the operational software from the potentially transient availability of the Device Gateway and Wi-Fi network.

The Motor Check 4383 software may read a hardware counter or encoder 1202 (FIG. 60) that reports motor 1200 rotation. The software in this module may independently estimate the motor's 1200 movements, and compare them to the expected motion based on the user inputs for rate of infusion. This may be an independent check for proper motor control. However, the primary motor 1200 control software may executed on the RTP 3500.

Event information may be written to a log via the Logging Process 4386 during normal operation. These events may consist of internal machine status and measurements, as well as therapy history events. Due to the volume and frequency of event log data, these logging operations may be buffered in a FIFO queue while waiting to be written to the database.

A SQL database (PostgreSQL) may be used to store the Drug Administration Library, Local Machine Settings, Infusion History and Machine Log data. Stored procedures executed by the database server may be used to insulate the application from the internal database structures.

The database system 4350 may be used as a buffer for log data destined for the Device Gateway server, as well as a staging area for infusion settings and warnings sent to the pump from the Gateway.

Upon requesting the start of an infusion, the DAL entry and all user selected parameters may be sent to the Infusion Control Task 4220. All of the DAL validations and a recalculation of the infusion rate and volume based upon the requested dose may be performed. The result may be checked against the results calculated by the IM 4360 on the UIP 3600. These results may be required to match to continue.

When running an infusion, the Infusion Control Task 4220 may control the delivery of each infusion 'segment'; i.e. one part of an infusion consisting of a volume and a rate. Examples of segments are: a primary infusion, KVO, bolus, remainder of primary after bolus, primary after titration, etc. The infusion segments are sequenced by the IM Process 4360 on the UIP 3600.

The Pump Control Task 4250 may incorporate the controllers that drive the pumping mechanism. The desired pumping rate and amount (VTBI) may be specified in commands sent from the Infusion Control Task 4220.

The Pump Control 4250 may receive periodic sensor readings from the Sensor Task 4264. The new sensor readings may be used to determine the motor speed and position, and to calculate the desired command to send to the Brushless Motor Control IRQ 4262. The receipt of the sensor message may trigger a recalculation of the controller output.

While pumping fluid, the Pump Control Task 4250 may perform at least one of the following tasks: controlling pumping speed, measuring volume delivered, measuring air detected (over a rolling time window), measuring fluid pressure or other indications of occlusions, and detecting upstream occlusions.

Relevant measurements may be reported to the RTP Status Task 4230 periodically. The Pump Control 4250 may execute one infusion segment at a time, stopping when the commanded delivery volume has been reached. The Sensor Task 4264 may read and aggregate the sensor data used for the dynamic control of the pumping system.

The sensor task 4264 may be scheduled to run at a consistent 1 kHz rate (every 1.0 ms) via a dedicated counter/timer. After all of the relevant sensors are read, the data may be passed to the Pump Control Task 4250 via an asynchronous message 4120. The periodic receipt of this message may be used as the master time base to synchronize the syringe pump's 500 control loops.

The RTP Status Task 4230 may be the central repository for both the state and the status of the various tasks running on the RTP 3500. The RTP Status Task 4230 may distribute this information to both the IM 4360 running on the UIP 3600, as well as to tasks on the RTP 3500 itself.

The RTP Status Task 4230 may also be charged with fluid accounting for the ongoing infusion. Pump starts and stops, as well as pumping progress may be reported to RTP Status 4230 by the Pump Control Task 4256. The RTP Status Task 4230 may account for at least one of the following: total volume infused, primary volume delivered, primary VTBI (counted down), volume delivered and VTBI of a bolus while the bolus is in progress, and volume delivered and VTBI of a secondary infusion while the secondary infusion is in progress.

All alerts or alarms originating on the RTP 3500 may be funneled through the RTP Status Task 4230, and subsequently passed up to the UIP 3600.

While the unit is in operation, the program flash, and RAM memory may be continually tested by the Memory Checker Task 4240. This test may be non-destructive. This test may be scheduled so that the entire memory space on the RTP 3500 is tested every few hours. Additional periodic checks may be scheduled under this task if needed.

Tasks running on the RTP 3500 may be required to communicate with each other as well as to tasks that are executing on the UIP 3600.

The RTP 3500 messaging system may use a unified global addressing scheme to allow messages to be passed to any task in the system. Local messages may be passed in memory utilizing the facilities of the RTOS' message passing, with off-chip messages routed over the asynchronous serial link 3601 by the InterComm Task 4210.

The InterComm Task 4210 may manage the RTP 3500 side of the serial link 3601 between the two processors. The InterComm Task 4210 is the RTP 3500 equivalent of the InterComm Process 4310 on the UIP 3600. Messages received from the UIP 3600 may be relayed to their destination on the RTP 3500. Outbound messages may be forwarded to InterComm Process 4310 on the UIP 3600.

All messages between the RTP 3500 and the UIP 3600 may be checked for data corruption using an error-detecting code (32 bit CRC). Messages sent over the serial link 3601 may be re-sent if corruption is detected. This provides a communications system that is reasonably tolerant to ESD. Corrupted messages within the processor between processes may be handled as a hard system failure. All of the message payloads used with the messaging system may be data classes derived from a common baseclass (MessageBase) to assure consistency across all possible message destinations.

Brushless Motor Control IRQ 4262 may not run as a task; it may be implemented as a strict foreground (interrupt context) process. Interrupts are generated from the commutator or hall sensors 3436, and the commutation algorithm may be run entirely in the interrupt service routine.

Figure 84:
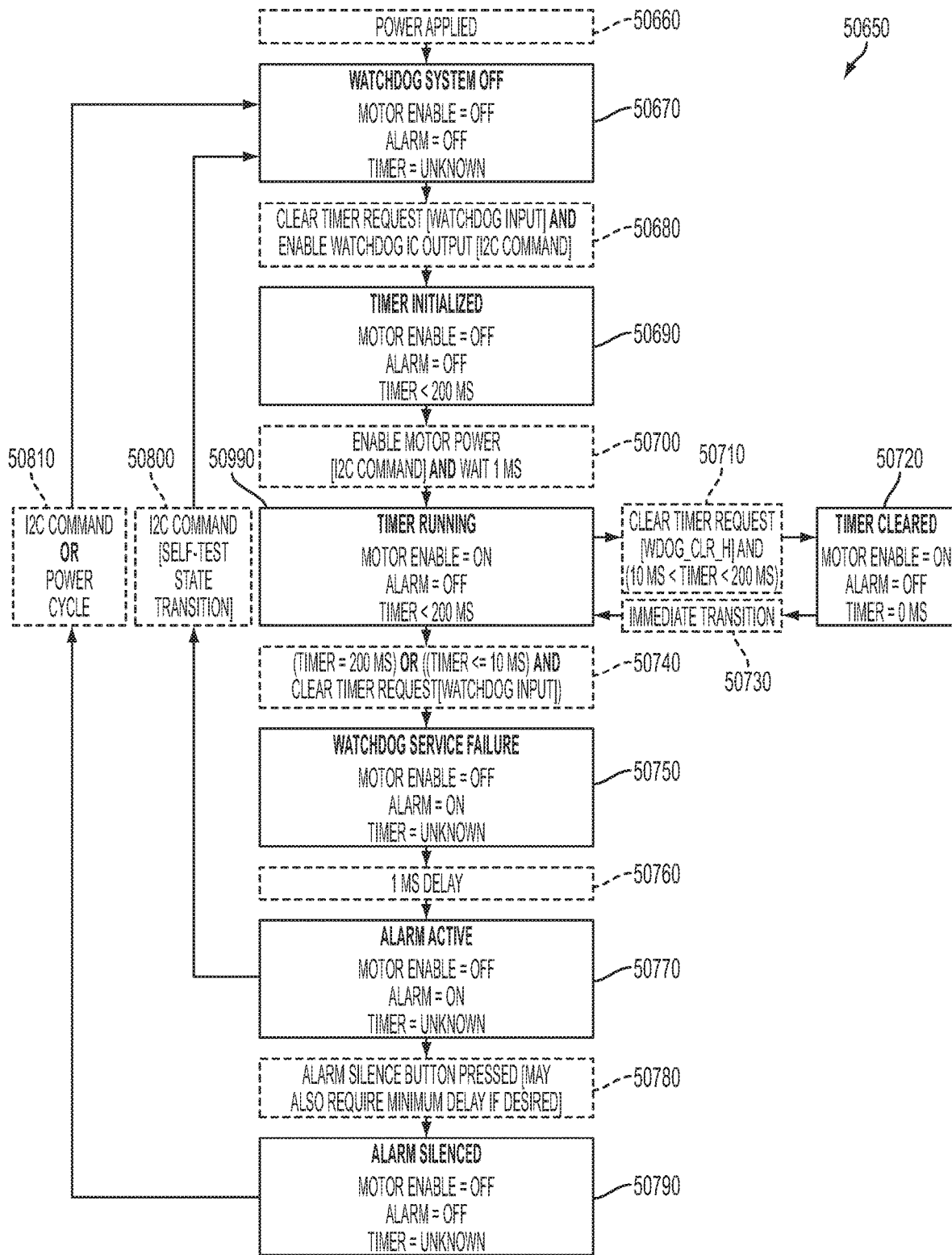
FIG. 84 shows a state diagram illustrating a method of providing a watchdog functionality in accordance with an embodiment of the present disclosure.
Figure 85A:
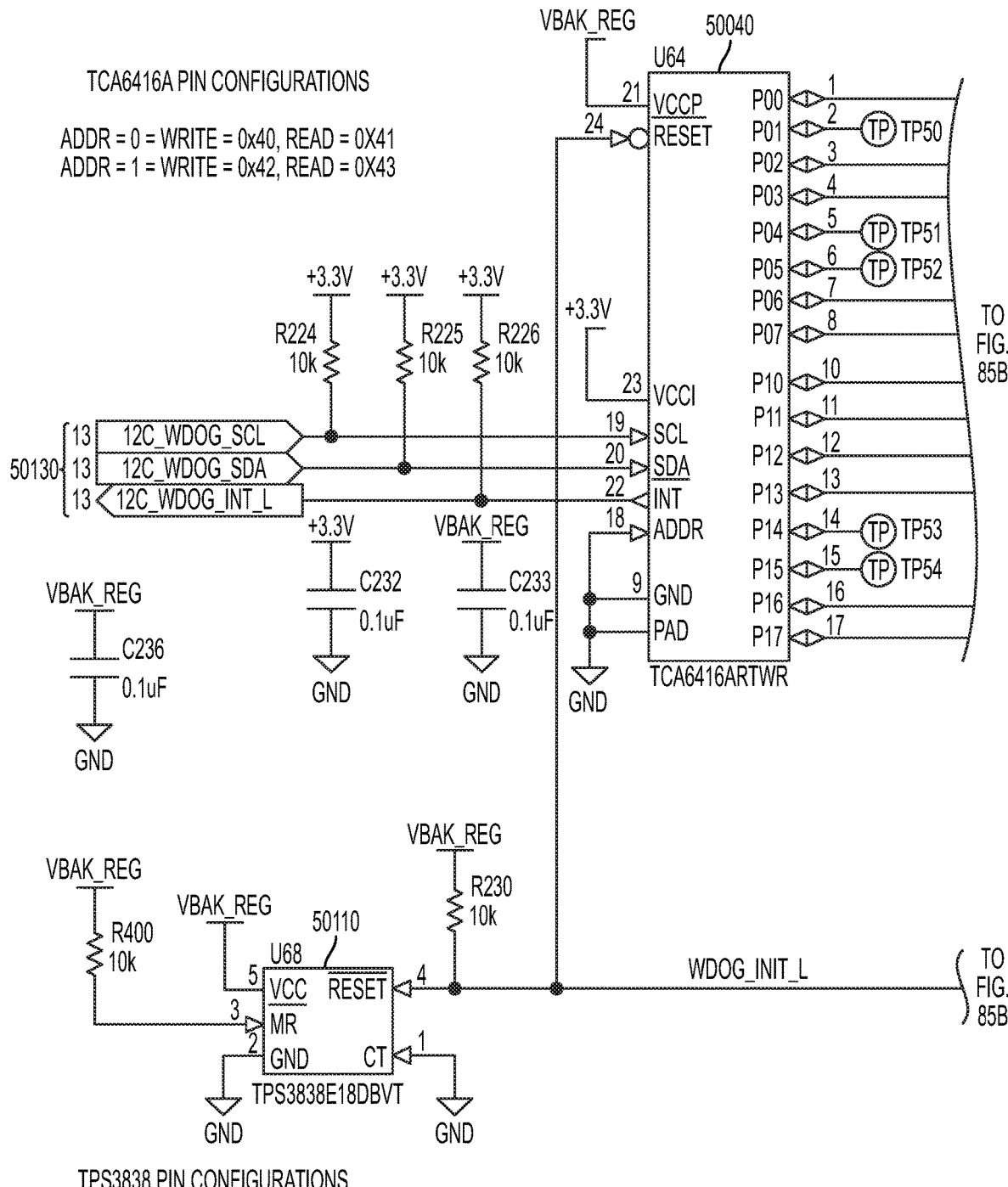
FIGS. 85A-85F show a circuit diagram of a watchdog system that is one embodiment that implements the watchdog functionality of the state diagram of FIG. 84 in accordance with another embodiment of the present disclosure.
Figure 85B:
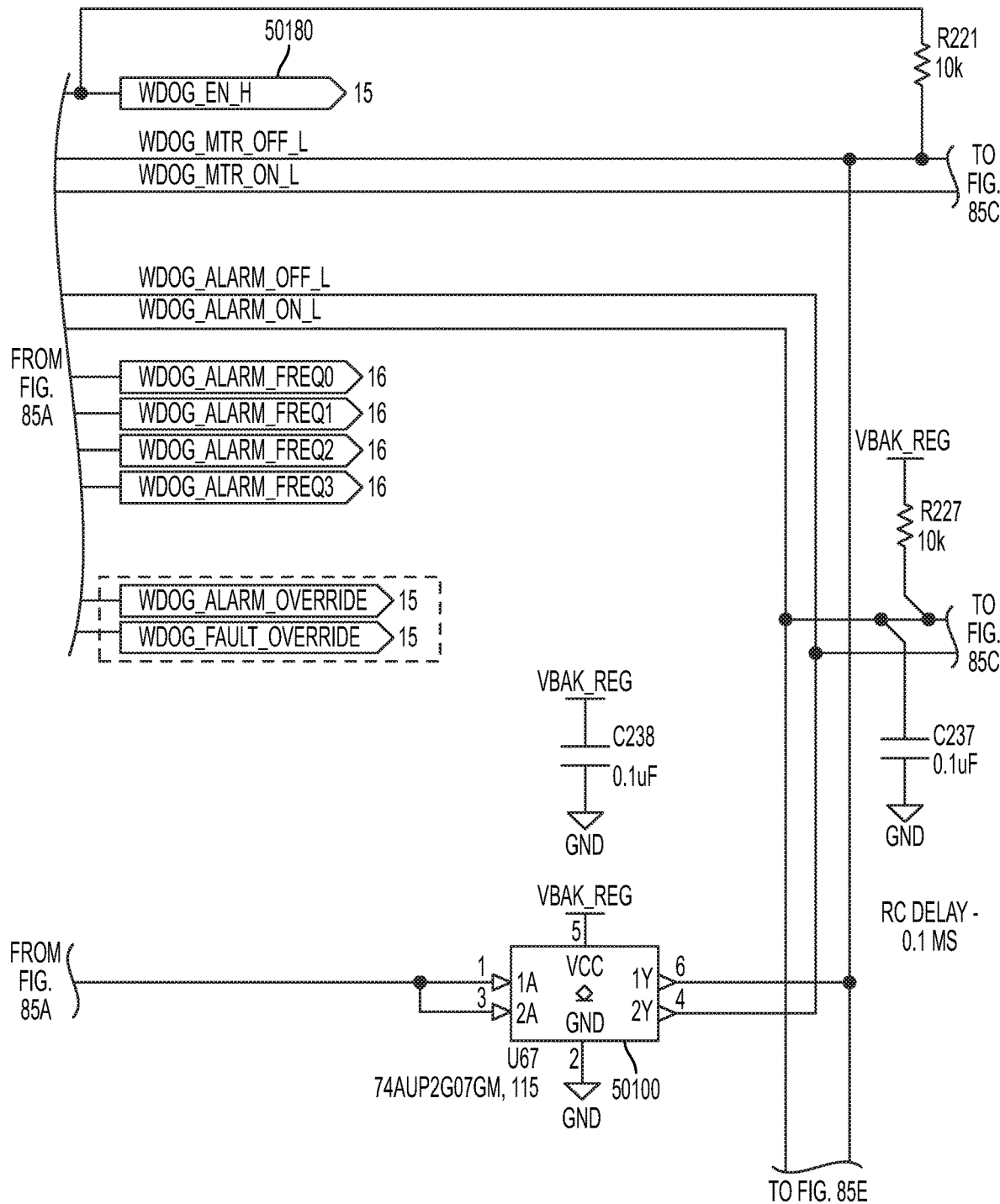
Figure 85C:
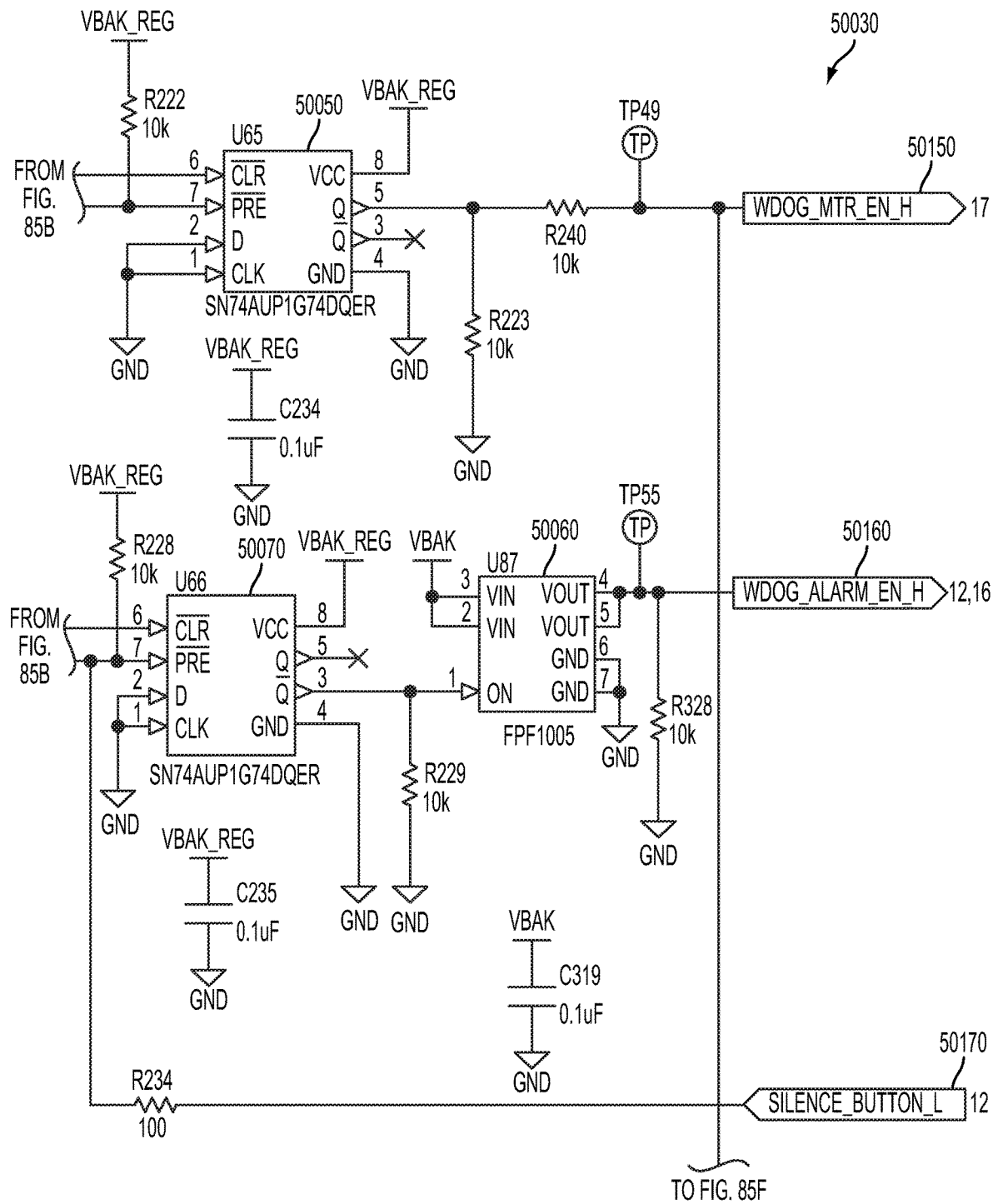
Figure 85D:
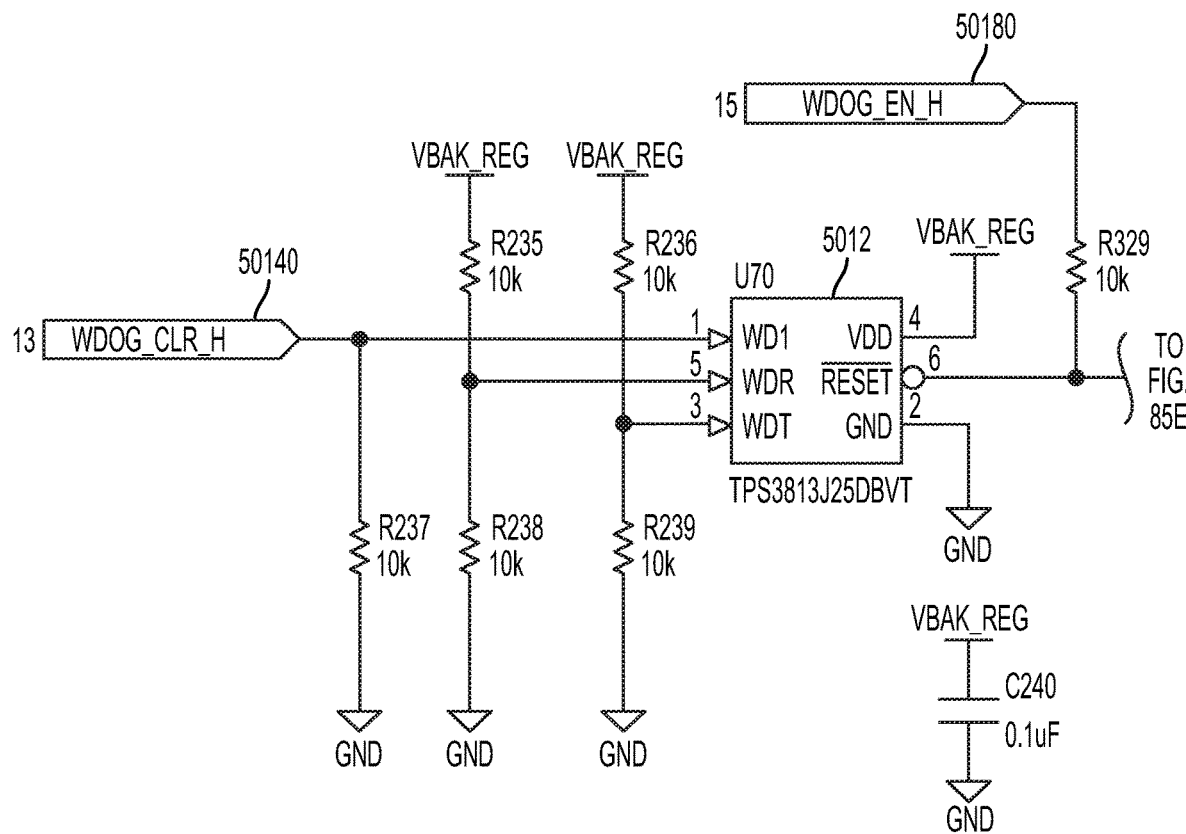
Figure 85E:
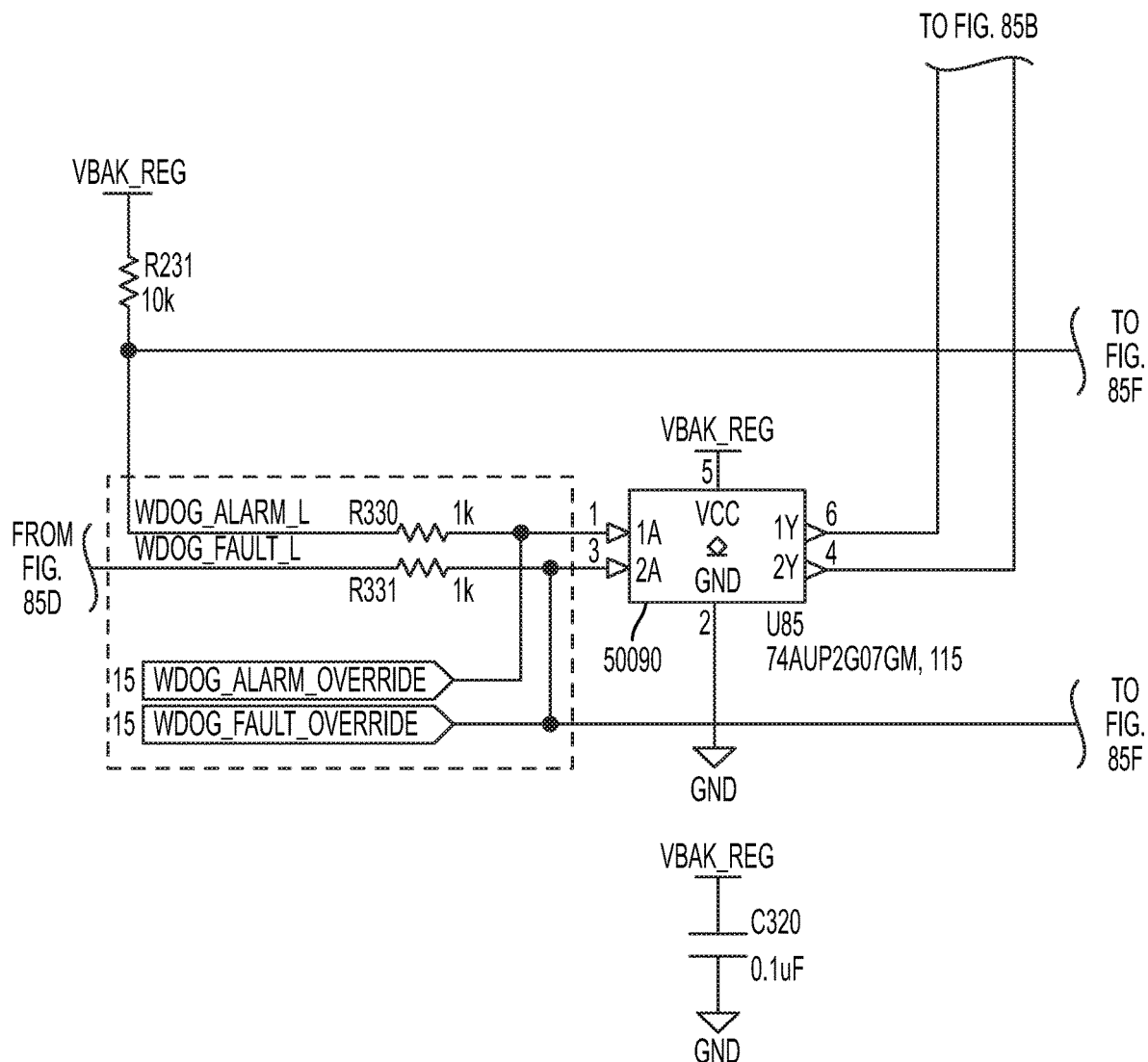
Figure 85F:
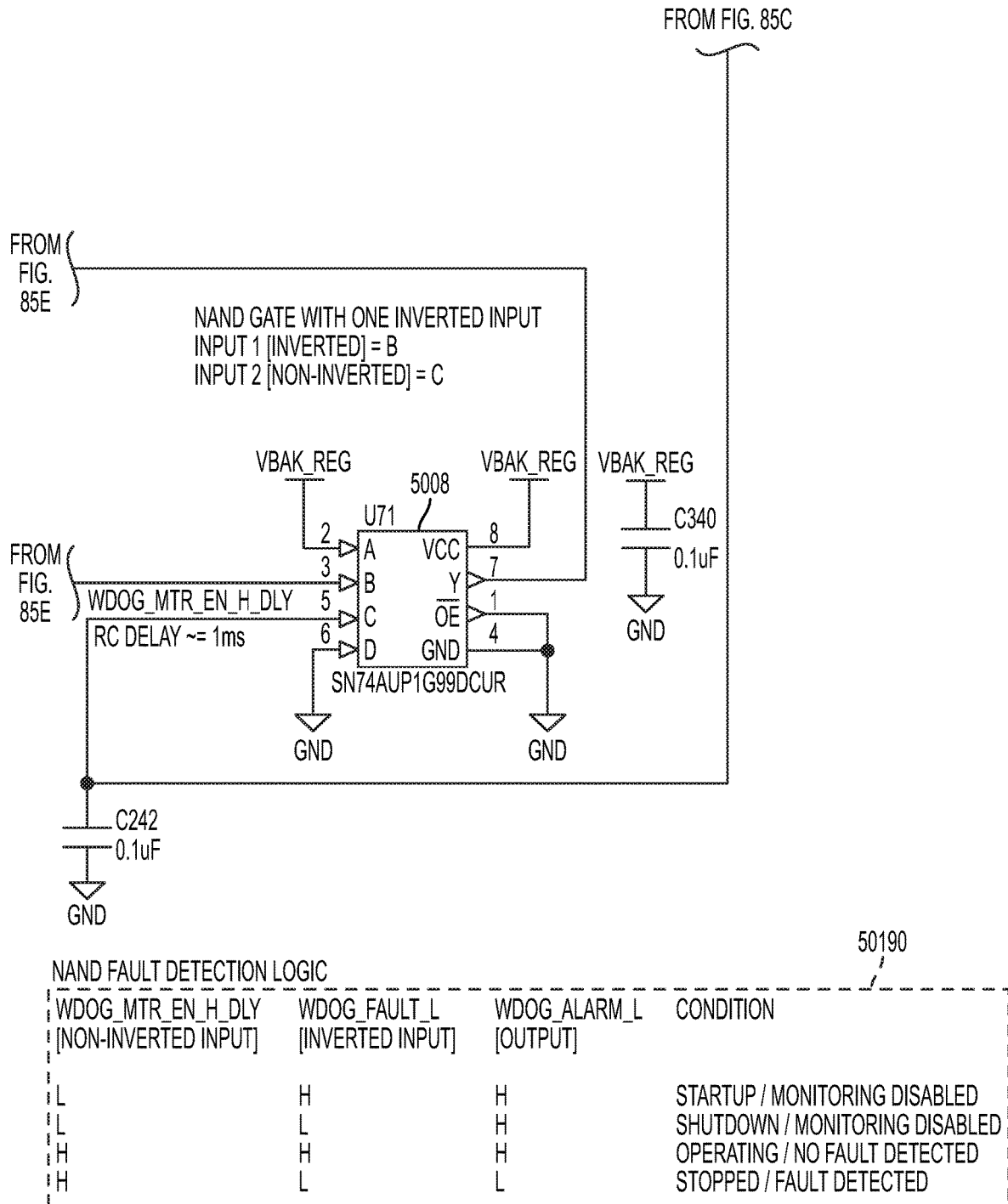

FIG. 84 shows a state diagram illustrating a method 50650 of providing a watchdog functionality in accordance with an embodiment of the present disclosure. The method 50650 is shown as a state diagram and includes states, 50670, 50690, 50990, 50720, 50750, 50770 and 50790, and transition conditions 50660, 50680, 50700, 50710, 50730, 50740, 50760, 50780, 50800, and 50810.

The method 50650 may be implemented by software, hardware, software in execution, or some combination thereof (e.g., as a hardware watchdog system). The method 5065 may be implemented by the watchdog 3460 of FIG. 59J such that it provides a motor enable signal to the motor controller 3431. FIGS. 85A-85F show one specific embodiment of a system that implements the method 50650 of FIG. 84.

Refer now to FIGS. 84, and 85A-85F. When the power is supplied to the watchdog system (e.g., system 50030), the method 50650 transitions 50660 to the watchdog system off state 50670 where the motor enable signal is off (e.g., line 50150), the alarm is off (e.g., line 50160), and the timer is in an unknown state. The timer may be part of the watchdog IC 50120. The watchdog IC 50120 is a window watchdog. The system 50030 also includes an I2C control lines 50130 that interface with an I/O expander 50040 (or other hardware latches). The I2C control lines 50130 may be part of the connections from the RTP 35000 to the watchdog 3460 of FIG. 59J. Additionally, a watchdog clear signal (line 50140 of FIG. 85D) may also be received from the RTP 35000 to the watchdog 34600. That is, the watchdog clear line 50140 "pets" the watchdog IC 50120.

In transition 50680, the RTP 3500 (see FIG. 59J) clears the watchdog IC's 50120 timer via the watchdog clear line 50140 and the RTP 35000 enables the watchdog IC's 50120 output via the I2C control lines 50130 by instructing the I/O expander 50040 to enable a watchdog enable line 50180. This causes the method 50650 to enter into the state 50690. In state 50690, the timer is initialized (set to zero), the motor enable line 50150 is set to off and the alarm line 50160 is set to off.

The RTP 3500 enables the motor power via the I2C control lines 50130 by setting the D-flip-flop to true (using the preset pin of a D-flip-flop 50050) and pauses for 1 ms in transition 50700. The method 50650 transitions to state 50990 where the watchdog IC's 5012 timer is running, the motor enable line 50150 is enabled, and the timer is less than 200 milliseconds. If the RTP 3500 sets the watchdog clear line 50140 when the watchdog is greater than 10 milliseconds and less than 200 milliseconds, the transition 50710 transitions the method 50650 to state 50720 wherein the timer is reset. The method 50650 will transition back to state 50990.

If the timer reaches 200 milliseconds or the timer is less than or equal to 10 milliseconds and the RTP 3500 sets the watchdog clear line 50140, transition 50740 transitions the method to state 50750. In state 50750, the watchdog IC 50120 sends out a fault signal that is buffered by a buffer 50090 which clears the D-flip-flop 50050 thereby turning the motor line 50150 off. In state 50750, the watchdog IC 50120 also sends out the fault signal which is received by a NAND gate 50080 via an inverted input, which outputs a signal to a logic buffer 50090 which clears a D-flip-flip 50070 and thereby turns on the a alarm line 50160. The output of the D-flip-flop 50070 is amplified by a load switch 50060.

When the motor enable signal line 50150 is set to turn the motor off, the off signal propagates through the non-inverting input of the NAND gate 50080 after about 1 millisecond, which causes the transition 50760 to transition to state 50770 thereby allowing the alarm to be disabled. An I2C command may cause transition 50800 to reset the system 50030 back to state 50670.

Otherwise, the alarm line 50160 will continue to alarm until a silence button 50170 is pressed which is coupled to the preset of the D-flip-flop 50070 to set the alarm line 50160 to off. That is, the button will cause the transition 50780 to transition the method 50650 to state 50790. An I2C signal via the I2C control lines 50140 to the IO expander 50040 may cause the method 50650 to transition to state 50670.

Figure 86:
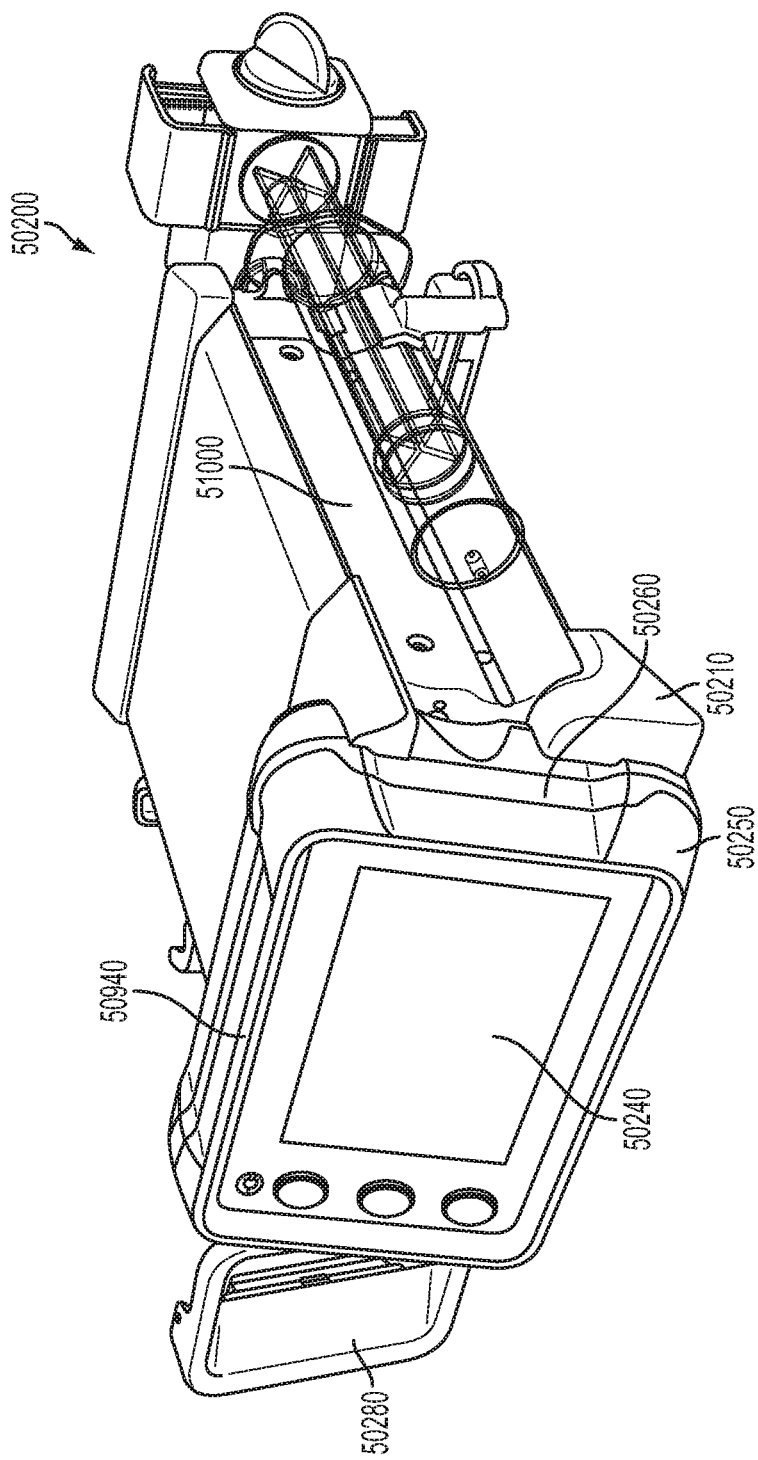
FIG. 86 shows another embodiment of syringe pump having a bumper in accordance with an embodiment of the present disclosure.

FIG. 86 shows another embodiment of syringe pump 50200 having a bumper 50210 in accordance with an embodiment of the present disclosure. The pump 50200 may couple to a pole via the clamp 50280. The pump 50200 includes a syringe seat 51000 that accommodates a bumper 50210.

The pump 50200 also includes a touchscreen 50240 coupled to the pump 50200 via an outer periphery 50250. The outer periphery 50250 includes an indicator light 50260. The indicator light 50260 may wholly wrap around the touchscreen 50240. The indicator light 50260 may include a diffuser wrapped around the touchscreen 50240 with a plurality of LED lights embedded therein (or optically coupled thereto). The indicator light 50260 may blink when the pump 50200 is running and/or it may be a specific color when the pump is running (e.g., red, blue, green, yellow, etc.). The indicator light 50260 may be continuously on when the pump 50200 is not running or is in a standby state. Additionally, alternatively, or optionally, the indicator light 50260 may be a specific color when the pump is not running or is in a standby state (e.g., red, blue, green, yellow, etc.).

The pump 50200 may also include a gesture-recognition apparatus 50940, which may be a camera. A processor of the pump 50200 may be coupled to the gesture-recognition apparatus 50940 to receive user input from a gesture by a user. That is, the processor may be configured to present a user with at least one option via the user interface 50240 and receive a selected one of the at least one option via the gesture-recognition apparatus 50940. The processor coupled to the user interface 50240 may be configured provide a plurality of pump parameter inputs where each of the plurality of pump parameter inputs is configured to receive a user inputted parameter. The processor may be configured to determine whether all of the user inputted parameters of all of the plurality of pump parameters meets at least one predetermined safety criterion. Each of the plurality of pump parameter inputs may be present without another one of the plurality of pump parameters inputs.

The processor may be configured to provide a plurality of pump parameter inputs where each of the plurality of pump parameter inputs is configured to receive a user inputted parameter. The processor may be configured to require that all of the plurality of pump parameter inputs are inputted within a predetermined amount of time. The processor may be configured to receive a corresponding user inputted parameter for the plurality of pump parameter inputs in any order.

Figure 87:
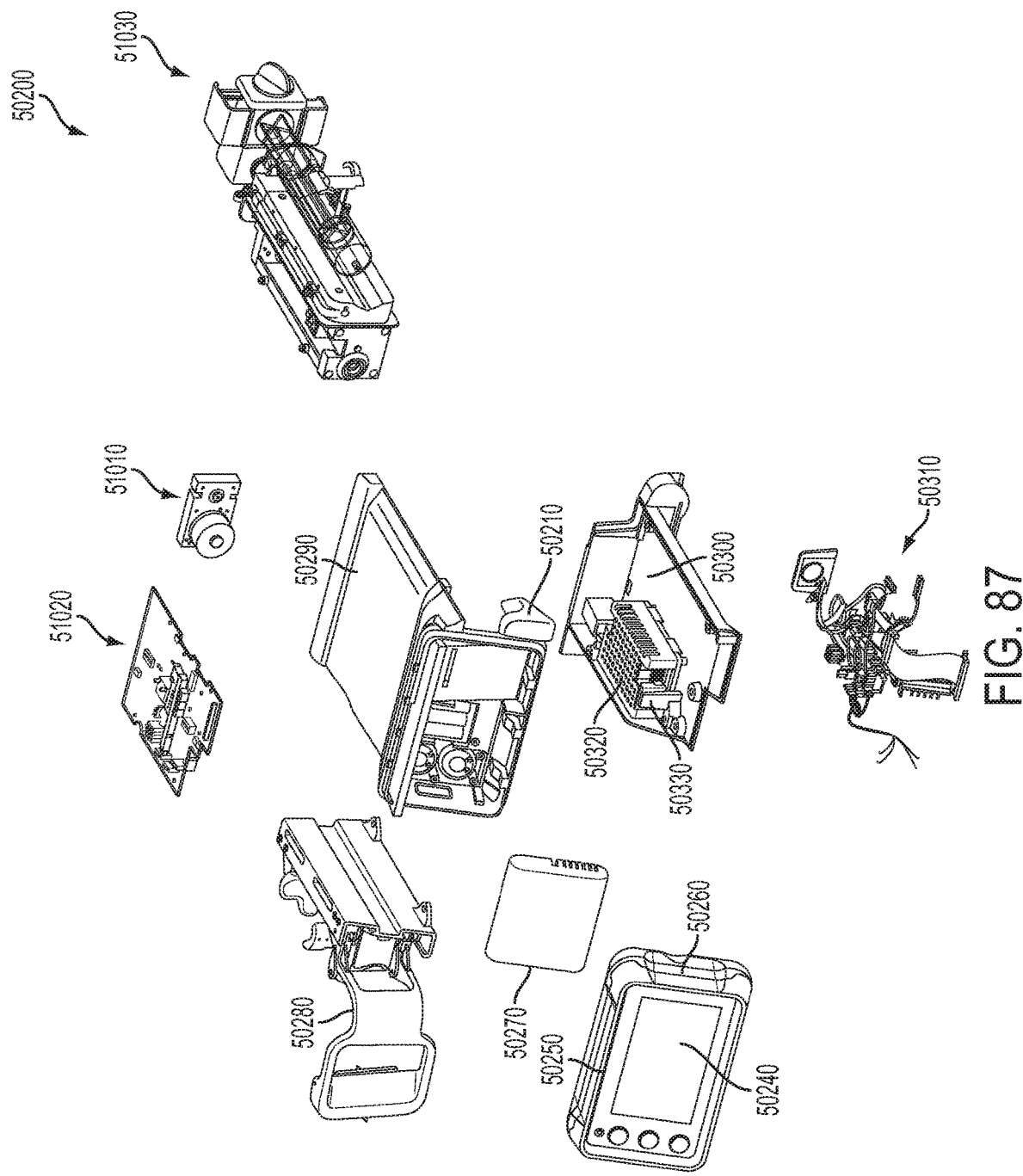
FIG. 87 shows an exploded view of the syringe pump of FIG. 86 in accordance with an embodiment of the present disclosure.
Figure 88:
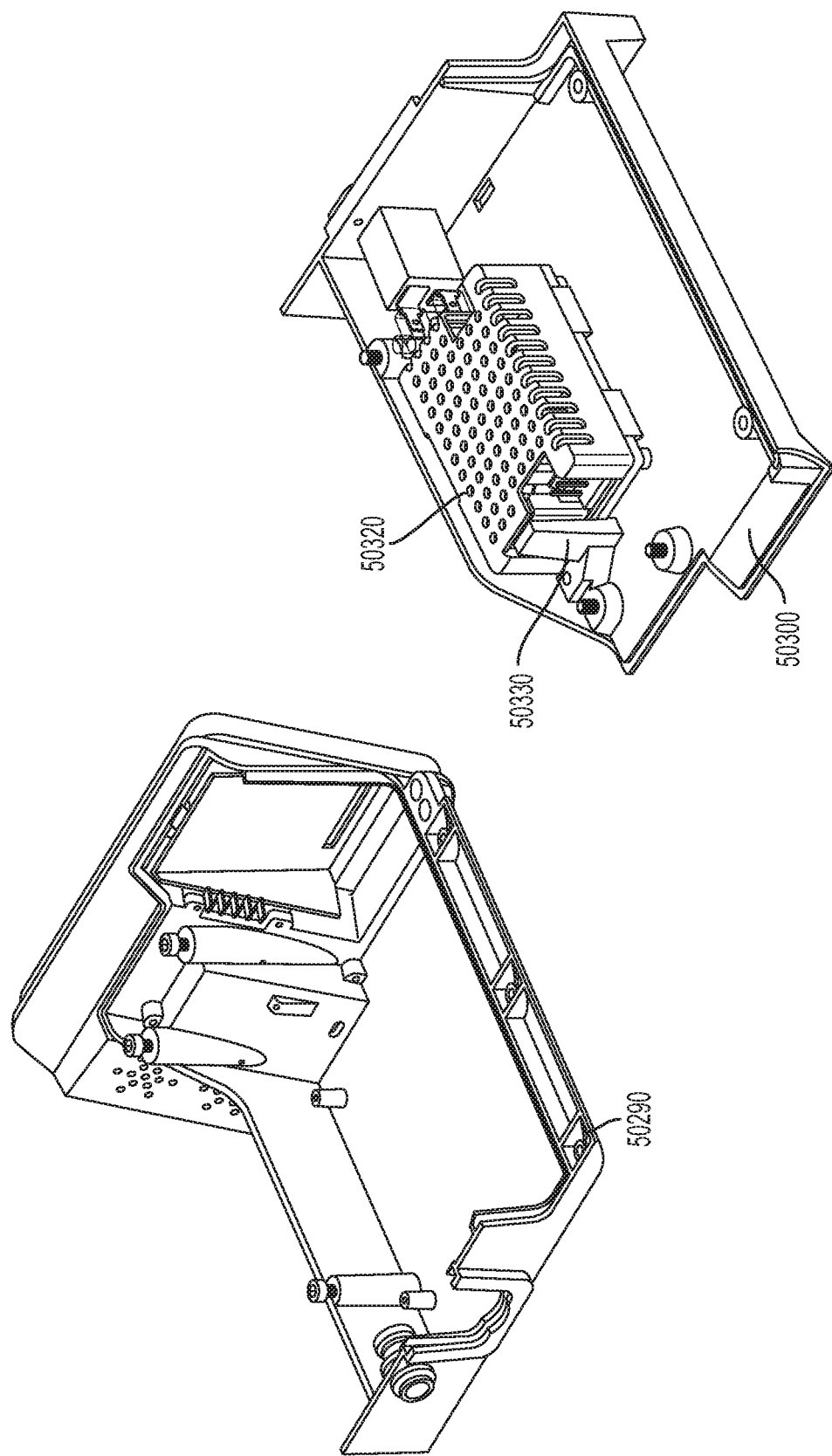
FIG. 88 shows a close-up view of the upper housing, the lower housing, and the power supply of the syringe pump of FIG. 86 in accordance with an embodiment of the present disclosure.

FIG. 87 shows an exploded view of the peristaltic pump 50200 of FIG. 86 in accordance with an embodiment of the present disclosure. The pump 50200 includes an upper housing portion 50290 and a lower portion housing 50300. Additionally or alternatively, the upper portion 50290 and the lower portion 50300 of the housing 50290, 50300 may be unitarily formed in some specific embodiments. A modular syringe pumping mechanism 51030 may be coupled to the housing 50290, 50300. A motor 51010 actuates the modular syringe pumping mechanism 51030. The motor 51010 may be controlled via a circuit board 51020 that is coupled to the motor 51010 and to various sensors, actuators, the touchscreen 5024, etc. The pump 50200 also includes cabling 50310 and a battery 50270 disposed behind the touchscreen 50240 (when assembled). FIG. 88 shows a close-up view of the upper housing 50290, the lower housing 50300, and the power supply 50320. Note how the power supply 50320 is thermally coupled to the lower housing portion 50600 via the conductive path 50330.

The pump 50200 includes a power supply 50320. The power supply 50320 is coupled to a conductive path 50330 to the housing 50300, 50290 (when assembled). The conductive path 50330 may be a piece of metal and may be unitarily formed with the housing 50300 (or 50290). The power supply 50320 may use the housing 50290, 50300 as a heat sink. The power supply 50320 may use any surface of the housing 50290, 50300 so that it is thermally coupled thereto and/or may be thermally coupled to the housing 50290, 50300 via the thermally conductive path 50330.

Figure 89B:
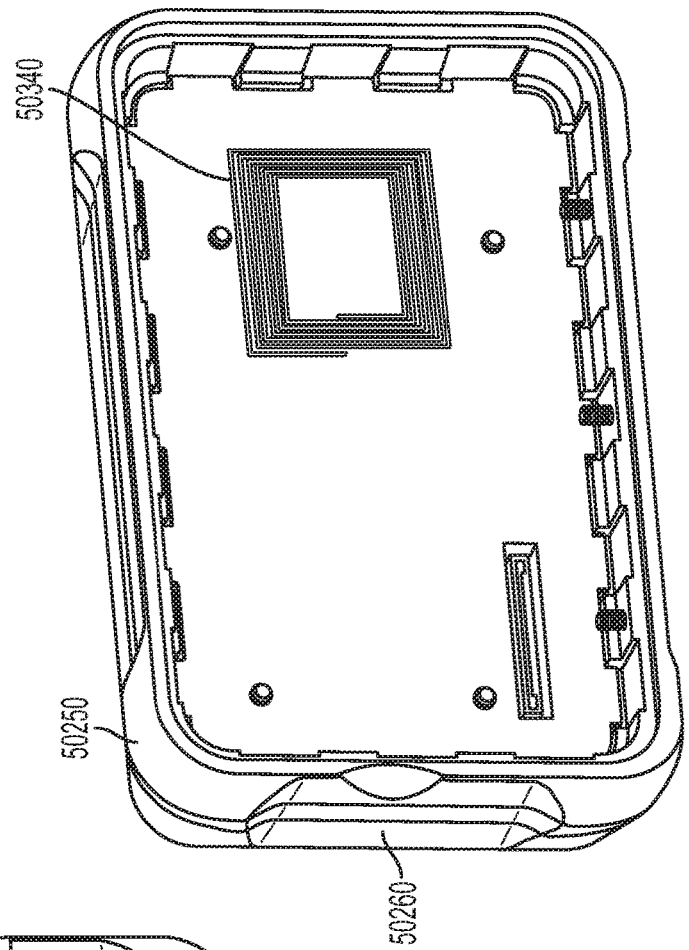
FIG. 89B shows a back view of the display of the pump of FIG. 86 in accordance with an embodiment of the present disclosure.
Figure 89A:
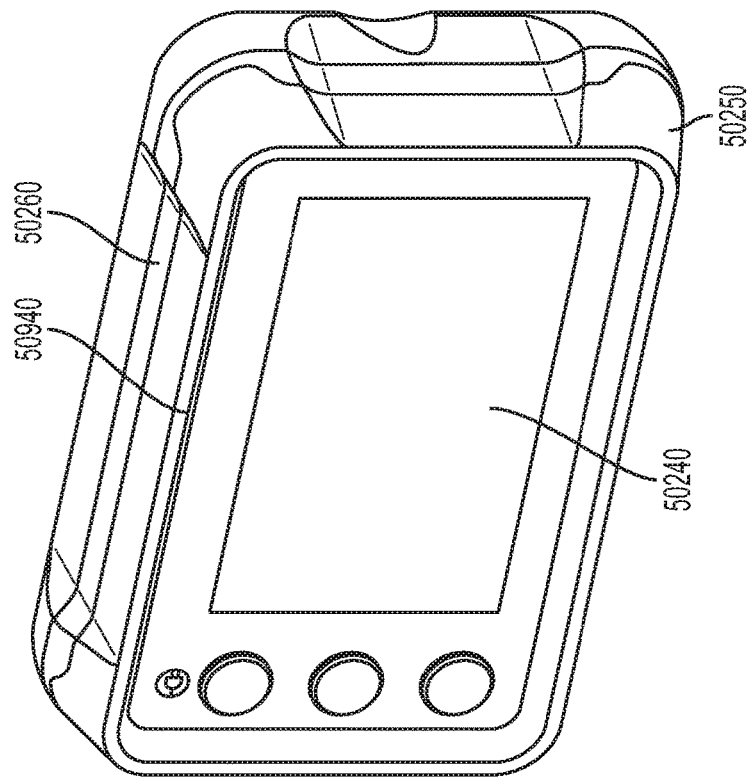
FIG. 89A shows a front view of the display of the pump of FIG. 86 in accordance with an embodiment of the present disclosure.
Figure 90:
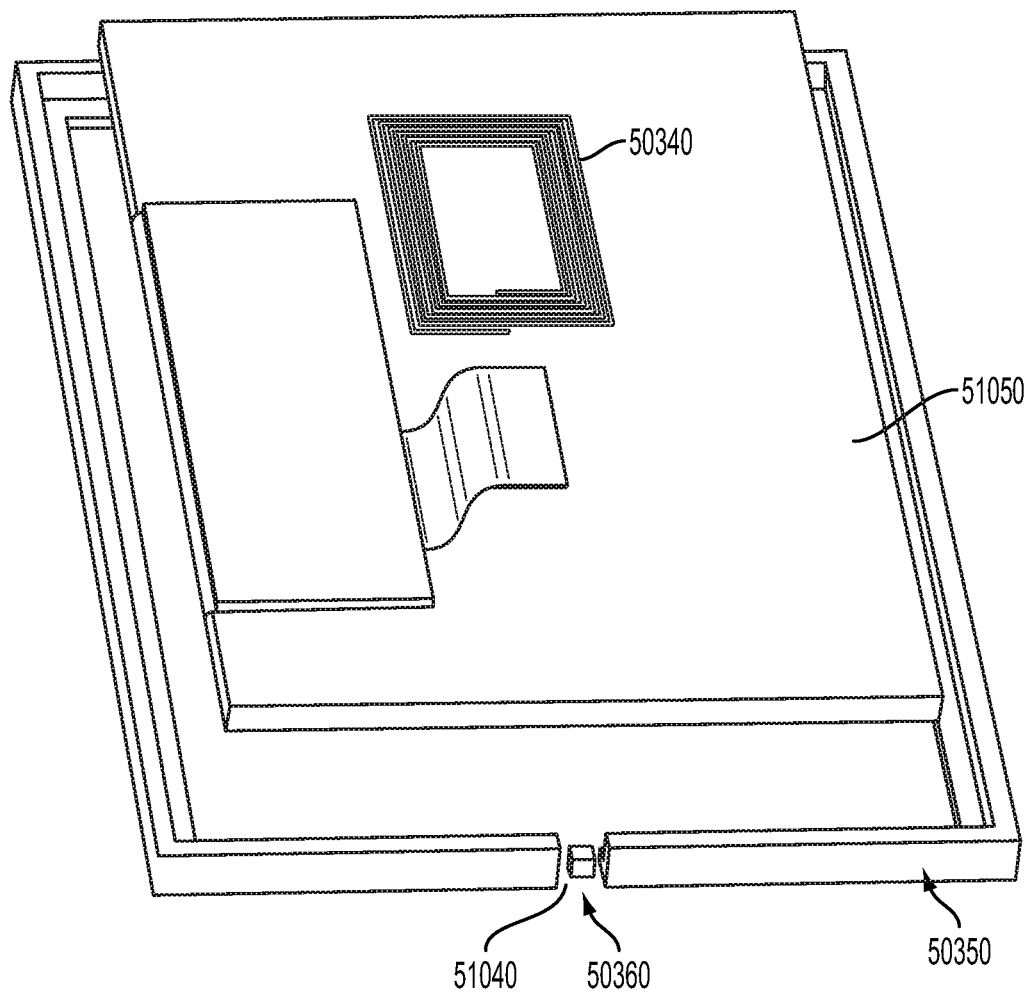
FIG. 90 shows the back of the sensor portion of the touchscreen and a frame-based split-ring resonator of for use with a near-field antenna in accordance with an embodiment of the present disclosure.

FIG. 89A shows a front view of the display of the pump 50200 and FIG. 89B shows a back view of the display of the pump 50200 in accordance with an embodiment of the present disclosure. On the back of the touchscreen 50240 (seen easily in FIG. 89B) a near-field antenna 50340 is disposed. FIG. 90 shows the sensor portion 51050 of the touchscreen with the near-filed antenna 50340 disposed adjacent to the backside of the sensor portion 51050 of the touchscreen 50240 (see FIGS. 89A-89B). A frame 50350 is shown that forms a loop of metal with a gap 51040 having a dielectric 50360 disposed within the gap 51040. The frame 50350 may be a frame of the sensor 51050 and/or the touchscreen 50240. The antenna 50340 may operate at 13.56 Megahertz and/or may be an NFC antenna. The metal frame 50350 in conjunction with the gap 51040 and the dielectric 50260 disposed within the gap may form a split-ring resonator. The metal frame 50350 forms an inductive element of the split-ring resonator, and the gap 50140 with the dielectric 50360 disposed therein form a capacitive element of the split-ring resonator.

Figure 91:
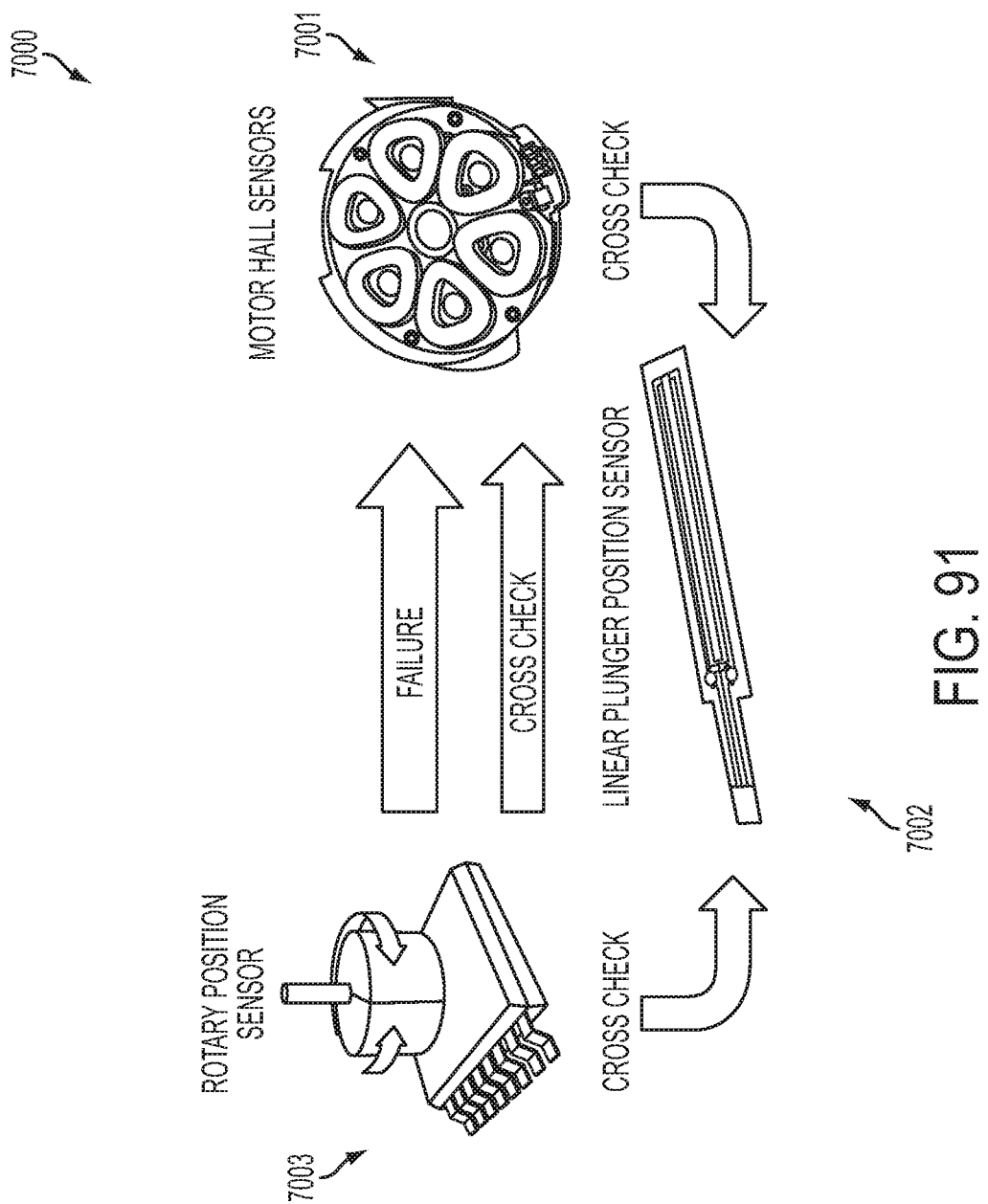
FIG. 91 shows a diagram illustrating the use of the sensors of the pump of FIG. 86 when one or more of the sensors are unavailable in accordance with an embodiment of the present disclosure.

FIG. 7000 shows a chart diagram illustrating the use of the sensors of the pump of FIG. 86 when one or more of the sensors are unavailable in accordance with an embodiment of the present disclosure. FIG. 91 shows sensors 7001, 7002, and 7003. The rotary position sensor 7003 may be the rotary sensor 1202 of FIGS. 59J and 60 (e.g., an encoder). The motor hall sensors 7001 may be the Hall Sensors 3436 on the motor 1200 of FIGS. 59J and 60. The linear plunger position sensor 7002 may be the linear sensor 3950 of FIG. 59B (to measure the position of the sliding block 800) such as the linear position sensor 1100 as shown in FIG. 57A.

FIG. 91 may be implemented as a method of using feedback sensors of a syringe pump 50206. The RTP 3500 of FIG. 59J may receive signals from the sensors 7001, 7002, 7003.

The RTP 3500 may cross-check the position of the sliding bock assembly 800 using all three sensors 7001, 7002, and 7003 relative to each other. The RTP 3500 will cross check the rotary position sensor 7003 with the motor hall sensors 7001, and if they are out of agreement by a predetermined amount, the RTP 3500 will compare them to the linear plunger position sensor 7002 to determine the operating one of the sensors 7001 and 7003. Thereafter, the RTP 3500 will use the operating one of the sensors 7001 and 7003. If the rotary position sensor 7003 is unavailable, the RTP 3500 will use the motor hall sensors 7001. The RTP 3500 also cross checks the rotary position sensor 5042 with the motor hall sensors 5043.

If it is determined that both of the motor hall sensors 7001 and the rotary position sensor 7003 are inoperative, the RTP 3500 will use only the linear plunger position sensor 7002.

Figure 93:
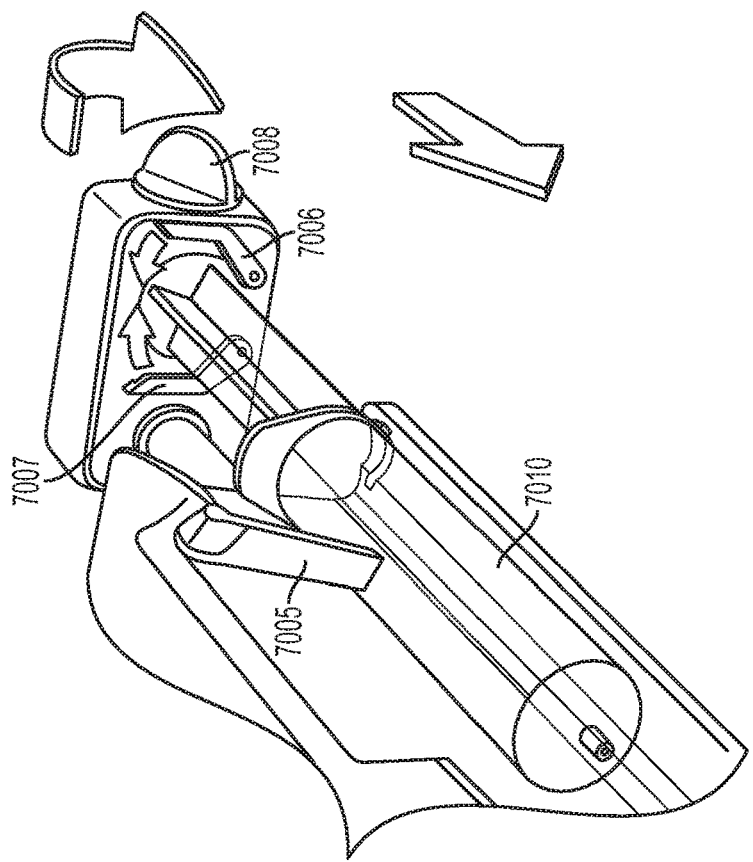
FIG. 93 shows a close-up view of the syringe pump of FIG. 92 in accordance with an embodiment of the present disclosure.
Figure 92:
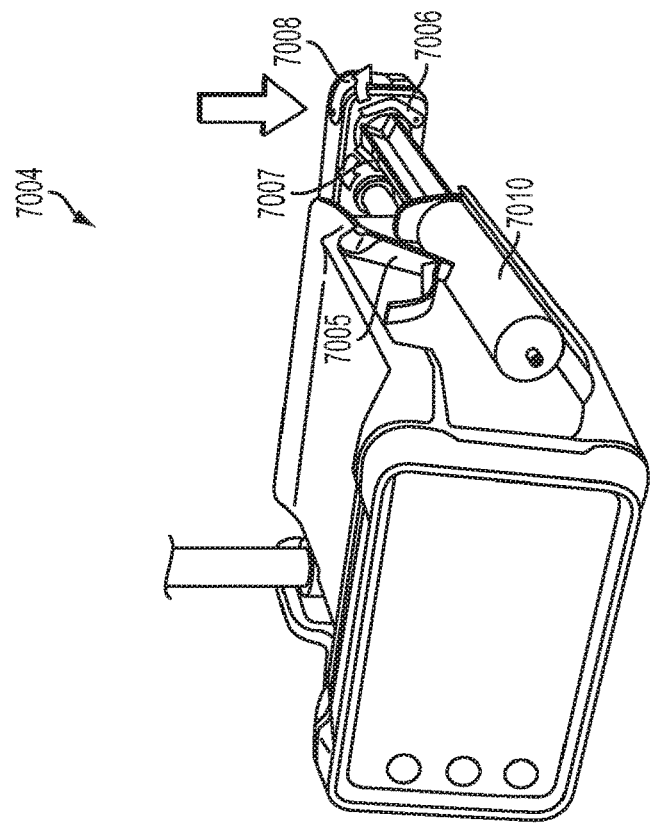
FIG. 92 shows a side view of a syringe pump having a retaining finger to retain a syringe in accordance with an embodiment of the present disclosure.

FIG. 92 shows a side view of a syringe pump 7004 having a retaining finger 7005 to retain a syringe and FIG. 93 shows a close-up view of the syringe pump 7004 of FIG. 92 in accordance with an embodiment of the present disclosure. The end of the syringe 7010 may be retained by pivotal jaw members 7006, and 7007. The pivotal jaw members 7006 and 7007 may include bends as shown. The knob 7008 may be operatively coupled to the pivotal jaw members 7006 and 7007 to cause them to pivot. The knob 7008 may be spring biased to rotate the knob 7008 to cause the pivotal jaw members 7006 and 7007 to rotate toward each other or to rotate away from each other.

Figure 94:
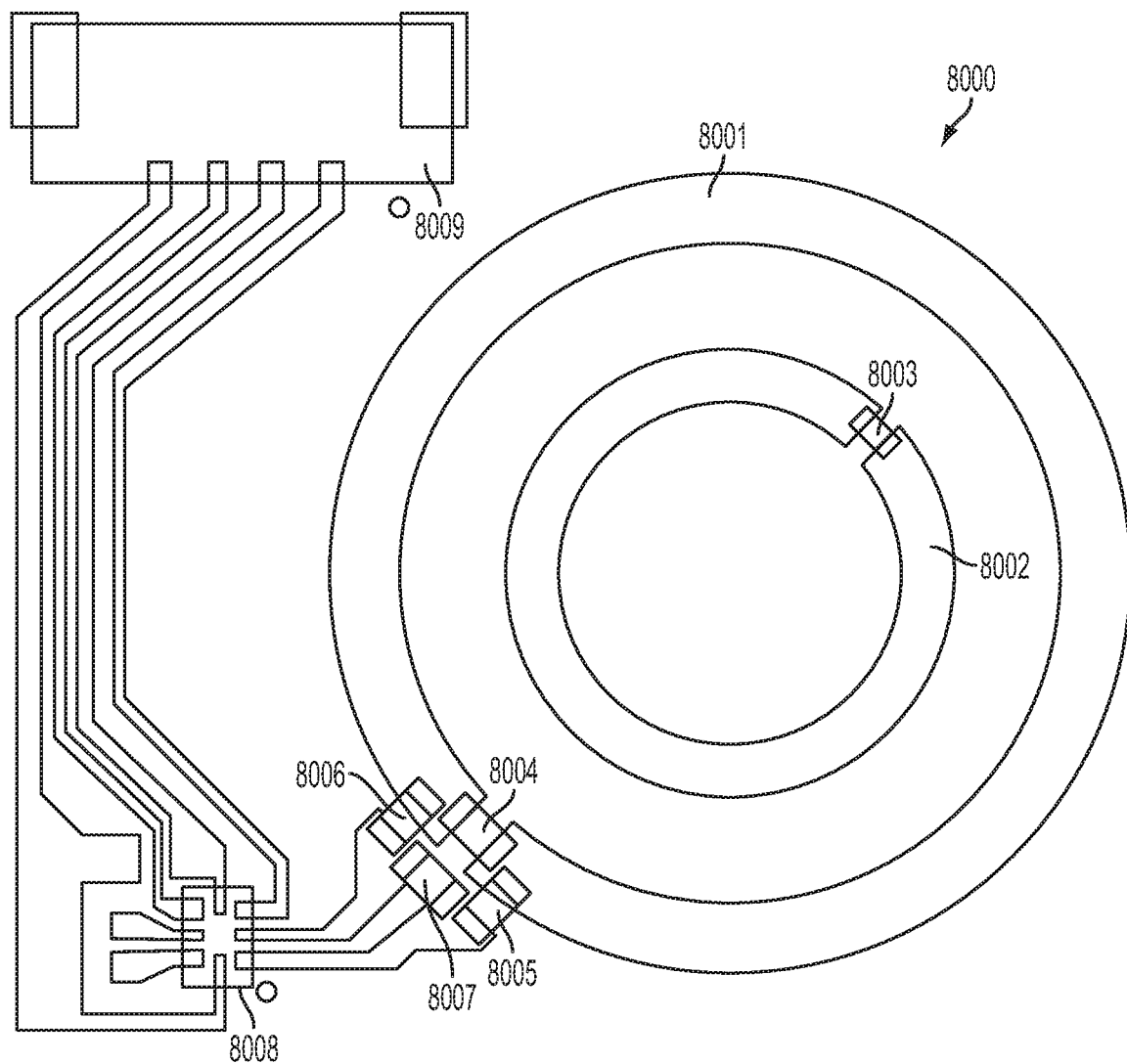
FIG. 94 shows a circuit for storing data within an RFID tag associated with a syringe pump in accordance with an embodiment of the present disclosure.

FIG. 94 shows a circuit 8000 for storing data within an RFID tag 8008 associated with an syringe pump (e.g., the syringe pump 500 of FIG. 29, the syringe pump 50200 of FIG. 86, or any other syringe pump) in accordance with an embodiment of the present disclosure. The RFID tag 8009 of FIG. 94 may be the RFID tag 3670 of FIG. 95E. The antenna 8001 of FIG. 94 may be the antenna 3955 of FIG. 59E.

The antenna 8001 is coupled to an RFID tag 8008 such that an RFID reader (i.e., RFID interrogator) can communicate with the RFID tag 8008. The circuit 8000 may be placed on a 1×1 PCB inch board with a solid-metal ground plane of the back side.

An inner loop 8002 with a capacitor 8003 may form a split-ring resonator to enhance the read range capability of the circuit 8000. The RFID tag 8008 may be coupled to the antenna 8001 via an impedance matching network 8004, 8005, 8006, 8007. The circuit 8000 may be configured for use with a 900 Megahertz RFID reader.

A reader chip 8009 may interface with the RFID tag 8008 to write data (e.g., log data) thereto. The reader chip 8009 may communicate with the RFID tag 8008 using I2C, a CAN bus, or other communications link. Alternatively, 8009 may be an electrical connector, in some embodiments.

Figure 95:
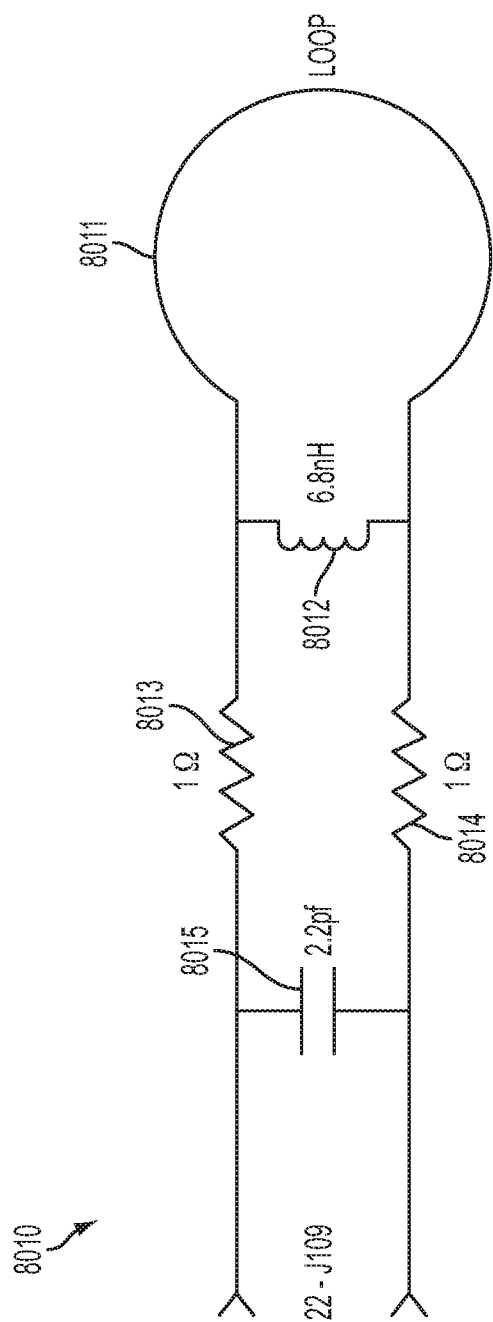
FIG. 95 shows an equivalent circuit for impedance as seen from the RFID tag of FIG. 94 in accordance with an embodiment of the present disclosure.

FIG. 95 shows an equivalent circuit 8010 for impedance as seen from the RFID tag 8008 of FIG. 94 in accordance with an embodiment of the present disclosure. A loop 8011 shows the antenna 8001 of FIG. 94. The inductor 8012 shows the inductor 8004 of FIG. 94. The resistors 8013 and 8014 are schematic representations of the resistors 8006 and 8005, respectively. The capacitor 8015 shows the capacitor 8007 of FIG. 94. The circuit elements 8012-8015 are used for impedance matching so that the RFID tag 8008 is efficiently coupled to the loop antenna 8001 such as in the circuit 8000 of FIG. 94.

Figure 96:
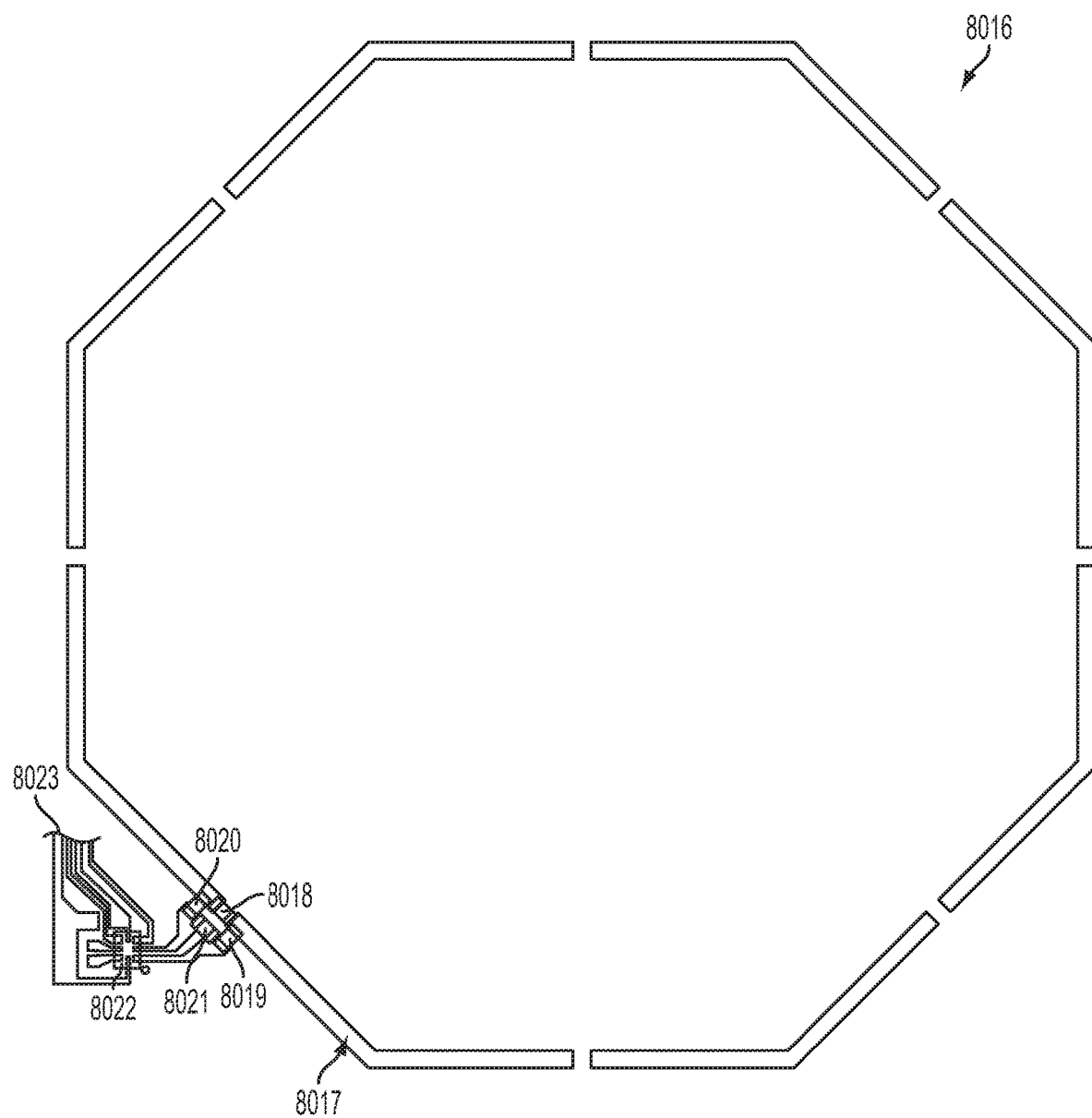
FIG. 96 shows another circuit for storing data within an RFID tag associated with a syringe pump in accordance with an embodiment of the present disclosure.

FIG. 96 shows another circuit 8016 for storing data within an RFID tag 8022 associated with an infusion pump (e.g., the syringe pump 500 of FIG. 29, the syringe pump 50200 of FIG. 86, or any other syringe pump) in accordance with an embodiment of the present disclosure. The antenna 8017 is shown. The RFID tag 8022 of FIG. 96 may be the RFID tag 3670 of FIG. 95E. The antenna 8017 of FIG. 96 may be the antenna 3955 of FIG. 59E.

Figure 97:
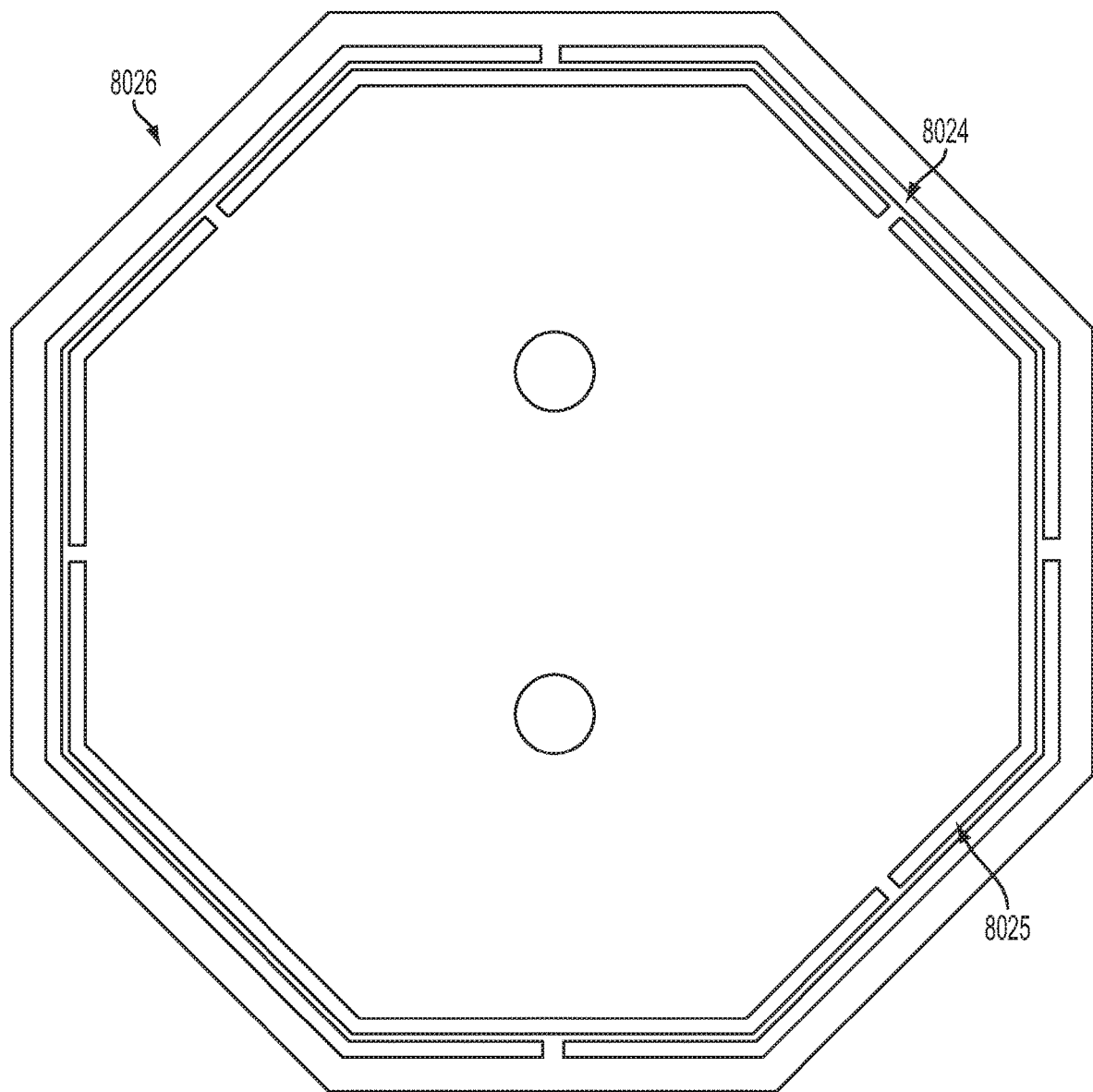
FIG. 97 shows a split-ring resonator used with the circuit of FIG. 96 in accordance with an embodiment of the present disclosure.

The antenna 8017 may have capacitors coupled to the gaps in the antenna 8017, in some embodiments. An impedance matching network 8018, 8020, 8021 may be used to efficiently couple the RFID tag 8022 to the antenna 8017. An interface 8023 may be used to communicate with the RFID tag 8022 (e.g., an I2C interface, a CAN interface, etc.). FIG. 97 shows a split-ring resonator 8026 used with the circuit 8016 of FIG. 96 in accordance with an embodiment of the present disclosure. The split-ring resonator 8026 may be printed on a PCB board with an inner loop 8025 and an outer loop 8024. The splint-ring resonator 8026 may be placed adjacent to the circuit 8016 of FIG. 96 to enhance its read range (e.g., the two planes defined by the two circuit's PCB boards may be parallel to each other).

Figure 98:
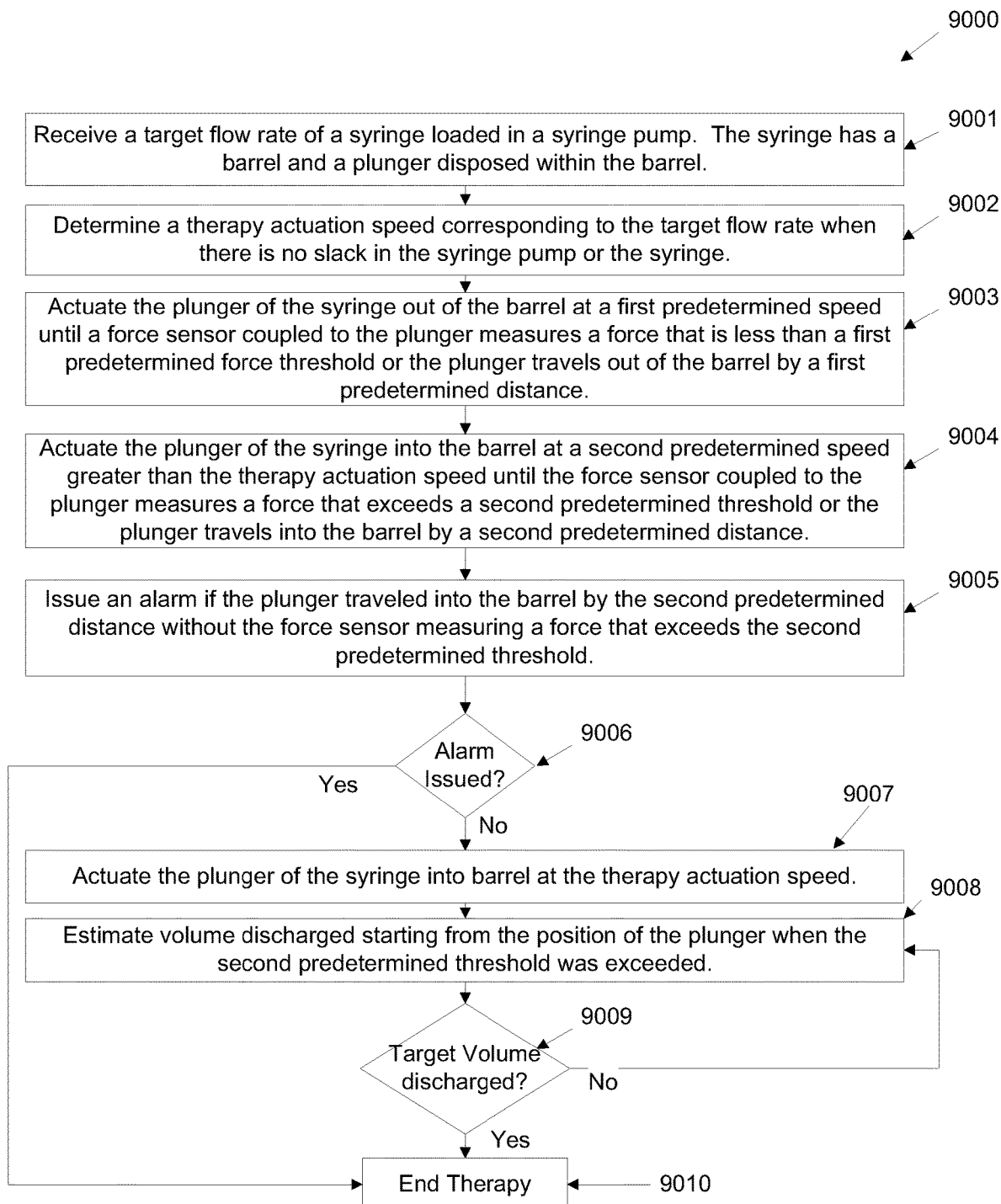
FIG. 98 shows a flow chart diagram illustrating a method for removing the effects of slack in a syringe pump having a syringe loaded on the syringe pump in accordance with an embodiment of the present disclosure.

FIG. 98 shows a flow chart diagram illustrating a method 9000 for removing the effects of slack in a syringe pump (e.g., the syringe pump 500 of FIG. 29, the syringe pump 50200 of FIG. 86, or any other syringe pump) having a syringe loaded on the syringe pump in accordance with an embodiment of the present disclosure. The Method 9000 includes acts 9001-9010 including two decision acts 9006 and 9009.

Act 9001 receives a target flow rate of a syringe loaded in a syringe pump. The syringe has a barrel and a plunger disposed within the barrel. Act 9002 determines a therapy actuation speed corresponding to the target flow rate when there is no slack in the syringe pump or the syringe. Act 9003 actuates the plunger of the syringe out of the barrel at a first predetermined speed until a force sensor coupled to the plunger measures a force that is less than a first predetermined force threshold or the plunger travels out of the barrel by a first predetermined distance. Act 9004 actuates the plunger of the syringe into the barrel at a second predetermined speed greater than the therapy actuation speed until the force sensor coupled to the plunger measures a force that exceeds a second predetermined threshold or the plunger travels into the barrel by a second predetermined distance. Act 9005 issues an alarm if the plunger traveled into the barrel by the second predetermined distance without the force sensor measuring a force that exceeds the second predetermined threshold. If an alarm is issued in act 9005, act 9006 branches the method 9000 to end the therapy 9010. Act 9007 actuates the plunger of the syringe into the barrel at the therapy actuation speed. Act 9008 estimates volume discharged starting from the position of the plunger when the second predetermined threshold was exceeded. Act 9009 will repeat act 9008 until the target volume is discharged, after which case, act 9009 will end the therapy 9010.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in the drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g., "a," "an," or "the," this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first," "second," "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A syringe pump, comprising:
   a motor operatively coupled to a lead screw and configured to rotate the lead screw, the motor having an integral motor rotation sensor configured to provide a motor rotation signal;
   a rotary position sensor operatively coupled to at least one of the motor and the lead screw to provide a rotation signal;
   a sliding block assembly configured to engage with the lead screw to actuate the sliding block assembly along the lead screw in accordance with rotation of the lead screw;
   a linear position sensor operatively coupled to the sliding block assembly and configured to provide a linear position signal; and
   at least one processor configured to control rotation of the motor, wherein the at least one processor operatively receives the motor rotation signal from the integral motor rotation sensor of the motor, the rotation signal from the rotary position sensor, and the linear position signal from the linear position sensor, wherein the at least one processor is configured to determine a discrepancy exists among the motor rotation signal, the rotation signal, and the linear position signal.

2. The syringe pump according to claim 1, wherein the rotary position sensor is operatively coupled to the motor.

3. The syringe pump according to claim 1, wherein the rotary position sensor is operatively coupled to the motor.

4. The syringe pump according to claim 1, wherein the at least one processor is further configured to continue an infusion treatment by ignoring an inoperative one of the integral motor rotation sensor, the rotary position sensor, and the linear position sensor.

5. The syringe pump according to claim 1, wherein the rotary position sensor is a magnetic encoder sensor.

6. The syringe pump according to claim 1, wherein the syringe pump is configured to communicate with a monitoring client.

7. The syringe pump according to claim 1, wherein the sliding block assembly comprises:
   a half-nut housing having a lead screw void configured to receive the lead screw;
   a half nut disposed within the half-nut housing, the half nut having half-nut threads at an end adjacent to the lead screw void, the half nut is slideable between an engagement position whereby the half-nut threads engage with threads of the lead screw and a disengagement position whereby the half-nut threads are disengaged from the threads of the lead screw, wherein the half nut includes a half-nut cam-follower surface and a half nut slot; and
   a barrel cam disposed within the half-nut housing and configured to engage with the half-nut cam-follower surface, the barrel cam includes a pin configured to fit within the half nut slot, wherein the barrel cam is configured to rotate between a first position and a second position to actuate the half nut between the engagement position and the disengagement position, respectively.

8. The syringe pump according to claim 7, wherein the half-nut cam-follower surface is positioned adjacent to the barrel cam.

9. The syringe pump according to claim 7, wherein the half-nut cam-follower surface is disposed near an opposite end of the half nut relative to the half-nut threads.

10. The syringe pump according to claim 7, wherein the half nut further includes a half-nut slot plate defining the half nut slot.

11. The syringe pump according to claim 10, wherein the half-nut slot plate extends away from the lead screw.

12. The syringe pump according to claim 10, wherein the half-nut slot plate is disposed near an edge of the half-nut cam-follower surface such that the half-nut slot plate engages the half-nut cam-follower surface at a right angle.

13. The syringe pump according to claim 12, wherein:
   the barrel cam is disposed adjacent to the half-nut cam-follower surface,
   the pin of the barrel cam is disposed on an end of the barrel cam, and
   the pin of the barrel cam engages with the half nut slot of the half-nut slot plate as the barrel cam engages with the half-nut cam-follower surface.

14. The syringe pump according to claim 13, wherein rotation of the barrel cam to the second position engages with the half nut slot to pull the half nut toward the barrel cam and away from the lead screw.

15. The syringe pump according to claim 14, wherein the barrel cam includes a barrel cam shoulder cylindrically shaped and having a first radius.

16. The syringe pump according to claim 15, wherein the barrel cam has a second radius that is substantially coextensive with the first radius, wherein the barrel cam includes a barrel cam flat wherein the second radius is less than the first radius, wherein the barrel cam flat is positioned to allow the half nut to extend closer to a center axis of the barrel cam than the distance of the first radius when the half nut is pulled toward the barrel cam and the barrel cam rotates to the second position.

17. The syringe pump according to claim 16, wherein the barrel cam flat is configured to be flush against the half-nut cam-follower surface when the barrel cam is in the second position.

18. The syringe pump according to claim 17, wherein the half-nut housing includes a barrel cam void configured to be adjacent a barrel cam surface of the barrel cam so that the barrel cam freely rotates within the barrel cam void.

19. The syringe pump according to claim 7, wherein the half nut includes a rod bushing void positioned between the half-nut threads and the half-nut cam-follower surface.

20. The syringe pump according to claim 7, wherein the syringe pump communicates a speed of a plunger to a monitoring client.

21. The syringe pump according to claim 7, wherein the half-nut housing defines a half-nut housing groove configured to cooperate with a syringe pump assembly guide rail.

22. The syringe pump according to claim 7, further comprising a half-nut slot plate disposed near an edge of the half-nut cam-follower surface such that the half-nut slot plate engages the half-nut cam-follower surface at a right angle.

23. The syringe pump according to claim 7, wherein:
   the barrel cam is disposed adjacent to the half-nut cam-follower surface,
   the pin of the barrel cam is disposed on an end of the barrel cam, and
   the pin of the barrel cam engages with the half nut slot as the barrel cam engages with the half-nut cam-follower surface.

24. The syringe pump according to claim 7, wherein rotation of the barrel cam to the second position engages with the half nut slot to pull the half nut toward the barrel cam and away from the lead screw.

25. The syringe pump according to claim 7, wherein the barrel cam includes a cylindrically shaped barrel cam shoulder.

26. The syringe pump according to claim 7, wherein the barrel cam has a second radius that is substantially coextensive with a first radius, wherein the barrel cam includes a barrel cam flat wherein the second radius is less than the first radius, wherein the barrel cam flat is positioned to allow the half nut to extend closer to a center axis of the barrel cam than the distance of the first radius when the half nut is pulled toward the barrel cam as the barrel cam rotates to the second position.

27. The syringe pump according to claim 7, wherein the barrel cam includes a barrel cam flat configured to be flush against the half-nut cam-follower surface when the barrel cam is in the second position.

28. The syringe pump according to claim 7, wherein the half-nut housing includes a barrel cam void configured to be adjacent a barrel cam surface of the barrel cam so that the barrel cam freely rotates within the barrel cam void.

29. The syringe pump according to claim 7, further comprising a retaining finger pivotally coupled to a housing of the syringe pump, wherein the retaining finger is configured to rotate toward a syringe disposed within a syringe seat to retain the syringe.

30. The syringe pump according to claim 1, further comprising
   a housing;
   a syringe seat coupled to the housing, the syringe seat configured to retain a syringe having a barrel and a plunger disposed within the barrel;
   a plunger head assembly coupled to the sliding block assembly and configured to drive the plunger of the syringe into the barrel of the syringe, the plunger head assembly having a force sensor operatively coupled to the plunger of the syringe to measure a force of the plunger head assembly on the plunger of the syringe; and
   a processor operatively coupled to the motor and configured to control rotation of the motor to thereby control actuation of the plunger head assembly, the processor is also operatively coupled to the force sensor to receive a measured force therefrom, wherein the processor is configured to:
      receive a target flow rate of the syringe loaded on the syringe pump;
      determine a therapy actuation speed corresponding to the target flow rate;
      command the motor to actuate the plunger of the syringe out of the barrel at a first predetermined speed until the force sensor coupled to the plunger measures a force that is less than a first predetermined force threshold or the plunger travels out of the barrel by a first predetermined distance;
      command the motor to actuate the plunger of the syringe into the barrel at a second predetermined speed greater than the therapy actuation speed until the force sensor coupled to the plunger measures a force that exceeds a second predetermined threshold or the plunger travels into the barrel by a second predetermined distance; and
      command the motor to actuate the plunger of the syringe into the barrel at the therapy actuation speed.

31. The syringe pump according to claim 30, wherein the therapy actuation speed corresponds to the target flow rate when there is no slack in the syringe pump or the syringe.

32. The syringe pump according to claim 30, wherein the processor is further configured issue an alarm if the plunger traveled into the barrel by the second predetermined distance without the force sensor measuring a force that exceeds the second predetermined threshold.

33. The syringe pump according to claim 30, further comprising a transceiver, wherein the processor is configured to communicate via the transceiver with a monitoring client.

34. A method of actuating a syringe pump, the method comprising:
   rotating a lead screw with a motor;
   monitoring the motor with an integral motor rotation sensor;
   monitoring a rotary position sensor operatively coupled to at least one of the motor and the lead screw;
   monitoring a position of a sliding block assembly using a linear position sensor;
   cross-checking the integral motor rotation sensor, the rotary position sensor, and the linear position sensor between each other;
   determining a discrepancy among the integral motor rotation sensor, the rotary position sensor, and the linear position sensor; and
   continuing an infusion treatment by ignoring an inoperative one of the integral motor rotation sensor, the rotary position sensor, and the linear position sensor.

* * * * *